US012578334B2

(12) United States Patent
Muthuswamy et al.

(10) Patent No.: US 12,578,334 B2
(45) Date of Patent: Mar. 17, 2026

(54) SENSOR FOR DETECTING BIOMARKERS IN A FLUID SAMPLE AND METHODS OF USE

(71) Applicants:Arizona Board of Regents on behalf of Arizona State University, Scottsdale, AZ (US); American University of Beirut, Beirut (LB)

(72) Inventors: Jitendran Muthuswamy, Scottsdale, AZ (US); Massoud Khraiche, Beirut (LB)

(73) Assignees: ARIZONA BOARD OF REGENTS ON BEHALF OF ARIZONA STATE UNIVERSITY, Scottsdale, AZ (US); AMERICAN UNIVERSITY OF BEIRUT, Beirut (LB)

( * ) Notice: Subject to any disclaimer, the term of this patent is extended or adjusted under 35 U.S.C. 154(b) by 0 days.

(21) Appl. No.: 18/566,986

(22) PCT Filed: Jun. 6, 2022

(86) PCT No.: PCT/US2022/032379
§ 371 (c)(1),
(2) Date: Dec. 4, 2023

(87) PCT Pub. No.: WO2022/256741
PCT Pub. Date: Dec. 8, 2022

(65) Prior Publication Data
US 2024/0272159 A1       Aug. 15, 2024

Related U.S. Application Data

(60) Provisional application No. 63/196,814, filed on Jun. 4, 2021.

(51) Int. Cl.
*G01N 33/53*       (2006.01)
*G01N 27/12*       (2006.01)
*G01N 33/543*       (2006.01)
*G01N 33/569*       (2006.01)

(52) U.S. Cl.
CPC ....... *G01N 33/56983* (2013.01); *G01N 27/12* (2013.01); *G01N 33/5438* (2013.01); *G01N 2333/165* (2013.01); *G01N 2469/20* (2013.01)

(58) Field of Classification Search
CPC ............. G01N 33/56983; G01N 27/12; G01N 33/5438; G01N 2333/165; G01N 2469/20
See application file for complete search history.

(56) References Cited

U.S. PATENT DOCUMENTS

| | | |
|---|---|---|
| 2006/0160134 A1 | 7/2006 | Melker et al. |
| 2009/0293590 A1 | 12/2009 | Zeng et al. |
| 2012/0003627 A1 | 1/2012 | Scholl et al. |
| 2016/0077086 A1 | 3/2016 | Holmes et al. |
| 2018/0356405 A1 | 12/2018 | Chou |
| 2019/0274599 A1 | 9/2019 | Polsky et al. |
| 2020/0158728 A1 | 5/2020 | Robinson et al. |

FOREIGN PATENT DOCUMENTS

WO     WO-2018067872 A1 *  4/2018

OTHER PUBLICATIONS

Afzal et al., Chemosensors, 2017, 5, 7, 25 pages (Year: 2017).*
Ainsworth, M. et al. Performance characteristics of five immunoassays for SARS-CoV-2: a head-to-head benchmark comparison. The Lancet Infectious Diseases, 2020, 20(12): p. 1390-1400.
Bartsch, Y.C. et al. Discrete SARS-CoV-2 antibody titers track with functional humoral stability. Nature Communications, 2021, 12(1).
Bastos, M.L. et al. Diagnostic accuracy of serological tests for covid-19: Systematic review and meta-analysis. The BMJ, 2020, 13 pages.
Cascella, M. et al. Features, Evaluation, and Treatment of Coronavirus (COVID-19) In: StatPearls [Internet]. Treasure Island (FL): StatPearls Publishing, published 2020, updated 2021, 20 pages.
Chan, J.F. et al., Improved molecular diagnosis of COVID-19 by the novel, highly sensitive and specific COVID-19-RdRp/Hel real-time reverse transcription-polymerase chain reaction assay validated in vitro and with clinical specimens. J Clin Microbial, 2020, 10 pages.
Chu, D.K.W. et al., Molecular Diagnosis of a Novel Coronavirus (2019-nCoV) Causing an Outbreak of Pneumonia. Clin Chem, 2020, 66(4): p. 549-555.
Corman, V.M. et al. Detection of 2019 novel coronavirus (2019-nCoV) by real-time RT•PCR. Euro Surveill, Jan. 2020, vol. 25(3), 8 pages.
Dobano, C., et al., Persistence and baseline determinants of seropositivity and reinfection rates in health care workers up to 12.5 months after COVID-19. Bmc Med, 2021. 19(1): p. 155.
Ergezen, E. et al., Real time monitoring of the effects of Heparan Sulfate Proteoglycan (HSPG) and surface charge on the cell adhesion process using thickness shear mode (TSM) sensor. Biosensors and Bioelectronics, 2007, 22(9-10): p. 2256-2260.
FDA. Policy for Coronavirus Disease—2019 Tests During the Public Health Emergency (Revised), issued May 2020, 3 pages.
(Continued)

*Primary Examiner* — Stacy B Chen
(74) *Attorney, Agent, or Firm* — Baker, Donelson, Bearman, Caldwell & Berkowitz, P.C.

(57) ABSTRACT

The invention relates to a diagnostic platform for detection of biomarkers associated with a particular condition, disease, or disorder and methods of making and using the same. In various embodiments, the diagnostic platform includes a sensing device and an electronic reading platform. Aspects of the invention are directed to a diagnostic platform for detection of at least one biomarker in a fluid sample. In embodiments, the diagnostic platform comprises a sensing device configured to receive the fluid sample. The platform can further comprise an electronic reading platform and a computing device. The electronic reading platform can be configured to activate the sensor.

30 Claims, 17 Drawing Sheets
Specification includes a Sequence Listing.

(56) References Cited

OTHER PUBLICATIONS

Grzelak, L. et al. A comparison of four serological assays for detecting anti-SARS-CoV-2 antibodies in human serum samples from different populations. Science Translational Medicine, 2020, 12(559).

Hagin, D., et al., Immunogenicity of Pfizer-BioNTech COVID-19 vaccine in patients with inborn errors of immunity. J Allergy Clin Immunol, 2021. 148(3): p. 739-749.

Harpaz, R. et al. Prevalence of Immunosuppression Among US Adults, 2013. JAMA, 2016, 316(23): p. 2547-2548.

Harris, E. K. Statistical principles underlying analytic goal-setting in clinical chemistry. Am J Clin Path, Aug. 1, 1979, 72 (2 Suppl):374-382.

Ivanov, A and E. Semenova, Long-term monitoring of the development and extinction of IgA and IgG responses to SARS-CoV-2 infection. J Med Virol, 2021. 93(10): p. 5953-5960.

Jacofsky, D. et al. Understanding Antibody Testing for COVID-19. Arthroplasty, 35 (2020) S74-S81, 8 pages.

Jiang, H.W., et al., SARS-CoV-2 proteome microarray for global profiling of COVID-19 specific IgG and IgM responses. Nat Commun, 2020. 11(1): p. 3581.

Khraiche M. et al. Multi-modal biochip for simultaneous, real-time measurement of adhesion and electrical activity of neurons in culture. Lab on Chip, 2012, 12, 2930-2941.

Khraiche, M.L. et al. Acoustic sensor for monitoring adhesion of Neuro-2A cells in real-time. J Neurosci Methods, 2005, 144(1): p. 1-10.

Khraiche, M.L. et al. Design and Development of Microscale Thickness Shear Mode (TSM) Resonators for Sensing Neuronal Adhesion. Front Neurosci, Jun. 2019, vol. 13, article 518, 15 pages.

Khraiche, M.L. et al. Early onset of electrical activity m developing neurons cultured on carbon nanotube immobilized microelectrodes. Conf Proc IEEE Eng Med Biol Soc, 2009, 2009: p. 777-80.

Kulikowska, J., et al., The Significance of COVID-19 Immunological Status in Severe Neurological Complications and Multiple Sclerosis—A Literature Review. Int J Mol Sci, 2021. 22(11).

Lauer, S.A. et al. The Incubation Period of Coronavirus Disease 2019 (COVID-19) From Publicly Reported Confirmed Cases: Estimation and Application. Ann Intern Med, Mar. 10, 2020: M20-0504, 7 pages.

Lee, C.Y.P. et al., Serological Approaches for COVID-19: Epidemiologic Perspective on Surveillance and Control. Frontiers in Immunology, Apr. 24, 2020: p. 1-7.

Li, R., et al. Substantial undocumented infection facilitates the rapid dissemination of novel coronavirus (SARS-CoV2). Science, Mar. 16, 2020, vol. 368, Issue 6490, pp. 489-493.

Li, X., et al. Molecular immune pathogenesis and diagnosis of COVID-19. J Pharm Anal, vol. 10, Issue 2, Apr. 2020, pp. 102-108.

Li, Z. et al. Development and clinical application of a rapid IgM-IgG combined antibody test for SARS-CoV-2 infection diagnosis. Journal of Medical Virology, 2020, 92(9): p. 1518-1524.

Liu, G. et al. COVID-19 Antibody Tests and Their Limitations. ACS Sensors, 2021, 6(3): p. 593-612.

Lu, F. et al., Finite element analysis of interference for the laterally coupled quartz crystal microbalances. Sensors and Actuators a-Physical, 2005, 119(1): p. 90-99.

Qiu, S. et al. Organic Printable Electronic Materials. Printed Electronics, 2016: p. 21-53.

Ricos, C. et al. Biological variations references database. Available online https://www.westgard.com/biodatabase2.htm, updated 2012, last accessed Nov. 30, 2023, 14 pages.

Rothan, H.A. et al. The epidemiology and pathogenesis of coronavirus disease (COVID-19) outbreak. J Autoimmun, vol. 109, May 2020, 102433, 4 pages.

Sauerbrey, G. The use of quartz crystal oscillators for weighing thin layers and for microweighing applications. Z. Phys, 1959. 155: p. 206-222.

Shahrabi, S.S. et al. Blood cell separation by novel PET/PVP blend electrospun membranes. Polymer Testing, 2018. 66: p. 94-104.

Shen, M. at al. Site-selective orientated immobilization of antibodies and conjugates for immunodiagnostics development. Methods (Mar. 2017 I), 116: 95-111.

Standard Guide for Accelerated Aging of Sterile Medical Device Packages. ASTM International Designation. F 1980-02, last updated Aug. 16, 2017, 2 pages.

Su, W. Encapsulation Technology for Organic Electronic Devices. Printed Electronics, 2016: p. 287-315.

Tan, W. et al., Viral Kinetics and Antibody Responses m Patients with COVID-19. medRxiv, 2020: p. 2020.03.24.20042382, 11 pages.

To, K.K. et al., Temporal profiles of viral load in posterior oropharyngeal saliva samples and serum antibody responses during infection by SARS-CoV-2: an observational cohort study. Lancet Infect Dis, 2020, vol. 20 Issue 5, pp. 565-574.

Vashist, S.K. In Vitro Diagnostic Assays for COVID-19: Recent Advances and Emerging Trends. Diagnostics, 2020, 10 (4): 202, 7 pages.

Wang, T. et al. Immunosensor for detection of inhibitory neurotransmitter gammaaminobutyric acid using quartz crystal microbalance. Anal Chem, 2008. 80(22): p. 8576- 82.

Wang, T.T. et al., Immobilization and characterization of gamma-aminobutyric acid on gold surface. Journal of Biomedical Materials Research Part A, 2006, 79A(I): p. 201-209.

Zhou, A. et al. Acoustic biosensor for monitoring antibody immobilization and neurotransmitter GABA in real-time. Sensors and Actuators B: Chemical, 2004, 101(1): p. 8-19.

International Search Report for PCT/US2022/032379 mailed Sep. 14, 2022, 3 pages.

Written Opinion for PCT/US2022/032379 mailed Sep. 14, 2022, 9 pages.

* cited by examiner

TABLE 1 | Summary of prototypes designs and their corresponding Q-factors.

| Δm (ng/mm2) | Freq (MHz) | Diameter | Electrode thickness (nm) | Q-factor |
|---|---|---|---|---|
| 0.54 | 42 | 1.2 mm | 33 | 7,020 |
| 0.49 | 42 | 1.2 mm | 230 | 7,620 |
| 0.22 | 42 | 800 μm | 230 | 7,600 |
| 0.35 | 42 | 800 μm | 33 | 4,800 |
| 0.073 | 42 | 400 μm | 230 | 5,695 |
| 0.084 | 42 | 400 μm | 33 | 4,965 |
| 0.081 | 50 | 400 μm | 33 | 4,340 |
| 0.023 | 50 | 200 μm | 230 | 3,880 |
| 0.016 | 50 | 150 μm | 230 | 3,000 |
| 0.182 | 77 | 800 μm | 230 | 3,000 |
| 0.049 | 90 | 400 μm | 230 | 5,000 |
| 0.13 | 90 | 800 μm | 230 | 4,000 |
| 70.13 | 10 | 8 mm | 230 | 6,000 |
| | | | | 10,000 |

*FIG. 3*

SEQUENCE LISTING

```
<160> NUMBER OF SEQ ID NOS: 16

<210> SEQ ID NO 1
<211> LENGTH: 1273
<212> TYPE: PRT
<213> ORGANISM: Severe acute respiratory syndrome coronavirus 2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30
```

-continued

```
Thr Arg Gly Val Tyr Tyr Pro Asp Lys Val Phe Arg Ser Ser Val Leu
    35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
                115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
                195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
    275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
    355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
    435                 440                 445

Tyr Asn Tyr Leu Tyr Arg Leu Phe Arg Lys Ser Asn Leu Lys Pro Phe
```

-continued

```
         450              455                460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
                 485              490              495

Phe Gln Pro Thr Asn Gly Val Gly Tyr Gln Pro Tyr Arg Val Val Val
             500              505              510

Leu Ser Phe Glu Leu Leu His Ala Pro Ala Thr Val Cys Gly Pro Lys
             515              520              525

Lys Ser Thr Asn Leu Val Lys Asn Lys Cys Val Asn Phe Asn Phe Asn
             530              535              540

Gly Leu Thr Gly Thr Gly Val Leu Thr Glu Ser Asn Lys Lys Phe Leu
545              550              555              560

Pro Phe Gln Gln Phe Gly Arg Asp Ile Ala Asp Thr Thr Asp Ala Val
             565              570              575

Arg Asp Pro Gln Thr Leu Glu Ile Leu Asp Ile Thr Pro Cys Ser Phe
             580              585              590

Gly Gly Val Ser Val Ile Thr Pro Gly Thr Asn Thr Ser Asn Gln Val
             595              600              605

Ala Val Leu Tyr Gln Asp Val Asn Cys Thr Glu Val Pro Val Ala Ile
             610              615              620

His Ala Asp Gln Leu Thr Pro Thr Trp Arg Val Tyr Ser Thr Gly Ser
625              630              635              640

Asn Val Phe Gln Thr Arg Ala Gly Cys Leu Ile Gly Ala Glu His Val
             645              650              655

Asn Asn Ser Tyr Glu Cys Asp Ile Pro Ile Gly Ala Gly Ile Cys Ala
             660              665              670

Ser Tyr Gln Thr Gln Thr Asn Ser Pro Arg Arg Ala Arg Ser Val Ala
             675              680              685

Ser Gln Ser Ile Ile Ala Tyr Thr Met Ser Leu Gly Ala Glu Asn Ser
             690              695              700

Val Ala Tyr Ser Asn Asn Ser Ile Ala Ile Pro Thr Asn Phe Thr Ile
705              710              715              720

Ser Val Thr Thr Glu Ile Leu Pro Val Ser Met Thr Lys Thr Ser Val
             725              730              735

Asp Cys Thr Met Tyr Ile Cys Gly Asp Ser Thr Glu Cys Ser Asn Leu
             740              745              750

Leu Leu Gln Tyr Gly Ser Phe Cys Thr Gln Leu Asn Arg Ala Leu Thr
             755              760              765

Gly Ile Ala Val Glu Gln Asp Lys Asn Thr Gln Glu Val Phe Ala Gln
             770              775              780

Val Lys Gln Ile Tyr Lys Thr Pro Pro Ile Lys Asp Phe Gly Gly Phe
785              790              795              800

Asn Phe Ser Gln Ile Leu Pro Asp Pro Ser Lys Pro Ser Lys Arg Ser
                 805              810              815

Phe Ile Glu Asp Leu Leu Phe Asn Lys Val Thr Leu Ala Asp Ala Gly
             820              825              830

Phe Ile Lys Gln Tyr Gly Asp Cys Leu Gly Asp Ile Ala Ala Arg Asp
             835              840              845

Leu Ile Cys Ala Gln Lys Phe Asn Gly Leu Thr Val Leu Pro Pro Leu
             850              855              860

Leu Thr Asp Glu Met Ile Ala Gln Tyr Thr Ser Ala Leu Leu Ala Gly
865              870              875              880
```

-continued

```
Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270
```

-continued

```
<210> SEQ ID NO 2
<211> LENGTH: 222
<212> TYPE: PRT
<213> ORGANISM: Severe acute respiratory syndrome coronavirus 2

<400> SEQUENCE: 2

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
            115                 120                 125

Leu Thr Arg Pro Leu Leu Glu Ser Glu Leu Val Ile Gly Ala Val Ile
        130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
            195                 200                 205

Asp His Ser Ser Ser Ser Asp Asn Ile Ala Leu Leu Val Gln
    210                 215                 220

<210> SEQ ID NO 3
<211> LENGTH: 75
<212> TYPE: PRT
<213> ORGANISM: Severe acute respiratory syndrome coronavirus 2

<400> SEQUENCE: 3

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75

<210> SEQ ID NO 4
<211> LENGTH: 419
<212> TYPE: PRT
<213> ORGANISM: Severe acute respiratory syndrome coronavirus 2
```

-continued

```
<400> SEQUENCE: 4

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
            115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
            275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
            405                 410                 415
```

-continued

Thr Gln Ala

<210> SEQ ID NO 5
<211> LENGTH: 601
<212> TYPE: PRT
<213> ORGANISM: Severe acute respiratory syndrome coronavirus 2

<400> SEQUENCE: 5

Ala Val Gly Ala Cys Val Leu Cys Asn Ser Gln Thr Ser Leu Arg Cys
1               5                   10                  15

Gly Ala Cys Ile Arg Arg Pro Phe Leu Cys Cys Lys Cys Cys Tyr Asp
            20                  25                  30

His Val Ile Ser Thr Ser His Lys Leu Val Leu Ser Val Asn Pro Tyr
        35                  40                  45

Val Cys Asn Ala Pro Gly Cys Asp Val Thr Asp Val Thr Gln Leu Tyr
    50                  55                  60

Leu Gly Gly Met Ser Tyr Tyr Cys Lys Ser His Lys Pro Pro Ile Ser
65                  70                  75                  80

Phe Pro Leu Cys Ala Asn Gly Gln Val Phe Gly Leu Tyr Lys Asn Thr
                85                  90                  95

Cys Val Gly Ser Asp Asn Val Thr Asp Phe Asn Ala Ile Ala Thr Cys
                100                 105                 110

Asp Trp Thr Asn Ala Gly Asp Tyr Ile Leu Ala Asn Thr Cys Thr Glu
            115                 120                 125

Arg Leu Lys Leu Phe Ala Ala Glu Thr Leu Lys Ala Thr Glu Glu Thr
        130                 135                 140

Phe Lys Leu Ser Tyr Gly Ile Ala Thr Val Arg Glu Val Leu Ser Asp
145                 150                 155                 160

Arg Glu Leu His Leu Ser Trp Glu Val Gly Lys Pro Arg Pro Pro Leu
                165                 170                 175

Asn Arg Asn Tyr Val Phe Thr Gly Tyr Arg Val Thr Lys Asn Ser Lys
                180                 185                 190

Val Gln Ile Gly Glu Tyr Thr Phe Glu Lys Gly Asp Tyr Gly Asp Ala
                195                 200                 205

Val Val Tyr Arg Gly Thr Thr Thr Tyr Lys Leu Asn Val Gly Asp Tyr
        210                 215                 220

Phe Val Leu Thr Ser His Thr Val Met Pro Leu Ser Ala Pro Thr Leu
225                 230                 235                 240

Val Pro Gln Glu His Tyr Val Arg Ile Thr Gly Leu Tyr Pro Thr Leu
                245                 250                 255

Asn Ile Ser Asp Glu Phe Ser Ser Asn Val Ala Asn Tyr Gln Lys Val
                260                 265                 270

Gly Met Gln Lys Tyr Ser Thr Leu Gln Gly Pro Pro Gly Thr Gly Lys
                275                 280                 285

Ser His Phe Ala Ile Gly Leu Ala Leu Tyr Tyr Pro Ser Ala Arg Ile
        290                 295                 300

Val Tyr Thr Ala Cys Ser His Ala Ala Val Asp Ala Leu Cys Glu Lys
305                 310                 315                 320

Ala Leu Lys Tyr Leu Pro Ile Asp Lys Cys Ser Arg Ile Ile Pro Ala
                325                 330                 335

Arg Ala Arg Val Glu Cys Phe Asp Lys Phe Lys Val Asn Ser Thr Leu
            340                 345                 350

Glu Gln Tyr Val Phe Cys Thr Val Asn Ala Leu Pro Glu Thr Thr Ala
            355                 360                 365

-continued

```
Asp Ile Val Val Phe Asp Glu Ile Ser Met Ala Thr Asn Tyr Asp Leu
    370             375             380

Ser Val Val Asn Ala Arg Leu Arg Ala Lys His Tyr Val Tyr Ile Gly
385             390             395             400

Asp Pro Ala Gln Leu Pro Ala Pro Arg Thr Leu Leu Thr Lys Gly Thr
                405             410             415

Leu Glu Pro Glu Tyr Phe Asn Ser Val Cys Arg Leu Met Lys Thr Ile
                420             425             430

Gly Pro Asp Met Phe Leu Gly Thr Cys Arg Arg Cys Pro Ala Glu Ile
            435             440             445

Val Asp Thr Val Ser Ala Leu Val Tyr Asp Asn Lys Leu Lys Ala His
    450             455             460

Lys Asp Lys Ser Ala Gln Cys Phe Lys Met Phe Tyr Lys Gly Val Ile
465             470             475             480

Thr His Asp Val Ser Ser Ala Ile Asn Arg Pro Gln Ile Gly Val Val
            485             490             495

Arg Glu Phe Leu Thr Arg Asn Pro Ala Trp Arg Lys Ala Val Phe Ile
            500             505             510

Ser Pro Tyr Asn Ser Gln Asn Ala Val Ala Ser Lys Ile Leu Gly Leu
            515             520             525

Pro Thr Gln Thr Val Asp Ser Ser Gln Gly Ser Glu Tyr Asp Tyr Val
    530             535             540

Ile Phe Thr Gln Thr Thr Glu Thr Ala His Ser Cys Asn Val Asn Arg
545             550             555             560

Phe Asn Val Ala Ile Thr Arg Ala Lys Val Gly Ile Leu Cys Ile Met
            565             570             575

Ser Asp Arg Asp Leu Tyr Asp Lys Leu Gln Phe Thr Ser Leu Glu Ile
            580             585             590

Pro Arg Arg Asn Val Ala Thr Leu Gln
        595             600
```

<210> SEQ ID NO 6
<211> LENGTH: 932
<212> TYPE: PRT
<213> ORGANISM: Severe acute respiratory syndrome coronavirus 2

<400> SEQUENCE: 6

```
Ser Ala Asp Ala Gln Ser Phe Leu Asn Arg Val Cys Gly Val Ser Ala
1               5               10              15

Ala Arg Leu Thr Pro Cys Gly Thr Gly Thr Ser Thr Asp Val Val Tyr
            20              25              30

Arg Ala Phe Asp Ile Tyr Asn Asp Lys Val Ala Gly Phe Ala Lys Phe
        35              40              45

Leu Lys Thr Asn Cys Cys Arg Phe Gln Glu Lys Asp Glu Asp Asp Asn
    50              55              60

Leu Ile Asp Ser Tyr Phe Val Val Lys Arg His Thr Phe Ser Asn Tyr
65              70              75              80

Gln His Glu Glu Thr Ile Tyr Asn Leu Leu Lys Asp Cys Pro Ala Val
                85              90              95

Ala Lys His Asp Phe Phe Lys Phe Arg Ile Asp Gly Asp Met Val Pro
            100             105             110

His Ile Ser Arg Gln Arg Leu Thr Lys Tyr Thr Met Ala Asp Leu Val
        115             120             125

Tyr Ala Leu Arg His Phe Asp Glu Gly Asn Cys Asp Thr Leu Lys Glu
```

-continued

```
              130                 135                 140

Ile Leu Val Thr Tyr Asn Cys Cys Asp Asp Asp Tyr Phe Asn Lys Lys
145                 150                 155                 160

Asp Trp Tyr Asp Phe Val Glu Asn Pro Asp Ile Leu Arg Val Tyr Ala
                165                 170                 175

Asn Leu Gly Glu Arg Val Arg Gln Ala Leu Leu Lys Thr Val Gln Phe
                180                 185                 190

Cys Asp Ala Met Arg Asn Ala Gly Ile Val Gly Val Leu Thr Leu Asp
                195                 200                 205

Asn Gln Asp Leu Asn Gly Asn Trp Tyr Asp Phe Gly Asp Phe Ile Gln
            210                 215                 220

Thr Thr Pro Gly Ser Gly Val Pro Val Val Asp Ser Tyr Tyr Ser Leu
225                 230                 235                 240

Leu Met Pro Ile Leu Thr Leu Thr Arg Ala Leu Thr Ala Glu Ser His
                245                 250                 255

Val Asp Thr Asp Leu Thr Lys Pro Tyr Ile Lys Trp Asp Leu Leu Lys
                260                 265                 270

Tyr Asp Phe Thr Glu Glu Arg Leu Lys Leu Phe Asp Arg Tyr Phe Lys
                275                 280                 285

Tyr Trp Asp Gln Thr Tyr His Pro Asn Cys Val Asn Cys Leu Asp Asp
            290                 295                 300

Arg Cys Ile Leu His Cys Ala Asn Phe Asn Val Leu Phe Ser Thr Val
305                 310                 315                 320

Phe Pro Pro Thr Ser Phe Gly Pro Leu Val Arg Lys Ile Phe Val Asp
                325                 330                 335

Gly Val Pro Phe Val Val Ser Thr Gly Tyr His Phe Arg Glu Leu Gly
                340                 345                 350

Val Val His Asn Gln Asp Val Asn Leu His Ser Ser Arg Leu Ser Phe
                355                 360                 365

Lys Glu Leu Leu Val Tyr Ala Ala Asp Pro Ala Met His Ala Ala Ser
            370                 375                 380

Gly Asn Leu Leu Leu Asp Lys Arg Thr Thr Cys Phe Ser Val Ala Ala
385                 390                 395                 400

Leu Thr Asn Asn Val Ala Phe Gln Thr Val Lys Pro Gly Asn Phe Asn
                405                 410                 415

Lys Asp Phe Tyr Asp Phe Ala Val Ser Lys Gly Phe Phe Lys Glu Gly
            420                 425                 430

Ser Ser Val Glu Leu Lys His Phe Phe Phe Ala Gln Asp Gly Asn Ala
            435                 440                 445

Ala Ile Ser Asp Tyr Asp Tyr Tyr Arg Tyr Asn Leu Pro Thr Met Cys
    450                 455                 460

Asp Ile Arg Gln Leu Leu Phe Val Val Glu Val Val Asp Lys Tyr Phe
465                 470                 475                 480

Asp Cys Tyr Asp Gly Gly Cys Ile Asn Ala Asn Gln Val Ile Val Asn
                485                 490                 495

Asn Leu Asp Lys Ser Ala Gly Phe Pro Phe Asn Lys Trp Gly Lys Ala
            500                 505                 510

Arg Leu Tyr Tyr Asp Ser Met Ser Tyr Glu Asp Gln Asp Ala Leu Phe
            515                 520                 525

Ala Tyr Thr Lys Arg Asn Val Ile Pro Thr Ile Thr Gln Met Asn Leu
    530                 535                 540

Lys Tyr Ala Ile Ser Ala Lys Asn Arg Ala Arg Thr Val Ala Gly Val
545                 550                 555                 560
```

-continued

Ser Ile Cys Ser Thr Met Thr Asn Arg Gln Phe His Gln Lys Leu Leu
            565             570             575

Lys Ser Ile Ala Ala Thr Arg Gly Ala Thr Val Val Ile Gly Thr Ser
            580             585             590

Lys Phe Tyr Gly Gly Trp His Asn Met Leu Lys Thr Val Tyr Ser Asp
            595             600             605

Val Glu Asn Pro His Leu Met Gly Trp Asp Tyr Pro Lys Cys Asp Arg
        610             615             620

Ala Met Pro Asn Met Leu Arg Ile Met Ala Ser Leu Val Leu Ala Arg
625             630             635             640

Lys His Thr Thr Cys Cys Ser Leu Ser His Arg Phe Tyr Arg Leu Ala
                645             650             655

Asn Glu Cys Ala Gln Val Leu Ser Glu Met Val Met Cys Gly Gly Ser
            660             665             670

Leu Tyr Val Lys Pro Gly Gly Thr Ser Ser Gly Asp Ala Thr Thr Ala
            675             680             685

Tyr Ala Asn Ser Val Phe Asn Ile Cys Gln Ala Val Thr Ala Asn Val
        690             695             700

Asn Ala Leu Leu Ser Thr Asp Gly Asn Lys Ile Ala Asp Lys Tyr Val
705             710             715             720

Arg Asn Leu Gln His Arg Leu Tyr Glu Cys Leu Tyr Arg Asn Arg Asp
            725             730             735

Val Asp Thr Asp Phe Val Asn Glu Phe Tyr Ala Tyr Leu Arg Lys His
            740             745             750

Phe Ser Met Met Ile Leu Ser Asp Asp Ala Val Val Cys Phe Asn Ser
            755             760             765

Thr Tyr Ala Ser Gln Gly Leu Val Ala Ser Ile Lys Asn Phe Lys Ser
        770             775             780

Val Leu Tyr Tyr Gln Asn Asn Val Phe Met Ser Glu Ala Lys Cys Trp
785             790             795             800

Thr Glu Thr Asp Leu Thr Lys Gly Pro His Glu Phe Cys Ser Gln His
            805             810             815

Thr Met Leu Val Lys Gln Gly Asp Asp Tyr Val Tyr Leu Pro Tyr Pro
            820             825             830

Asp Pro Ser Arg Ile Leu Gly Ala Gly Cys Phe Val Asp Asp Ile Val
            835             840             845

Lys Thr Asp Gly Thr Leu Met Ile Glu Arg Phe Val Ser Leu Ala Ile
        850             855             860

Asp Ala Tyr Pro Leu Thr Lys His Pro Asn Gln Glu Tyr Ala Asp Val
865             870             875             880

Phe His Leu Tyr Leu Gln Tyr Ile Arg Lys Leu His Asp Glu Leu Thr
            885             890             895

Gly His Met Leu Asp Met Tyr Ser Val Met Leu Thr Asn Asp Asn Thr
            900             905             910

Ser Arg Tyr Trp Glu Pro Glu Phe Tyr Glu Ala Met Tyr Thr Pro His
            915             920             925

Thr Val Leu Gln
    930

<210> SEQ ID NO 7
<211> LENGTH: 7530
<212> TYPE: PRT
<213> ORGANISM: Severe acute respiratory syndrome coronavirus 2

<400> SEQUENCE: 7

Val Gln Pro Val Leu His Arg Ala Ala Gln Ala Leu Val Leu Met Ser
1               5                   10                  15

Tyr Thr Gly Leu Leu Thr Ser Thr Met Ile Lys Leu Val Leu Leu Asn
            20                  25                  30

Ser Lys Leu Ile Val Val Ala Ser Lys Lys Arg Thr Lys Met Thr Ile
        35                  40                  45

Leu Ile Leu Thr Leu Leu Arg Asp Thr Leu Ser Leu Thr Thr Asn Met
    50                  55                  60

Lys Lys Gln Phe Ile Ile Tyr Leu Arg Ile Val Gln Leu Leu Leu Asn
65                  70                  75                  80

Met Thr Ser Leu Ser Leu Glu Thr Val Thr Trp Tyr His Ile Tyr His
                85                  90                  95

Val Asn Val Leu Leu Asn Thr Gln Trp Gln Thr Ser Ser Met Leu Gly
            100                 105                 110

Ile Leu Met Lys Val Ile Val Thr His Lys Lys Tyr Leu Ser His Thr
            115                 120                 125

Ile Val Val Met Met Ile Ile Ser Ile Lys Arg Thr Gly Met Ile Leu
    130                 135                 140

Lys Thr Gln Ile Tyr Tyr Ala Tyr Thr Pro Thr Val Asn Val Tyr Ala
145                 150                 155                 160

Lys Leu Cys Lys Gln Tyr Asn Ser Val Met Pro Cys Glu Met Leu Val
            165                 170                 175

Leu Leu Val Tyr His Ile Ile Lys Ile Ser Met Val Thr Gly Met Ile
            180                 185                 190

Ser Val Ile Ser Tyr Lys Pro Arg Gln Val Val Glu Phe Leu Leu Ile
            195                 200                 205

Leu Ile Ile His Cys Cys Leu Tyr Pro Pro Gly Leu Leu Gln Ser His
    210                 215                 220

Met Leu Thr Leu Thr Gln Ser Leu Thr Leu Ser Gly Ile Cys Asn Met
225                 230                 235                 240

Thr Ser Arg Lys Arg Gly Asn Ser Leu Thr Val Ile Leu Asn Ile Gly
            245                 250                 255

Ile Arg His Thr Thr Gln Ile Val Leu Thr Val Trp Met Thr Asp Ala
            260                 265                 270

Phe Cys Ile Val Gln Thr Leu Met Phe Tyr Ser Leu Gln Cys Ser His
            275                 280                 285

Leu Gln Val Leu Asp His Glu Lys Tyr Leu Leu Met Val Phe His Leu
    290                 295                 300

Phe Gln Leu Asp Thr Thr Ser Glu Ser Val Leu Tyr Ile Ile Arg Met
305                 310                 315                 320

Thr Tyr Ile Ala Leu Asp Leu Val Leu Arg Asn Tyr Leu Cys Met Leu
            325                 330                 335

Leu Thr Leu Leu Cys Thr Leu Leu Leu Val Ile Tyr Tyr Ile Asn Ala
            340                 345                 350

Leu Arg Ala Phe Gln Leu His Leu Leu Thr Met Leu Leu Phe Lys Leu
            355                 360                 365

Ser Asn Pro Val Ile Leu Thr Lys Thr Ser Met Thr Leu Leu Cys Leu
            370                 375                 380

Arg Val Ser Leu Arg Lys Glu Val Leu Leu Asn Asn Thr Ser Ser Leu
385                 390                 395                 400

Leu Arg Met Val Met Leu Leu Ser Ala Ile Met Thr Thr Ile Val Ile
            405                 410                 415

```
Ile Tyr Gln Gln Cys Val Ile Ser Asp Asn Tyr Tyr Leu Leu Lys Leu
            420                 425                 430

Leu Ile Ser Thr Leu Ile Val Thr Met Val Ala Val Leu Met Leu Thr
            435                 440                 445

Lys Ser Ser Ser Thr Thr Thr Asn Gln Leu Val Phe His Leu Ile Asn
            450                 455                 460

Gly Val Arg Leu Asp Phe Ile Met Ile Gln Val Met Arg Ile Lys Met
465                 470                 475                 480

His Phe Ser His Ile Gln Asn Val Met Ser Ser Leu Leu Leu Lys Ile
                    485                 490                 495

Leu Ser Met Pro Leu Val Gln Arg Ile Glu Leu Ala Pro Leu Val Ser
                500                 505                 510

Leu Ser Val Val Leu Pro Ile Asp Ser Phe Ile Lys Asn Tyr Asn Gln
            515                 520                 525

Pro Pro Leu Glu Glu Leu Leu Leu Glu Gln Ala Asn Ser Met Val Val
    530                 535                 540

Gly Thr Thr Cys Lys Leu Phe Ile Val Met Lys Thr Leu Thr Leu Trp
545                 550                 555                 560

Val Gly Ile Ile Leu Asn Val Ile Glu Pro Cys Leu Thr Cys Leu Glu
                565                 570                 575

Leu Trp Pro His Leu Phe Leu Leu Ala Asn Ile Gln Arg Val Val Ala
            580                 585                 590

Cys His Thr Val Ser Ile Asp Leu Met Ser Val Leu Lys Tyr Val Lys
            595                 600                 605

Trp Ser Cys Val Ala Val His Tyr Met Leu Asn Gln Val Glu Pro His
    610                 615                 620

Gln Glu Met Pro Gln Leu Leu Met Leu Ile Val Phe Leu Thr Phe Val
625                 630                 635                 640

Lys Leu Ser Arg Pro Met Leu Met His Phe Tyr Leu Leu Met Val Thr
                645                 650                 655

Lys Leu Pro Ile Ser Met Ser Ala Ile Tyr Asn Thr Asp Phe Met Ser
                660                 665                 670

Val Ser Ile Glu Ile Glu Met Leu Thr Gln Thr Leu Met Ser Phe Thr
            675                 680                 685

His Ile Cys Val Asn Ile Ser Gln Tyr Ser Leu Thr Met Leu Leu Cys
    690                 695                 700

Val Ser Ile Ala Leu Met His Leu Lys Val Trp Leu Ala Arg Thr Leu
705                 710                 715                 720

Ser Gln Phe Phe Ile Ile Lys Thr Met Phe Leu Cys Leu Lys Gln Asn
                725                 730                 735

Val Gly Leu Arg Leu Thr Leu Leu Lys Asp Leu Met Asn Phe Ala Leu
            740                 745                 750

Asn Ile Gln Cys Leu Asn Arg Val Met Ile Met Cys Thr Phe Leu Thr
            755                 760                 765

Gln Ile His Gln Glu Ser Gly Pro Ala Val Leu Met Ile Ser Lys Gln
    770                 775                 780

Met Val His Leu Leu Asn Gly Ser Cys Leu Leu Met Leu Thr His Leu
785                 790                 795                 800

Leu Asn Ile Leu Ile Arg Ser Met Leu Met Ser Phe Ile Cys Thr Tyr
                805                 810                 815

Asn Thr Glu Ser Tyr Met Met Ser Gln Asp Thr Cys Thr Cys Ile Leu
            820                 825                 830
```

```
Leu Cys Leu Leu Met Ile Thr Leu Gln Gly Ile Gly Asn Leu Ser Phe
        835                 840                 845

Met Arg Leu Cys Thr His Arg Ile Gln Ser Tyr Arg Leu Leu Gly Leu
    850                 855                 860

Val Phe Phe Ala Ile His Arg Leu His Asp Val Val Leu Ala Tyr Val
865                 870                 875                 880

Asp His Ser Tyr Val Val Asn Ala Val Thr Thr Met Ser Tyr Gln His
                885                 890                 895

His Ile Asn Ser Cys Leu Leu Ile Arg Met Phe Ala Met Leu Gln Val
                900                 905                 910

Val Met Ser Gln Met Leu Asn Phe Thr Glu Val Ala Ile Ile Val Asn
        915                 920                 925

His Ile Asn His Pro Leu Val Phe His Cys Val Leu Met Asp Lys Phe
    930                 935                 940

Leu Val Tyr Ile Lys Ile His Val Leu Val Ala Ile Met Leu Leu Thr
945                 950                 955                 960

Leu Met Gln Leu Gln His Val Thr Gly Gln Met Leu Val Ile Thr Phe
                965                 970                 975

Leu Thr Pro Val Leu Lys Asp Ser Ser Phe Leu Gln Gln Lys Arg Ser
            980                 985                 990

Lys Leu Leu Arg Arg His Leu Asn  Cys Leu Met Val Leu  Leu Leu Tyr
        995                 1000                1005

Val Lys  Cys Cys Leu Thr Glu  Asn Tyr Ile Phe His  Gly Lys Leu
    1010                1015                1020

Val Asn  Leu Asp His His Leu  Thr Glu Ile Met Ser  Leu Leu Val
    1025                1030                1035

Ile Val  Leu Lys Thr Val Lys  Tyr Lys Glu Ser Thr  Pro Leu Lys
    1040                1045                1050

Lys Val  Thr Met Val Met Leu  Leu Phe Thr Glu Val  Gln Gln Leu
    1055                1060                1065

Thr Asn  Met Leu Val Ile Ile  Leu Cys His His Ile  Gln Cys His
    1070                1075                1080

Val His  Leu His Cys His Lys  Ser Thr Met Leu Glu  Leu Leu Ala
    1085                1090                1095

Tyr Thr  Gln His Ser Ile Ser  Gln Met Ser Phe Leu  Ala Met Leu
    1100                1105                1110

Gln Ile  Ile Lys Arg Leu Val  Cys Lys Ser Ile Leu  His Ser Arg
    1115                1120                1125

Asp His  Leu Val Leu Val Arg  Val Ile Leu Leu Leu  Ala Leu Ser
    1130                1135                1140

Thr Thr  Leu Leu Leu Ala Cys  Ile Gln Leu Ala Leu  Met Pro Leu
    1145                1150                1155

Leu Met  His Tyr Val Arg Arg  His Asn Ile Cys Leu  Ile Asn Val
    1160                1165                1170

Val Glu  Leu Tyr Leu His Val  Leu Val Ser Val Leu  Ile Asn Ser
    1175                1180                1185

Lys Ile  Gln His Asn Ser Met  Ser Phe Val Leu Met  His Cys Leu
    1190                1195                1200

Arg Arg  Gln Gln Ile Leu Ser  Leu Met Lys Phe Gln  Trp Pro Gln
    1205                1210                1215

Ile Met  Ile Val Leu Ser Met  Pro Asp Tyr Val Leu  Ser Thr Met
    1220                1225                1230

Cys Thr  Leu Ala Thr Leu Leu  Asn Tyr Leu His His  Ala His Cys
```

```
            1235                1240                1245

Leu Arg  Ala His Asn Gln Asn  Ile Ser Ile Gln Cys  Val Asp Leu
    1250                1255                1260

Lys Leu  Val Gln Thr Cys Ser  Ser Glu Leu Val Gly  Val Val Leu
    1265                1270                1275

Leu Lys  Leu Leu Thr Leu Val  Leu Trp Phe Met Ile  Ile Ser Leu
    1280                1285                1290

Lys His  Ile Lys Thr Asn Gln  Leu Asn Ala Leu Lys  Cys Phe Ile
    1295                1300                1305

Arg Val  Leu Ser Arg Met Met  Phe His Leu Gln Leu  Thr Gly His
    1310                1315                1320

Lys Ala  Trp Glu Asn Ser Leu  His Val Thr Leu Leu  Gly Glu Lys
    1325                1330                1335

Leu Ser  Leu Phe His Leu Ile  Ile His Arg Met Leu  Pro Gln Arg
    1340                1345                1350

Phe Trp  Asp Tyr Gln Leu Lys  Leu Leu Ile His His  Arg Ala Gln
    1355                1360                1365

Asn Met  Thr Met Ser Tyr Ser  Leu Lys Pro Leu Lys  Gln Leu Thr
    1370                1375                1380

Leu Val  Met Thr Asp Leu Met  Leu Leu Leu Pro Glu  Gln Lys Ala
    1385                1390                1395

Tyr Phe  Ala Cys Leu Ile Glu  Thr Phe Met Thr Ser  Cys Asn Leu
    1400                1405                1410

Gln Val  Leu Lys Phe His Val  Gly Met Trp Gln Leu  Tyr Lys Leu
    1415                1420                1425

Lys Met  Gln Asp Ser Leu Lys  Ile Val Val Arg Ser  Leu Gly Tyr
    1430                1435                1440

Ile Leu  His Arg His Leu His  Thr Ser Val Leu Thr  Leu Asn Ser
    1445                1450                1455

Lys Leu  Lys Val Tyr Val Leu  Thr Tyr Leu Ala Tyr  Leu Arg Thr
    1460                1465                1470

Pro Ile  Glu Asp Ser Ser Leu  Trp Val Leu Lys Ile  Ile Lys Leu
    1475                1480                1485

Met Val  Thr Leu Thr Cys Leu  Ser Pro Ala Lys Lys  Leu Asp Met
    1490                1495                1500

Tyr Val  His Gly Leu Ala Ser  Met Ser Arg Gly Val  Met Leu Leu
    1505                1510                1515

Glu Lys  Leu Leu Val Pro Ile  Tyr Leu Tyr Ser Val  Phe Leu Gln
    1520                1525                1530

Val Leu  Thr Leu Leu Tyr Leu  Gln Val Met Leu Ile  His Leu Ile
    1535                1540                1545

Ile Gln  Ile Phe Pro Glu Leu  Val Leu Asn His Arg  Leu Glu Ile
    1550                1555                1560

Asn Leu  Asn Thr Ser Tyr His  Leu Cys Thr Lys Asp  Phe Leu Gly
    1565                1570                1575

Met Cys  Val Arg Leu Tyr Lys  Cys Val Thr His Leu  Lys Ile Ser
    1580                1585                1590

Leu Thr  Glu Ser Tyr Leu Ser  Tyr Gly His Met Ala  Leu Ser His
    1595                1600                1605

Leu Ser  Ile Leu Lys Asp Leu  Ser Ala Pro Val Val  Tyr Val Ile
    1610                1615                1620

Asp Val  Pro His Ala Phe Pro  Leu Leu Gln Thr Leu  Met Pro Val
    1625                1630                1635
```

-continued

```
Gly Ile  Ile Leu Leu Asp Leu  Ile Thr Ser Ile Ile  Arg Leu Leu
    1640               1645               1650

Met Phe  Asn Asn Gly Val Leu  Gln Val Thr Tyr Lys  Ala Thr Met
    1655               1660               1665

Ile Cys  Ile Val Lys Ser Met  Val Met His Met Leu  Val Val Met
    1670               1675               1680

Gln Ser  Leu Gly Val Leu Ser  Thr Ser Ala Leu Leu  Ser Val Leu
    1685               1690               1695

Thr Gly  Leu Leu Asn Ile Leu  Leu Val Met Asn Arg  Leu Met Arg
    1700               1705               1710

Leu Val  Glu Arg Phe Asn Thr  Trp Leu Leu Lys Leu  His Tyr Gln
    1715               1720               1725

Thr Asn  Ser Gln Phe Phe Thr  Thr Leu Val Thr Leu  Lys Leu Leu
    1730               1735               1740

Ser Val  Tyr Leu Lys Leu Met  Asn Gly Ser Ser Met  Met His Ser
    1745               1750               1755

Leu Val  Val Thr Lys Leu Ile  Lys Lys Asn Tyr Ser  Ile Leu Met
    1760               1765               1770

Pro His  Ile Leu Thr Asn Ser  Gln Met Val Tyr Ala  Tyr Phe Gly
    1775               1780               1785

Ile Ala  Met Ser Ile Asp Ile  Leu Leu Ile Pro Leu  Phe Val Asp
    1790               1795               1800

Leu Thr  Leu Glu Cys Tyr Leu  Thr Leu Thr Cys Leu  Val Val Met
    1805               1810               1815

Val Ala  Val Cys Met Ile Asn  Met His Ser Thr His  Gln Leu Leu
    1820               1825               1830

Ile Lys  Val Leu Leu Leu Ile  Asn Asn Tyr His Phe  Ser Ile Thr
    1835               1840               1845

Leu Thr  Val His Val Ser Leu  Met Glu Asn Lys Cys  Gln Ile Ile
    1850               1855               1860

Met Tyr  His Ser Leu Leu Arg  Val His Val Ala Ile  Val Val Leu
    1865               1870               1875

Ser Val  Asp Ile Met Leu Met  Ser Thr Asp Cys Ile  Ser Met Leu
    1880               1885               1890

Ile Thr  Ser Gln Leu Ala Leu  Ala Cys Gly Phe Thr  Asn Asn Leu
    1895               1900               1905

Ile Leu  Ile Thr Ser Gly Thr  Leu Leu Gln Asp Phe  Arg Val Lys
    1910               1915               1920

Met Trp  Leu Leu Met Leu Ile  Arg Asp Thr Leu Met  Asp Asn Arg
    1925               1930               1935

Val Lys  Tyr Gln Phe Leu Ser  Leu Ile Thr Leu Phe  Thr Gln Lys
    1940               1945               1950

Leu Met  Val Leu Met Asn Cys  Leu Lys Ile Lys Gln  His Tyr Leu
    1955               1960               1965

Leu Met  His Leu Ser Phe Gly  Leu Ser Ala Thr Leu  Asn Gln Tyr
    1970               1975               1980

Gln Arg  Lys Tyr Ser Ile Ile  Trp Val Trp Thr Leu  Leu Leu Ile
    1985               1990               1995

Leu Ser  Gly Thr Thr Lys Glu  Met Leu Gln His Ile  Tyr Leu Leu
    2000               2005               2010

Leu Val  Phe Val Leu Leu Thr  Pro Arg Asn Gln Leu  Lys Arg Phe
    2015               2020               2025
```

```
Val His  His Ser Leu Ser Phe  Leu Met Val Glu Leu  Met Val Lys
    2030                 2035                 2040

Thr Tyr  Leu Glu Met Pro Val  Met Val Phe Leu Leu  Gln Lys Val
    2045                 2050                 2055

Val Leu  Lys Val Tyr Asn His  Leu Val Pro Asn Lys  Leu Val Leu
    2060                 2065                 2070

Met Glu  Ser His Leu Glu Lys  Pro Lys His Ser Ser  Ile Ile Ile
    2075                 2080                 2085

Arg Lys  Leu Met Val Leu Ser  Asn Asn Tyr Leu Lys  Leu Thr Leu
    2090                 2095                 2100

Leu Arg  Val Glu Ile Tyr Lys  Asn Leu Asn Pro Gly  Val Lys Trp
    2105                 2110                 2115

Lys Leu  Ile Ser Asn Leu Trp  Met Asn Ser Leu Asn  Gly Ile Asn
    2120                 2125                 2130

Lys Ala  Met Pro Ser Asn Ile  Ser Phe Met Glu Ile  Leu Val Ile
    2135                 2140                 2145

Val Ser  Val Val Tyr Ile Tyr  Leu Asp Leu Asn Val  Leu Arg Asn
    2150                 2155                 2160

His Leu  Leu Asn Lys Ile Leu  Phe Leu Trp Thr Val  Gln Leu Lys
    2165                 2170                 2175

Thr Ile  Ser Gln Met Arg Lys  Gln Val His Leu Ser  Val Cys Val
    2180                 2185                 2190

Leu Leu  Leu Ile Tyr Tyr Leu  Met Ile Leu Leu Lys  Asn Pro Lys
    2195                 2200                 2205

Ile Tyr  Leu Phe Leu Arg Leu  Ser Lys Leu Leu Thr  Ile Gln Lys
    2210                 2215                 2220

Phe His  Leu Cys Phe Gly Val  Lys Met Ala Met Lys  His Phe Thr
    2225                 2230                 2235

Gln Asn  Tyr Asn Leu Val Lys  Arg Gly Asn Arg Val  Leu Leu Cys
    2240                 2245                 2250

Leu Ile  Phe Thr Lys Cys Lys  Glu Cys Tyr Lys Ser  Val Thr Phe
    2255                 2260                 2265

Lys Ile  Met Val Ile Val Gln  His Tyr Leu Lys Ala  Met Ser Gln
    2270                 2275                 2280

Asn Ile  Leu Asn Cys Val Asn  Ile Thr His His Leu  Tyr Pro Ile
    2285                 2290                 2295

Ile Glu  Leu Tyr Ile Leu Val  Leu Val Leu Ile Lys  Glu Leu His
    2300                 2305                 2310

Gln Val  Gln Leu Phe Asp Ser  Gly Cys Leu Arg Val  Arg Cys Leu
    2315                 2320                 2325

Ser Ile  Gln Ile Leu Met Thr  Leu Ser Leu Met Gln  Ile Gln Leu
    2330                 2335                 2340

Leu Val  Ile Val Gln Leu Tyr  Ile Gln Leu Ile Asn  Gly Ile Ser
    2345                 2350                 2355

Leu Leu  Val Ile Cys Thr Thr  Leu Arg Leu Lys Met  Leu Gln Lys
    2360                 2365                 2370

Lys Met  Thr Leu Lys Arg Val  Phe Ser Leu Thr Phe  Val Gly Leu
    2375                 2380                 2385

Tyr Asn  Lys Ser Leu Leu Glu  Val Pro Trp Leu Arg  Gln Asn Ile
    2390                 2395                 2400

Leu Gly  Met Leu Ile Phe Ile  Ser Ser Trp Asp Thr  Ser His Gly
    2405                 2410                 2415

Gly Gln  Pro Leu Leu Leu Met  Met Arg His His Leu  Lys His Phe
```

-continued

```
           2420                2425                2430

Leu Asp  Val Ile Ile Leu Ala  Asn His Ala Asn Lys  Met Val Met
    2435                2440                2445

Ser Cys  Met Gln Ile Thr Tyr  Phe Gly Gly Ile Gln  Ile Gln Phe
    2450                2455                2460

Ser Cys  Leu Pro Ile Leu Tyr  Leu Thr Val Asn Phe  Pro Leu Asn
    2465                2470                2475

Gly Val  Leu Leu Leu Cys Leu  Lys Lys Val Lys Ser  Met Ile Phe
    2480                2485                2490

Tyr Leu  Phe Leu Val Lys Val  Asp Leu Leu Glu Lys  Thr Thr Glu
    2495                2500                2505

Leu Leu  Phe Leu Val Met Phe  Leu Leu Thr Thr Cys  Ser Pro Ser
    2510                2515                2520

Tyr Thr  Val Arg His Arg His  Tyr Cys Arg Ile Gln  Gly Phe His
    2525                2530                2535

Leu Gln  Ser Ser Trp Phe Cys  Ile Pro Lys Asn Leu  Leu Ser Leu
    2540                2545                2550

Pro Arg  Lys Gly Arg Arg Gln  Phe Asn Phe Leu Leu  Cys Ser Glu
    2555                2560                2565

Thr His  Phe Leu Leu Pro Thr  Arg Asn Asn Leu Phe  Thr Gly Leu
    2570                2575                2580

Ser Ser  Cys Cys Thr Leu Leu  Val Asn Arg Arg His  Gly Thr Thr
    2585                2590                2595

Tyr Ile  Thr Ser Thr Ser Tyr  Ile His Asn Gly Arg  Pro Arg Leu
    2600                2605                2610

Cys Phe  Lys Ala Phe Arg Leu  His Ile Lys Arg Asn  Thr Cys His
    2615                2620                2625

Ile Gln  Leu Leu Leu Phe Gln  Lys Gly Leu Val Phe  Cys Arg Lys
    2630                2635                2640

Pro Arg  Tyr Ile Thr Arg Ile  Arg Gln Leu Arg Thr  Cys Thr Pro
    2645                2650                2655

Ser Phe  Val Lys Asn Ser Thr  Ile Leu Cys His Ala  Lys Cys Trp
    2660                2665                2670

Tyr Cys  Trp Cys Thr Asp Ile  Arg Ser Arg Ser Gln  Trp Leu Val
    2675                2680                2685

Phe Arg  Phe His Thr Asn His  Ala Arg Trp Ser Ser  Cys Cys Arg
    2690                2695                2700

Phe Leu  Leu Phe Ile Val Asn  Ala Tyr Ile Asn Leu  Asp Gln Gly
    2705                2710                2715

Phe Asn  Cys Arg Val Thr Cys  His Leu Asn Lys Ala  Leu His Val
    2720                2725                2730

Gly Phe  Val Lys Ile Leu His  Gly Arg Glu Val Lys  Thr Leu Pro
    2735                2740                2745

Leu Phe  Ile Leu Gly Ser Asp  Ile Pro Pro Lys Leu  Cys Leu Phe
    2750                2755                2760

Gly Gln  Met His Ser Ala Leu  Cys Lys Leu Cys Phe  Ile Leu Tyr
    2765                2770                2775

Ser Val  Pro Thr Tyr Lys Phe  Trp Thr Thr Ser Glu  Lys Asn Ile
    2780                2785                2790

Cys Trp  Cys Ser Ile Cys Ser  Phe Asn Trp Ile Pro  Leu Gln Arg
    2795                2800                2805

Ala Arg  Cys Cys Thr Ser Gly  Cys Lys Leu Thr Leu  Thr Phe Gly
    2810                2815                2820
```

-continued

```
Ile Thr Cys Val Cys Cys Pro  Cys Tyr Ala Arg Cys  Phe Trp Ser
2825                2830                2835

Ile Thr Arg Thr His Tyr Val  Leu Phe Ser Ser Cys  Thr Tyr Gln
2840                2845                2850

Cys Cys Phe Ser Asn Cys Gln  Thr Arg Phe Gln Arg  Leu Leu Leu
2855                2860                2865

Cys Cys Val Gly Phe Leu Gly  Arg Lys Phe Cys Ile  Lys Thr Leu
2870                2875                2880

Leu Leu Cys Ser Gly Trp Cys  Cys Tyr Gln Arg Leu  Leu Leu Ser
2885                2890                2895

Leu Ser Thr Asn Asn Val Tyr  Gln Thr Thr Thr Ile  Cys Ser Ser
2900                2905                2910

Cys Val Leu Leu Leu Arg Trp  Trp Leu Tyr Cys Pro  Ser His Arg
2915                2920                2925

Gln Gln Pro Arg Gln Ile Ser  Trp Phe Ser Ile Met  Gly Gly Thr
2930                2935                2940

Leu Leu Phe Asn Glu Leu Gly  Ser Arg Cys Thr Phe  Arg Ile Tyr
2945                2950                2955

Lys Thr Cys His Pro Tyr Tyr  Asn Ser Asn Glu Ser  Val Cys His
2960                2965                2970

Cys Lys Glu Ser Ser His Arg  Ser Trp Cys Leu Tyr  Leu Tyr Tyr
2975                2980                2985

Asp Gln Thr Val Ser Ser Lys  Ile Ile Glu Ile Asn  Ser Arg His
2990                2995                3000

Arg Ser Tyr Cys Ser Asn Trp  Asn Lys Gln Ile Leu  Trp Trp Leu
3005                3010                3015

Ala Gln His Val Lys Asn Cys  Leu Cys Arg Lys Pro  Ser Pro Tyr
3020                3025                3030

Gly Leu Gly Leu Ser Met Ser  His Ala His Ala Asn  Tyr Gly Leu
3035                3040                3045

Thr Cys Ser Cys Ser Gln Thr  Tyr Asn Val Leu Leu  Val Thr Pro
3050                3055                3060

Phe Leu Ile Ser Val Cys Ser  Ser Ile Glu Asn Gly  His Val Trp
3065                3070                3075

Arg Phe Thr Ile Cys Thr Arg  Trp Asn Leu Ile Arg  Arg Cys His
3080                3085                3090

Asn Cys Leu Cys Cys Phe His  Leu Ser Ser Cys His  Gly Gln Cys
3095                3100                3105

Cys Thr Phe Ile Tyr Trp Gln  Asn Cys Arg Val Cys  Pro Gln Phe
3110                3115                3120

Thr Thr Gln Thr Leu Val Ser  Leu Lys Arg Cys His  Arg Leu Cys
3125                3130                3135

Glu Val Leu Arg Ile Phe Ala  Thr Phe Leu Asn Asp  Asp Thr Leu
3140                3145                3150

Arg Cys Cys Cys Val Phe Gln  His Leu Cys Ile Ser  Arg Ser Ser
3155                3160                3165

Gly His Lys Glu Leu Val Ser  Ser Leu Leu Ser Lys  Gln Cys Phe
3170                3175                3180

Tyr Val Ser Lys Met Leu Asp  Asp Pro Tyr Arg Thr  Ser Ile Leu
3185                3190                3195

Leu Ser Thr Tyr Asn Ala Ser  Thr Gly Leu Cys Val  Pro Ser Leu
3200                3205                3210
```

-continued

```
Pro Arg Ser Ile Lys Asn Pro Arg Gly Arg Leu Phe Cys Arg Tyr
    3215                3220              3225

Arg Lys Asn Arg Trp Tyr Thr Tyr Asp Thr Val Arg Val Phe Ser
    3230            3235              3240

Tyr Arg Cys Leu Pro Thr Tyr Thr Ser Ser Gly Val Cys Cys Leu
    3245            3250              3255

Ser Phe Val Leu Thr Ile His Lys Lys Ala Thr Val Asn Arg Thr
    3260            3265              3270

His Val Arg His Val Phe Cys Tyr Ala Tyr His Phe Lys Val Leu
    3275            3280              3285

Gly Thr Val Leu Gly Tyr Val His Thr Ala Tyr Ser Leu Thr Gly
    3290            3295              3300

Cys Trp Gly Leu Cys Ser Leu Gln Phe Thr Asp Phe Ile Lys Met
    3305            3310              3315

Trp Cys Leu His Thr Thr Ile Leu Met Leu Met Leu Leu Arg Pro
    3320            3325              3330

Cys His Ile Asn Ile Thr Ile Ser Leu Val Cys Ser Val Cys Leu
    3335            3340              3345

Gln Cys Ser Arg Leu Cys His Arg Cys Asp Ser Thr Leu Leu Arg
    3350            3355              3360

Arg Tyr Glu Leu Leu Leu Ile Thr Thr Thr His Phe Ser Ile Val
    3365            3370              3375

Cys Trp Thr Ser Phe Trp Phe Ile Lys Tyr Met Cys Trp Arg Cys
    3380            3385              3390

Tyr Leu Cys Asn Cys Asn Met Leu Asp Lys Cys Trp Leu His Phe
    3395            3400              3405

Ser His Leu Tyr Lys Thr Gln Ala Phe Cys Ser Arg Asn Ala Gln
    3410            3415              3420

Ser Tyr Gly Asp Ile Thr Val Leu Trp Tyr Cys Tyr Cys Thr Ser
    3425            3430              3435

Ala Val Gln Arg Ile Thr Ser Phe Met Gly Ser Trp Thr Thr Thr
    3440            3445              3450

Thr Pro Lys Leu Cys Leu Tyr Trp Leu Ser Cys Asn Lys Gln Ser
    3455            3460              3465

Thr Asn Arg Arg Val His Leu Lys Arg Leu Trp Cys Cys Cys Leu
    3470            3475              3480

Pro Arg Tyr Asn Asn Leu Gln Ile Lys Cys Trp Leu Phe Cys Ala
    3485            3490              3495

Asp Ile Thr Tyr Ser Asn Ala Ile Lys Cys Thr Tyr Thr Ser Ala
    3500            3505              3510

Thr Arg Ala Leu Cys Asn Tyr Trp Leu Ile Pro Asn Thr Gln Tyr
    3515            3520              3525

Leu Arg Val Phe Gln Cys Cys Lys Leu Ser Lys Gly Trp Tyr Ala
    3530            3535              3540

Lys Val Phe Tyr Thr Pro Gly Thr Thr Trp Tyr Trp Glu Ser Phe
    3545            3550              3555

Cys Tyr Trp Pro Ser Ser Leu Leu Pro Phe Cys Ser His Ser Val
    3560            3565              3570

Tyr Ser Leu Leu Ser Cys Arg Cys Cys Thr Met Glu Gly Ile Lys
    3575            3580              3585

Ile Phe Ala Tyr Arg Met Asn Tyr Thr Cys Thr Cys Ser Cys Arg
    3590            3595              3600

Val Phe Ile Gln Ser Glu Phe Asn Ile Arg Thr Val Cys Leu Leu
```

-continued

```
      3605                3610                3615

Tyr Cys Lys Cys Ile Ala Asp Asp Ser Arg Tyr Ser Cys Leu Asn
    3620            3625            3630

Phe Asn Gly His Lys Leu Phe Glu Cys Cys Gln Cys Gln Ile Thr
    3635            3640            3645

Cys Ala Leu Cys Val His Trp Arg Pro Cys Ser Ile Thr Cys Thr
    3650            3655            3660

Thr His Ile Ala Asn Gly His Thr Arg Thr Arg Ile Phe Gln Phe
    3665            3670            3675

Ser Val Thr Tyr Glu Asn Tyr Arg Ser Arg His Val Pro Arg Asn
    3680            3685            3690

Leu Ser Ala Leu Ser Cys Asn Cys His Cys Glu Cys Phe Gly Leu
    3695            3700            3705

Ala Ser Thr Arg Gln Ile Ser Ser Met Leu Asn Val Leu Gly Cys
    3710            3715            3720

Tyr His Ala Cys Phe Ile Cys Asn Gln Ala Thr Asn Arg Arg Gly
    3725            3730            3735

Lys Arg Ile Pro Tyr Thr Pro Cys Leu Glu Lys Ser Cys Leu Tyr
    3740            3745            3750

Phe Thr Leu Phe Thr Glu Cys Cys Ser Leu Lys Asp Phe Gly Thr
    3755            3760            3765

Thr Asn Ser Asn Cys Phe Ile Thr Gly Leu Arg Ile Leu Cys His
    3770            3775            3780

Ile His Ser Asn His Asn Ser Ser Leu Leu Cys Lys Gln Ile Cys
    3785            3790            3795

Cys Tyr Tyr Gln Ser Lys Ser Arg His Thr Leu His Asn Val Arg
    3800            3805            3810

Pro Leu Gln Val Ala Ile Tyr Lys Ser Asn Ser Thr Glu Cys Gly
    3815            3820            3825

Asn Phe Thr Ser Lys Cys Asn Arg Thr Leu Arg Leu Gly Asn His
    3830            3835            3840

Trp Val Thr Ser Tyr Thr Gly Thr Tyr Thr Pro Gln Cys His Ile
    3845            3850            3855

Gln Asn Arg Phe Met Cys His Thr Trp His Thr Gly His Asp Leu
    3860            3865            3870

Lys Thr His Leu Tyr Asp Gly Phe Asn Glu Leu Ser Ser Trp Leu
    3875            3880            3885

Pro His Val Tyr His Pro Arg Arg Ser Tyr Lys Thr Cys Thr Cys
    3890            3895            3900

Met Asp Trp Leu Arg Cys Arg Gly Val Ser Cys Tyr Arg Ser Cys
    3905            3910            3915

Trp Tyr Gln Phe Thr Phe Thr Ala Arg Phe Phe Tyr Arg Cys Pro
    3920            3925            3930

Ser Cys Cys Thr Tyr Arg Leu Cys Tyr Thr Tyr Arg Phe Phe Gln
    3935            3940            3945

Ser Cys Thr Thr Ala Trp Arg Ser Ile Thr Pro His Thr Thr Tyr
    3950            3955            3960

Val Gln Arg Thr Ser Leu Glu Cys Ser Ala Tyr Lys Asp Cys Thr
    3965            3970            3975

Asn Val Lys His Thr Lys Ser Leu Gln Ser Arg Ile Cys Leu Met
    3980            3985            3990

Gly Thr Trp Leu Val Asp Ile Tyr Glu Val Phe Cys Glu Asn Arg
    3995            4000            4005
```

-continued

```
Thr Ala His Leu Leu Ser Met  Thr Cys His Met Leu  Phe His Cys
    4010             4015              4020

Phe Arg His Leu Cys Leu Leu  Ala Ser Phe Tyr Trp  Ile Leu Arg
    4025             4030              4035

Leu Ser Val Tyr Asp Cys Ser  Thr Met Gly Phe Tyr  Arg Pro Thr
    4040             4045              4050

Lys Gln Pro Ser Val Leu Ser  Ser Pro Trp Cys Thr  Cys Ser Leu
    4055             4060              4065

Cys Asn His Asp Val Ser Ser  Cys Pro Arg Val Leu  Cys Ala Cys
    4070             4075              4080

Leu Asp Tyr Ile Ser Tyr Asn  Trp Thr Glu Asp Cys  Gly Leu Lys
    4085             4090              4095

Gly Ser Thr His Gly Cys Ser  Cys Ile Ile Ser Arg  Gln Ile Pro
    4100             4105              4110

Ser Ser Ser Arg His Trp Pro  Ser Tyr Val Cys Thr  Ser Ser Cys
    4115             4120              4125

Arg Met Glu Val Leu Cys Thr  Ala Leu Gln Ser Leu  Asn Arg Arg
    4130             4135              4140

Ile Ile Leu Phe Leu Cys His  Thr Phe Gln Ile His  Arg Trp Cys
    4145             4150              4155

Met Pro Ile Leu Glu Leu Gln  Cys Arg Ile Ser Cys  Phe His Cys
    4160             4165              4170

Leu Ile His Ser Ala Ile Pro  Leu Ala Trp Leu Trp  Trp Gln Phe
    4175             4180              4185

Val Cys Lys Thr Cys Ile Pro  His Thr Ser Phe Lys  Cys Phe Cys
    4190             4195              4200

Phe Lys Thr Ile Thr Ile Phe  Leu Leu Leu Gln Ser  Met Val Ser
    4205             4210              4215

Trp Lys Thr Ser Ser Val Arg  Tyr Arg Leu Cys Thr  Thr Lys Val
    4220             4225              4230

Cys Tyr Val Tyr Asn Thr Leu  Gln Phe Arg Trp Cys  Cys Leu Thr
    4235             4240              4245

Ser Cys Val Gln Ile Val Ser  Arg Cys Leu His Asp  Asp Leu Ser
    4250             4255              4260

Trp Leu Leu Val Gly Leu Gln  Thr Ile Tyr Leu Pro  Leu Glu His
    4265             4270              4275

Phe Tyr Lys Thr Ser Glu Phe  Arg Lys Cys Gly Phe  Cys Cys Lys
    4280             4285              4290

Gly Thr Leu Trp Thr Thr Gly  Ser Thr Ser Phe Tyr  His His Cys
    4295             4300              4305

Leu His Lys Ser Trp Cys Cys  Arg Ile Val Lys Asn  Asn Ile Thr
    4310             4315              4320

Cys Cys Ser Ile Ala Leu Gly  Ala Gln His Thr Ser  Thr Arg Gly
    4325             4330              4335

Glu Asn Thr Gln Phe Gly Cys  Gly His Cys Cys Tyr  Cys Asp Leu
    4340             4345              4350

Gly Leu Gln Lys Arg Cys Ser  Ser Thr Tyr Ile Tyr  Tyr Trp Cys
    4355             4360              4365

Leu Phe Tyr Asp His Ser Gln  Glu Thr Asn Asn Asp  Leu Cys Thr
    4370             4375              4380

Thr His Cys Leu Phe Trp Ser  Trp Ser Ser Arg Leu  Ile Lys Cys
    4385             4390              4395
```

-continued

```
Pro Trp Cys Ser Tyr Tyr Arg  Arg Cys Arg Phe Thr  Thr Ile Cys
    4400                 4405             4410

Arg Ser Gln Thr Ser Ser Trp  Ser His Ile Asn Trp  Arg Ser Arg
    4415                 4420             4425

Lys Asn Thr Val Gln Leu Leu  Glu Ser Trp Cys Cys  Pro Thr Ile
    4430                 4435             4440

Thr Asn Leu Leu Tyr Ser Glu  Lys Phe Thr Arg Ile  Thr Gln Glu
    4445                 4450             4455

Ser Asn Gly Asn Phe Leu Arg  Ile Ser Tyr Gly Ile  His Thr Val
    4460                 4465             4470

Ile Arg Arg Leu Cys Leu Arg  Thr Tyr Arg Leu Trp  Arg Phe Ser
    4475                 4480             4485

Ser Val Arg Trp Phe Thr Ser  Thr Asp Trp Thr Ser  Thr Phe Gly
    4490                 4495             4500

Ile Thr Phe Ile Arg Arg Phe  Tyr Ser Tyr Gly Gln  Tyr Ser Lys
    4505                 4510             4515

Leu Phe His Asn Arg Cys Ala  Asn Arg Phe Ile Val  Cys Val Phe
    4520                 4525             4530

Cys Tyr Phe Ile Thr Phe Cys  Asn Asn Lys Ile Pro  Arg Phe Ile
    4535                 4540             4545

Cys Ser Phe Gly Cys Gln Ser  Asp Tyr Leu Tyr Arg  Asn Phe Ile
    4550                 4555             4560

Tyr Ala Leu Val Arg Trp Pro  Cys Arg Asn Ile Leu  Pro Lys Ile
    4565                 4570             4575

Thr Ile Ser Ser Val Ala Thr  Gly Cys Cys Tyr Ala  Ser Leu Gln
    4580                 4585             4590

Asn Ala Lys Asn Ala Ile Arg  Lys Val Pro Ser Lys  Leu Trp Cys
    4595                 4600             4605

Asn Ile Thr Arg His Asn Asp  Glu Cys Arg Lys Ile  Tyr Ser Thr
    4610                 4615             4620

Val Ser Ile Phe Lys His Ile  Asn Ile Ser Cys Thr  Leu Tyr Glu
    4625                 4630             4635

Ser Tyr Thr Phe Trp Cys Trp  Phe Arg Ser Cys Thr  Arg Tyr Ser
    4640                 4645             4650

Cys Phe Lys Thr Val Val Ala  Tyr Gly Tyr Ala Ala  Cys Arg Phe
    4655                 4660             4665

Arg Ser Leu Cys Leu Cys Arg  Phe Asn Phe Asp Trp  Leu Cys Asn
    4670                 4675             4680

Cys Thr Tyr Ser Met Gly Ser  His Tyr Tyr Val Arg  Pro Asp Lys
    4685                 4690             4695

Cys Tyr Lys Arg Lys Leu Arg  Gly Phe Phe His Leu  His Leu Trp
    4700                 4705             4710

Val Tyr Thr Thr Lys Ala Ser  Ser Trp Arg Phe Arg  Gly Tyr Lys
    4715                 4720             4725

Asp Asn Arg Thr Phe Leu Glu  Cys Ser Leu Ala His  Gly Thr Leu
    4730                 4735             4740

Arg Met Val Asp Ser Leu Cys  Tyr Cys Glu Cys Val  Ile Ile Ser
    4745                 4750             4755

Ile Phe Asn Trp Met Leu Ser  Trp Gln Thr Thr Arg  Thr Asn Arg
    4760                 4765             4770

Trp Leu Cys His Ala Cys Lys  Leu His Ile Leu Glu  Glu Tyr Lys
    4775                 4780             4785

Ser Asn Ser Val Val Phe Leu  Phe Phe Ile His Glu  Ile Ser Pro
```

-continued

```
                4790                    4795                    4800

Ile Lys  Gly Tyr Cys Cys Tyr  Val Phe Lys Arg Arg  Ser Asn Gln
    4805                 4810                 4815

Tyr Asp  Phe Ile Ser Ser Arg  Thr Tyr Asn Arg Lys  Gln Gln Ser
    4820                 4825                 4830

Cys Tyr  Phe Cys Ser Cys Gln  Leu Ala Ala Arg Leu  Thr Pro Cys
    4835                 4840                 4845

Gly Thr  Gly Thr Ser Thr Asp  Val Val Tyr Arg Ala  Phe Asp Ile
    4850                 4855                 4860

Tyr Asn  Asp Lys Val Ala Gly  Phe Ala Lys Phe Leu  Lys Thr Asn
    4865                 4870                 4875

Cys Cys  Arg Phe Gln Glu Lys  Asp Glu Asp Asp Asn  Leu Ile Asp
    4880                 4885                 4890

Ser Tyr  Phe Val Val Lys Arg  His Thr Phe Ser Asn  Tyr Gln His
    4895                 4900                 4905

Glu Glu  Thr Ile Tyr Asn Leu  Leu Lys Asp Cys Pro  Ala Val Ala
    4910                 4915                 4920

Lys His  Asp Phe Phe Lys Phe  Arg Ile Asp Gly Asp  Met Val Pro
    4925                 4930                 4935

His Ile  Ser Arg Gln Arg Leu  Thr Lys Tyr Thr Met  Ala Asp Leu
    4940                 4945                 4950

Val Tyr  Ala Leu Arg His Phe  Asp Glu Gly Asn Cys  Asp Thr Leu
    4955                 4960                 4965

Lys Glu  Ile Leu Val Thr Tyr  Asn Cys Cys Asp Asp  Asp Tyr Phe
    4970                 4975                 4980

Asn Lys  Lys Asp Trp Tyr Asp  Phe Val Glu Asn Pro  Asp Ile Leu
    4985                 4990                 4995

Arg Val  Tyr Ala Asn Leu Gly  Glu Arg Val Arg Gln  Ala Leu Leu
    5000                 5005                 5010

Lys Thr  Val Gln Phe Cys Asp  Ala Met Arg Asn Ala  Gly Ile Val
    5015                 5020                 5025

Gly Val  Leu Thr Leu Asp Asn  Gln Asp Leu Asn Gly  Asn Trp Tyr
    5030                 5035                 5040

Asp Phe  Gly Asp Phe Ile Gln  Thr Thr Pro Gly Ser  Gly Val Pro
    5045                 5050                 5055

Val Val  Asp Ser Tyr Tyr Ser  Leu Leu Met Pro Ile  Leu Thr Leu
    5060                 5065                 5070

Thr Arg  Ala Leu Thr Ala Glu  Ser His Val Asp Thr  Asp Leu Thr
    5075                 5080                 5085

Lys Pro  Tyr Ile Lys Trp Asp  Leu Leu Lys Tyr Asp  Phe Thr Glu
    5090                 5095                 5100

Glu Arg  Leu Lys Leu Phe Asp  Arg Tyr Phe Lys Tyr  Trp Asp Gln
    5105                 5110                 5115

Thr Tyr  His Pro Asn Cys Val  Asn Cys Leu Asp Asp  Arg Cys Ile
    5120                 5125                 5130

Leu His  Cys Ala Asn Phe Asn  Val Leu Phe Ser Thr  Val Phe Pro
    5135                 5140                 5145

Pro Thr  Ser Phe Gly Pro Leu  Val Arg Lys Ile Phe  Val Asp Gly
    5150                 5155                 5160

Val Pro  Phe Val Val Ser Thr  Gly Tyr His Phe Arg  Glu Leu Gly
    5165                 5170                 5175

Val Val  His Asn Gln Asp Val  Asn Leu His Ser Ser  Arg Leu Ser
    5180                 5185                 5190
```

-continued

```
Phe Lys  Glu Leu Leu Val Tyr  Ala Ala Asp Pro Ala  Met His Ala
    5195             5200              5205

Ala Ser  Gly Asn Leu Leu Leu  Asp Lys Arg Thr Thr  Cys Phe Ser
    5210             5215              5220

Val Ala  Ala Leu Thr Asn Asn  Val Ala Phe Gln Thr  Val Lys Pro
    5225             5230              5235

Gly Asn  Phe Asn Lys Asp Phe  Tyr Asp Phe Ala Val  Ser Lys Gly
    5240             5245              5250

Phe Phe  Lys Glu Gly Ser Ser  Val Glu Leu Lys His  Phe Phe Phe
    5255             5260              5265

Ala Gln  Asp Gly Asn Ala Ala  Ile Ser Asp Tyr Asp  Tyr Tyr Arg
    5270             5275              5280

Tyr Asn  Leu Pro Thr Met Cys  Asp Ile Arg Gln Leu  Leu Phe Val
    5285             5290              5295

Val Glu  Val Val Asp Lys Tyr  Phe Asp Cys Tyr Asp  Gly Gly Cys
    5300             5305              5310

Ile Asn  Ala Asn Gln Val Ile  Val Asn Asn Leu Asp  Lys Ser Ala
    5315             5320              5325

Gly Phe  Pro Phe Asn Lys Trp  Gly Lys Ala Arg Leu  Tyr Tyr Asp
    5330             5335              5340

Ser Met  Ser Tyr Glu Asp Gln  Asp Ala Leu Phe Ala  Tyr Thr Lys
    5345             5350              5355

Arg Asn  Val Ile Pro Thr Ile  Thr Gln Met Asn Leu  Lys Tyr Ala
    5360             5365              5370

Ile Ser  Ala Lys Asn Arg Ala  Arg Thr Val Ala Gly  Val Ser Ile
    5375             5380              5385

Cys Ser  Thr Met Thr Asn Arg  Gln Phe His Gln Lys  Leu Leu Lys
    5390             5395              5400

Ser Ile  Ala Ala Thr Arg Gly  Ala Thr Val Val Ile  Gly Thr Ser
    5405             5410              5415

Lys Phe  Tyr Gly Gly Trp His  Asn Met Leu Lys Thr  Val Tyr Ser
    5420             5425              5430

Asp Val  Glu Asn Pro His Leu  Met Gly Trp Asp Tyr  Pro Lys Cys
    5435             5440              5445

Asp Arg  Ala Met Pro Asn Met  Leu Arg Ile Met Ala  Ser Leu Val
    5450             5455              5460

Leu Ala  Arg Lys His Thr Thr  Cys Cys Ser Leu Ser  His Arg Phe
    5465             5470              5475

Tyr Arg  Leu Ala Asn Glu Cys  Ala Gln Val Leu Ser  Glu Met Val
    5480             5485              5490

Met Cys  Gly Gly Ser Leu Tyr  Val Lys Pro Gly Gly  Thr Ser Ser
    5495             5500              5505

Gly Asp  Ala Thr Thr Ala Tyr  Ala Asn Ser Val Phe  Asn Ile Cys
    5510             5515              5520

Gln Ala  Val Thr Ala Asn Val  Asn Ala Leu Leu Ser  Thr Asp Gly
    5525             5530              5535

Asn Lys  Ile Ala Asp Lys Tyr  Val Arg Asn Leu Gln  His Arg Leu
    5540             5545              5550

Tyr Glu  Cys Leu Tyr Arg Asn  Arg Asp Val Asp Thr  Asp Phe Val
    5555             5560              5565

Asn Glu  Phe Tyr Ala Tyr Leu  Arg Lys His Phe Ser  Met Met Ile
    5570             5575              5580
```

-continued

```
Leu Ser Asp Asp Ala Val Val Cys Phe Asn Ser Thr Tyr Ala Ser
    5585             5590             5595

Gln Gly Leu Val Ala Ser Ile Lys Asn Phe Lys Ser Val Leu Tyr
    5600             5605             5610

Tyr Gln Asn Asn Val Phe Met Ser Glu Ala Lys Cys Trp Thr Glu
    5615             5620             5625

Thr Asp Leu Thr Lys Gly Pro His Glu Phe Cys Ser Gln His Thr
    5630             5635             5640

Met Leu Val Lys Gln Gly Asp Asp Tyr Val Tyr Leu Pro Tyr Pro
    5645             5650             5655

Asp Pro Ser Arg Ile Leu Gly Ala Gly Cys Phe Val Asp Asp Ile
    5660             5665             5670

Val Lys Thr Asp Gly Thr Leu Met Ile Glu Arg Phe Val Ser Leu
    5675             5680             5685

Ala Ile Asp Ala Tyr Pro Leu Thr Lys His Pro Asn Gln Glu Tyr
    5690             5695             5700

Ala Asp Val Phe His Leu Tyr Leu Gln Tyr Ile Arg Lys Leu His
    5705             5710             5715

Asp Glu Leu Thr Gly His Met Leu Asp Met Tyr Ser Val Met Leu
    5720             5725             5730

Thr Asn Asp Asn Thr Ser Arg Tyr Trp Glu Pro Glu Phe Tyr Glu
    5735             5740             5745

Ala Met Tyr Thr Pro His Thr Val Leu Gln Ala Val Gly Ala Cys
    5750             5755             5760

Val Leu Cys Asn Ser Gln Thr Ser Leu Arg Cys Gly Ala Cys Ile
    5765             5770             5775

Arg Arg Pro Phe Leu Cys Cys Lys Cys Cys Tyr Asp His Val Ile
    5780             5785             5790

Ser Thr Ser His Lys Leu Val Leu Ser Val Asn Pro Tyr Val Cys
    5795             5800             5805

Asn Ala Pro Gly Cys Asp Val Thr Asp Val Thr Gln Leu Tyr Leu
    5810             5815             5820

Gly Gly Met Ser Tyr Tyr Cys Lys Ser His Lys Pro Pro Ile Ser
    5825             5830             5835

Phe Pro Leu Cys Ala Asn Gly Gln Val Phe Gly Leu Tyr Lys Asn
    5840             5845             5850

Thr Cys Val Gly Ser Asp Asn Val Thr Asp Phe Asn Ala Ile Ala
    5855             5860             5865

Thr Cys Asp Trp Thr Asn Ala Gly Asp Tyr Ile Leu Ala Asn Thr
    5870             5875             5880

Cys Thr Glu Arg Leu Lys Leu Phe Ala Ala Glu Thr Leu Lys Ala
    5885             5890             5895

Thr Glu Glu Thr Phe Lys Leu Ser Tyr Gly Ile Ala Thr Val Arg
    5900             5905             5910

Glu Val Leu Ser Asp Arg Glu Leu His Leu Ser Trp Glu Val Gly
    5915             5920             5925

Lys Pro Arg Pro Pro Leu Asn Arg Asn Tyr Val Phe Thr Gly Tyr
    5930             5935             5940

Arg Val Thr Lys Asn Ser Lys Val Gln Ile Gly Glu Tyr Thr Phe
    5945             5950             5955

Glu Lys Gly Asp Tyr Gly Asp Ala Val Val Tyr Arg Gly Thr Thr
    5960             5965             5970

Thr Tyr Lys Leu Asn Val Gly Asp Tyr Phe Val Leu Thr Ser His
```

-continued

```
    5975              5980              5985

Thr Val Met Pro Leu Ser Ala Pro Thr Leu Val Pro Gln Glu His
    5990              5995              6000

Tyr Val Arg Ile Thr Gly Leu Tyr Pro Thr Leu Asn Ile Ser Asp
    6005              6010              6015

Glu Phe Ser Ser Asn Val Ala Asn Tyr Gln Lys Val Gly Met Gln
    6020              6025              6030

Lys Tyr Ser Thr Leu Gln Gly Pro Pro Gly Thr Gly Lys Ser His
    6035              6040              6045

Phe Ala Ile Gly Leu Ala Leu Tyr Tyr Pro Ser Ala Arg Ile Val
    6050              6055              6060

Tyr Thr Ala Cys Ser His Ala Ala Val Asp Ala Leu Cys Glu Lys
    6065              6070              6075

Ala Leu Lys Tyr Leu Pro Ile Asp Lys Cys Ser Arg Ile Ile Pro
    6080              6085              6090

Ala Arg Ala Arg Val Glu Cys Phe Asp Lys Phe Lys Val Asn Ser
    6095              6100              6105

Thr Leu Glu Gln Tyr Val Phe Cys Thr Val Asn Ala Leu Pro Glu
    6110              6115              6120

Thr Thr Ala Asp Ile Val Val Phe Asp Glu Ile Ser Met Ala Thr
    6125              6130              6135

Asn Tyr Asp Leu Ser Val Val Asn Ala Arg Leu Arg Ala Lys His
    6140              6145              6150

Tyr Val Tyr Ile Gly Asp Pro Ala Gln Leu Pro Ala Pro Arg Thr
    6155              6160              6165

Leu Leu Thr Lys Gly Thr Leu Glu Pro Glu Tyr Phe Asn Ser Val
    6170              6175              6180

Cys Arg Leu Met Lys Thr Ile Gly Pro Asp Met Phe Leu Gly Thr
    6185              6190              6195

Cys Arg Arg Cys Pro Ala Glu Ile Val Asp Thr Val Ser Ala Leu
    6200              6205              6210

Val Tyr Asp Asn Lys Leu Lys Ala His Lys Asp Lys Ser Ala Gln
    6215              6220              6225

Cys Phe Lys Met Phe Tyr Lys Gly Val Ile Thr His Asp Val Ser
    6230              6235              6240

Ser Ala Ile Asn Arg Pro Gln Ile Gly Val Val Arg Glu Phe Leu
    6245              6250              6255

Thr Arg Asn Pro Ala Trp Arg Lys Ala Val Phe Ile Ser Pro Tyr
    6260              6265              6270

Asn Ser Gln Asn Ala Val Ala Ser Lys Ile Leu Gly Leu Pro Thr
    6275              6280              6285

Gln Thr Val Asp Ser Ser Gln Gly Ser Glu Tyr Asp Tyr Val Ile
    6290              6295              6300

Phe Thr Gln Thr Thr Glu Thr Ala His Ser Cys Asn Val Asn Arg
    6305              6310              6315

Phe Asn Val Ala Ile Thr Arg Ala Lys Val Gly Ile Leu Cys Ile
    6320              6325              6330

Met Ser Asp Arg Asp Leu Tyr Asp Lys Leu Gln Phe Thr Ser Leu
    6335              6340              6345

Glu Ile Pro Arg Arg Asn Val Ala Thr Leu Gln Ala Glu Asn Val
    6350              6355              6360

Thr Gly Leu Phe Lys Asp Cys Ser Lys Val Ile Thr Gly Leu His
    6365              6370              6375
```

-continued

```
Pro Thr  Gln Ala Pro Thr His  Leu Ser Val Asp Thr  Lys Phe Lys
    6380             6385             6390

Thr Glu  Gly Leu Cys Val Asp  Ile Pro Gly Ile Pro  Lys Asp Met
    6395             6400             6405

Thr Tyr  Arg Arg Leu Ile Ser  Met Met Gly Phe Lys  Met Asn Tyr
    6410             6415             6420

Gln Val  Asn Gly Tyr Pro Asn  Met Phe Ile Thr Arg  Glu Glu Ala
    6425             6430             6435

Ile Arg  His Val Arg Ala Trp  Ile Gly Phe Asp Val  Glu Gly Cys
    6440             6445             6450

His Ala  Thr Arg Glu Ala Val  Gly Thr Asn Leu Pro  Leu Gln Leu
    6455             6460             6465

Gly Phe  Ser Thr Gly Val Asn  Leu Val Ala Val Pro  Thr Gly Tyr
    6470             6475             6480

Val Asp  Thr Pro Asn Asn Thr  Asp Phe Ser Arg Val  Ser Ala Lys
    6485             6490             6495

Pro Pro  Pro Gly Asp Gln Phe  Lys His Leu Ile Pro  Leu Met Tyr
    6500             6505             6510

Lys Gly  Leu Pro Trp Asn Val  Val Arg Ile Lys Ile  Val Gln Met
    6515             6520             6525

Leu Ser  Asp Thr Leu Lys Asn  Leu Ser Asp Arg Val  Val Phe Val
    6530             6535             6540

Leu Trp  Ala His Gly Phe Glu  Leu Thr Ser Met Lys  Tyr Phe Val
    6545             6550             6555

Lys Ile  Gly Pro Glu Arg Thr  Cys Cys Leu Cys Asp  Arg Arg Ala
    6560             6565             6570

Thr Cys  Phe Ser Thr Ala Ser  Asp Thr Tyr Ala Cys  Trp His His
    6575             6580             6585

Ser Ile  Gly Phe Asp Tyr Val  Tyr Asn Pro Phe Met  Ile Asp Val
    6590             6595             6600

Gln Gln  Trp Gly Phe Thr Gly  Asn Leu Gln Ser Asn  His Asp Leu
    6605             6610             6615

Tyr Cys  Gln Val His Gly Asn  Ala His Val Ala Ser  Cys Asp Ala
    6620             6625             6630

Ile Met  Thr Arg Cys Leu Ala  Val His Glu Cys Phe  Val Lys Arg
    6635             6640             6645

Val Asp  Trp Thr Ile Glu Tyr  Pro Ile Ile Gly Asp  Glu Leu Lys
    6650             6655             6660

Ile Asn  Ala Ala Cys Arg Lys  Val Gln His Met Val  Val Lys Ala
    6665             6670             6675

Ala Leu  Leu Ala Asp Lys Phe  Pro Val Leu His Asp  Ile Gly Asn
    6680             6685             6690

Pro Lys  Ala Ile Lys Cys Val  Pro Gln Ala Asp Val  Glu Trp Lys
    6695             6700             6705

Phe Tyr  Asp Ala Gln Pro Cys  Ser Asp Lys Ala Tyr  Lys Ile Glu
    6710             6715             6720

Glu Leu  Phe Tyr Ser Tyr Ala  Thr His Ser Asp Lys  Phe Thr Asp
    6725             6730             6735

Gly Val  Cys Leu Phe Trp Asn  Cys Asn Val Asp Arg  Tyr Pro Ala
    6740             6745             6750

Asn Ser  Ile Val Cys Arg Phe  Asp Thr Arg Val Leu  Ser Asn Leu
    6755             6760             6765
```

-continued

```
Asn Leu Pro Gly Cys Asp Gly  Gly Ser Leu Tyr Val  Asn Lys His
    6770             6775              6780

Ala Phe His Thr Pro Ala Phe  Asp Lys Ser Ala Phe  Val Asn Leu
    6785             6790              6795

Lys Gln Leu Pro Phe Phe Tyr  Tyr Ser Asp Ser Pro  Cys Glu Ser
    6800             6805              6810

His Gly Lys Gln Val Val Ser  Asp Ile Asp Tyr Val  Pro Leu Lys
    6815             6820              6825

Ser Ala Thr Cys Ile Thr Arg  Cys Asn Leu Gly Gly  Ala Val Cys
    6830             6835              6840

Arg His His Ala Asn Glu Tyr  Arg Leu Tyr Leu Asp  Ala Tyr Asn
    6845             6850              6855

Met Met Ile Ser Ala Gly Phe  Ser Leu Trp Val Tyr  Lys Gln Phe
    6860             6865              6870

Asp Thr Tyr Asn Leu Trp Asn  Thr Phe Thr Arg Leu  Gln Ser Leu
    6875             6880              6885

Glu Asn Val Ala Phe Asn Val  Val Asn Lys Gly His  Phe Asp Gly
    6890             6895              6900

Gln Gln Gly Glu Val Pro Val  Ser Ile Ile Asn Asn  Thr Val Tyr
    6905             6910              6915

Thr Lys Val Asp Gly Val Asp  Val Glu Leu Phe Glu  Asn Lys Thr
    6920             6925              6930

Thr Leu Pro Val Asn Val Ala  Phe Glu Leu Trp Ala  Lys Arg Asn
    6935             6940              6945

Ile Lys Pro Val Pro Glu Val  Lys Ile Leu Asn Asn  Leu Gly Val
    6950             6955              6960

Asp Ile Ala Ala Asn Thr Val  Ile Trp Asp Tyr Lys  Arg Asp Ala
    6965             6970              6975

Pro Ala His Ile Ser Thr Ile  Gly Val Cys Ser Met  Thr Asp Ile
    6980             6985              6990

Ala Lys Lys Pro Thr Glu Thr  Ile Cys Ala Pro Leu  Thr Val Phe
    6995             7000              7005

Phe Asp Gly Arg Val Asp Gly  Gln Val Asp Leu Phe  Arg Asn Ala
    7010             7015              7020

Arg Asn Gly Val Leu Ile Thr  Glu Gly Ser Val Lys  Gly Leu Gln
    7025             7030              7035

Pro Ser Val Gly Pro Lys Gln  Ala Ser Leu Asn Gly  Val Thr Leu
    7040             7045              7050

Ile Gly Glu Ala Val Lys Thr  Gln Phe Asn Tyr Tyr  Lys Lys Val
    7055             7060              7065

Asp Gly Val Val Gln Gln Leu  Pro Glu Thr Tyr Phe  Thr Gln Ser
    7070             7075              7080

Arg Asn Leu Gln Glu Phe Lys  Pro Arg Ser Gln Met  Glu Ile Asp
    7085             7090              7095

Phe Leu Glu Leu Ala Met Asp  Glu Phe Ile Glu Arg  Tyr Lys Leu
    7100             7105              7110

Glu Gly Tyr Ala Phe Glu His  Ile Val Tyr Gly Asp  Phe Ser His
    7115             7120              7125

Ser Gln Leu Gly Gly Leu His  Leu Leu Ile Gly Leu  Ala Lys Arg
    7130             7135              7140

Phe Lys Glu Ser Pro Phe Glu  Leu Glu Asp Phe Ile  Pro Met Asp
    7145             7150              7155

Ser Thr Val Lys Asn Tyr Phe  Ile Thr Asp Ala Gln  Thr Gly Ser
```

-continued

```
            7160                 7165                 7170

Ser Lys Cys Val Cys Ser Val  Ile Asp Leu Leu Leu  Asp Asp Phe
    7175                 7180                 7185

Val Glu Ile Ile Lys Ser Gln  Asp Leu Ser Val Val  Ser Lys Val
    7190                 7195                 7200

Val Lys Val Thr Ile Asp Tyr  Thr Glu Ile Ser Phe  Met Leu Trp
    7205                 7210                 7215

Cys Lys Asp Gly His Val Glu  Thr Phe Tyr Pro Lys  Leu Gln Ser
    7220                 7225                 7230

Ser Gln Ala Trp Gln Pro Gly  Val Ala Met Pro Asn  Leu Tyr Lys
    7235                 7240                 7245

Met Gln Arg Met Leu Leu Glu  Lys Cys Asp Leu Gln  Asn Tyr Gly
    7250                 7255                 7260

Asp Ser Ala Thr Leu Pro Lys  Gly Ile Met Met Asn  Val Ala Lys
    7265                 7270                 7275

Tyr Thr Gln Leu Cys Gln Tyr  Leu Asn Thr Leu Thr  Leu Ala Val
    7280                 7285                 7290

Pro Tyr Asn Met Arg Val Ile  His Phe Gly Ala Gly  Ser Asp Lys
    7295                 7300                 7305

Gly Val Ala Pro Gly Thr Ala  Val Leu Arg Gln Trp  Leu Pro Thr
    7310                 7315                 7320

Gly Thr Leu Leu Val Asp Ser  Asp Leu Asn Asp Phe  Val Ser Asp
    7325                 7330                 7335

Ala Asp Ser Thr Leu Ile Gly  Asp Cys Ala Thr Val  His Thr Ala
    7340                 7345                 7350

Asn Lys Trp Asp Leu Ile Ile  Ser Asp Met Tyr Asp  Pro Lys Thr
    7355                 7360                 7365

Lys Asn Val Thr Lys Glu Asn  Asp Ser Lys Glu Gly  Phe Phe Thr
    7370                 7375                 7380

Tyr Ile Cys Gly Phe Ile Gln  Gln Lys Leu Ala Leu  Gly Gly Ser
    7385                 7390                 7395

Val Ala Ile Lys Ile Thr Glu  His Ser Trp Asn Ala  Asp Leu Tyr
    7400                 7405                 7410

Lys Leu Met Gly His Phe Ala  Trp Trp Thr Ala Phe  Val Thr Asn
    7415                 7420                 7425

Val Asn Ala Ser Ser Ser Glu  Ala Phe Leu Ile Gly  Cys Asn Tyr
    7430                 7435                 7440

Leu Gly Lys Pro Arg Glu Gln  Ile Asp Gly Tyr Val  Met His Ala
    7445                 7450                 7455

Asn Tyr Ile Phe Trp Arg Asn  Thr Asn Pro Ile Gln  Leu Ser Ser
    7460                 7465                 7470

Tyr Ser Leu Phe Asp Met Ser  Lys Phe Pro Leu Lys  Leu Arg Gly
    7475                 7480                 7485

Thr Ala Val Met Ser Leu Lys  Glu Gly Gln Ile Asn  Asp Met Ile
    7490                 7495                 7500

Leu Ser Leu Leu Ser Lys Gly  Arg Leu Ile Ile Arg  Glu Asn Asn
    7505                 7510                 7515

Arg Val Val Ile Ser Ser Asp  Val Leu Val Asn Asn
    7520                 7525                 7530
```

<210> SEQ ID NO 8
<211> LENGTH: 828
<212> TYPE: DNA
<213> ORGANISM: Severe acute respiratory syndrome coronavirus 2

-continued

```
<400> SEQUENCE: 8
atggatttgt ttatgagaat cttcacaatt ggaactgtaa ctttgaagca aggtgaaatc      60
aaggatgcta ctccttcaga tttttgttcgc gctactgcaa cgataccgat acaagcctca     120 ctcccttcg gatggcttat tgttggcgtt gcacttcttg ctgtttttca gagcgcttcc      180
aaaatcataa ccctcaaaaa gagatggcaa ctagcactct ccaagggtgt tcactttgtt     240
tgcaacttgc tgttgttgtt tgtaacagtt tactcacacc ttttgctcgt tgctgctggc     300
cttgaagccc ctttctcta tctttatgct ttagtctact tcttgcagag tataaacttt     360
gtaagaataa taatgaggct ttggctttgc tggaaatgcc gttccaaaaa cccattactt     420
tatgatgcca actattttct ttgctggcat actaattgtt acgactattg tataccttac     480
aatagtgtaa cttcttcaat tgtcattact tcaggtgatg gcacaacaag tcctatttct     540
gaacatgact accagattgg tggttatact gaaaaatggg aatctggagt aaaagactgt     600
gttgtattac acagttactt cacttcagac tattaccagc tgtactcaac tcaattgagt     660
acagacactg tgttgaaca tgttaccttc ttcatctaca ataaaattgt tgatgagcct     720
gaagaacatg tccaaattca cacaatcgac ggttcatccg gagttgttaa tccagtaatg     780
gaaccaattt atgatgaacc gacgacgact actagcgtgc ctttgtaa               828

<210> SEQ ID NO 9
<211> LENGTH: 186
<212> TYPE: DNA
<213> ORGANISM: Severe acute respiratory syndrome coronavirus 2

<400> SEQUENCE: 9
atgtttcatc tcgttgactt tcaggttact atagcagaga tattactaat tattatgagg      60
acttttaaag tttccatttg gaatcttgat tacatcataa acctcataat taaaaattta     120
tctaagtcac taactgagaa taaatattct caattagatg aagagcaacc aatggagatt     180
gattaa                                                              186

<210> SEQ ID NO 10
<211> LENGTH: 669
<212> TYPE: DNA
<213> ORGANISM: Severe acute respiratory syndrome coronavirus 2

<400> SEQUENCE: 10
atggcagatt ccaacggtac tattaccgtt gaagagctta aaaagctcct tgaacaatgg      60
aacctagtaa taggtttcct attccttaca tggatttgtc ttctacaatt tgcctatgcc     120
aacaggaata ggttttttgta tataattaag ttaattttcc tctggctgtt atggccagta     180
actttagctt gttttgtgct tgctgctgtt tacagaataa attggatcac cggtggaatt     240
gctatcgcaa tggcttgtct tgtaggcttg atgtggctca gctacttcat tgcttctttc     300
agactgtttg cgcgtacgcg ttccatgtgg tcattcaatc cagaaactaa cattcttctc     360
aacgtgccac tccatggcac tattctgacc agaccgcttc tagaaagtga actcgtaatc     420
ggagctgtga tccttcgtgg acatcttcgt attgctggac accatctagg acgctgtgac     480
atcaaggacc tgcctaaaga aatcactgtt gctacatcac gaacgctttc ttattacaaa     540
ttgggagctt cgcagcgtgt agcaggtgac tcaggttttg ctgcatacag tcgctacagg     600
attggcaact ataaattaaa cacagaccat tccagtagca gtgacaatat tgctttgctt     660
gtacagtaa                                                            669
```

```
<210> SEQ ID NO 11
<211> LENGTH: 1260
<212> TYPE: DNA
<213> ORGANISM: Severe acute respiratory syndrome coronavirus 2

<400> SEQUENCE: 11
atgtctgata atggacccca aaatcagcga aatgcacccc gcattacgtt tggtggaccc          60
tcagattcaa ctggcagtaa ccagaatgga gaacgcagtg gggcgcgatc aaaacaacgt         120
cggccccaag gtttacccaa taatactgcg tcttggttca ccgctctcac tcaacatggc         180
aaggaagacc ttaaattccc tcgaggacaa ggcgttccaa ttaacaccaa tagcagtcca         240
gatgaccaaa ttggctacta ccgaagagct accagacgaa ttcgtggtgg tgacggtaaa         300
atgaaagatc tcagtccaag atggtatttc tactacctag gaactgggcc agaagctgga         360
cttccctatg gtgctaacaa agacggcatc atatgggttg caactgaggg agccttgaat         420
acaccaaaag atcacattgg cacccgcaat cctgctaaca atgctgcaat cgtgctacaa         480
cttcctcaag gaacaacatt gccaaaaggc ttctacgcag aagggagcag aggcggcagt         540
caagcctctt ctcgttcctc atcacgtagt cgcaacagtt caagaaattc aactccaggc         600
agcagtaggg gaacttctcc tgctagaatg gctggcaatg gcggtgatgc tgctcttgct         660
ttgctgctgc ttgacagatt gaaccagctt gagagcaaaa tgtctggtaa aggccaacaa         720
caacaaggcc aaactgtcac taagaaatct gctgctgagg cttctaagaa gcctcggcaa         780
aaacgtactg ccactaaagc atacaatgta acacaagctt tcggcagacg tggtccagaa         840
caaacccaag gaaattttgg ggaccaggaa ctaatcagac aaggaactga ttacaaacat         900
tggccgcaaa ttgcacaatt gcccccagc gcttcagcgt tcttcggaat gtcgcgcatt         960
ggcatggaag tcacaccttc gggaacgtgg ttgacctaca caggtgccat caaattggat        1020
gacaaagatc caaatttcaa agatcaagtc attttgctga ataagcatat tgacgcatac        1080
aaaacattcc caccaacaga gcctaaaaag gacaaaaaga agaaggctga tgaaactcaa        1140
gccttaccgc agagacagaa gaaacagcaa actgtgactc ttcttcctgc tgcagatttg        1200
gatgatttct ccaaacaatt gcaacaatcc atgagcagtg ctgactcaac tcaggcctaa        1260
```

```
<210> SEQ ID NO 12
<211> LENGTH: 1803
<212> TYPE: DNA
<213> ORGANISM: Severe acute respiratory syndrome coronavirus 2

<400> SEQUENCE: 12
gctgttgggg cttgtgttct ttgcaattca cagacttcat taagatgtgg tgcttgcata          60
cgtagaccat tcttatgttg taaatgctgt tacgaccatg tcatatcaac atcacataaa         120
ttagtcttgt ctgttaatcc gtatgtttgc aatgctccag ttgtgatgt cacagatgtg         180 actcaacttt acttaggagg tatgagctat tattgtaaat cacataaacc acccattagt         240
tttccattgt gtgctaatgg acaagttttt ggtttatata aaaatacatg tgttggtagc         300
gataatgtta ctgactttaa tgcaattgca acatgtgact ggacaaatgc tggtgattac         360
attttagcta acacctgtac tgaaagactc aagcttttg cagcagaaac gctcaaagct         420
actgaggaga catttaaact gtcttatggt attgctactg tacgtgaagt gctgtctgac         480
agagaattac atcttccatg ggaagttggt aaacctagac caccacttaa ccgaaattat         540
gtctttactg gttatcgtgt aactaaaaac agtaaagtac aaataggaga gtacaccttt         600
gaaaaaggtg actatggtga tgctgttgtt taccgaggta caacaacta caaattaaat         660
```

-continued

```
gttggtgatt attttgtgct gacatcacat acagtaatgc cattaagtgc acctacacta        720
gtgccacaag agcactatgt tagaattact ggcttatacc caacactcaa tatctcagat        780
gagttttcta gcaatgttgc aaattatcaa aaggttggta tgcaaaagta ttctacactc        840
cagggaccac ctggtactgg taagagtcat tttgctattg gcctagctct ctactaccct        900
tctgctcgca tagtgtatac agcttgctct catgccgctg ttgatgcact atgtgagaag        960
gcattaaaat atttgcctat agataaatgt agtagaatta tacctgcacg tgctcgtgta       1020
gagtgttttg ataaattcaa agtgaattca acattagaac agtatgtctt ttgtactgta       1080
aatgcattgc ctgagacgac agcagatata gttgtctttg atgaaatttc aatggccaca       1140
aattatgatt tgagtgttgt caatgccaga ttacgtgcta agcactatgt gtacattggc       1200
gaccctgctc aattacctgc accacgcaca ttgctaacta agggcacact agaaccagaa       1260
tatttcaatt cagtgtgtag acttatgaaa actataggtc cagacatgtt cctcggaact       1320
tgtcggcgtt gtcctgctga aattgttgac actgtgagtg ctttggttta tgataataag       1380
cttaaagcac ataaagacaa atcagctcaa tgctttaaaa tgttttataa gggtgttatc       1440
acgcatgatg tttcatctgc aattaacagg ccacaaatag gcgtggtaag agaattcctt       1500
acacgtaacc ctgcttggag aaaagctgtc tttatttcac cttataattc acagaatgct       1560
gtagcctcaa agattttggg actaccaact caaactgttg attcatcaca gggctcagaa       1620
tatgactatg tcatattcac tcaaaccact gaaacagctc actcttgtaa tgtaaacaga       1680
tttaatgttg ctattaccag agcaaaagta ggcatacttt gcataatgtc tgatagagac       1740
ctttatgaca agttgcaatt tacaagtctt gaaattccac gtaggaatgt ggcaacttta       1800
caa                                                                     1803
```

<210> SEQ ID NO 13
<211> LENGTH: 2795
<212> TYPE: DNA
<213> ORGANISM: Severe acute respiratory syndrome coronavirus 2

<400> SEQUENCE: 13

```
tcagctgatg cacaatcgtt tttaaacggg tttgcggtgt aagtgcagcc cgtcttacac         60
cgtgcggcac aggcactagt actgatgtcg tatacagggc ttttgacatc tacaatgata        120
aagtagctgg ttttgctaaa ttcctaaaaa ctaattgttg tcgcttccaa gaaaaggacg        180
aagatgacaa tttaattgat tcttactttg tagttaagag acacactttc tctaactacc        240
aacatgaaga aacaatttat aatttactta aggattgtcc agctgttgct aaacatgact        300
tctttaagtt tagaatagac ggtgacatgg taccacatat atcacgtcaa cgtcttacta        360
aatacacaat ggcagacctc gtctatgctt taaggcattt tgatgaaggt aattgtgaca        420
cattaaaaga aatacttgtc acatacaatt gttgtgatga tgattatttc aataaaaagg        480
actggtatga ttttgtagaa aacccagata tattacgcgt atacgccaac ttaggtgaac        540
gtgtacgcca agctttgtta aaaacagtac aattctgtga tgccatgcga aatgctggta        600
ttgttggtgt actgacatta gataatcaag atctcaatgg taactggtat gatttcggtg        660
atttcataca aaccacgcca ggtagtggag ttcctgttgt agattcttat tattcattgt        720
taatgcctat attaaccttg accagggctt taactgcaga gtcacatgtt gacactgact        780
taacaaagcc ttacattaag tgggatttgt taaaatatga cttcacggaa gagaggttaa        840
aactctttga ccgttatttt aaatattggg atcagacata ccacccaaat tgtgttaact        900
```

-continued

```
gtttggatga cagatgcatt ctgcattgtg caaactttaa tgtttattc tctacagtgt       960 tcccacctac aagttttgga ccactagtga gaaaaatatt tgttgatggt gttccatttg      1020
tagtttcaac tggataccac ttcagagagc taggtgttgt acataatcag gatgtaaact      1080
tacatagctc tagacttagt tttaaggaat tacttgtgta tgctgctgac cctgctatgc      1140
acgctgcttc tggtaatcta ttactagata aacgcactac gtgctttca gtagctgcac       1200 ttactaacaa tgttgctttt caaactgtca aacccggtaa ttttaacaaa gacttctatg      1260
actttgctgt gtctaagggt ttctttaagg aaggaagttc tgttgaatta aaacacttct      1320
tctttgctca ggatggtaat gctgctatca gcgattatga ctactatcgt tataatctac      1380
caacaatgtg tgatatcaga caactactat ttgtagttga agttgttgat aagtactttg      1440
attgttacga tggtggctgt attaatgcta accaagtcat cgtcaacaac ctagacaaat      1500
cagctggttt tccatttaat aaatggggta aggctagact ttattatgat tcaatgagtt      1560
atgaggatca agatgcactt ttcgcatata caaaacgtaa tgtcatccct actataactc      1620
aaatgaatct taagtatgcc attagtgcaa agaatagagc tcgcaccgta gctggtgtct      1680
ctatctgtag tactatgacc aatagacagt ttcatcaaaa attattgaaa tcaatagccg      1740
ccactagagg agctactgta gtaattggaa caagcaaatt ctatggtggt tggcacaaca      1800
tgttaaaaac tgtttatagt gatgtagaaa accctcacct tatgggttgg gattatccta      1860
aatgtgatag agccatgcct aacatgctta gaattatggc ctcacttgtt cttgctcgca      1920
aacatacaac gtgttgtagc ttgtcacacc gtttctatag attagctaat gagtgtgctc      1980
aagtattgag tgaaatggtc atgtgtggcg gttcactata tgttaaacca ggtggaacct      2040
catcaggaga tgccacaact gcttatgcta atagtgtttt taacatttgt caagctgtca      2100
cggccaatgt taatgcactt ttatctactg atggtaacaa aattgccgat aagtatgtcc      2160
gcaatttaca acacagactt tatgagtgtc tctatagaaa tagagatgtt gacacagact      2220
ttgtgaatga gttttacgca tatttgcgta aacatttctc aatgatgata ctctctgacg      2280
atgctgttgt gtgtttcaat agcacttatg catctcaagg tctagtggct agcataaaga      2340
actttaagtc agttctttat tatcaaaaca atgttttta t gtctgaagca aaatgttgga      2400
ctgagactga ccttactaaa ggacctcatg aattttgctc tcaacataca atgctagtta      2460
aacagggtga tgattatgtg taccttcctt acccagatcc atcaagaatc ctaggggccg      2520 gctgtttttgt agatgatatc gtaaaaacag atggtacact tatgattgaa cggttcgtgt      2580
ctttagctat agatgcttac ccacttacta aacatcctaa tcaggagtat gctgatgtct      2640
ttcatttgta cttacaatac ataagaaagc tacatgatga gttaacagga cacatgttag      2700
acatgtattc tgttatgctt actaatgata acacttcaag gtattgggaa cctgagtttt      2760
atgaggctat gtacacaccg catacagtct tacag                                 2795
```

<210> SEQ ID NO 14
<211> LENGTH: 8072
<212> TYPE: DNA
<213> ORGANISM: Severe acute respiratory syndrome coronavirus 2

<400> SEQUENCE: 14

```
gtgcagcccg tcttacaccg tgcggcacag gcactagtac tgatgtcgta tacagggctt        60
ttgacatcta caatgataaa gtagctggtt ttgctaaatt cctaaaaact aattgttgtc       120
gcttccaaga aaaggacgaa gatgacaatt taattgattc ttactttgta gttaagagac       180
acactttctc taactaccaa catgaagaaa caatttataa tttacttaag gattgtccag       240
```

-continued

```
ctgttgctaa acatgacttc tttaagttta gaatagacgg tgacatggta ccacatatat      300
cacgtcaacg tcttactaaa tacacaatgg cagacctcgt ctatgcttta aggcattttg      360
atgaaggtaa ttgtgacaca ttaaaagaaa tacttgtcac atacaattgt tgtgatgatg      420
attatttcaa taaaaaggac tggtatgatt ttgtagaaaa cccagatata ttacgcgtat      480
acgccaactt aggtgaacgt gtacgccaag ctttgttaaa aacagtacaa ttctgtgatg      540
ccatgcgaaa tgctggtatt gttggtgtac tgacattaga taatcaagat ctcaatggta      600
actggtatga tttcggtgat ttcatacaaa ccacgccagg tagtggagtt cctgttgtag      660
attcttatta ttcattgtta atgcctatat taaccttgac cagggcttta actgcagagt      720
cacatgttga cactgactta acaaagcctt acattaagtg ggatttgtta aaatatgact      780
tcacggaaga gaggttaaaa ctctttgacc gttattttaa atattgggat cagacatacc      840
acccaaattg tgttaactgt ttggatgaca gatgcattct gcattgtgca aactttaatg      900
ttttattctc tacagtgttc ccacctacaa gtttttggacc actagtgaga aaaatatttg      960
ttgatggtgt tccatttgta gtttcaactg gataccactt cagagagcta ggtgttgtac     1020
ataatcagga tgtaaactta catagctcta gacttagttt taaggaatta cttgtgtatg     1080
ctgctgaccc tgctatgcac gctgcttctg gtaatctatt actagataaa cgcactacgt     1140
gcttttcagt agctgcactt actaacaatg ttgcttttca aactgtcaaa cccggtaatt     1200
ttaacaaaga cttctatgac tttgctgtgt ctaagggttt ctttaaggaa ggaagttctg     1260
ttgaattaaa acacttcttc tttgctcagg atggtaatgc tgctatcagc gattatgact     1320
actatcgtta taatctacca acaatgtgtg atatcagaca actactattt gtagttgaag     1380
ttgttgataa gtactttgat tgttacgatg gtggctgtat taatgctaac caagtcatcg     1440
tcaacaacct agacaaatca gctggttttc catttaataa atgggggtaag gctagacttt     1500 attatgattc aatgagttat gaggatcaag atgcactttt cgcatataca aaacgtaatg     1560
tcatccctac tataactcaa atgaatctta agtatgccat tagtgcaaag aatagagctc     1620
gcaccgtagc tggtgtctct atctgtagta ctatgaccaa tagacagttt catcaaaaat     1680
tattgaaatc aatagccgcc actagaggag ctactgtagt aattggaaca agcaaattct     1740
atggtggttg gcacaacatg ttaaaaactg tttatagtga tgtagaaaac cctcacctta     1800
tgggttggga ttatcctaaa tgtgatagag ccatgcctaa catgcttaga attatggcct     1860
cacttgttct tgctcgcaaa catacaacgt gttgtagctt gtcacaccgt ttctatagat     1920
tagctaatga gtgtgctcaa gtattgagtg aaatggtcat gtgtggcggt tcactatatg     1980
ttaaaccagg tggaacctca tcaggagatg ccacaactgc ttatgctaat agtgtttta     2040 acatttgtca agctgtcacg gccaatgtta atgcactttt atctactgat ggtaacaaaa     2100
ttgccgataa gtatgtccgc aatttacaac acagacttta tgagtgtctc tatagaaata     2160
gagatgttga cacagacttt gtgaatgagt tttacgcata tttgcgtaaa catttctcaa     2220
tgatgatact ctctgacgat gctgttgtgt gtttcaatag cacttatgca tctcaaggtc     2280
tagtggctag cataaagaac tttaagtcag ttctttatta tcaaaacaat gttttttatgt     2340 ctgaagcaaa atgttggact gagactgacc ttactaaagg acctcatgaa ttttgctctc     2400
aacatacaat gctagttaaa cagggtgatg attatgtgta ccttccttac ccagatccat     2460
caagaatcct aggggccggc tgttttgtag atgatatcgt aaaaacagat ggtacactta     2520
tgattgaacg gttcgtgtct ttagctatag atgcttaccc acttactaaa catcctaatc     2580
```

-continued

```
aggagtatgc tgatgtcttt catttgtact tacaatacat aagaaagcta catgatgagt    2640
taacaggaca catgttagac atgtattctg ttatgcttac taatgataac acttcaaggt    2700
attgggaacc tgagttttat gaggctatgt acacaccgca tacagtctta caggctgttg    2760
gggcttgtgt tctttgcaat tcacagactt cattaagatg tggtgcttgc atacgtagac    2820
cattcttatg ttgtaaatgc tgttacgacc atgtcatatc aacatcacat aaattagtct    2880
tgtctgttaa tccgtatgtt tgcaatgctc caggttgtga tgtcacagat gtgactcaac    2940
tttacttagg aggtatgagc tattattgta aatcacataa accacccatt agttttccat    3000
tgtgtgctaa tggacaagtt tttggtttat ataaaaatac atgtgttggt agcgataatg    3060
ttactgactt taatgcaatt gcaacatgtg actggacaaa tgctggtgat tacatttttag    3120 ctaacacctg tactgaaaga ctcaagcttt ttgcagcaga aacgctcaaa gctactgagg    3180
agacatttaa actgtcttat ggtattgcta ctgtacgtga agtgctgtct gacagagaat    3240
tacatctttc atgggaagtt ggtaaaccta gaccaccact taaccgaaat tatgtctttta    3300 ctggttatcg tgtaactaaa aacagtaaag tacaaatagg agagtacacc tttgaaaaag    3360
gtgactatgg tgatgctgtt gtttaccgag gtacaacaac ttacaaatta aatgttggtg    3420
attattttgt gctgacatca catacagtaa tgccattaag tgcacctaca ctagtgccac    3480
aagagcacta tgttagaatt actggcttat acccaacact caatatctca gatgagtttt    3540
ctagcaatgt tgcaaattat caaaaggttg gtatgcaaaa gtattctaca ctccagggac    3600
cacctggtac tggtaagagt cattttgcta ttggcctagc tctctactac ccttctgctc    3660
gcatagtgta tacagcttgc tctcatgccg ctgttgatgc actatgtgag aaggcattaa    3720
aatatttgcc tatagataaa tgtagtagaa ttatacctgc acgtgctcgt gtagagtgtt    3780
ttgataaatt caaagtgaat tcaacattag aacagtatgt cttttgtact gtaaatgcat    3840
tgcctgagac gacagcagat atagttgtct ttgatgaaat ttcaatggcc acaaattatg    3900
atttgagtgt tgtcaatgcc agattacgtg ctaagcacta tgtgtacatt ggcgaccctg    3960
ctcaattacc tgcaccacgc acattgctaa ctaagggcac actagaacca gaatatttca    4020
attcagtgtg tagacttatg aaaactatag gtccagacat gttcctcgga acttgtcggc    4080
gttgtcctgc tgaaattgtt gacactgtga gtgctttggt ttatgataat aagcttaaag    4140
cacataaaga caaatcagct caatgcttta aaatgttttta taaggtgtgtt atcacgcatg    4200 atgtttcatc tgcaattaac aggccacaaa taggcgtggt aagagaattc cttacacgta    4260
accctgcttg gagaaaagct gtctttattt caccttataa ttcacagaat gctgtagcct    4320
caaagatttt gggactacca actcaaactg ttgattcatc acagggctca gaatatgact    4380
atgtcatatt cactcaaacc actgaaacag ctcactcttg taatgtaaac agatttaatg    4440
ttgctattac cagagcaaaa gtaggcatac tttgcataat gtctgataga gacctttatg    4500
acaagttgca atttacaagt cttgaaattc cacgtaggaa tgtggcaact ttacaagctg    4560
aaaatgtaac aggactcttt aaagattgta gtaaggtaat cactgggtta catcctacac    4620
aggcacctac acacctcagt gttgacacta aattcaaaac tgaaggttta tgtgttgaca    4680
tacctggcat acctaaggac atgacctata gaagactcat ctctatgatg ggttttaaaa    4740
tgaattatca agttaatggt taccctaaca tgtttatcac ccgcgaagaa gctataagac    4800
atgtacgtgc atggattggc ttcgatgtcg aggggtgtca tgctactaga gaagctgttg    4860
gtaccaattt accttttacag ctaggttttt ctacaggtgt taacctagtt gctgtaccta    4920
caggttatgt tgatacacct aataatacag attttttccag agttagtgct aaaccaccgc    4980
```

-continued

```
ctggagatca atttaaacac ctcataccac ttatgtacaa aggacttcct tggaatgtag    5040
tgcgtataaa gattgtacaa atgttaagtg acacacttaa aaatctctct gacagagtcg    5100
tatttgtctt atgggcacat ggctttgagt tgacatctat gaagtatttt gtgaaaatag    5160
gacctgagcg cacctgttgt ctatgtgata gacgtgccac atgctttttcc actgcttcag    5220 acacttatgc ctgttggcat cattctattg gatttgatta cgtctataat ccgtttatga    5280
ttgatgttca acaatggggt tttacaggta acctacaaag caaccatgat ctgtattgtc    5340
aagtccatgg taatgcacat gtagctagtt gtgatgcaat catgactagg tgtctagctg    5400
tccacgagtg ctttgttaag cgtgttgact ggactattga atatcctata attggtgatg    5460
aactgaagat taatgcggct tgtagaaagg ttcaacacat ggttgttaaa gctgcattat    5520
tagcagacaa attcccagtt cttcacgaca ttggtaaccc taaagctatt aagtgtgtac    5580
ctcaagctga tgtagaatgg aagttctatg atgcacagcc ttgtagtgac aaagcttata    5640
aaatagaaga attattctat tcttatgcca cacattctga caaattcaca gatggtgtat    5700
gcctattttg gaattgcaat gtcgatagat atcctgctaa ttccattgtt tgtagatttg    5760
acactagagt gctatctaac cttaacttgc ctggttgtga tggtggcagt ttgtatgtaa    5820
ataaacatgc attccacaca ccagcttttg ataaaagtgc ttttgttaat ttaaaacaat    5880
taccattttt ctattactct gacagtccat gtgagtctca tggaaaacaa gtagtgtcag    5940
atatagatta tgtaccacta aagtctgcta cgtgtataac acgttgcaat ttaggtggtg    6000
ctgtctgtag acatcatgct aatgagtaca gattgtatct cgatgcttat aacatgatga    6060
tctcagctgg ctttagcttg tgggtttaca aacaatttga tacttataac ctctggaaca    6120
cttttacaag acttcagagt ttagaaaatg tggctttttaa tgttgtaaat aagggacact    6180
ttgatggaca acagggtgaa gtaccagttt ctatcattaa taacactgtt tacacaaaag    6240
ttgatggtgt tgatgtagaa ttgtttgaaa ataaaacaac attacctgtt aatgtagcat    6300
ttgagctttg ggctaagcgc aacattaaac cagtaccaga ggtgaaaata ctcaataatt    6360
tgggtgtgga cattgctgct aatactgtga tctgggacta caaaagagat gctccagcac    6420
atatatctac tattggtgtt tgttctatga ctgacatagc caagaaacca actgaaacga    6480
tttgtgcacc actcactgtc tttttttgatg gtagagttga tggtcaagta gacttatttta    6540 gaaatgcccg taatggtgtt cttattacag aaggtagtgt taaaggttta caaccatctg    6600
taggtcccaa acaagctagt cttaatggag tcacattaat tggagaagcc gtaaaaacac    6660
agttcaatta ttataagaaa gttgatggtg ttgtccaaca attacctgaa acttacttta    6720
ctcagagtag aaatttacaa gaatttaaac ccaggagtca aatggaaatt gatttcttag    6780
aattagctat ggatgaattc attgaacggg ataaattaga aggctatgcc ttcgaacata    6840
tcgtttatgg agattttagt catagtcagt taggtggttt acatctactg attggactag    6900
ctaaacgttt taaggaatca ccttttgaat tagaagattt tattcctatg gacagtacag    6960
ttaaaaacta tttcataaca gatgcgcaaa caggttcatc taagtgtgtg tgttctgtta    7020
ttgatttatt acttgatgat tttgttgaaa taataaaatc ccaagattta tctgtagttt    7080
ctaaggttgt caaagtgact attgactata cagaaatttc atttatgctt tggtgtaaag    7140
atggccatgt agaaacattt tacccaaaat tacaatctag tcaagcgtgg caaccgggtg    7200
ttgctatgcc taatctttac aaaatgcaaa gaatgctatt agaaaagtgt gaccttcaaa    7260
attatggtga tagtgcaaca ttacctaaag gcataatgat gaatgtcgca aaatatactc    7320
```

```
aactgtgtca atatttaaac acattaacat tagctgtacc ctataatatg agagttatac   7380
attttggtgc tggttctgat aaaggagttg caccaggtac agctgttttta agacagtggt   7440 tgcctacggg tacgctgctt gtcgattcag atcttaatga ctttgtctct gatgcagatt   7500
caactttgat tggtgattgt gcaactgtac atacagctaa taaatgggat ctcattatta   7560
gtgatatgta cgaccctaag actaaaaatg ttacaaaaga aaatgactct aaagagggtt   7620
ttttcactta catttgtggg tttatacaac aaaagctagc tcttggaggt tccgtggcta   7680
taaagataac agaacattct tggaatgctg atctttataa gctcatggga cacttcgcat   7740
ggtggacagc ctttgttact aatgtgaatg cgtcatcatc tgaagcattt ttaattggat   7800
gtaattatct tggcaaacca cgcgaacaaa tagatggtta tgtcatgcat gcaaattaca   7860
tattttggag gaatacaaat ccaattcagt tgtcttccta ttctttattt gacatgagta   7920
aatttcccct taaattaagg ggtactgctg ttatgtcttt aaaagaaggt caaatcaatg   7980
atatgatttt atctcttctt agtaaaggta gacttataat tagagaaaac aacagagttg   8040
ttatttctag tgatgttctt gttaacaact aa                                 8072
```

```
<210> SEQ ID NO 15
<211> LENGTH: 12422
<212> TYPE: PRT
<213> ORGANISM: Severe acute respiratory syndrome coronavirus 2

<400> SEQUENCE: 15

Met Glu Ser Leu Val Pro Gly Phe Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Val Leu Ser Glu Ala Arg Gln His Leu Lys Asp
        35                  40                  45

Gly Thr Cys Gly Leu Val Glu Val Glu Lys Gly Val Leu Pro Gln Leu
    50                  55                  60

Glu Gln Pro Tyr Val Phe Ile Lys Arg Ser Asp Ala Arg Thr Ala Pro
65                  70                  75                  80

His Gly His Val Met Val Glu Leu Val Ala Glu Leu Glu Gly Ile Gln
                85                  90                  95

Tyr Gly Arg Ser Gly Glu Thr Leu Gly Val Leu Val Pro His Val Gly
            100                 105                 110

Glu Ile Pro Val Ala Tyr Arg Lys Val Leu Leu Arg Lys Asn Gly Asn
        115                 120                 125

Lys Gly Ala Gly Gly His Ser Tyr Gly Ala Asp Leu Lys Ser Phe Asp
    130                 135                 140

Leu Gly Asp Glu Leu Gly Thr Asp Pro Tyr Glu Asp Phe Gln Glu Asn
145                 150                 155                 160

Trp Asn Thr Lys His Ser Ser Gly Val Thr Arg Glu Leu Met Arg Glu
                165                 170                 175

Leu Asn Gly Gly Ala Tyr Thr Arg Tyr Val Asp Asn Asn Phe Cys Gly
            180                 185                 190

Pro Asp Gly Tyr Pro Leu Glu Cys Ile Lys Asp Leu Leu Ala Arg Ala
        195                 200                 205

Gly Lys Ala Ser Cys Thr Leu Ser Glu Gln Leu Asp Phe Ile Asp Thr
    210                 215                 220

Lys Arg Gly Val Tyr Cys Cys Arg Glu His Glu His Glu Ile Ala Trp
225                 230                 235                 240
```

-continued

```
Tyr Thr Glu Arg Ser Glu Lys Ser Tyr Glu Leu Gln Thr Pro Phe Glu
                245                 250                 255

Ile Lys Leu Ala Lys Lys Phe Asp Thr Phe Asn Gly Glu Cys Pro Asn
                260                 265                 270

Phe Val Phe Pro Leu Asn Ser Ile Ile Lys Thr Ile Gln Pro Arg Val
                275                 280                 285

Glu Lys Lys Lys Leu Asp Gly Phe Met Gly Arg Ile Arg Ser Val Tyr
    290                 295                 300

Pro Val Ala Ser Pro Asn Glu Cys Asn Gln Met Cys Leu Ser Thr Leu
305                 310                 315                 320

Met Lys Cys Asp His Cys Gly Glu Thr Ser Trp Gln Thr Gly Asp Phe
                325                 330                 335

Val Lys Ala Thr Cys Glu Phe Cys Gly Thr Glu Asn Leu Thr Lys Glu
                340                 345                 350

Gly Ala Thr Thr Cys Gly Tyr Leu Pro Gln Asn Ala Val Val Lys Ile
                355                 360                 365

Tyr Cys Pro Ala Cys His Asn Ser Glu Val Gly Pro Glu His Ser Leu
    370                 375                 380

Ala Glu Tyr His Asn Glu Ser Gly Leu Lys Thr Ile Leu Arg Lys Gly
385                 390                 395                 400

Gly Arg Thr Ile Ala Phe Gly Gly Cys Val Phe Ser Tyr Val Gly Cys
                405                 410                 415

His Asn Lys Cys Ala Tyr Trp Val Pro Arg Ala Ser Ala Asn Ile Gly
                420                 425                 430

Cys Asn His Thr Gly Val Val Gly Glu Gly Ser Glu Gly Leu Asn Asp
                435                 440                 445

Asn Leu Leu Glu Ile Leu Gln Lys Glu Lys Val Asn Ile Asn Ile Val
    450                 455                 460

Gly Asp Phe Lys Leu Asn Glu Glu Ile Ala Ile Ile Leu Ala Ser Phe
465                 470                 475                 480

Ser Ala Ser Thr Ser Ala Phe Val Glu Thr Val Lys Gly Leu Asp Tyr
                485                 490                 495

Lys Ala Phe Lys Gln Ile Val Glu Ser Cys Gly Asn Phe Lys Val Thr
                500                 505                 510

Lys Gly Lys Ala Lys Lys Gly Ala Trp Asn Ile Gly Glu Gln Lys Ser
                515                 520                 525

Ile Leu Ser Pro Leu Tyr Ala Phe Ala Ser Glu Ala Ala Arg Val Val
    530                 535                 540

Arg Ser Ile Phe Ser Arg Thr Leu Glu Thr Ala Gln Asn Ser Val Arg
545                 550                 555                 560

Val Leu Gln Lys Ala Ala Ile Thr Ile Leu Asp Gly Ile Ser Gln Tyr
                565                 570                 575

Ser Leu Arg Leu Ile Asp Ala Met Met Phe Thr Ser Asp Leu Ala Thr
                580                 585                 590

Asn Asn Leu Val Val Met Ala Tyr Ile Thr Gly Gly Val Val Gln Leu
                595                 600                 605

Thr Ser Gln Trp Leu Thr Asn Ile Phe Gly Thr Val Tyr Glu Lys Leu
    610                 615                 620

Lys Pro Val Leu Asp Trp Leu Glu Glu Lys Phe Lys Glu Gly Val Glu
625                 630                 635                 640

Phe Leu Arg Asp Gly Trp Glu Ile Val Lys Phe Ile Ser Thr Cys Ala
                645                 650                 655

Cys Glu Ile Val Gly Gly Gln Ile Val Thr Cys Ala Lys Glu Ile Lys
```

-continued

```
              660              665              670

Glu Ser Val Gln Thr Phe Phe Lys Leu Val Asn Lys Phe Leu Ala Leu
         675              680              685

Cys Ala Asp Ser Ile Ile Ile Gly Gly Ala Lys Leu Lys Ala Leu Asn
     690              695              700

Leu Gly Glu Thr Phe Val Thr His Ser Lys Gly Leu Tyr Arg Lys Cys
705              710              715              720

Val Lys Ser Arg Glu Glu Thr Gly Leu Leu Met Pro Leu Lys Ala Pro
         725              730              735

Lys Glu Ile Ile Phe Leu Glu Gly Glu Thr Leu Pro Thr Glu Val Leu
         740              745              750

Thr Glu Glu Val Val Leu Lys Thr Gly Asp Leu Gln Pro Leu Glu Gln
         755              760              765

Pro Thr Ser Glu Ala Val Glu Ala Pro Leu Val Gly Thr Pro Val Cys
     770              775              780

Ile Asn Gly Leu Met Leu Leu Glu Ile Lys Asp Thr Glu Lys Tyr Cys
785              790              795              800

Ala Leu Ala Pro Asn Met Met Val Thr Asn Asn Thr Phe Thr Leu Lys
         805              810              815

Gly Gly Ala Pro Thr Lys Val Thr Phe Gly Asp Asp Thr Val Ile Glu
         820              825              830

Val Gln Gly Tyr Lys Ser Val Asn Ile Thr Phe Glu Leu Asp Glu Arg
         835              840              845

Ile Asp Lys Val Leu Asn Glu Lys Cys Ser Ala Tyr Thr Val Glu Leu
     850              855              860

Gly Thr Glu Val Asn Glu Phe Ala Cys Val Val Ala Asp Ala Val Ile
865              870              875              880

Lys Thr Leu Gln Pro Val Ser Glu Leu Leu Thr Pro Leu Gly Ile Asp
         885              890              895

Leu Asp Glu Trp Ser Met Ala Thr Tyr Tyr Leu Phe Asp Glu Ser Gly
         900              905              910

Glu Phe Lys Leu Ala Ser His Met Tyr Cys Ser Phe Tyr Pro Pro Asp
         915              920              925

Glu Asp Glu Glu Glu Gly Asp Cys Glu Glu Glu Glu Phe Glu Pro Ser
     930              935              940

Thr Gln Tyr Glu Tyr Gly Thr Glu Asp Asp Tyr Gln Gly Lys Pro Leu
945              950              955              960

Glu Phe Gly Ala Thr Ser Ala Ala Leu Gln Pro Glu Glu Gln Glu
         965              970              975

Glu Asp Trp Leu Asp Asp Asp Ser Gln Gln Thr Val Gly Gln Gln Asp
         980              985              990

Gly Ser Glu Asp Asn Gln Thr Thr  Thr Ile Gln Thr Ile  Val Glu Val
         995              1000              1005

Gln Pro  Gln Leu Glu Met Glu  Leu Thr Pro Val Val  Gln Thr Ile
     1010              1015              1020

Glu Val  Asn Ser Phe Ser Gly  Tyr Leu Lys Leu Thr  Asp Asn Val
     1025              1030              1035

Tyr Ile  Lys Asn Ala Asp Ile  Val Glu Glu Ala Lys  Lys Val Lys
     1040              1045              1050

Pro Thr  Val Val Val Asn Ala  Ala Asn Val Tyr Leu  Lys His Gly
     1055              1060              1065

Gly Gly  Val Ala Gly Ala Leu  Asn Lys Ala Thr Asn  Asn Ala Met
     1070              1075              1080
```

```
Gln Val Glu Ser Asp Asp Tyr  Ile Ala Thr Asn Gly  Pro Leu Lys
    1085                1090                1095

Val Gly Gly Ser Cys Val Leu  Ser Gly His Asn Leu  Ala Lys His
    1100                1105                1110

Cys Leu His Val Val Gly Pro  Asn Val Asn Lys Gly  Glu Asp Ile
    1115                1120                1125

Gln Leu Leu Lys Ser Ala Tyr  Glu Asn Phe Asn Gln  His Glu Val
    1130                1135                1140

Leu Leu Ala Pro Leu Leu Ser  Ala Gly Ile Phe Gly  Ala Asp Pro
    1145                1150                1155

Ile His Ser Leu Arg Val Cys  Val Asp Thr Val Arg  Thr Asn Val
    1160                1165                1170

Tyr Leu Ala Val Phe Asp Lys  Asn Leu Tyr Asp Lys  Leu Val Ser
    1175                1180                1185

Ser Phe Leu Glu Met Lys Ser  Glu Lys Gln Val Glu  Gln Lys Ile
    1190                1195                1200

Ala Glu Ile Pro Lys Glu Glu  Val Lys Pro Phe Ile  Thr Glu Ser
    1205                1210                1215

Lys Pro Ser Val Glu Gln Arg  Lys Gln Asp Asp Lys  Lys Ile Lys
    1220                1225                1230

Ala Cys Val Glu Glu Val Thr  Thr Thr Leu Glu Glu  Thr Lys Phe
    1235                1240                1245

Leu Thr Glu Asn Leu Leu Leu  Tyr Ile Asp Ile Asn  Gly Asn Leu
    1250                1255                1260

His Pro Asp Ser Ala Thr Leu  Val Ser Asp Ile Asp  Ile Thr Phe
    1265                1270                1275

Leu Lys Lys Asp Ala Pro Tyr  Ile Val Gly Asp Val  Val Gln Glu
    1280                1285                1290

Gly Val Leu Thr Ala Val Val  Ile Pro Thr Lys Lys  Ala Gly Gly
    1295                1300                1305

Thr Thr Glu Met Leu Ala Lys  Ala Leu Arg Lys Val  Pro Thr Asp
    1310                1315                1320

Asn Tyr Ile Thr Thr Tyr Pro  Gly Gln Gly Leu Asn  Gly Tyr Thr
    1325                1330                1335

Val Glu Glu Ala Lys Thr Val  Leu Lys Lys Cys Lys  Ser Ala Phe
    1340                1345                1350

Tyr Ile Leu Pro Ser Ile Ile  Ser Asn Glu Lys Gln  Glu Ile Leu
    1355                1360                1365

Gly Thr Val Ser Trp Asn Leu  Arg Glu Met Leu Ala  His Ala Glu
    1370                1375                1380

Glu Thr Arg Lys Leu Met Pro  Val Cys Val Glu Thr  Lys Ala Ile
    1385                1390                1395

Val Ser Thr Ile Gln Arg Lys  Tyr Lys Gly Ile Lys  Ile Gln Glu
    1400                1405                1410

Gly Val Val Asp Tyr Gly Ala  Arg Phe Tyr Phe Tyr  Thr Ser Lys
    1415                1420                1425

Thr Thr Val Ala Ser Leu Ile  Asn Thr Leu Asn Asp  Leu Asn Glu
    1430                1435                1440

Thr Leu Val Thr Met Pro Leu  Gly Tyr Val Thr His  Gly Leu Asn
    1445                1450                1455

Leu Glu Glu Ala Ala Arg Tyr  Met Arg Ser Leu Lys  Val Pro Ala
    1460                1465                1470
```

```
Thr Val Ser Val Ser Ser Pro Asp Ala Val Thr Ala Tyr Asn Gly
    1475             1480             1485

Tyr Leu Thr Ser Ser Ser Lys Thr Pro Glu Glu His Phe Ile Glu
    1490             1495             1500

Thr Ile Ser Leu Ala Gly Ser Tyr Lys Asp Trp Ser Tyr Ser Gly
    1505             1510             1515

Gln Ser Thr Gln Leu Gly Ile Glu Phe Leu Lys Arg Gly Asp Lys
    1520             1525             1530

Ser Val Tyr Tyr Thr Ser Asn Pro Thr Thr Phe His Leu Asp Gly
    1535             1540             1545

Glu Val Ile Thr Phe Asp Asn Leu Lys Thr Leu Leu Ser Leu Arg
    1550             1555             1560

Glu Val Arg Thr Ile Lys Val Phe Thr Thr Val Asp Asn Ile Asn
    1565             1570             1575

Leu His Thr Gln Val Val Asp Met Ser Met Thr Tyr Gly Gln Gln
    1580             1585             1590

Phe Gly Pro Thr Tyr Leu Asp Gly Ala Asp Val Thr Lys Ile Lys
    1595             1600             1605

Pro His Asn Ser His Glu Gly Lys Thr Phe Tyr Val Leu Pro Asn
    1610             1615             1620

Asp Asp Thr Leu Arg Val Glu Ala Phe Glu Tyr Tyr His Thr Thr
    1625             1630             1635

Asp Pro Ser Phe Leu Gly Arg Tyr Met Ser Ala Leu Asn His Thr
    1640             1645             1650

Lys Lys Trp Lys Tyr Pro Gln Val Asn Gly Leu Thr Ser Ile Lys
    1655             1660             1665

Trp Ala Asp Asn Asn Cys Tyr Leu Ala Thr Ala Leu Leu Thr Leu
    1670             1675             1680

Gln Gln Ile Glu Leu Lys Phe Asn Pro Pro Ala Leu Gln Asp Ala
    1685             1690             1695

Tyr Tyr Arg Ala Arg Ala Gly Glu Ala Ala Asn Phe Cys Ala Leu
    1700             1705             1710

Ile Leu Ala Tyr Cys Asn Lys Thr Val Gly Glu Leu Gly Asp Val
    1715             1720             1725

Arg Glu Thr Met Ser Tyr Leu Phe Gln His Ala Asn Leu Asp Ser
    1730             1735             1740

Cys Lys Arg Val Leu Asn Val Val Cys Lys Thr Cys Gly Gln Gln
    1745             1750             1755

Gln Thr Thr Leu Lys Gly Val Glu Ala Val Met Tyr Met Gly Thr
    1760             1765             1770

Leu Ser Tyr Glu Gln Phe Lys Lys Gly Val Gln Ile Pro Cys Thr
    1775             1780             1785

Cys Gly Lys Gln Ala Thr Lys Tyr Leu Val Gln Gln Glu Ser Pro
    1790             1795             1800

Phe Val Met Met Ser Ala Pro Pro Ala Gln Tyr Glu Leu Lys His
    1805             1810             1815

Gly Thr Phe Thr Cys Ala Ser Glu Tyr Thr Gly Asn Tyr Gln Cys
    1820             1825             1830

Gly His Tyr Lys His Ile Thr Ser Lys Glu Thr Leu Tyr Cys Ile
    1835             1840             1845

Asp Gly Ala Leu Leu Thr Lys Ser Ser Glu Tyr Lys Gly Pro Ile
    1850             1855             1860

Thr Asp Val Phe Tyr Lys Glu Asn Ser Tyr Thr Thr Thr Ile Lys
```

-continued

```
      1865                1870                1875

Pro Val Thr Tyr Lys Leu Asp Gly Val Val Cys Thr Glu Ile Asp
      1880                1885                1890

Pro Lys Leu Asp Asn Tyr Tyr Lys Lys Asp Asn Ser Tyr Phe Thr
      1895                1900                1905

Glu Gln Pro Ile Asp Leu Val Pro Asn Gln Pro Tyr Pro Asn Ala
      1910                1915                1920

Ser Phe Asp Asn Phe Lys Phe Val Cys Asp Asn Ile Lys Phe Ala
      1925                1930                1935

Asp Asp Leu Asn Gln Leu Thr Gly Tyr Lys Lys Pro Ala Ser Arg
      1940                1945                1950

Glu Leu Lys Val Thr Phe Phe Pro Asp Leu Asn Gly Asp Val Val
      1955                1960                1965

Ala Ile Asp Tyr Lys His Tyr Thr Pro Ser Phe Lys Lys Gly Ala
      1970                1975                1980

Lys Leu Leu His Lys Pro Ile Val Trp His Val Asn Asn Ala Thr
      1985                1990                1995

Asn Lys Ala Thr Tyr Lys Pro Asn Thr Trp Cys Ile Arg Cys Leu
      2000                2005                2010

Trp Ser Thr Lys Pro Val Glu Thr Ser Asn Ser Phe Asp Val Leu
      2015                2020                2025

Lys Ser Glu Asp Ala Gln Gly Met Asp Asn Leu Ala Cys Glu Asp
      2030                2035                2040

Leu Lys Pro Val Ser Glu Glu Val Val Glu Asn Pro Thr Ile Gln
      2045                2050                2055

Lys Asp Val Leu Glu Cys Asn Val Lys Thr Thr Glu Val Val Gly
      2060                2065                2070

Asp Ile Ile Leu Lys Pro Ala Asn Asn Ser Leu Lys Ile Thr Glu
      2075                2080                2085

Glu Val Gly His Thr Asp Leu Met Ala Ala Tyr Val Asp Asn Ser
      2090                2095                2100

Ser Leu Thr Ile Lys Lys Pro Asn Glu Leu Ser Arg Val Leu Gly
      2105                2110                2115

Leu Lys Thr Leu Ala Thr His Gly Leu Ala Ala Val Asn Ser Val
      2120                2125                2130

Pro Trp Asp Thr Ile Ala Asn Tyr Ala Lys Pro Phe Leu Asn Lys
      2135                2140                2145

Val Val Ser Thr Thr Thr Asn Ile Val Thr Arg Cys Leu Asn Arg
      2150                2155                2160

Val Cys Thr Asn Tyr Met Pro Tyr Phe Phe Thr Leu Leu Leu Gln
      2165                2170                2175

Leu Cys Thr Phe Thr Arg Ser Thr Asn Ser Arg Ile Lys Ala Ser
      2180                2185                2190

Met Pro Thr Thr Ile Ala Lys Asn Thr Val Lys Ser Val Gly Lys
      2195                2200                2205

Phe Cys Leu Glu Ala Ser Phe Asn Tyr Leu Lys Ser Pro Asn Phe
      2210                2215                2220

Ser Lys Leu Ile Asn Ile Ile Ile Trp Phe Leu Leu Leu Ser Val
      2225                2230                2235

Cys Leu Gly Ser Leu Ile Tyr Ser Thr Ala Ala Leu Gly Val Leu
      2240                2245                2250

Met Ser Asn Leu Gly Met Pro Ser Tyr Cys Thr Gly Tyr Arg Glu
      2255                2260                2265
```

-continued

```
Gly Tyr Leu Asn Ser Thr Asn  Val Thr Ile Ala Thr  Tyr Cys Thr
    2270                 2275             2280

Gly Ser Ile Pro Cys Ser Val  Cys Leu Ser Gly Leu  Asp Ser Leu
    2285                 2290             2295

Asp Thr Tyr Pro Ser Leu Glu  Thr Ile Gln Ile Thr  Ile Ser Ser
    2300                 2305             2310

Phe Lys Trp Asp Leu Thr Ala  Phe Gly Leu Val Ala  Glu Trp Phe
    2315                 2320             2325

Leu Ala Tyr Ile Leu Phe Thr  Arg Phe Phe Tyr Val  Leu Gly Leu
    2330                 2335             2340

Ala Ala Ile Met Gln Leu Phe  Phe Ser Tyr Phe Ala  Val His Phe
    2345                 2350             2355

Ile Ser Asn Ser Trp Leu Met  Trp Leu Ile Ile Asn  Leu Val Gln
    2360                 2365             2370

Met Ala Pro Ile Ser Ala Met  Val Arg Met Tyr Ile  Phe Phe Ala
    2375                 2380             2385

Ser Phe Tyr Tyr Val Trp Lys  Ser Tyr Val His Val  Val Asp Gly
    2390                 2395             2400

Cys Asn Ser Ser Thr Cys Met  Met Cys Tyr Lys Arg  Asn Arg Ala
    2405                 2410             2415

Thr Arg Val Glu Cys Thr Thr  Ile Val Asn Gly Val  Arg Arg Ser
    2420                 2425             2430

Phe Tyr Val Tyr Ala Asn Gly  Gly Lys Gly Phe Cys  Lys Leu His
    2435                 2440             2445

Asn Trp Asn Cys Val Asn Cys  Asp Thr Phe Cys Ala  Gly Ser Thr
    2450                 2455             2460

Phe Ile Ser Asp Glu Val Ala  Arg Asp Leu Ser Leu  Gln Phe Lys
    2465                 2470             2475

Arg Pro Ile Asn Pro Thr Asp  Gln Ser Ser Tyr Ile  Val Asp Ser
    2480                 2485             2490

Val Thr Val Lys Asn Gly Ser  Ile His Leu Tyr Phe  Asp Lys Ala
    2495                 2500             2505

Gly Gln Lys Thr Tyr Glu Arg  His Ser Leu Ser His  Phe Val Asn
    2510                 2515             2520

Leu Asp Asn Leu Arg Ala Asn  Asn Thr Lys Gly Ser  Leu Pro Ile
    2525                 2530             2535

Asn Val Ile Val Phe Asp Gly  Lys Ser Lys Cys Glu  Glu Ser Ser
    2540                 2545             2550

Ala Lys Ser Ala Ser Val Tyr  Tyr Ser Gln Leu Met  Cys Gln Pro
    2555                 2560             2565

Ile Leu Leu Leu Asp Gln Ala  Leu Val Ser Asp Val  Gly Asp Ser
    2570                 2575             2580

Ala Glu Val Ala Val Lys Met  Phe Asp Ala Tyr Val  Asn Thr Phe
    2585                 2590             2595

Ser Ser Thr Phe Asn Val Pro  Met Glu Lys Leu Lys  Thr Leu Val
    2600                 2605             2610

Ala Thr Ala Glu Ala Glu Leu  Ala Lys Asn Val Ser  Leu Asp Asn
    2615                 2620             2625

Val Leu Ser Thr Phe Ile Ser  Ala Ala Arg Gln Gly  Phe Val Asp
    2630                 2635             2640

Ser Asp Val Glu Thr Lys Asp  Val Val Glu Cys Leu  Lys Leu Ser
    2645                 2650             2655
```

-continued

```
His Gln  Ser Asp Ile Glu Val  Thr Gly Asp Ser Cys  Asn Asn Tyr
2660             2665             2670

Met Leu  Thr Tyr Asn Lys Val  Glu Asn Met Thr Pro  Arg Asp Leu
2675             2680             2685

Gly Ala  Cys Ile Asp Cys Ser  Ala Arg His Ile Asn  Ala Gln Val
2690             2695             2700

Ala Lys  Ser His Asn Ile Ala  Leu Ile Trp Asn Val  Lys Asp Phe
2705             2710             2715

Met Ser  Leu Ser Glu Gln Leu  Arg Lys Gln Ile Arg  Ser Ala Ala
2720             2725             2730

Lys Lys  Asn Asn Leu Pro Phe  Lys Leu Thr Cys Ala  Thr Thr Arg
2735             2740             2745

Gln Val  Val Asn Val Val Thr  Thr Lys Ile Ala Leu  Lys Gly Gly
2750             2755             2760

Lys Ile  Val Asn Asn Trp Leu  Lys Gln Leu Ile Lys  Val Thr Leu
2765             2770             2775

Val Phe  Leu Phe Val Ala Ala  Ile Phe Tyr Leu Ile  Thr Pro Val
2780             2785             2790

His Val  Met Ser Lys His Thr  Asp Phe Ser Ser Glu  Ile Ile Gly
2795             2800             2805

Tyr Lys  Ala Ile Asp Gly Gly  Val Thr Arg Asp Ile  Ala Ser Thr
2810             2815             2820

Asp Thr  Cys Phe Ala Asn Lys  His Ala Asp Phe Asp  Thr Trp Phe
2825             2830             2835

Ser Gln  Arg Gly Gly Ser Tyr  Thr Asn Asp Lys Ala  Cys Pro Leu
2840             2845             2850

Ile Ala  Ala Val Ile Thr Arg  Glu Val Gly Phe Val  Val Pro Gly
2855             2860             2865

Leu Pro  Gly Thr Ile Leu Arg  Thr Thr Asn Gly Asp  Phe Leu His
2870             2875             2880

Phe Leu  Pro Arg Val Phe Ser  Ala Val Gly Asn Ile  Cys Tyr Thr
2885             2890             2895

Pro Ser  Lys Leu Ile Glu Tyr  Thr Asp Phe Ala Thr  Ser Ala Cys
2900             2905             2910

Val Leu  Ala Ala Glu Cys Thr  Ile Phe Lys Asp Ala  Ser Gly Lys
2915             2920             2925

Pro Val  Pro Tyr Cys Tyr Asp  Thr Asn Val Leu Glu  Gly Ser Val
2930             2935             2940

Ala Tyr  Glu Ser Leu Arg Pro  Asp Thr Arg Tyr Val  Leu Met Asp
2945             2950             2955

Gly Ser  Ile Ile Gln Phe Pro  Asn Thr Tyr Leu Glu  Gly Ser Val
2960             2965             2970

Arg Val  Val Thr Thr Phe Asp  Ser Glu Tyr Cys Arg  His Gly Thr
2975             2980             2985

Cys Glu  Arg Ser Glu Ala Gly  Val Cys Val Ser Thr  Ser Gly Arg
2990             2995             3000

Trp Val  Leu Asn Asn Asp Tyr  Tyr Arg Ser Leu Pro  Gly Val Phe
3005             3010             3015

Cys Gly  Val Asp Ala Val Asn  Leu Leu Thr Asn Met  Phe Thr Pro
3020             3025             3030

Leu Ile  Gln Pro Ile Gly Ala  Leu Asp Ile Ser Ala  Ser Ile Val
3035             3040             3045

Ala Gly  Gly Ile Val Ala Ile  Val Val Thr Cys Leu  Ala Tyr Tyr
```

-continued

```
        3050              3055                3060

Phe Met  Arg Phe Arg Arg Ala  Phe Gly Glu Tyr Ser  His Val Val
    3065             3070                3075

Ala Phe  Asn Thr Leu Leu Phe  Leu Met Ser Phe Thr  Val Leu Cys
    3080             3085                3090

Leu Thr  Pro Val Tyr Ser Phe  Leu Pro Gly Val Tyr  Ser Val Ile
    3095             3100                3105

Tyr Leu  Tyr Leu Thr Phe Tyr  Leu Thr Asn Asp Val  Ser Phe Leu
    3110             3115                3120

Ala His  Ile Gln Trp Met Val  Met Phe Thr Pro Leu  Val Pro Phe
    3125             3130                3135

Trp Ile  Thr Ile Ala Tyr Ile  Ile Cys Ile Ser Thr  Lys His Phe
    3140             3145                3150

Tyr Trp  Phe Phe Ser Asn Tyr  Leu Lys Arg Arg Val  Val Phe Asn
    3155             3160                3165

Gly Val  Ser Phe Ser Thr Phe  Glu Glu Ala Ala Leu  Cys Thr Phe
    3170             3175                3180

Leu Leu  Asn Lys Glu Met Tyr  Leu Lys Leu Arg Ser  Asp Val Leu
    3185             3190                3195

Leu Pro  Leu Thr Gln Tyr Asn  Arg Tyr Leu Ala Leu  Tyr Asn Lys
    3200             3205                3210

Tyr Lys  Tyr Phe Ser Gly Ala  Met Asp Thr Thr Ser  Tyr Arg Glu
    3215             3220                3225

Ala Ala  Cys Cys His Leu Ala  Lys Ala Leu Asn Asp  Phe Ser Asn
    3230             3235                3240

Ser Gly  Ser Asp Val Leu Tyr  Gln Pro Pro Gln Thr  Ser Ile Thr
    3245             3250                3255

Ser Ala  Val Leu Gln Ser Gly  Phe Arg Lys Met Ala  Phe Pro Ser
    3260             3265                3270

Gly Lys  Val Glu Gly Cys Met  Val Gln Val Thr Cys  Gly Thr Thr
    3275             3280                3285

Thr Leu  Asn Gly Leu Trp Leu  Asp Asp Val Val Tyr  Cys Pro Arg
    3290             3295                3300

His Val  Ile Cys Thr Ser Glu  Asp Met Leu Asn Pro  Asn Tyr Glu
    3305             3310                3315

Asp Leu  Leu Ile Arg Lys Ser  Asn His Asn Phe Leu  Val Gln Ala
    3320             3325                3330

Gly Asn  Val Gln Leu Arg Val  Ile Gly His Ser Met  Gln Asn Cys
    3335             3340                3345

Val Leu  Lys Leu Lys Val Asp  Thr Ala Asn Pro Lys  Thr Pro Lys
    3350             3355                3360

Tyr Lys  Phe Val Arg Ile Gln  Pro Gly Gln Thr Phe  Ser Val Leu
    3365             3370                3375

Ala Cys  Tyr Asn Gly Ser Pro  Ser Gly Val Tyr Gln  Cys Ala Met
    3380             3385                3390

Arg Pro  Asn Phe Thr Ile Lys  Gly Ser Phe Leu Asn  Gly Ser Cys
    3395             3400                3405

Gly Ser  Val Gly Phe Asn Ile  Asp Tyr Asp Cys Val  Ser Phe Cys
    3410             3415                3420

Tyr Met  His His Met Glu Leu  Pro Thr Gly Val His  Ala Gly Thr
    3425             3430                3435

Asp Leu  Glu Gly Asn Phe Tyr  Gly Pro Phe Val Asp  Arg Gln Thr
    3440             3445                3450
```

-continued

```
Ala Gln Ala Ala Gly Thr Asp  Thr Thr Ile Thr Val  Asn Val Leu
    3455             3460          3465

Ala Trp Leu Tyr Ala Ala Val  Ile Asn Gly Asp Arg  Trp Phe Leu
    3470             3475          3480

Asn Arg Phe Thr Thr Thr Leu  Asn Asp Phe Asn Leu  Val Ala Met
    3485             3490          3495

Lys Tyr Asn Tyr Glu Pro Leu  Thr Gln Asp His Val  Asp Ile Leu
    3500             3505          3510

Gly Pro Leu Ser Ala Gln Thr  Gly Ile Ala Val Leu  Asp Met Cys
    3515             3520          3525

Ala Ser Leu Lys Glu Leu Leu  Gln Asn Gly Met Asn  Gly Arg Thr
    3530             3535          3540

Ile Leu Gly Ser Ala Leu Leu  Glu Asp Glu Phe Thr  Pro Phe Asp
    3545             3550          3555

Val Val Arg Gln Cys Ser Gly  Val Thr Phe Gln Ser  Ala Val Lys
    3560             3565          3570

Arg Thr Ile Lys Gly Thr His  His Trp Leu Leu Leu  Thr Ile Leu
    3575             3580          3585

Thr Ser Leu Leu Val Leu Val  Gln Ser Thr Gln Trp  Ser Leu Phe
    3590             3595          3600

Phe Phe Leu Tyr Glu Asn Ala  Phe Leu Pro Phe Ala  Met Gly Ile
    3605             3610          3615

Ile Ala Met Ser Ala Phe Ala  Met Met Phe Val Lys  His Lys His
    3620             3625          3630

Ala Phe Leu Cys Leu Phe Leu  Leu Pro Ser Leu Ala  Thr Val Ala
    3635             3640          3645

Tyr Phe Asn Met Val Tyr Met  Pro Ala Ser Trp Val  Met Arg Ile
    3650             3655          3660

Met Thr Trp Leu Asp Met Val  Asp Thr Ser Leu Ser  Gly Phe Lys
    3665             3670          3675

Leu Lys Asp Cys Val Met Tyr  Ala Ser Ala Val Val  Leu Leu Ile
    3680             3685          3690

Leu Met Thr Ala Arg Thr Val  Tyr Asp Asp Gly Ala  Arg Arg Val
    3695             3700          3705

Trp Thr Leu Met Asn Val Leu  Thr Leu Val Tyr Lys  Val Tyr Tyr
    3710             3715          3720

Gly Asn Ala Leu Asp Gln Ala  Ile Ser Met Trp Ala  Leu Ile Ile
    3725             3730          3735

Ser Val Thr Ser Asn Tyr Ser  Gly Val Val Thr Thr  Val Met Phe
    3740             3745          3750

Leu Ala Arg Gly Ile Val Phe  Met Cys Val Glu Tyr  Cys Pro Ile
    3755             3760          3765

Phe Phe Ile Thr Gly Asn Thr  Leu Gln Cys Ile Met  Leu Val Tyr
    3770             3775          3780

Cys Phe Leu Gly Tyr Phe Cys  Thr Cys Tyr Phe Gly  Leu Phe Cys
    3785             3790          3795

Leu Leu Asn Arg Tyr Phe Arg  Leu Thr Leu Gly Val  Tyr Asp Tyr
    3800             3805          3810

Leu Val Ser Thr Gln Glu Phe  Arg Tyr Met Asn Ser  Gln Gly Leu
    3815             3820          3825

Leu Pro Pro Lys Asn Ser Ile  Asp Ala Phe Lys Leu  Asn Ile Lys
    3830             3835          3840
```

-continued

```
Leu Leu  Gly Val Gly Gly Lys  Pro Cys Ile Lys Val  Ala Thr Val
    3845              3850              3855

Gln Ser  Lys Met Ser Asp Val  Lys Cys Thr Ser Val  Val Leu Leu
    3860              3865              3870

Ser Val  Leu Gln Gln Leu Arg  Val Glu Ser Ser Ser  Lys Leu Trp
    3875              3880              3885

Ala Gln  Cys Val Gln Leu His  Asn Asp Ile Leu Leu  Ala Lys Asp
    3890              3895              3900

Thr Thr  Glu Ala Phe Glu Lys  Met Val Ser Leu Leu  Ser Val Leu
    3905              3910              3915

Leu Ser  Met Gln Gly Ala Val  Asp Ile Asn Lys Leu  Cys Glu Glu
    3920              3925              3930

Met Leu  Asp Asn Arg Ala Thr  Leu Gln Ala Ile Ala  Ser Glu Phe
    3935              3940              3945

Ser Ser  Leu Pro Ser Tyr Ala  Ala Phe Ala Thr Ala  Gln Glu Ala
    3950              3955              3960

Tyr Glu  Gln Ala Val Ala Asn  Gly Asp Ser Glu Val  Val Leu Lys
    3965              3970              3975

Lys Leu  Lys Lys Ser Leu Asn  Val Ala Lys Ser Glu  Phe Asp Arg
    3980              3985              3990

Asp Ala  Ala Met Gln Arg Lys  Leu Glu Lys Met Ala  Asp Gln Ala
    3995              4000              4005

Met Thr  Gln Met Tyr Lys Gln  Ala Arg Ser Glu Asp  Lys Arg Ala
    4010              4015              4020

Lys Val  Thr Ser Ala Met Gln  Thr Met Leu Phe Thr  Met Leu Arg
    4025              4030              4035

Lys Leu  Asp Asn Asp Ala Leu  Asn Asn Ile Ile Asn  Asn Ala Arg
    4040              4045              4050

Asp Gly  Cys Val Pro Leu Asn  Ile Ile Pro Leu Thr  Thr Ala Ala
    4055              4060              4065

Lys Leu  Met Val Val Ile Pro  Asp Tyr Asn Thr Tyr  Lys Asn Thr
    4070              4075              4080

Cys Asp  Gly Thr Thr Phe Thr  Tyr Ala Ser Ala Leu  Trp Glu Ile
    4085              4090              4095

Gln Gln  Val Val Asp Ala Asp  Ser Lys Ile Val Gln  Leu Ser Glu
    4100              4105              4110

Ile Ser  Met Asp Asn Ser Pro  Asn Leu Ala Trp Pro  Leu Ile Val
    4115              4120              4125

Thr Ala  Leu Arg Ala Asn Ser  Ala Val Lys Leu Gln  Asn Asn Glu
    4130              4135              4140

Leu Ser  Pro Val Ala Leu Arg  Gln Met Ser Cys Ala  Ala Gly Thr
    4145              4150              4155

Thr Gln  Thr Ala Cys Thr Asp  Asp Asn Ala Leu Ala  Tyr Tyr Asn
    4160              4165              4170

Thr Thr  Lys Gly Gly Arg Phe  Val Leu Ala Leu Leu  Ser Asp Leu
    4175              4180              4185

Gln Asp  Leu Lys Trp Ala Arg  Phe Pro Lys Ser Asp  Gly Thr Gly
    4190              4195              4200

Thr Ile  Tyr Thr Glu Leu Glu  Pro Pro Cys Arg Phe  Val Thr Asp
    4205              4210              4215

Thr Pro  Lys Gly Pro Lys Val  Lys Tyr Leu Tyr Phe  Ile Lys Gly
    4220              4225              4230

Leu Asn  Asn Leu Asn Arg Gly  Met Val Leu Gly Ser  Leu Ala Ala
```

```
            4235                4240                4245

Thr Val  Arg Leu Gln Ala Gly  Asn Ala Thr Glu Val  Pro Ala Asn
    4250                4255                4260

Ser Thr  Val Leu Ser Phe Cys  Ala Phe Ala Val Asp  Ala Ala Lys
    4265                4270                4275

Ala Tyr  Lys Asp Tyr Leu Ala  Ser Gly Gly Gln Pro  Ile Thr Asn
    4280                4285                4290

Cys Val  Lys Met Leu Cys Thr  His Thr Gly Thr Gly  Gln Ala Ile
    4295                4300                4305

Thr Val  Thr Pro Glu Ala Asn  Met Asp Gln Glu Ser  Phe Gly Gly
    4310                4315                4320

Ala Ser  Cys Cys Leu Tyr Cys  Arg Cys His Ile Asp  His Pro Asn
    4325                4330                4335

Pro Lys  Gly Phe Cys Asp Leu  Lys Gly Lys Tyr Val  Gln Ile Pro
    4340                4345                4350

Thr Thr  Cys Ala Asn Asp Pro  Val Gly Phe Thr Leu  Lys Asn Thr
    4355                4360                4365

Val Cys  Thr Val Cys Gly Met  Trp Lys Gly Tyr Gly  Cys Ser Cys
    4370                4375                4380

Asp Gln  Leu Arg Glu Pro Met  Leu Gln Ser Ala Asp  Ala Gln Ser
    4385                4390                4395

Phe Leu  Asn Gly Phe Ala Val  Trp Arg Ala Leu Ser  Leu Val Ser
    4400                4405                4410

Thr Arg  Lys His Thr Ser Asn  Ser Val Cys Leu Phe  Tyr Arg Phe
    4415                4420                4425

Ala Thr  Cys Ser Tyr Val Ala  Leu Glu Thr Pro Trp  Arg Arg Ser
    4430                4435                4440

Tyr Gln  Arg His Val Asn Ile  Leu Lys Met Ala Leu  Val Ala Lys
    4445                4450                4455

Leu Lys  Lys Ala Phe Cys Leu  Asn Leu Asn Ser Pro  Met Cys Ser
    4460                4465                4470

Ser Asn  Val Arg Met Leu Glu  Leu His Leu Met Val  Met Leu Trp
    4475                4480                4485

Leu Ser  Trp Gln Asn Ser Lys  Ala Phe Ser Thr Val  Val Val Val
    4490                4495                4500

Arg His  Leu Val Ser Leu Ser  Leu Met Trp Ala Lys  Tyr Gln Trp
    4505                4510                4515

Leu Thr  Ala Arg Phe Phe Phe  Val Arg Thr Val Ile  Lys Glu Leu
    4520                4525                4530

Val Ala  Ile Val Thr Ala Pro  Ile Ser His Leu Thr  Ala Thr Ser
    4535                4540                4545

Leu Ala  Leu Ile Leu Met Lys  Ile Phe Lys Lys Thr  Gly Thr Leu
    4550                4555                4560

Asn Ile  Ala Val Val Leu Pro  Val Asn Ser Cys Val  Ser Leu Thr
    4565                4570                4575

Glu Gly  His Thr Leu Ala Met  Ser Ile Thr Thr Ser  Val Ala Leu
    4580                4585                4590

Met Ala  Thr Leu Leu Ser Ala  Leu Lys Thr Phe His  Val Leu Val
    4595                4600                4605

Lys Leu  His Ala Leu Cys Pro  Asn Asn Trp Thr Leu  Leu Thr Leu
    4610                4615                4620

Arg Gly  Val Tyr Thr Ala Ala  Val Asn Met Ser Met  Lys Leu Leu
    4625                4630                4635
```

-continued

```
Gly Thr Arg Asn Val Leu Lys  Arg Ala Met Asn Cys  Arg His Leu
    4640            4645              4650

Leu Lys Leu Asn Trp Gln Arg  Asn Leu Thr Pro Ser  Met Gly Asn
    4655            4660              4665

Val Gln Ile Leu Tyr Phe Pro  Ile Pro Ser Arg Leu  Phe Asn Gln
    4670            4675              4680

Gly Leu Lys Arg Lys Ser Leu  Met Ala Leu Trp Val  Glu Phe Asp
    4685            4690              4695

Leu Ser Ile Gln Leu Arg His  Gln Met Asn Ala Thr  Lys Cys Ala
    4700            4705              4710

Phe Gln Leu Ser Ser Val Ile  Ile Val Val Lys Leu  His Gly Arg
    4715            4720              4725

Arg Ala Ile Leu Leu Lys Pro  Leu Ala Asn Phe Val  Ala Leu Arg
    4730            4735              4740

Ile Leu Lys Lys Val Pro Leu  Leu Val Val Thr Tyr  Pro Lys Met
    4745            4750              4755

Leu Leu Leu Lys Phe Ile Val  Gln His Val Thr Ile  Gln Lys Asp
    4760            4765              4770

Leu Ser Ile Val Leu Pro Asn  Thr Ile Met Asn Leu  Ala Lys Pro
    4775            4780              4785

Phe Phe Val Arg Val Val Ala  Leu Leu Pro Leu Glu  Ala Val Cys
    4790            4795              4800

Ser Leu Met Leu Val Ala Ile  Thr Ser Val Pro Ile  Gly Phe His
    4805            4810              4815

Val Leu Ala Leu Thr Val Val  Thr Ile Gln Val Leu  Leu Glu Lys
    4820            4825              4830

Val Pro Lys Val Leu Met Thr  Thr Phe Leu Lys Tyr  Ser Lys Lys
    4835            4840              4845

Arg Lys Ser Thr Ser Ile Leu  Leu Val Thr Leu Asn  Leu Met Lys
    4850            4855              4860

Arg Ser Pro Leu Phe Trp His  Leu Phe Leu Leu Pro  Gln Val Leu
    4865            4870              4875

Leu Trp Lys Leu Lys Val Trp  Ile Ile Lys His Ser  Asn Lys Leu
    4880            4885              4890

Leu Asn Pro Val Val Ile Leu  Lys Leu Gln Lys Glu  Lys Leu Lys
    4895            4900              4905

Lys Val Pro Gly Ile Leu Val  Asn Arg Asn Gln Tyr  Val Leu Phe
    4910            4915              4920

Met His Leu His Gln Arg Leu  Leu Val Leu Tyr Asp  Gln Phe Ser
    4925            4930              4935

Pro Ala Leu Leu Lys Leu Leu  Lys Ile Leu Cys Val  Phe Tyr Arg
    4940            4945              4950

Arg Pro Leu Gln Tyr Met Glu  Phe His Ser Ile His  Asp Ser Leu
    4955            4960              4965

Met Leu Cys Ser His Leu Ile  Trp Leu Leu Thr Ile  Leu Trp Pro
    4970            4975              4980

Thr Leu Gln Val Val Leu Phe  Ser Leu Arg Ser Gly  Leu Thr Ser
    4985            4990              4995

Leu Ala Leu Phe Met Lys Asn  Ser Asn Pro Ser Leu  Ile Gly Leu
    5000            5005              5010

Lys Arg Ser Leu Arg Lys Val  Ser Phe Leu Glu Thr  Val Gly Lys
    5015            5020              5025
```

-continued

```
Leu Leu  Asn Leu Ser Gln Pro  Val Leu Val Lys Leu  Ser Val Asp
    5030             5035              5040

Lys Leu  Ser Pro Val Gln Arg  Lys Leu Arg Arg Val  Phe Arg His
    5045             5050              5055

Ser Leu  Ser Leu Ile Asn Phe  Trp Leu Cys Val Leu  Thr Leu Ser
    5060             5065              5070

Leu Leu  Val Glu Leu Asn Leu  Lys Pro Ile Val Lys  His Leu Ser
    5075             5080              5085

Arg Thr  Gln Arg Asp Cys Thr  Glu Ser Val Leu Asn  Pro Glu Lys
    5090             5095              5100

Lys Leu  Ala Tyr Ser Cys Leu  Lys Pro Gln Lys Lys  Leu Ser Ser
    5105             5110              5115

Arg Glu  Lys His Phe Pro Gln  Lys Cys Gln Arg Lys  Leu Ser Lys
    5120             5125              5130

Leu Val  Ile Tyr Asn His Asn  Asn Leu Leu Val Lys  Leu Leu Lys
    5135             5140              5145

Leu His  Trp Leu Val His Gln  Phe Val Leu Thr Gly  Leu Cys Cys
    5150             5155              5160

Ser Lys  Ser Lys Thr Gln Lys  Ser Thr Val Pro Leu  His Leu Ile
    5165             5170              5175

Trp Gln  Thr Ile Pro Ser His  Ser Lys Ala Val His  Gln Gln Arg
    5180             5185              5190

Leu Leu  Leu Val Met Thr Leu  Lys Cys Lys Val Thr  Arg Val Ile
    5195             5200              5205

Ser Leu  Leu Asn Leu Met Lys  Gly Leu Ile Lys Tyr  Leu Met Arg
    5210             5215              5220

Ser Ala  Leu Pro Ile Gln Leu  Asn Ser Val Gln Lys  Met Ser Ser
    5225             5230              5235

Pro Val  Leu Trp Gln Met Leu  Ser Lys Leu Cys Asn  Gln Tyr Leu
    5240             5245              5250

Asn Tyr  Leu His His Trp Ala  Leu Ile Met Ser Gly  Val Trp Leu
    5255             5260              5265

His Thr  Thr Tyr Leu Met Ser  Leu Val Ser Leu Asn  Trp Leu His
    5270             5275              5280

Ile Cys  Ile Val Leu Ser Thr  Leu Gln Met Arg Met  Lys Lys Lys
    5285             5290              5295

Val Ile  Val Lys Lys Lys Ser  Leu Ser His Gln Leu  Asn Met Ser
    5300             5305              5310

Met Val  Leu Lys Met Ile Thr  Lys Val Asn Leu Trp  Asn Leu Val
    5315             5320              5325

Pro Leu  Leu Leu Leu Phe Asn  Leu Lys Lys Ser Lys  Lys Lys Ile
    5330             5335              5340

Gly Met  Met Ile Val Asn Lys  Leu Leu Val Asn Lys  Thr Ala Val
    5345             5350              5355

Arg Thr  Ile Arg Gln Leu Leu  Phe Lys Gln Leu Leu  Arg Phe Asn
    5360             5365              5370

Leu Asn  Arg Trp Asn Leu His  Gln Leu Phe Arg Leu  Leu Lys Ile
    5375             5380              5385

Val Leu  Val Val Ile Asn Leu  Leu Thr Met Tyr Thr  Leu Lys Met
    5390             5395              5400

Gln Thr  Leu Trp Lys Lys Leu  Lys Arg Asn Gln Gln  Trp Leu Leu
    5405             5410              5415

Met Gln  Pro Met Phe Thr Leu  Asn Met Glu Glu Val  Leu Gln Glu
```

-continued

```
        5420              5425              5430

Pro Ile Arg Leu Leu Thr Met Pro Cys Lys Leu Asn Leu Met Ile
    5435              5440              5445

Thr Leu Leu Met Asp His Leu Lys Trp Val Val Val Val Phe Ala
    5450              5455              5460

Asp Thr Ile Leu Leu Asn Thr Val Phe Met Leu Ser Ala Gln Met
    5465              5470              5475

Leu Thr Lys Val Lys Thr Phe Asn Phe Leu Arg Val Leu Met Lys
    5480              5485              5490

Ile Leu Ile Ser Thr Lys Phe Tyr Leu His His Tyr Tyr Gln Leu
    5495              5500              5505

Val Phe Leu Val Leu Thr Leu Tyr Ile Leu Glu Phe Val Ile Leu
    5510              5515              5520

Phe Ala Gln Met Ser Thr Leu Ser Leu Ile Lys Ile Ser Met Thr
    5525              5530              5535

Asn Leu Phe Gln Ala Phe Trp Lys Arg Val Lys Ser Lys Leu Asn
    5540              5545              5550

Lys Arg Ser Leu Arg Phe Leu Lys Arg Lys Leu Ser His Leu Leu
    5555              5560              5565

Lys Val Asn Leu Gln Leu Asn Arg Glu Asn Lys Met Ile Arg Lys
    5570              5575              5580

Ser Lys Leu Val Leu Lys Lys Leu Gln Gln Leu Trp Lys Lys Leu
    5585              5590              5595

Ser Ser Ser Gln Lys Thr Cys Tyr Phe Ile Leu Thr Leu Met Ala
    5600              5605              5610

Ile Phe Ile Gln Ile Leu Pro Leu Leu Leu Val Thr Leu Thr Ser
    5615              5620              5625

Leu Ser Arg Lys Met Leu His Ile Trp Val Met Leu Phe Lys Arg
    5630              5635              5640

Val Phe Leu Leu Trp Leu Tyr Leu Leu Lys Arg Leu Val Ala Leu
    5645              5650              5655

Leu Lys Cys Arg Lys Leu Glu Lys Cys Gln Gln Thr Ile Ile Pro
    5660              5665              5670

Leu Thr Arg Val Arg Val Met Val Thr Leu Arg Arg Gln Arg Gln
    5675              5680              5685

Cys Leu Lys Ser Val Lys Val Pro Phe Thr Phe Tyr His Leu Leu
    5690              5695              5700

Ser Leu Met Arg Ser Lys Lys Phe Leu Glu Leu Phe Leu Gly Ile
    5705              5710              5715

Cys Glu Lys Cys Leu His Met Gln Lys Lys His Ala Asn Cys Leu
    5720              5725              5730

Ser Val Trp Lys Leu Lys Pro Phe Gln Leu Tyr Ser Val Asn Ile
    5735              5740              5745

Arg Val Leu Lys Tyr Lys Arg Val Trp Leu Ile Met Val Leu Asp
    5750              5755              5760

Phe Thr Phe Thr Pro Val Lys Gln Leu Arg His Leu Ser Thr His
    5765              5770              5775

Leu Thr Ile Met Lys Leu Leu Leu Gln Cys His Leu Ala Met His
    5780              5785              5790

Met Ala Ile Trp Lys Lys Leu Leu Gly Ile Asp Leu Ser Lys Cys
    5795              5800              5805

Gln Leu Gln Phe Leu Phe Leu His Leu Met Leu Leu Gln Arg Ile
    5810              5815              5820
```

-continued

```
Met Val  Ile Leu Leu Leu Leu  Leu Lys His Leu Lys  Asn Ile Leu
5825                 5830             5835

Leu Lys  Pro Ser His Leu Leu  Val Pro Ile Lys Ile  Gly Pro Ile
5840                 5845             5850

Leu Asp  Asn Leu His Asn Val  Asn Phe Leu Arg Glu  Val Ile Lys
5855                 5860             5865

Val Tyr  Ile Thr Leu Val Ile  Leu Pro His Ser Thr  Met Val Lys
5870                 5875             5880

Leu Ser  Pro Leu Thr Ile Leu  Arg His Phe Phe Leu  Glu Lys Gly
5885                 5890             5895

Leu Leu  Arg Cys Leu Gln Gln  Thr Thr Leu Thr Ser  Thr Arg Lys
5900                 5905             5910

Leu Trp  Thr Cys Gln His Met  Asp Asn Ser Leu Val  Gln Leu Ile
5915                 5920             5925

Trp Met  Glu Leu Met Leu Leu  Lys Asn Leu Ile Ile  His Met Lys
5930                 5935             5940

Val Lys  His Phe Met Phe Tyr  Leu Met Met Thr Leu  Tyr Val Leu
5945                 5950             5955

Arg Leu  Leu Ser Thr Thr Thr  Gln Leu Ile Leu Val  Phe Trp Val
5960                 5965             5970

Gly Thr  Cys Gln His Ile Thr  Leu Lys Ser Gly Asn  Thr His Lys
5975                 5980             5985

Leu Met  Val Leu Leu Leu Asn  Gly Gln Ile Thr Thr  Val Ile Leu
5990                 5995             6000

Pro Leu  His Cys His Ser Asn  Lys Ser Ser Leu Ile  His Leu Leu
6005                 6010             6015

Tyr Lys  Met Leu Ile Thr Glu  Gln Gly Leu Val Lys  Leu Leu Thr
6020                 6025             6030

Phe Val  His Leu Ser Pro Thr  Val Ile Arg Gln Val  Ser Val Met
6035                 6040             6045

Leu Glu  Lys Gln Val Thr Cys  Phe Asn Met Pro Ile  Ile Leu Ala
6050                 6055             6060

Lys Glu  Ser Thr Trp Cys Val  Lys Leu Val Asp Asn  Ser Arg Gln
6065                 6070             6075

Pro Leu  Arg Val Lys Leu Leu  Cys Thr Trp Ala His  Phe Leu Met
6080                 6085             6090

Asn Asn  Leu Arg Lys Val Phe  Arg Tyr Leu Val Arg  Val Val Asn
6095                 6100             6105

Lys Leu  Gln Asn Ile Tyr Asn  Arg Ser His Leu Leu  Leu Cys Gln
6110                 6115             6120

His His  Leu Leu Ser Met Asn  Leu Ser Met Val His  Leu Leu Val
6125                 6130             6135

Leu Val  Ser Thr Leu Val Ile  Thr Ser Val Val Thr  Ile Asn Ile
6140                 6145             6150

Leu Leu  Lys Lys Leu Cys Ile  Ala Thr Val Leu Tyr  Leu Gln Ser
6155                 6160             6165

Pro Gln  Asn Thr Lys Val Leu  Leu Arg Met Phe Ser  Thr Lys Lys
6170                 6175             6180

Thr Val  Thr Gln Gln Pro Asn  Gln Leu Leu Ile Asn  Trp Met Val
6185                 6190             6195

Leu Phe  Val Gln Lys Leu Thr  Leu Ser Trp Thr Ile  Ile Ile Arg
6200                 6205             6210
```

-continued

```
Lys Thr  Ile Leu Ile Ser Gln  Ser Asn Gln Leu Ile  Leu Tyr Gln
    6215              6220              6225

Thr Asn  His Ile Gln Thr Gln  Ala Ser Ile Ile Leu  Ser Leu Tyr
    6230              6235              6240

Val Ile  Ile Ser Asn Leu Leu  Met Ile Thr Ser Leu  Val Ile Arg
    6245              6250              6255

Asn Leu  Leu Gln Glu Ser Leu  Lys Leu His Phe Ser  Leu Thr Met
    6260              6265              6270

Val Met  Trp Trp Leu Leu Ile  Ile Asn Thr Thr His  Pro Leu Leu
    6275              6280              6285

Arg Lys  Glu Leu Asn Cys Tyr  Ile Asn Leu Leu Phe  Gly Met Leu
    6290              6295              6300

Thr Met  Gln Leu Ile Lys Pro  Arg Ile Asn Gln Ile  Pro Gly Val
    6305              6310              6315

Tyr Val  Val Phe Gly Ala Gln  Asn Gln Leu Lys His  Gln Ile Arg
    6320              6325              6330

Leu Met  Tyr Ser Gln Arg Thr  Arg Arg Glu Trp Ile  Ile Leu Pro
    6335              6340              6345

Ala Lys  Ile Asn Gln Ser Leu  Lys Lys Trp Lys Ile  Leu Pro Tyr
    6350              6355              6360

Arg Lys  Thr Phe Leu Ser Val  Met Lys Leu Pro Lys  Leu Glu Thr
    6365              6370              6375

Leu Tyr  Leu Asn Gln Gln Ile  Ile Val Lys Leu Gln  Lys Arg Leu
    6380              6385              6390

Ala Thr  Gln Ile Trp Leu Leu  Met Thr Ile Leu Val  Leu Leu Leu
    6395              6400              6405

Arg Asn  Leu Met Asn Tyr Leu  Glu Tyr Val Lys Pro  Leu Leu Leu
    6410              6415              6420

Met Val  Leu Leu Leu Ile Val  Ser Leu Gly Ile Leu  Leu Ile Met
    6425              6430              6435

Leu Ser  Leu Phe Leu Thr Lys  Leu Leu Val Gln Leu  Leu Thr Leu
    6440              6445              6450

His Gly  Val Thr Val Phe Val  Leu Ile Ile Cys Leu  Ile Ser Leu
    6455              6460              6465

Leu Tyr  Cys Tyr Asn Cys Val  Leu Leu Leu Glu Val  Gln Ile Leu
    6470              6475              6480

Glu Leu  Lys His Leu Cys Arg  Leu Leu Gln Arg Ile  Leu Leu Arg
    6485              6490              6495

Val Ser  Val Asn Phe Val Arg  Leu His Leu Ile Ile  Ser His Leu
    6500              6505              6510

Ile Phe  Leu Asn Ile Leu Phe  Gly Phe Tyr Tyr Val  Phe Ala Val
    6515              6520              6525

Leu Ser  Thr Gln Pro Leu Leu  Val Phe Cys Leu Ile  Ala Cys Leu
    6530              6535              6540

Leu Thr  Val Leu Val Thr Glu  Lys Ala Ile Thr Leu  Leu Met Ser
    6545              6550              6555

Leu Leu  Gln Pro Thr Val Leu  Val Leu Tyr Leu Val  Val Phe Val
    6560              6565              6570

Leu Val  Val Ile Leu Thr Pro  Ile Leu Leu Lys Leu  Tyr Lys Leu
    6575              6580              6585

Pro Phe  His Leu Leu Asn Gly  Ile Leu Leu Leu Ala  Leu Gln Ser
    6590              6595              6600

Gly Phe  Trp His Ile Phe Phe  Ser Leu Gly Phe Ser  Met Tyr Leu
```

```
        6605                6610                6615

Asp Trp Leu Gln Ser Cys Asn  Cys Phe Ser Ala Ile  Leu Gln Tyr
    6620                6625                6630

Ile Leu Leu Val Ile Leu Gly  Leu Cys Gly Leu Ile  Leu Tyr Lys
    6635                6640                6645

Trp Pro Arg Phe Gln Leu Trp  Leu Glu Cys Thr Ser  Ser Leu His
    6650                6655                6660

His Phe Ile Met Tyr Gly Lys  Val Met Cys Met Leu  Thr Val Val
    6665                6670                6675

Ile His Gln Leu Val Cys Val  Thr Asn Val Ile Glu  Gln Gln Glu
    6680                6685                6690

Ser Asn Val Gln Leu Leu Leu  Met Val Leu Glu Gly  Pro Phe Met
    6695                6700                6705

Ser Met Leu Met Glu Val Lys  Ala Phe Ala Asn Tyr  Thr Ile Gly
    6710                6715                6720

Ile Val Leu Ile Val Ile His  Ser Val Leu Val Val  His Leu Leu
    6725                6730                6735

Val Met Lys Leu Arg Glu Thr  Cys His Tyr Ser Leu  Lys Asp Gln
    6740                6745                6750

Ile Leu Leu Thr Ser Leu Leu  Thr Ser Leu Ile Val  Leu Gln Arg
    6755                6760                6765

Met Val Pro Ser Ile Phe Thr  Leu Ile Lys Leu Val  Lys Arg Leu
    6770                6775                6780

Met Lys Asp Ile Leu Ser Leu  Ile Leu Leu Thr Thr  Thr Glu Leu
    6785                6790                6795

Ile Thr Leu Lys Val His Cys  Leu Leu Met Leu Phe  Leu Met Val
    6800                6805                6810

Asn Gln Asn Val Lys Asn His  Leu Gln Asn Gln Arg  Leu Phe Thr
    6815                6820                6825

Thr Val Ser Leu Cys Val Asn  Leu Tyr Cys Tyr Ile  Arg His Cys
    6830                6835                6840

Leu Met Leu Val Ile Val Arg  Lys Leu Gln Leu Lys  Cys Leu Met
    6845                6850                6855

Leu Thr Leu Ile Arg Phe His  Gln Leu Leu Thr Tyr  Gln Trp Lys
    6860                6865                6870

Asn Ser Lys His Leu Gln Leu  Gln Lys Leu Asn Leu  Gln Arg Met
    6875                6880                6885

Cys Pro Thr Met Ser Tyr Leu  Leu Leu Phe Gln Gln  Leu Gly Lys
    6890                6895                6900

Gly Leu Leu Ile Gln Met Lys  Leu Lys Met Leu Leu  Asn Val Leu
    6905                6910                6915

Asn Cys His Ile Asn Leu Thr  Lys Leu Leu Ala Ile  Val Val Ile
    6920                6925                6930

Thr Ile Cys Ser Pro Ile Thr  Lys Leu Lys Thr His  Pro Val Thr
    6935                6940                6945

Leu Val Leu Val Leu Thr Val  Val Arg Val Ile Leu  Met Arg Arg
    6950                6955                6960

Gln Lys Val Thr Thr Leu Leu  Tyr Gly Thr Leu Lys  Ile Ser Cys
    6965                6970                6975

His Cys Leu Asn Asn Tyr Glu  Asn Lys Tyr Val Val  Leu Leu Lys
    6980                6985                6990

Arg Ile Thr Tyr Leu Leu Ser  His Val Gln Leu Leu  Asp Lys Leu
    6995                7000                7005
```

-continued

```
Leu Met  Leu Gln Gln Arg His  Leu Arg Val Val Lys  Leu Leu Ile
    7010             7015             7020

Ile Gly  Ser Ser Leu Lys Leu  His Leu Cys Ser Phe  Leu Leu Leu
    7025             7030             7035

Leu Phe  Ser Ile His Leu Phe  Met Ser Cys Leu Asn  Ile Leu Thr
    7040             7045             7050

Phe Gln  Val Lys Ser Asp Thr  Arg Leu Leu Met Val  Val Ser Leu
    7055             7060             7065

Val Thr  His Leu Gln Ile Leu  Val Leu Leu Thr Asn  Met Leu Ile
    7070             7075             7080

Leu Thr  His Gly Leu Ala Ser  Val Val Val Val Ile  Leu Met Thr
    7085             7090             7095

Lys Leu  Ala His Leu Leu Gln  Ser Gln Glu Lys Trp  Val Leu Ser
    7100             7105             7110

Cys Leu  Val Cys Leu Ala Arg  Tyr Tyr Ala Gln Leu  Met Val Thr
    7115             7120             7125

Phe Cys  Ile Ser Tyr Leu Glu  Phe Leu Val Gln Leu  Val Thr Ser
    7130             7135             7140

Val Thr  His His Gln Asn Leu  Ser Thr Leu Thr Leu  Gln His Gln
    7145             7150             7155

Leu Val  Phe Trp Leu Leu Asn  Val Gln Phe Leu Lys  Met Leu Leu
    7160             7165             7170

Val Ser  Gln Tyr His Ile Val  Met Ile Pro Met Tyr  Lys Val Leu
    7175             7180             7185

Leu Leu  Met Lys Val Tyr Ala  Leu Thr His Val Met  Cys Ser Trp
    7190             7195             7200

Met Ala  Leu Leu Phe Asn Phe  Leu Thr Pro Thr Leu  Lys Val Leu
    7205             7210             7215

Leu Glu  Trp Gln Leu Leu Ile  Leu Ser Thr Val Gly  Thr Ala Leu
    7220             7225             7230

Val Lys  Asp Gln Lys Leu Val  Phe Val Tyr Leu Leu  Val Val Asp
    7235             7240             7245

Gly Tyr  Leu Thr Met Ile Ile  Thr Asp Leu Tyr Gln  Glu Phe Ser
    7250             7255             7260

Val Val  Met Leu Ile Tyr Leu  Leu Ile Cys Leu His  His Phe Asn
    7265             7270             7275

Leu Leu  Val Leu Trp Thr Tyr  Gln His Leu Leu Val  Val Leu Leu
    7280             7285             7290

Ser His  Ala Leu Pro Thr Ile  Leu Gly Leu Glu Glu  Leu Leu Val
    7295             7300             7305

Asn Thr  Val Met Leu Pro Leu  Ile Leu Tyr Tyr Ser  Leu Cys His
    7310             7315             7320

Ser Leu  Tyr Ser Val His Gln  Phe Thr His Ser Tyr  Leu Val Phe
    7325             7330             7335

Ile Leu  Leu Phe Thr Cys Thr  His Phe Ile Leu Leu  Met Met Phe
    7340             7345             7350

Leu Phe  His Ile Phe Ser Gly  Trp Leu Cys Ser His  Leu Tyr Leu
    7355             7360             7365

Ser Gly  Gln Leu Leu Ile Ser  Phe Val Phe Pro Gln  Ser Ile Ser
    7370             7375             7380

Ile Gly  Ser Leu Val Ile Thr  Arg Asp Val Ser Leu  Met Val Phe
    7385             7390             7395
```

-continued

```
Pro Leu  Val Leu Leu Lys Lys  Leu Arg Cys Ala Pro  Phe Cys Ile
    7400             7405             7410

Lys Lys  Cys Ile Ser Cys Val  Val Met Cys Tyr Tyr  Leu Leu Arg
    7415             7420             7425

Asn Ile  Ile Asp Thr Leu Phe  Ile Ile Ser Thr Ser  Ile Leu Val
    7430             7435             7440

Glu Gln  Trp Ile Gln Leu Ala  Thr Glu Lys Leu Leu  Val Val Ile
    7445             7450             7455

Ser Gln  Arg Leu Ser Met Thr  Ser Val Thr Gln Val  Leu Met Phe
    7460             7465             7470

Phe Thr  Asn His His Lys Pro  Leu Ser Pro Gln Leu  Phe Cys Arg
    7475             7480             7485

Val Val  Leu Glu Lys Trp His  Ser His Leu Val Lys  Leu Arg Val
    7490             7495             7500

Val Trp  Tyr Lys Leu Val Val  Gln Leu His Leu Thr  Val Phe Gly
    7505             7510             7515

Leu Met  Thr Phe Thr Val Gln  Asp Met Ser Ala Pro  Leu Lys Thr
    7520             7525             7530

Cys Leu  Thr Leu Ile Met Lys  Ile Tyr Ser Phe Val  Ser Leu Ile
    7535             7540             7545

Ile Ile  Ser Trp Tyr Arg Leu  Val Met Phe Asn Ser  Gly Leu Leu
    7550             7555             7560

Asp Ile  Leu Cys Lys Ile Val  Tyr Leu Ser Leu Arg  Leu Ile Gln
    7565             7570             7575

Pro Ile  Leu Arg His Leu Ser  Ile Ser Leu Phe Ala  Phe Asn Gln
    7580             7585             7590

Asp Arg  Leu Phe Gln Cys Leu  Val Thr Met Val His  His Leu Val
    7595             7600             7605

Phe Thr  Asn Val Leu Gly Pro  Ile Ser Leu Leu Arg  Val His Ser
    7610             7615             7620

Leu Met  Val His Val Val Val  Leu Val Leu Thr Ile  Met Thr Val
    7625             7630             7635

Ser Leu  Phe Val Thr Cys Thr  Ile Trp Asn Tyr Gln  Leu Glu Phe
    7640             7645             7650

Met Leu  Ala Gln Thr Lys Val  Thr Phe Met Asp Leu  Leu Leu Thr
    7655             7660             7665

Gly Lys  Gln His Lys Gln Leu  Val Arg Thr Gln Leu  Leu Gln Leu
    7670             7675             7680

Met Phe  Leu Gly Cys Thr Leu  Leu Leu Met Glu Thr  Gly Gly Phe
    7685             7690             7695

Ser Ile  Asp Leu Pro Gln Leu  Leu Met Thr Leu Thr  Leu Trp Leu
    7700             7705             7710

Ser Thr  Ile Met Asn Leu His  Lys Thr Met Leu Thr  Tyr Asp Leu
    7715             7720             7725

Phe Leu  Leu Lys Leu Glu Leu  Pro Phe Ile Cys Val  Leu His Lys
    7730             7735             7740

Asn Tyr  Cys Lys Met Val Met  Asp Val Pro Tyr Trp  Val Val Leu
    7745             7750             7755

Tyr Lys  Met Asn Leu His Leu  Leu Met Leu Leu Asp  Asn Ala Gln
    7760             7765             7770

Val Leu  Leu Ser Lys Val Gln  Lys Glu Gln Ser Arg  Val His Thr
    7775             7780             7785

Thr Gly  Cys Tyr Ser Gln Phe  Leu His Phe Phe Ser  Arg Val Leu
```

-continued

```
          7790              7795              7800

Asn Gly Leu Cys Ser Phe Phe  Cys Met Lys Met Pro  Phe Tyr Leu
    7805              7810              7815

Leu Leu Trp Val Leu Leu Leu  Cys Leu Leu Leu Gln  Cys Leu Ser
    7820              7825              7830

Asn Ile Ser Met His Phe Ser  Val Cys Phe Cys Tyr  Leu Leu Leu
    7835              7840              7845

Pro Leu Leu Ile Leu Ile Trp  Ser Ile Cys Leu Leu  Val Gly Cys
    7850              7855              7860

Val Leu His Gly Trp Ile Trp  Leu Ile Leu Val Cys  Leu Val Leu
    7865              7870              7875

Ser Lys Thr Val Leu Cys Met  His Gln Leu Cys Tyr  Ser Leu Gln
    7880              7885              7890

Gln Glu Leu Cys Met Met Met  Val Leu Gly Glu Cys  Gly His Leu
    7895              7900              7905

Met Ser His Ser Phe Ile Lys  Phe Ile Met Val Met  Leu Ile Lys
    7910              7915              7920

Pro Phe Pro Cys Gly Leu Leu  Ser Leu Leu Leu Leu  Thr Thr Gln
    7925              7930              7935

Val Leu Gln Leu Ser Cys Phe  Trp Pro Glu Val Leu  Phe Leu Cys
    7940              7945              7950

Val Leu Ser Ile Ala Leu Phe  Ser Ser Leu Val Ile  His Phe Ser
    7955              7960              7965

Val Cys Phe Ile Val Ser Ala  Ile Phe Val Leu Val  Thr Leu Ala
    7970              7975              7980

Ser Phe Val Tyr Ser Thr Ala  Thr Leu Asp Leu Leu  Val Phe Met
    7985              7990              7995

Ile Thr Phe Leu His Arg Ser  Leu Asp Ile Ile His  Arg Asp Tyr
    8000              8005              8010

Ser His Pro Arg Ile Ala Met  Pro Ser Asn Ser Thr  Leu Asn Cys
    8015              8020              8025

Trp Val Leu Val Ala Asn Leu  Val Ser Lys Pro Leu  Tyr Ser Leu
    8030              8035              8040

Lys Cys Gln Met Ser Ala His  Gln Ser Tyr Ser Gln  Phe Cys Asn
    8045              8050              8055

Asn Ser Glu Asn His His Leu  Asn Cys Gly Leu Asn  Val Ser Ser
    8060              8065              8070

Tyr Thr Met Thr Phe Ser Leu  Lys Ile Leu Leu Lys  Pro Leu Lys
    8075              8080              8085

Lys Trp Phe His Tyr Phe Leu  Phe Cys Phe Pro Cys  Arg Val Leu
    8090              8095              8100

Thr Thr Ser Phe Val Lys Lys  Cys Trp Thr Thr Gly  Gln Pro Tyr
    8105              8110              8115

Lys Leu Pro Gln Ser Leu Val  Pro Phe His His Met  Gln Leu Leu
    8120              8125              8130

Leu Leu Leu Lys Lys Leu Met  Ser Arg Leu Leu Leu  Met Val Ile
    8135              8140              8145

Leu Lys Leu Phe Leu Lys Ser  Arg Ser Leu Met Trp  Leu Asn Leu
    8150              8155              8160

Asn Leu Thr Val Met Gln Pro  Cys Asn Val Ser Trp  Lys Arg Trp
    8165              8170              8175

Leu Ile Lys Leu Pro Lys Cys  Ile Asn Arg Leu Asp  Leu Arg Thr
    8180              8185              8190
```

```
Arg Gly Gln Lys Leu Leu Val  Leu Cys Arg Gln Cys  Phe Ser Leu
    8195             8200          8205

Cys Leu Glu Ser Trp Ile Met  Met His Ser Thr Thr  Leu Ser Thr
    8210             8215          8220

Met Gln Glu Met Val Val Phe  Pro Thr Tyr Leu Leu  Gln Gln Gln
    8225             8230          8235

Pro Asn Trp Leu Ser Tyr Gln  Thr Ile Thr His Ile  Lys Ile Arg
    8240             8245          8250

Val Met Val Gln His Leu Leu  Met His Gln His Cys  Gly Lys Ser
    8255             8260          8265

Asn Arg Leu Met Gln Ile Val  Lys Leu Phe Asn Leu  Val Lys Leu
    8270             8275          8280

Val Trp Thr Ile His Leu Ile  His Gly Leu Leu Leu  Gln Leu Gly
    8285             8290          8295

Pro Ile Leu Leu Ser Asn Tyr  Arg Ile Met Ser Leu  Val Leu Leu
    8300             8305          8310

His Tyr Asp Arg Cys Leu Val  Leu Pro Val Leu His  Lys Leu Leu
    8315             8320          8325

Ala Leu Met Thr Met Arg Leu  Thr Thr Thr Gln Gln  Arg Glu Val
    8330             8335          8340

Gly Leu Tyr Leu His Cys Tyr  Pro Ile Tyr Arg Ile  Asn Gly Leu
    8345             8350          8355

Asp Ser Leu Arg Val Met Glu  Leu Val Leu Ser Ile  Gln Asn Trp
    8360             8365          8370

Asn His Leu Val Gly Leu Leu  Gln Thr His Leu Lys  Val Leu Lys
    8375             8380          8385

Ser Ile Tyr Thr Leu Leu Lys  Asp Thr Thr Ile Glu  Val Trp Tyr
    8390             8395          8400

Leu Val Val Leu Pro Gln Tyr  Val Tyr Lys Leu Val  Met Gln Gln
    8405             8410          8415

Lys Cys Leu Pro Ile Gln Leu  Tyr Tyr Leu Ser Val  Leu Leu Leu
    8420             8425          8430

Met Leu Leu Lys Leu Thr Lys  Ile Ile Leu Val Gly  Asp Asn Gln
    8435             8440          8445

Ser Leu Ile Val Leu Arg Cys  Cys Val His Thr Leu  Val Leu Val
    8450             8455          8460

Arg Gln Gln Leu His Arg Lys  Pro Ile Trp Ile Lys  Asn Pro Leu
    8465             8470          8475

Val Val His Arg Val Val Cys  Thr Ala Val Ala Thr  Ile Ile Gln
    8480             8485          8490

Ile Leu Lys Asp Phe Val Thr  Lys Val Ser Met Tyr  Lys Tyr Leu
    8495             8500          8505

Gln Leu Val Leu Met Thr Leu  Trp Val Leu His Leu  Lys Thr Gln
    8510             8515          8520

Ser Val Pro Ser Ala Val Cys  Gly Lys Val Met Ala  Val Val Val
    8525             8530          8535

Ile Asn Ser Ala Asn Pro Cys  Phe Ser Gln Leu Met  His Asn Arg
    8540             8545          8550

Phe Thr Gly Leu Arg Cys Gly  Glu Pro Cys Pro Trp  Phe Gln Arg
    8555             8560          8565

Glu Asn Thr Arg Pro Thr Gln  Phe Ala Cys Phe Thr  Gly Ser Arg
    8570             8575          8580
```

-continued

```
Arg Ala  Arg Thr Trp Leu Trp  Arg Leu Arg Gly Gly  Gly Leu Ile
    8585             8590             8595

Arg Gly  Thr Ser Thr Ser Arg  Trp His Leu Trp Leu  Ser Arg Ser
    8600             8605             8610

Lys Arg  Arg Phe Ala Ser Thr  Thr Ala Leu Cys Val  His Gln Thr
    8615             8620             8625

Phe Gly  Cys Ser Asn Cys Thr  Ser Trp Ser Cys Tyr  Gly Ala Gly
    8630             8635             8640

Ser Arg  Thr Arg Arg His Ser  Val Arg Ser Trp Asp  Thr Trp Cys
    8645             8650             8655

Pro Cys  Pro Ser Cys Gly Arg  Asn Thr Ser Gly Leu  Pro Gln Gly
    8660             8665             8670

Ser Ser  Ser Glu Arg Arg Ser  Trp Trp Pro Leu Arg  Arg Arg Ser
    8675             8680             8685

Lys Val  Ile Leu Arg Arg Arg  Ala Trp His Ser Leu  Arg Phe Ser
    8690             8695             8700

Arg Lys  Leu Glu His Thr Gln  Trp Cys Tyr Pro Thr  His Ala Ala
    8705             8710             8715

Arg Arg  Gly Ile His Ser Leu  Cys Arg Gln Leu Leu  Trp Pro Trp
    8720             8725             8730

Leu Pro  Ser Val His Arg Pro  Ser Ser Thr Cys Trp  Ser Phe Met
    8735             8740             8745

His Phe  Val Arg Thr Thr Gly  Leu Tyr His Glu Gly  Cys Ile Leu
    8750             8755             8760

Leu Pro  Thr Ala Asn Cys Leu  Val His Gly Thr Phe  Lys Glu Leu
    8765             8770             8775

Ile Ala  Asp Thr Phe Asn Ile  Gly Lys Glu Ile His  Leu Gln Trp
    8780             8785             8790

Gly Met  Ser Lys Phe Cys Ile  Ser Leu Lys Phe His  Asn Gln Asp
    8795             8800             8805

Tyr Ser  Thr Lys Gly Lys Glu  Lys Ala Trp Leu Tyr  Gly Asn Ser
    8810             8815             8820

Ile Cys  Leu Ser Ser Cys Val  Thr Lys Met Gln Pro  Asn Val Pro
    8825             8830             8835

Phe Asn  Ser His Glu Val Ser  Leu Trp Asn Phe Met  Ala Asp Gly
    8840             8845             8850

Arg Phe  Cys Ser His Leu Arg  Ile Leu Trp His Glu  Phe Asp Arg
    8855             8860             8865

Arg Cys  His Tyr Leu Trp Leu  Leu Thr Pro Lys Cys  Cys Cys Asn
    8870             8875             8880

Leu Leu  Ser Ser Met Ser Gln  Phe Arg Ser Arg Thr  Ala Ser Cys
    8885             8890             8895

Arg Ile  Pro Ile Trp Leu Glu  Asn His Ser Ser Gly  Trp Ser His
    8900             8905             8910

Tyr Cys  Leu Trp Arg Leu Cys  Val Leu Leu Cys Trp  Leu Pro Gln
    8915             8920             8925

Val Cys  Leu Leu Gly Ser Thr  Cys Arg His Arg Leu  Pro Tyr Arg
    8930             8935             8940

Cys Cys  Trp Arg Arg Phe Arg  Arg Ser Gln Pro Ser  Asn Thr Pro
    8945             8950             8955

Lys Arg  Glu Ser Gln His Gln  Tyr Cys Trp Leu Thr  Arg Asp Arg
    8960             8965             8970

His Tyr  Phe Gly Ile Phe Phe  Cys Phe His Lys Cys  Phe Cys Gly
```

-continued

```
         8975                  8980                  8985

Asn Cys Glu Arg Phe Gly Leu  Ser Ile Gln Thr Asn  Cys Ile Leu
    8990                  8995                  9000

Trp Phe Ser Tyr Lys Arg Lys  Ser Lys Arg Cys Leu  Glu Tyr Trp
    9005                  9010                  9015

Thr Glu Ile Asn Thr Glu Ser  Ser Leu Cys Ile Cys  Ile Arg Gly
    9020                  9025                  9030

Cys Ser Cys Cys Thr Ile Asn  Phe Leu Pro His Ser  Asn Cys Ser
    9035                  9040                  9045

Lys Phe Cys Ala Cys Phe Thr  Glu Gly Arg Tyr Asn  Asn Thr Arg
    9050                  9055                  9060

Trp Asn Phe Thr Val Phe Thr  Glu Thr His Cys Tyr  Asp Val His
    9065                  9070                  9075

Ile Phe Gly Tyr Gln Ser Ser  Cys Asn Gly Leu His  Tyr Arg Trp
    9080                  9085                  9090

Cys Cys Ser Val Asp Phe Ala  Val Ala Asn His Leu  Trp His Cys
    9095                  9100                  9105

Leu Lys Thr Gln Thr Arg Pro  Leu Ala Arg Glu Val  Gly Arg Cys
    9110                  9115                  9120

Arg Val Ser Arg Arg Leu Gly  Asn Cys Ile Tyr Leu  Asn Leu Cys
    9125                  9130                  9135

Leu Asn Cys Arg Trp Thr Asn  Cys His Leu Cys Lys  Gly Asn Gly
    9140                  9145                  9150

Glu Cys Ser Asp Ile Leu Ala  Cys Lys Ile Phe Gly  Phe Val Cys
    9155                  9160                  9165

Leu Tyr His Tyr Trp Trp Ser  Thr Ser Leu Glu Phe  Arg Asn Ile
    9170                  9175                  9180

Cys His Ala Leu Lys Gly Ile  Val Gln Lys Val Cys  Ile Gln Arg
    9185                  9190                  9195

Arg Asn Trp Pro Thr His Ala  Ser Lys Ser Pro Lys  Arg Asn Tyr
    9200                  9205                  9210

Leu Leu Arg Gly Arg Asn Thr  Ser His Arg Ser Val  Asn Arg Gly
    9215                  9220                  9225

Ser Cys Leu Glu Asn Trp Phe  Thr Thr Ile Arg Thr  Thr Tyr Ser
    9230                  9235                  9240

Cys Ser Ser Ile Gly Trp Tyr  Thr Ser Leu Tyr Arg  Ala Tyr Val
    9245                  9250                  9255

Ala Arg Asn Gln Arg His Arg  Lys Val Leu Cys Pro  Cys Thr Tyr
    9260                  9265                  9270

Asp Gly Asn Lys Gln Tyr Leu  His Thr Gln Arg Arg  Cys Thr Asn
    9275                  9280                  9285

Lys Gly Tyr Phe Trp His Cys  Asp Arg Ser Ala Arg  Leu Gln Glu
    9290                  9295                  9300

Cys Glu Tyr His Phe Thr Lys  Asp Ser Thr Glu Val  Leu Cys Leu
    9305                  9310                  9315

Tyr Ser Thr Arg Tyr Arg Ser  Lys Val Arg Leu Cys  Cys Gly Arg
    9320                  9325                  9330

Cys Cys His Lys Asn Phe Ala  Thr Ser Ile Ile Thr  Tyr Thr Thr
    9335                  9340                  9345

Gly His Phe Arg Val Glu Tyr  Gly Tyr Ile Leu Leu  Ile Val Trp
    9350                  9355                  9360

Val Ile Gly Phe Thr Tyr Val  Leu Phe Phe Leu Pro  Ser Arg Gly
    9365                  9370                  9375
```

```
Arg Arg Arg Leu Arg Arg Arg  Val Ala Ile Asn Ser  Ile Val Trp
    9380            9385          9390

Tyr Arg Leu Pro Arg Thr Phe  Gly Ile Trp Cys His  Phe Cys Cys
    9395            9400          9405

Ser Ser Thr Arg Arg Ala Arg  Arg Arg Leu Val Arg  Ser Thr Asn
    9410            9415          9420

Cys Trp Ser Thr Arg Arg Gln  Gly Gln Ser Asp Asn  Tyr Tyr Ser
    9425            9430          9435

Asn Asn Cys Gly Ser Thr Ser  Ile Arg Asp Gly Thr  Tyr Thr Ser
    9440            9445          9450

Cys Ser Asp Tyr Ser Glu Phe  Trp Leu Phe Lys Thr  Tyr Gln Cys
    9455            9460          9465

Ile His Lys Cys Arg His Cys  Gly Arg Ser Lys Gly  Lys Thr Asn
    9470            9475          9480

Ser Gly Cys Cys Ser Gln Cys  Leu Pro Thr Trp Arg  Arg Cys Cys
    9485            9490          9495

Arg Ser Leu Lys Gly Tyr Gln  Cys His Ala Ser Ile  Leu His Ser
    9500            9505          9510

Tyr Trp Thr Thr Ser Gly Trp  Leu Cys Phe Lys Arg  Thr Gln Ser
    9515            9520          9525

Cys Thr Leu Ser Ser Cys Cys  Arg Pro Lys Cys Gln  Arg Arg His
    9530            9535          9540

Ser Thr Ser Glu Cys Leu Lys  Phe Ser Ala Arg Ser  Ser Thr Cys
    9545            9550          9555

Thr Ile Ile Ile Ser Trp Tyr  Phe Trp Cys Pro Tyr  Thr Phe Phe
    9560            9565          9570

Lys Ser Leu Cys Arg Tyr Cys  Ser His Lys Cys Leu  Leu Ser Cys
    9575            9580          9585

Leu Lys Ser Leu Gln Thr Cys  Phe Lys Leu Phe Gly  Asn Glu Glu
    9590            9595          9600

Lys Ala Ser Thr Lys Asp Arg  Asp Ser Arg Gly Ser  Ala Ile Tyr
    9605            9610          9615

Asn Lys Thr Phe Ser Thr Glu  Lys Thr Arg Glu Asn  Gln Ser Leu
    9620            9625          9630

Cys Arg Ser Tyr Asn Asn Ser  Gly Arg Asn Val Pro  His Arg Lys
    9635            9640          9645

Leu Val Thr Leu Tyr His Trp  Gln Ser Ser Ser Arg  Phe Cys His
    9650            9655          9660

Ser Cys His His His Phe Leu  Lys Glu Arg Cys Ser  Ile Tyr Ser
    9665            9670          9675

Gly Cys Cys Ser Arg Gly Cys  Phe Asn Cys Cys Gly  Tyr Thr Tyr
    9680            9685          9690

Lys Gly Trp Trp His Tyr Asn  Ala Ser Glu Ser Phe  Glu Lys Ser
    9695            9700          9705

Ala Asn Arg Gln Leu Tyr Asn  His Leu Pro Gly Ser  Gly Phe Lys
    9710            9715          9720

Trp Leu His Cys Arg Gly Gly  Lys Asp Ser Ala Lys  Val Lys Cys
    9725            9730          9735

Leu Leu His Ser Thr Ile Tyr  Tyr Leu Glu Ala Arg  Asn Ser Trp
    9740            9745          9750

Asn Cys Phe Leu Glu Phe Ala  Arg Asn Ala Cys Thr  Cys Arg Arg
    9755            9760          9765
```

-continued

```
Asn Thr  Gln Ile Asn Ala Cys  Leu Cys Gly Asn Ser  His Ser Phe
    9770             9775             9780

Asn Tyr  Thr Ala Ile Gly Tyr  Asn Thr Arg Gly Cys  Gly Leu Trp
    9785             9790             9795

Cys Ile  Leu Leu Leu His Gln  Asn Asn Cys Ser Val  Thr Tyr Gln
    9800             9805             9810

His Thr  Arg Ser Lys Asn Ser  Cys Tyr Asn Ala Thr  Trp Leu Cys
    9815             9820             9825

Asn Thr  Trp Leu Lys Phe Gly  Arg Ser Cys Ser Val  Tyr Glu Ile
    9830             9835             9840

Ser Gln  Ser Ala Ser Tyr Ser  Phe Cys Phe Phe Thr  Cys Cys Tyr
    9845             9850             9855

Ser Val  Trp Leu Ser Tyr Phe  Phe Phe Asn Thr Arg  Thr Phe Tyr
    9860             9865             9870

Asn His  Leu Thr Cys Trp Phe  Leu Arg Leu Val Leu  Phe Trp Thr
    9875             9880             9885

Ile Tyr  Thr Thr Arg Tyr Arg  Ile Ser Glu Arg Lys  Cys Ile Leu
    9890             9895             9900

His Ser  Tyr His Ile Pro Pro  Arg Trp Ser Tyr His  Leu Gln Ser
    9905             9910             9915

Asp Thr  Ser Phe Phe Glu Arg  Ser Glu Asp Tyr Gly  Val Tyr Asn
    9920             9925             9930

Ser Arg  Gln His Pro Pro His  Ala Ser Cys Gly His  Val Asn Asp
    9935             9940             9945

Ile Trp  Thr Thr Val Trp Ser  Asn Leu Phe Gly Trp  Ser Cys Tyr
    9950             9955             9960

Asn Lys  Thr Ser Phe Thr Arg  Asn Ile Leu Cys Phe  Thr His Ser
    9965             9970             9975

Thr Cys  Gly Phe Val Leu Pro  His Asn Ser Phe Ser  Gly Val His
    9980             9985             9990

Val Ser  Ile Lys Ser His Lys   Val Glu Ile Pro Thr   Ser Trp Phe
    9995             10000              10005

Asn Phe  Tyr Met Gly Arg Gln   Leu Leu Ser Cys His   Cys Ile Val
    10010             10015              10020

Asn Thr  Pro Thr Asn Arg Val   Glu Val Ser Thr Cys   Ser Thr Arg
    10025             10030              10035

Cys Leu  Leu Gln Ser Lys Gly   Trp Ser Cys Leu Leu   Cys Thr Tyr
    10040             10045              10050

Leu Ser  Leu Leu Asp Ser Arg   Val Arg Cys Arg Asn   Asn Glu Leu
    10055             10060              10065

Leu Val  Ser Thr Cys Gln Phe   Arg Phe Leu Gln Lys   Ser Leu Glu
    10070             10075              10080

Arg Gly  Val Asn Leu Trp Thr   Thr Ala Asp Asn Pro   Gly Cys Arg
    10085             10090              10095

Ser Cys  Tyr Val His Gly His   Thr Phe Leu Thr Ile   Glu Arg Cys
    10100             10105              10110

Ser Asp  Thr Leu Tyr Val Trp   Thr Ser Tyr Lys Ile   Ser Ser Thr
    10115             10120              10125

Thr Gly  Val Thr Phe Cys Tyr   Asp Val Ser Thr Thr   Cys Ser Val
    10130             10135              10140

Thr Ala  Trp Tyr Ile Tyr Leu   Cys Val His Trp Leu   Pro Val Trp
    10145             10150              10155

Ser Leu  Thr Tyr Asn Phe Arg   Asn Phe Val Leu His   Arg Arg Cys
```

-continued

```
    10160                10165                10170

Phe Thr  Tyr Lys Val Leu Arg  Ile Gln Arg Ser Tyr  Tyr Gly Cys
    10175                10180                10185

Phe Leu  Gln Arg Lys Gln Leu  His Asn Asn His Lys  Thr Ser Tyr
    10190                10195                10200

Leu Ile  Gly Trp Cys Cys Leu  Tyr Arg Asn Pro Val  Gly Gln Leu
    10205                10210                10215

Leu Glu  Arg Gln Phe Leu Phe  His Arg Ala Thr Asn  Ser Cys Thr
    10220                10225                10230

Lys Pro  Thr Ile Ser Lys Arg  Lys Leu Arg Phe Val  Cys Met Tyr
    10235                10240                10245

Gln Ile  Cys Phe Lys Pro Val  Asn Trp Leu Glu Thr  Cys Phe Lys
    10250                10255                10260

Arg Ala  Ser Tyr Ile Phe Pro  Leu Lys Trp Cys Gly  Gly Tyr Leu
    10265                10270                10275

Thr Leu  His Thr Leu Phe Glu  Arg Ser Ile Val Thr  Thr Tyr Cys
    10280                10285                10290

Leu Ala  Cys Gln Cys Asn Ser  His Val Thr Lys Tyr  Leu Val Tyr
    10295                10300                10305

Thr Leu  Ser Leu Glu His Lys  Thr Ser Asn Ile Lys  Phe Val Cys
    10310                10315                10320

Thr Glu  Val Arg Gly Arg Ala  Gly Asn Gly Ser Cys  Leu Arg Arg
    10325                10330                10335

Ser Lys  Thr Ser Leu Arg Ser  Ser Gly Lys Ser Tyr  His Thr Glu
    10340                10345                10350

Arg Arg  Ser Val Cys Glu Asn  Tyr Arg Ser Cys Arg  Arg His Tyr
    10355                10360                10365

Thr Thr  Ser Lys Phe Lys Asn  Tyr Arg Arg Gly Trp  Pro His Arg
    10370                10375                10380

Ser Asn  Gly Cys Leu Cys Arg  Gln Phe Ser Tyr Tyr  Glu Thr Ile
    10385                10390                10395

Ile Ser  Ile Arg Phe Glu Asn  Pro Cys Tyr Ser Trp  Phe Ser Cys
    10400                10405                10410

Cys Cys  Pro Leu Gly Tyr Tyr  Ser Leu Cys Ala Phe  Ser Gln Ser
    10415                10420                10425

Cys Tyr  Asn Tyr His Ser Tyr  Thr Val Phe Lys Pro  Cys Leu Tyr
    10430                10435                10440

Leu Tyr  Ala Leu Phe Leu Tyr  Phe Ile Ala Thr Ile  Val Tyr Phe
    10445                10450                10455

Tyr Lys  Tyr Lys Phe Asn Ser  Ile Tyr Ala Asp Tyr  Tyr Ser Lys
    10460                10465                10470

Glu Tyr  Cys Glu Cys Arg Ile  Leu Ser Arg Gly Phe  Ile Leu Phe
    10475                10480                10485

Glu Val  Thr Phe Phe Thr Asp  Lys Tyr Tyr Asn Leu  Val Phe Thr
    10490                10495                10500

Ile Lys  Cys Leu Pro Arg Phe  Phe Asn Leu Leu Asn  Arg Cys Phe
    10505                10510                10515

Arg Cys  Phe Asn Val Phe Arg  His Ala Phe Leu Leu  Tyr Trp Leu
    10520                10525                10530

Gln Arg  Arg Leu Phe Glu Leu  Tyr Cys His Tyr Cys  Asn Leu Leu
    10535                10540                10545

Tyr Trp  Phe Tyr Thr Leu Cys  Leu Ser Trp Phe Arg  Phe Phe Arg
    10550                10555                10560
```

-continued

His Leu   Ser Phe Phe Arg Asn   Tyr Thr Asn Tyr His   Phe Ile Phe
   10565            10570               10575

Met Gly   Phe Asn Cys Phe Trp   Leu Ser Cys Arg Val   Val Phe Gly
   10580            10585               10590

Ile Tyr   Ser Phe His Val Phe   Leu Cys Thr Trp Ile   Gly Cys Asn
   10595            10600               10605

His Ala   Ile Val Phe Gln Leu   Phe Cys Ser Thr Phe   Tyr Phe Leu
   10610            10615               10620

Ala Tyr   Val Val Asn Asn Ser   Cys Thr Asn Gly Pro   Asp Phe Ser
   10625            10630               10635

Tyr Gly   Asn Val His Leu Leu   Cys Ile Ile Leu Leu   Cys Met Glu
   10640            10645               10650

Lys Leu   Cys Ala Cys Cys Arg   Arg Leu Phe Ile Asn   Leu Tyr Asp
   10655            10660               10665

Val Leu   Gln Thr Ser Asn Lys   Ser Arg Met Tyr Asn   Tyr Cys Trp
   10670            10675               10680

Cys Lys   Val Leu Leu Cys Leu   Cys Trp Arg Arg Leu   Leu Gln Thr
   10685            10690               10695

Thr Gln   Leu Glu Leu Cys Leu   Tyr Ile Leu Cys Trp   Tyr Ile Tyr
   10700            10705               10710

Ser Cys   Glu Arg Leu Val Thr   Thr Val Lys Thr Asn   Lys Ser Tyr
   10715            10720               10725

Pro Val   Phe Leu His Arg Cys   Tyr Ser Glu Glu Trp   Phe His Pro
   10730            10735               10740

Ser Leu   Leu Ser Trp Ser Lys   Asp Leu Lys Thr Phe   Ser Leu Ser
   10745            10750               10755

Phe Cys   Leu Arg Gln Pro Glu   Ser His Arg Phe Ile   Ala Tyr Cys
   10760            10765               10770

Tyr Ser   Phe Trp Ile Lys Met   Arg Ile Ile Cys Lys   Ile Ser Val
   10775            10780               10785

Cys Leu   Leu Gln Ser Ala Tyr   Val Ser Thr Tyr Thr   Val Thr Arg
   10790            10795               10800

Ser Gly   Ile Ser Val Cys Trp   Cys Gly Ser Cys Ser   Asn Val Cys
   10805            10810               10815

Leu Arg   Tyr Val Phe Ile Asn   Phe Arg Thr Asn Gly   Lys Thr Gln
   10820            10825               10830

Asn Thr   Ser Cys Asn Cys Arg   Ser Thr Cys Lys Glu   Cys Val Leu
   10835            10840               10845

Arg Gln   Cys Leu Ile Tyr Phe   Tyr Phe Ser Ser Ser   Ala Arg Val
   10850            10855               10860

Cys Phe   Arg Cys Arg Asn Arg   Cys Cys Met Ser Ile   Val Thr Ser
   10865            10870               10875

Ile His   Arg Ser Tyr Trp Arg   Leu Leu Tyr Ala His   Leu Gln Ser
   10880            10885               10890

Lys His   Asp Thr Pro Pro Trp   Cys Leu Tyr Leu Cys   Ala Ser Tyr
   10895            10900               10905

Cys Ala   Gly Ser Lys Lys Ser   Gln His Cys Phe Asp   Met Glu Arg
   10910            10915               10920

Arg Phe   His Val Ile Val Thr   Thr Thr Lys Thr Asn   Thr Cys Cys
   10925            10930               10935

Lys Glu   Leu Thr Phe Val Asp   Met Cys Asn Tyr Thr   Ser Cys Cys
   10940            10945               10950

-continued

```
Cys Asn   Asn Lys Asp Ser Thr   Gly Trp Asn Cys Leu   Val Glu Ala
    10955             10960               10965

Val Asn   Ser Tyr Thr Cys Val   Pro Phe Cys Cys Cys   Tyr Phe Leu
    10970             10975               10980

Phe Asn   Asn Thr Cys Ser Cys   His Val Thr Tyr Leu   Phe Lys Asn
    10985             10990               10995

His Arg   Ile Gln Gly Tyr Trp   Trp Cys His Ser His   Ser Ile Tyr
    11000             11005               11010

Arg Tyr   Leu Phe Cys Gln Thr   Cys Phe His Met Val   Pro Ala Trp
    11015             11020               11025

Trp Leu   Tyr Gln Ser Leu Pro   Ile Asp Cys Cys Ser   His Asn Lys
    11030             11035               11040

Arg Ser   Gly Phe Cys Arg Ala   Trp Phe Ala Trp His   Asp Ile Thr
    11045             11050               11055

His Asn   Trp Leu Phe Ala Phe   Leu Thr Ser Phe Cys   Ser Trp His
    11060             11065               11070

Leu Leu   His Thr Ile Lys Thr   Tyr Arg Val His Leu   Cys Asn Ile
    11075             11080               11085

Ser Leu   Cys Phe Gly Cys Met   Tyr Asn Phe Arg Cys   Phe Trp Ala
    11090             11095               11100

Ser Thr   Ile Leu Leu Tyr Gln   Cys Thr Arg Arg Phe   Cys Cys Leu
    11105             11110               11115

Lys Phe   Thr Pro His Thr Leu   Cys Ala His Gly Trp   Leu Tyr Tyr
    11120             11125               11130

Ser Ile   Ser His Leu Pro Arg   Phe Cys Ser Gly Asn   Asn Phe Phe
    11135             11140               11145

Val Leu   Ala Arg His Leu Lys   Ile Arg Ser Trp Cys   Leu Cys Ile
    11150             11155               11160

Tyr Trp   Met Gly Thr Gln Leu   Leu Gln Ile Phe Thr   Arg Ser Phe
    11165             11170               11175

Leu Trp   Cys Arg Cys Cys Lys   Phe Thr Tyr Tyr Val   Tyr Thr Thr
    11180             11185               11190

Asn Ser   Thr Tyr Trp Cys Phe   Gly His Ile Ser Ile   Tyr Ser Ser
    11195             11200               11205

Trp Trp   Tyr Cys Ser Tyr Arg   Ser Asn Met Pro Cys   Leu Leu Phe
    11210             11215               11220

Tyr Glu   Val Lys Ser Phe Trp   Ile Gln Ser Cys Ser   Cys Leu Tyr
    11225             11230               11235

Phe Thr   Ile Pro Tyr Val Ile   His Cys Thr Leu Phe   Asn Thr Ser
    11240             11245               11250

Leu Leu   Ile Leu Thr Trp Cys   Leu Phe Cys Tyr Leu   Leu Val Leu
    11255             11260               11265

Asp Ile   Leu Ser Tyr Cys Phe   Phe Phe Ser Thr Tyr   Ser Val Asp
    11270             11275               11280

Gly Tyr   Val His Thr Phe Ser   Thr Phe Leu Asp Asn   Asn Cys Leu
    11285             11290               11295

Tyr His   Leu Tyr Phe His Lys   Ala Phe Leu Leu Val   Leu Leu Pro
    11300             11305               11310

Lys Glu   Thr Cys Ser Leu Trp   Cys Phe Leu Tyr Phe   Arg Ser Cys
    11315             11320               11325

Ala Val   His Leu Phe Val Lys   Arg Asn Val Ser Lys   Val Ala Cys
    11330             11335               11340

Ala Ile   Thr Ser Tyr Ala Ile   Ile Leu Ser Ser Leu   Val Gln Val
```

-continued

```
          11345              11350              11355

Phe Trp  Ser Asn Gly Tyr Asn  Leu Gln Arg Ser Cys  Leu Leu Ser
    11360              11365              11370

Ser Arg  Lys Gly Ser Gln Leu  Gln Leu Arg Phe Cys  Ser Leu Pro
    11375              11380              11385

Thr Thr  Thr Asn Leu Tyr His  Leu Ser Cys Phe Ala  Glu Trp Phe
    11390              11395              11400

Lys Asn  Gly Ile Pro Ile Trp  Ser Gly Leu Tyr Gly  Thr Ser Asn
    11405              11410              11415

Leu Trp  Tyr Asn Tyr Thr Arg  Ser Leu Ala Arg Ser  Leu Leu Ser
    11420              11425              11430

Lys Thr  Cys Asp Leu His Leu  Arg His Ala Pro Leu  Arg Phe Thr
    11435              11440              11445

His Ser  Val Ser Phe Leu Gly  Thr Gly Trp Cys Ser  Thr Gln Gly
    11450              11455              11460

Tyr Trp  Thr Phe Tyr Ala Lys  Leu Cys Thr Ala Gly  Tyr Ser Gln
    11465              11470              11475

Ser Asp  Thr Val Val Cys Ser  His Ser Thr Arg Thr  Asp Phe Phe
    11480              11485              11490

Ser Val  Ser Leu Leu Gln Trp  Phe Thr Ile Trp Cys  Leu Pro Met
    11495              11500              11505

Cys Tyr  Glu Ala Gln Phe His  Tyr Gly Phe Ile Pro  Trp Phe Met
    11510              11515              11520

Trp Cys  Trp Phe His Arg Leu  Leu Cys Leu Phe Leu  Leu His Ala
    11525              11530              11535

Pro Tyr  Gly Ile Thr Asn Trp  Ser Ser Cys Trp His  Arg Leu Arg
    11540              11545              11550

Arg Leu  Leu Trp Thr Phe Cys  Gln Ala Asn Ser Thr  Ser Ser Trp
    11555              11560              11565

Tyr Gly  His Asn Tyr Tyr Ser  Cys Phe Ser Leu Val  Val Arg Cys
    11570              11575              11580

Cys Tyr  Lys Trp Arg Gln Val  Val Ser Gln Ser Ile  Tyr His Asn
    11585              11590              11595

Ser Leu  Pro Cys Gly Tyr Glu  Val Gln Leu Thr Ser  Asn Thr Arg
    11600              11605              11610

Pro Cys  His Thr Arg Thr Ser  Phe Cys Ser Asn Trp  Asn Cys Arg
    11615              11620              11625

Phe Arg  Tyr Val Cys Phe Ile  Lys Arg Ile Thr Ala  Lys Trp Tyr
    11630              11635              11640

Glu Trp  Thr Tyr His Ile Gly  Cys Phe Ile Arg Arg  Ile Tyr Thr
    11645              11650              11655

Phe Cys  Cys Thr Met Leu Arg  Cys Tyr Phe Pro Lys  Cys Ser Glu
    11660              11665              11670

Lys Asn  Asn Gln Gly Tyr Thr  Pro Leu Val Val Thr  His Asn Phe
    11675              11680              11685

Asp Phe  Thr Phe Ser Phe Ser  Pro Glu Tyr Ser Met  Val Phe Val
    11690              11695              11700

Leu Phe  Phe Val Lys Cys Leu  Phe Thr Phe Cys Tyr  Gly Tyr Tyr
    11705              11710              11715

Cys Tyr  Val Cys Phe Cys Asn  Asp Val Cys Gln Thr  Ala Cys Ile
    11720              11725              11730

Ser Leu  Phe Val Phe Val Thr  Phe Ser Cys His Cys  Ser Leu Phe
    11735              11740              11745
```

-continued

```
Tyr Gly   Leu Tyr Ala Cys Leu   Gly Asp Ala Tyr Tyr   Asp Met Val
    11750             11755               11760

Gly Tyr   Gly Tyr Phe Val Trp   Phe Ala Lys Arg Leu   Cys Tyr Val
    11765             11770               11775

Cys Ile   Ser Cys Ser Val Thr   Asn Pro Tyr Asp Ser   Lys Asn Cys
    11780             11785               11790

Val Trp   Cys Glu Ser Val Asp   Thr Tyr Glu Cys Leu   Asp Thr Arg
    11795             11800               11805

Leu Ser   Leu Leu Trp Cys Phe   Arg Ser Ser His Phe   His Val Gly
    11810             11815               11820

Ser Tyr   Asn Leu Cys Tyr Phe   Leu Leu Arg Cys Ser   Tyr Asn Cys
    11825             11830               11835

His Val   Phe Gly Gln Arg Tyr   Cys Phe Tyr Val Cys   Val Leu Pro
    11840             11845               11850

Tyr Phe   Leu His Asn Trp Tyr   Thr Ser Val Tyr Asn   Ala Ser Leu
    11855             11860               11865

Leu Phe   Leu Arg Leu Phe Leu   Tyr Leu Leu Leu Trp   Pro Leu Leu
    11870             11875               11880

Phe Thr   Gln Pro Leu Leu Thr   Asp Ser Trp Cys Leu   Leu Leu Ser
    11885             11890               11895

Phe Tyr   Thr Gly Val Ile Tyr   Glu Phe Thr Gly Thr   Thr Pro Thr
    11900             11905               11910

Gln Glu   His Arg Cys Leu Gln   Thr Gln His Ile Val   Gly Cys Trp
    11915             11920               11925

Trp Gln   Thr Leu Tyr Gln Ser   Ser His Cys Thr Val   Asn Val Arg
    11930             11935               11940

Cys Lys   Val His Ile Ser Ser   Leu Thr Leu Ser Phe   Ala Thr Thr
    11945             11950               11955

Gln Ser   Arg Ile Ile Ile Ile   Val Gly Ser Met Cys   Pro Val Thr
    11960             11965               11970

Gln His   Ser Leu Ser Arg Tyr   Tyr Ser Leu Lys Asn   Gly Phe Thr
    11975             11980               11985

Thr Phe   Cys Phe Ala Phe His   Ala Gly Cys Cys Arg   His Lys Gln
    11990             11995               12000

Ala Leu   Arg Asn Ala Gly Gln   Gln Gly Asn Leu Thr   Ser Tyr Ser
    12005             12010               12015

Leu Arg   Val Phe Pro Ser Ile   Ile Cys Ser Phe Cys   Tyr Cys Ser
    12020             12025               12030

Arg Ser   Leu Ala Gly Cys Cys   Trp Phe Ser Cys Ser   Lys Val Glu
    12035             12040               12045

Glu Val   Phe Glu Cys Gly Ile   Ile Pro Cys Ser His   Ala Thr Val
    12050             12055               12060

Gly Lys   Asp Gly Ser Ser Tyr   Asp Pro Asn Val Thr   Gly Ile Gly
    12065             12070               12075

Gln Glu   Gly Lys Ser Tyr Cys   Tyr Ala Asp Asn Ala   Phe His Tyr
    12080             12085               12090

Ala Lys   Val Gly Cys Thr Gln   Gln His Tyr Gln Gln   Cys Lys Arg
    12095             12100               12105

Trp Leu   Cys Ser Leu Glu His   Asn Thr Ser Tyr Asn   Ser Ser Gln
    12110             12115               12120

Thr Asn   Gly Cys His Thr Arg   Leu His Ile Lys Tyr   Val Trp Tyr
    12125             12130               12135
```

-continued

```
Asn Ile  Tyr Leu Cys Ile Ser  Ile Val Gly Asn Pro  Thr Gly Cys
    12140                 12145             12150

Arg Cys  Arg Asn Cys Ser Thr  Asn Tyr Gly Gln Phe  Thr Phe Ser
    12155                 12160             12165

Met Ala  Ser Tyr Cys Asn Ser  Phe Lys Gly Gln Phe  Cys Cys Gln
    12170                 12175             12180

Ile Thr  Glu Ala Ser Cys Cys  Thr Thr Thr Asp Val  Leu Cys Cys
    12185                 12190             12195

Arg Tyr  Tyr Thr Asn Cys Leu  His Gln Cys Val Ser  Leu Leu Gln
    12200                 12205             12210

His Asn  Lys Gly Arg Val Cys  Thr Cys Thr Val Ile  Arg Phe Thr
    12215                 12220             12225

Gly Phe  Glu Met Gly Ile Pro  Glu Trp Asn Trp Tyr  Tyr Leu Tyr
    12230                 12235             12240

Arg Thr  Gly Thr Thr Leu Val  Cys Tyr Arg His Thr  Arg Ser Ser
    12245                 12250             12255

Glu Val  Phe Ile Leu Tyr Arg  Ile Lys Gln Pro Lys  Arg Tyr Gly
    12260                 12265             12270

Thr Trp  Phe Ser Cys His Ser  Thr Ser Thr Ser Trp  Cys Asn Arg
    12275                 12280             12285

Ser Ala  Cys Gln Phe Asn Cys  Ile Ile Phe Leu Cys  Phe Cys Cys
    12290                 12295             12300

Arg Cys  Cys Ser Leu Gln Arg  Leu Ser Ser Trp Gly  Thr Thr Asn
    12305                 12310             12315

His Leu  Cys Asp Val Val Tyr  Thr His Trp Tyr Trp  Ser Gly Asn
    12320                 12325             12330

Asn Ser  Tyr Thr Gly Ser Gln  Tyr Gly Ser Arg Ile  Leu Trp Trp
    12335                 12340             12345

Cys Ile  Val Leu Ser Val Leu  Pro Leu Pro His Arg  Ser Ser Lys
    12350                 12355             12360

Ser Arg  Ile Leu Leu Lys Arg  Val Cys Thr Asn Thr  Tyr Asn Leu
    12365                 12370             12375

Cys Pro  Cys Gly Phe Tyr Thr  Lys His Ser Leu Tyr  Arg Leu Arg
    12380                 12385             12390

Tyr Val  Glu Arg Leu Trp Leu  Leu Ser Thr Pro Arg  Thr His Ala
    12395                 12400             12405

Ser Val  Ser Cys Thr Ile Val  Phe Lys Arg Val Cys  Gly Val
    12410                 12415             12420
```

```
<210> SEQ ID NO 16
<211> LENGTH: 13218
<212> TYPE: DNA
<213> ORGANISM: Severe acute respiratory syndrome coronavirus 2

<400> SEQUENCE: 16
atggagagcc ttgtccctgg tttcaacgag aaaacacacg tccaactcag tttgcctgtt      60
ttacaggttc gcgacgtgct cgtacgtggc tttggagact ccgtggagga ggtcttatca     120
gaggcacgtc aacatcttaa agatggcact tgtggcttag tagaagttga aaaaggcgtt     180
ttgcctcaac ttgaacagcc ctatgtgttc atcaaacgtt cggatgctcg aactgcacct     240
catggtcatg ttatggttga ctggtagca gaactcgaag gcattcagta cggtcgtagt     300
ggtgagacac ttggtgtcct tgtccctcat gtgggcgaaa taccagtggc ttaccgcaag     360
gttcttcttc gtaagaacgg taataaagga gctggtggcc atagttacgg cgccgatcta     420
```

-continued

```
aagtcatttg acttaggcga cgagcttggc actgatcctt atgaagattt tcaagaaaac   480
tggaacacta aacatagcag tggtgttacc cgtgaactca tgcgtgagct taacggaggg   540
gcatacactc gctatgtcga taacaacttc tgtggccctg atggctaccc tcttgagtgc   600
attaaagacc ttctagcacg tgctggtaaa gcttcatgca cttttgtccga acaactggac   660 tttattgaca ctaagagggg tgtatactgc tgccgtgaac atgagcatga aattgcttgg   720
tacacggaac gttctgaaaa gagctatgaa ttgcagacac cttttgaaat taaattggca   780
aagaaatttg acaccttcaa tggggaatgt ccaaattttg tatttccctt aaattccata   840
atcaagacta ttcaaccaag ggttgaaaag aaaaagcttg atggctttat gggtagaatt   900
cgatctgtct atccagttgc gtcaccaaat gaatgcaacc aaatgtgcct ttcaactctc   960
atgaagtgtg atcattgtgg tgaaacttca tggcagacgg gcgattttgt taaagccact  1020
tgcgaatttt gtggcactga gaatttgact aaagaaggtg ccactacttg tggttactta  1080
ccccaaaatg ctgttgttaa aatttattgt ccagcatgtc acaattcaga agtaggacct  1140
gagcatagtc ttgccgaata ccataatgaa tctggcttga aaaccattct tcgtaagggt  1200
ggtcgcacta ttgcctttgg aggctgtgtg ttctcttatg ttggttgcca taacaagtgt  1260
gcctattggg ttccacgtgc tagcgctaac ataggttgta accatacagg tgttgttgga  1320
gaaggttccg aagtgtcttaa tgacaacctt cttgaaatac tccaaaaaga gaaagtcaac  1380
atcaatattg ttggtgactt taaacttaat gaagagatcg ccattatttt ggcatctttt  1440
tctgcttcca caagtgcttt tgtggaaact gtgaaaggtt tggattataa agcattcaaa  1500
caaattgttg aatcctgtgg taattttaaa gttacaaaag gaaagctaa aaaaggtgcc  1560 tggaatattg gtgaacagaa atcaatactg agtcctcttt atgcatttgc atcagaggct  1620
gctcgtgttg tacgatcaat tttctcccgc actcttgaaa ctgctcaaaa ttctgtgcgt  1680
gttttacaga aggccgctat aacaatacta gatggaattt cacagtattc actgagactc  1740
attgatgcta tgatgttcac atctgatttg gctactaaca atctagttgt aatggcctac  1800
attacaggtg gtgttgttca gttgacttcg cagtggctaa ctaacatctt tggcactgtt  1860
tatgaaaaac tcaaacccgt ccttgattgg cttgaagaga gtttaaggaa ggtgtagag  1920 tttcttagag acggttggga aattgttaaa tttatctcaa cctgtgcttg tgaaattgtc  1980
ggtggacaaa ttgtcacctg tgcaaaggaa attaaggaga gtgttcagac attctttaag  2040
cttgtaaata aattttttggc tttgtgtgct gactctatca ttattggtgg agctaaactt  2100
aaagccttga atttaggtga aacatttgtc acgcactcaa agggattgta cagaaagtgt  2160
gttaaatcca gagaagaaac tggcctactc atgcctctaa aagccccaaa agaaattatc  2220
ttcttagagg gagaaacact tcccacagaa gtgttaacag aggaagttgt cttgaaaact  2280
ggtgatttac aaccattaga caacctact agtgaagctg ttgaagctcc attggttggt  2340
acaccagttt gtattaacgg gcttatgttg ctcgaaatca aagacacaga aaagtactgt  2400
gcccttgcac ctaatatgat ggtaacaaac aatacccttca cactcaaagg cggtgcacca  2460
acaaaggtta cttttggtga tgacactgtg atagaagtgc aaggttacaa gagtgtgaat  2520 atcactttg aacttgatga aaggattgat aaagtactta atgagaagtg ctctgcctat  2580
acagttgaac tcggtacaga agtaaatgag ttcgcctgtg ttgtggcaga tgctgtcata  2640
aaaactttgc aaccagtatc tgaattactt acaccactgg gcattgattt agatgagtgg  2700
agtatggcta catactactt atttgatgag tctggtgagt ttaaattggc ttcacatatg  2760
tattgttctt ctaccctcc agatgaggat gaagaagaag gtgattgtga agaagaagag  2820
```

-continued

```
tttgagccat caactcaata tgagtatggt actgaagatg attaccaagg taaacctttg      2880
gaatttggtg ccacttctgc tgctcttcaa cctgaagaag agcaagaaga agattggtta      2940
gatgatgata gtcaacaaac tgttggtcaa caagacggca gtgaggacaa tcagacaact      3000
actattcaaa caattgttga ggttcaacct caattagaga tggaacttac accagttgtt      3060
cagactattg aagtgaatag ttttagtggt tatttaaaac ttactgacaa tgtatacatt      3120
aaaaatgcag acattgtgga agaagctaaa aaggtaaaac caacagtggt tgttaatgca      3180
gccaatgttt accttaaaca tggaggaggt gttgcaggag ccttaaataa ggctactaac      3240
aatgccatgc aagttgaatc tgatgattac atagctacta atggaccact taaagtgggt      3300
ggtagttgtg tttttaagcgg acacaatctt gctaaacact gtcttcatgt tgtcggccca      3360
aatgttaaca aaggtgaaga cattcaactt cttaagagtg cttatgaaaa ttttaatcag      3420
cacgaagttc tacttgcacc attattatca gctggtattt ttggtgctga ccctatacat      3480
tctttaagag tttgtgtaga tactgttcgc acaaatgtct acttagctgt ctttgataaa      3540
aatctctatg acaaacttgt ttcaagcttt ttggaaatga agagtgaaaa gcaagttgaa      3600
caaaagatcg ctgagattcc taaagaggaa gttaagccat ttataactga agtaaacct      3660 tcagttgaac agagaaaaca agatgataag aaaatcaaag cttgtgttga agaagttaca      3720
acaactctgg aagaaactaa gttcctcaca gaaaacttgt tactttatat tgacattaat      3780
ggcaatcttc atccagattc tgccactctt gttagtgaca ttgacatcac tttcttaaag      3840
aaagatgctc catatatagt gggtgatgtt gttcaagagg gtgtttttaac tgctgtggtt      3900 atacctacta aaaaggctgg tggcactact gaaatgctag cgaaagcttt gagaaaagtg      3960
ccaacagaca attatataac cacttacccg ggtcagggtt taaatggtta cactgtagag      4020
gaggcaaaga cagtgcttaa aaagtgtaaa agtgcctttt acattctacc atctattatc      4080
tctaatgaga agcaagaaat tcttggaact gtttcttgga atttgcgaga aatgcttgca      4140
catgcagaag aaacacgcaa attaatgcct gtctgtgtgg aaactaaagc catagtttca      4200
actatacagc gtaaatataa gggtattaaa atacaagagg gtgtggttga ttatggtgct      4260
agattttact tttacaccag taaaacaact gtagcgtcac ttatcaacac acttaacgat      4320
ctaaatgaaa ctcttgttac aatgccactt ggctatgtaa cacatggctt aaatttggaa      4380
gaagctgctc ggtatatgag atctctcaaa gtgccagcta cagtttctgt ttcttcacct      4440
gatgctgtta cagcgtataa tggttatctt acttcttctt ctaaaacacc tgaagaacat      4500
tttattgaaa ccatctcact tgctggttcc tataaagatt ggtcctattc tggacaatct      4560
acacaactag gtatagaatt tcttaagaga ggtgataaaa gtgtatatta cactagtaat      4620
cctaccacat tccacctaga tggtgaagtt atcacctttg acaatcttaa gacacttctt      4680
tctttgagag aagtgaggac tattaaggtg tttacaacag tagacaacat taacctccac      4740
acgcaagttg tggacatgtc aatgacatat ggacaacagt ttggtccaac ttatttggat      4800
ggagctgatg ttactaaaat aaaacctcat aattcacatg aaggtaaaac attttatgtt      4860
ttacctaatg atgacactct acgtgttgag gcttttgagt actaccacac aactgatcct      4920
agttttctgg gtaggtacat gtcagcatta aatcacacta aaaagtggaa atacccacaa      4980
gttaatggtt taacttctat taaatgggca gataacaact gttatcttgc cactgcattg      5040
ttaacactcc aacaaataga gttgaagttt aatccacctg ctctacaaga tgcttattac      5100
agagcaaggg ctggtgaagc tgctaacttt tgtgcactta tcttagccta ctgtaataag      5160
```

-continued

```
acagtaggtg agttaggtga tgttagagaa acaatgagtt acttgtttca acatgccaat      5220
ttagattctt gcaaaagagt cttgaacgtg gtgtgtaaaa cttgtggaca acagcagaca      5280
acccttaagg gtgtagaagc tgttatgtac atgggcacac tttcttatga acaatttaag      5340
aaaggtgttc agataccttg tacgtgtggt aaacaagcta caaaatatct agtacaacag      5400
gagtcacctt ttgttatgat gtcagcacca cctgctcagt atgaacttaa gcatggtaca      5460
tttacttgtg ctagtgagta cactggtaat taccagtgtg gtcactataa acatataact      5520
tctaaagaaa ctttgtattg catagacggt gctttactta caaagtcctc agaatacaaa      5580
ggtcctatta cggatgtttt ctacaaagaa aacagttaca caacaaccat aaaaccagtt      5640
acttataaat tggatggtgt tgtttgtaca gaaattgacc ctaagttgga caattattat      5700
aagaaagaca attcttattt cacagagcaa ccaattgatc ttgtaccaaa ccaaccatat      5760
ccaaacgcaa gcttcgataa tttaagttt gtatgtgata atatcaaatt tgctgatgat      5820
ttaaaccagt taactggtta taagaaacct gcttcaagag agcttaaagt tacattttc      5880 cctgacttaa atggtgatgt ggtggctatt gattataaac actacacacc ctctttaag      5940 aaaggagcta aattgttaca taaacctatt gtttggcatg ttaacaatgc aactaataaa      6000
gccacgtata aaccaaatac ctggtgtata cgttgtcttt ggagcacaaa accagttgaa      6060
acatcaaatt cgtttgatgt actgaagtca gaggacgcgc agggaatgga taatcttgcc      6120
tgcgaagatc taaaaccagt ctctgaagaa gtagtggaaa atcctaccat acagaaagac      6180
gttcttgagt gtaatgtgaa aactaccgaa gttgtaggag acattatact taaaccagca      6240
aataatagtt taaaaattac agaagaggtt ggccacacag atctaatggc tgcttatgta      6300
gacaattcta gtcttactat taagaaacct aatgaattat ctagagtatt aggtttgaaa      6360
acccttgcta ctcatggttt agctgctgtt aatagtgtcc cttgggatac tatagctaat      6420
tatgctaagc ctttcttaa caaagttgtt agtacaacta ctaacatagt tacacggtgt      6480
ttaaaccgtg tttgtactaa ttatatgcct tatttcttta ctttattgct acaattgtgt      6540
actttactta gaagtacaaa ttctagaatt aaagcatcta tgccgactac tatagcaaag      6600
aatactgtta agagtgtcgg taaatttgt ctagaggctt catttaatta tttgaagtca      6660 cctaatttt ctaaactgat aaatattata atttggtttt tactattaag tgtttgccta      6720
ggttctttaa tctactcaac cgctgcttta ggtgttttaa tgtctaattt aggcatgcct      6780
tcttactgta ctggttacag agaaggctat ttgaactcta ctaatgtcac tattgcaacc      6840
tactgtactg gttctatacc ttgtagtgtt tgtcttagtg gtttagattc tttagacacc      6900
tatccttctt tagaaactat acaaattacc atttcatctt ttaaatggga tttaactgct      6960
tttggcttag ttgcagagtg gttttttggca tatattcttt tcactaggtt ttttctatgta      7020 cttggattgg ctgcaatcat gcaattgttt ttcagctatt ttgcagtaca ttttattagt      7080
aattcttggc ttatgtggtt aataattaat cttgtacaaa tggccccgat ttcagctatg      7140
gttagaatgt acatcttctt tgcatcattt tattatgtat ggaaaagtta tgtgcatgtt      7200
gtagacggtt gtaattcatc aacttgtatg atgtgttaca acgtaatag agcaacaaga      7260 gtcgaatgta caactattgt taatggtgtt agaaggtcct tttatgtcta tgctaatgga      7320
ggtaaaggct tttgcaaact acacaattgg aattgtgtta attgtgatac attctgtgct      7380
ggtagtacat ttattagtga tgaagttgcg agagacttgt cactacagtt taaaagacca      7440
ataaatccta ctgaccagtc ttcttacatc gttgatagtg ttacagtgaa gaatggttcc      7500
atccatcttt actttgataa agctggtcaa aagacttatg aaagacattc tctctctcat      7560
```

-continued

```
tttgttaact tagacaacct gagagctaat aacactaaag gttcattgcc tattaatgtt      7620
atagtttttg atggtaaatc aaaatgtgaa gaatcatctg caaaatcagc gtctgtttac      7680
tacagtcagc ttatgtgtca acctatactg ttactagatc aggcattagt gtctgatgtt      7740
ggtgatagtg cggaagttgc agttaaaatg tttgatgctt acgttaatac gttttcatca      7800
acttttaacg taccaatgga aaaactcaaa acactagttg caactgcaga agctgaactt      7860
gcaaagaatg tgtccttaga caatgtctta tctactttta tttcagcagc tcggcaaggg      7920
tttgttgatt cagatgtaga aactaaagat gttgttgaat gtcttaaatt gtcacatcaa      7980
tctgacatag aagttactgg cgatagttgt aataactata tgctcaccta taacaaagtt      8040
gaaaacatga caccccgtga ccttggtgct tgtattgact gtagtgcgcg tcatattaat      8100
gcgcaggtag caaaaagtca caacattgct ttgatatgga acgttaaaga tttcatgtca      8160
ttgtctgaac aactacgaaa acaaatacgt agtgctgcta aaaagaataa cttacctttt      8220
aagttgacat gtgcaactac tagacaagtt gttaatgttg taacaacaaa gatagcactt      8280
aagggtggta aaattgttaa taattggttg aagcagttaa ttaaagttac acttgtgttc      8340
ctttttgttg ctgctatttt ctatttaata acacctgttc atgtcatgtc taaacatact      8400
gacttttcaa gtgaaatcat aggatacaag gctattgatg gtggtgtcac tcgtgacata      8460
gcatctacag atacttgttt tgctaacaaa catgctgatt ttgacacatg gtttagccag      8520
cgtggtggta gttatactaa tgacaaagct tgcccattga ttgctgcagt cataacaaga      8580 gaagtggggtt ttgtcgtgcc tggtttgcct ggcacgatat tacgcacaac taatggtgac      8640
tttttgcatt tcttacctag agtttttagt gcagttggta acatctgtta cacaccatca      8700
aaacttatag agtacactga ctttgcaaca tcagcttgtg ttttggctgc tgaatgtaca      8760 attttttaaag atgcttctgg taagccagta ccatattgtt atgataccaa tgtactagaa      8820
ggttctgttg cttatgaaag tttacgccct gacacacgtt atgtgctcat ggatggctct      8880
attattcaat ttcctaacac ctaccttgaa ggttctgtta gagtggtaac aactttttgat      8940 tctgagtact gtaggcacgg cacttgtgaa agatcagaag ctggtgtttg tgtatctact      9000
agtggtagat gggtacttaa caatgattat tacagatctt taccaggagt tttctgtggt      9060
gtagatgctg taaatttact tactaatatg tttacaccac taattcaacc tattggtgct      9120
ttggacatat cagcatctat agtagctggt ggtattgtag ctatcgtagt aacatgcctt      9180
gcctactatt ttatgaggtt tagaagagct tttggtgaat acagtcatgt agttgccttt      9240
aatactttac tattccttat gtcattcact gtactctgtt taacaccagt ttactcattc      9300
ttacctggtg tttattctgt tatttacttg tacttgacat tttatcttac taatgatgtt      9360
tcttttttag cacatattca gtggatggt atgttcacac ctttagtacc tttctggata      9420
acaattgctt atatcatttg tatttccaca aagcatttct attggttctt tagtaattac      9480
ctaaagagac gtgtagtctt taatggtgtt tcctttagta cttttgaaga agctgcgctg      9540
tgcacctttt tgttaaataa agaaatgtat ctaaagttgc gtagtgatgt gctattacct      9600
cttacgcaat ataatagata cttagctctt tataataagt acaagtattt tagtggagca      9660
atggatacaa ctagctacag agaagctgct tgttgtcatc tcgcaaaggc tctcaatgac      9720
ttcagtaact caggttctga tgttctttac caaccaccac aaacctctat cacctcagct      9780
gttttgcaga gtggtttag aaaaatggca ttcccatctg gtaaagttga gggttgtatg      9840
gtacaagtaa cttgtggtac aactacactt aacggtcttt ggcttgatga cgtagtttac      9900
```

-continued

```
tgtccaagac atgtgatctg cacctctgaa gacatgctta accctaatta tgaagattta      9960
ctcattcgta agtctaatca taatttcttg gtacaggctg gtaatgttca actcagggtt     10020
attggacatt ctatgcaaaa ttgtgtactt aagcttaagg ttgatacagc caatcctaag     10080
acacctaagt ataagtttgt tcgcattcaa ccaggacaga ctttttcagt gttagcttgt     10140
tacaatggtt caccatctgg tgtttaccaa tgtgctatga ggcccaattt cactattaag     10200
ggttcattcc ttaatggttc atgtggtagt gttggtttta acatagatta tgactgtgtc     10260
tctttttgtt acatgcacca tatggaatta ccaactggag ttcatgctgg cacagactta     10320
gaaggtaact tttatggacc ttttgttgac aggcaaacag cacaagcagc tggtacggac     10380
acaactatta cagttaatgt tttagcttgg ttgtacgctg ctgttataaa tggagacagg     10440
tggtttctca atcgatttac cacaactctt aatgacttta accttgtggc tatgaagtac     10500
aattatgaac ctctaacaca agaccatgtt gacatactag gacctctttc tgctcaaact     10560
ggaattgccg ttttagatat gtgtgcttca ttaaaagaat tactgcaaaa tggtatgaat     10620
ggacgtacca tattgggtag tgctttatta gaagatgaat ttacaccttt tgatgttgtt     10680
agacaatgct caggtgttac tttccaaagt gcagtgaaaa gaacaatcaa gggtacacac     10740
cactggttgt tactcacaat tttgacttca ctttttagttt tagtccagag tactcaatgg     10800
tctttgttct ttttttttgta tgaaaatgcc tttttacctt ttgctatggg tattattgct     10860
atgtctgctt ttgcaatgat gtttgtcaaa cataagcatg catttctctg tttgtttttg     10920
ttaccttctc ttgccactgt agcttatttt aatatggtct atatgcctgc tagttgggtg     10980
atgcgtatta tgacatggtt ggatatggtt gatactagtt tgtctggttt taagctaaaa     11040
gactgtgtta tgtatgcatc agctgtagtg ttactaatcc ttatgacagc aagaactgtg     11100
tatgatgatg gtgctaggag agtgtggaca cttatgaatg tcttgacact cgtttataaa     11160
gtttattatg gtaatgcttt agatcaagcc atttccatgt gggctcttat aatctctgtt     11220
acttctaact actcaggtgt agttacaact gtcatgtttt tggccagagg tattgttttt     11280
atgtgtgttg agtattgccc tatttttcttc ataactggta atacacttca gtgtataatg     11340
ctagtttatt gtttcttagg ctattttgt acttgttact ttggcctctt ttgtttactc     11400
aaccgctact ttagactgac tcttggtgtt tatgattact tagtttctac acaggagttt     11460
agatatatga attcacaggg actactccca cccaagaata gcatagatgc cttcaaactc     11520
aacattaaat tgttgggtgt tggtggcaaa ccttgtatca aagtagccac tgtacagtct     11580
aaaatgtcag atgtaaagtg cacatcagta gtcttactct cagttttgca acaactcaga     11640
gtagaatcat catctaaatt gtgggctcaa tgtgtccagt tacacaatga cattctctta     11700
gctaaagata ctactgaagc cttgaaaaa atggtttcac tactttctgt tttgctttcc     11760
atgcagggtg ctgtagacat aaacaagctt tgtgaagaaa tgctggacaa cagggcaacc     11820
ttacaagcta tagcctcaga gtttagttcc cttccatcat atgcagcttt tgctactgct     11880
caagaagctt atgagcaggc tgttgctaat ggtgattctg aagttgttct taaaaagttg     11940
aagaagtctt tgaatgtggc taaatctgaa tttgaccgtg atgcagccat gcaacgtaag     12000
ttggaaaaga tggctgatca agctatgacc caaatgtata acaggctag atctgaggac     12060 aagagggcaa aagttactag tgctatgcag acaatgcttt tcactatgct tagaaagttg     12120
gataatgatg cactcaacaa cattatcaac aatgcaagag atggttgtgt tccccttgaac     12180 ataatacctc ttacaacagc agccaaacta atggttgtca taccagacta taacacatat     12240
aaaaatacgt gtgatggtac aacatttact tatgcatcag cattgtggga aatccaacag     12300
```

-continued

```
gttgtagatg cagatagtaa aattgttcaa cttagtgaaa ttagtatgga caattcacct   12360
aatttagcat ggcctcttat tgtaacagct ttaagggcca attctgctgt caaattacag   12420
aataatgagc ttagtcctgt tgcactacga cagatgtctt gtgctgccgg tactacacaa   12480
actgcttgca ctgatgacaa tgcgttagct tactacaaca caacaaaggg aggtaggttt   12540
gtacttgcac tgttatccga tttacaggat ttgaaatggg ctagattccc taagagtgat   12600
ggaactggta ctatctatac agaactggaa ccaccttgta ggtttgttac agacacacct   12660
aaaggtccta aagtgaagta tttatacttt attaaaggat taaacaacct aaatagaggt   12720
atggtacttg gtagtttagc tgccacagta cgtctacaag ctggtaatgc aacagaagtg   12780
cctgccaatt caactgtatt atctttctgt gcttttgctg tagatgctgc taaagcttac   12840
aaagattatc tagctagtgg gggacaacca atcactaatt gtgttaagat gttgtgtaca   12900
cacactggta ctggtcaggc aataacagtt acaccggaag ccaatatgga tcaagaatcc   12960
tttggtggta catcgtgttg tctgtactgc cgttgccaca tagatcatcc aaatcctaaa   13020
ggattttgtg acttaaaagg taagtatgta caaataccta caacttgtgc taatgaccct   13080
gtgggtttta cacttaaaaa cacagtctgt accgtctgcg gtatgtggaa aggttatggc   13140
tgtagttgtg atcaactccg cgaacccatg cttcagtcag ctgatgcaca atcgttttta   13200
aacgggtttg cggtgtaa                                                  13218
```

SENSOR FOR DETECTING BIOMARKERS IN A FLUID SAMPLE AND METHODS OF USE

CROSS-REFERENCE TO RELATED APPLICATIONS

This application is a National Stage Entry of PCT Application No. PCT/US2022/032379, filed on Jun. 6, 2022, which is an International Application that claims priority from U.S. Provisional Application Ser. No. 63/196,814 filed on Jun. 4, 2021, the contents of each of which are incorporated herein by reference in their entireties.

STATEMENT OF GOVERNMENT SPONSORSHIP

N/A

REFERENCE TO A SEQUENCE LISTING

This application contains a Sequence Listing in computer readable form. The computer readable form is incorporated herein by reference. Said ASCII copy, created on Dec. 5, 2025, is named 2952332-000005-US2_SL.txt and is 248,295 bytes in size.

FIELD OF THE INVENTION

The invention relates to a sensor device for detection of biomarkers associated with a particular condition, disease, or disorder and methods of making and using the same. The invention further includes a diagnostic platform that employs the sensor device.

BACKGROUND OF THE INVENTION

Severe acute respiratory syndrome coronavirus 2 (SARS-CoV-2) leads to the infectious disease COVID-19, which was first reported in Wuhan, China in December 2019. The disease has since spread across the globe infecting over 200 countries. The lack of cheap, scalable, and rapid testing platform has contributed significantly to the spread of the diseases as countries struggle to identify patients and isolate them to prevent the wide spread of the disease before health care systems are overwhelmed. The problem is exacerbated by the presence of many asymptomatic infected patients. In the absence of proven antiviral drug therapies and vaccines, the current pandemic containment and mitigation strategy depends on isolation of the infected individuals and their close contacts in addition to social distancing through large scale lockdowns for the entire countries or communities. The latter has strained economies across the world, currently risks the availability of resources and has paralyzed the world in ways that will take years to recover from[5]. However, to mitigate the risk of having resurge in cases, increasing testing capacity and access is fundamental for the rapid identification and isolation of COVID-19 cases and containment of any new clusters.

SUMMARY OF THE INVENTION

Aspects of the invention are directed to a diagnostic platform for detection of at least one biomarker in a fluid sample. In embodiments, the diagnostic platform comprises a sensing device configured to receive the fluid sample. The platform can further comprise an electronic reading platform and a computing device. The electronic reading platform can be configured to activate the sensor. In embodiments, the sensing device comprises a layer of piezoelectric material comprising two faces; at least one electrode layer, wherein the at least one electrode layer is affixed to one face of the piezoelectric material; a second reference electrode layer that is affixed to a second face of the piezoelectric material; and a sensing layer disposed upon the electrode layer. In certain embodiments, the sensing layer is configured to bind the at least one biomarker for a disease or condition. The sensing device can be communicatively linked with the electronic reading platform, and the electronic reading platform can be configured to receive sensor data from the sensing device and to communicate the data to the computing device. The computing device is configured to determine the presence, absence, or amount of the at least one biomarker. The computing device can be integral with the electronic reading platform or external to the electronic reading platform.

In embodiments, the fluid sample comprises blood, saliva, nasal fluid, or a combination thereof. Certain embodiments comprise a fingerstick system configured to obtain the blood from a patient. The fingerstick system can be a belt-driven fingerstick system.

The diagnostic platform comprises a portable, hand-held device. In embodiments, the portable, hand-held device is configured to be worn by a user. The diagnostic platform configured to determine the presence, absence, or amount of the at least one biomarker within about 10 minutes after the fluid sample contacts the sensing device.

In certain embodiments, the piezoelectric material comprises a quartz crystal, PZT (lead zirconate titanate), lead titanate, Barium titanate, Zinc Oxide, lead magnesium niobate lead titanate (PMNPT), polyvinylidene difluoride, poly-vinylidene fluoride (PVDF), Aluminum nitride, Gallium nitride, or a combination thereof.

The piezoelectric material can comprise a diameter of at least about 1 mm. In embodiments, the piezoelectric material comprises a diameter of up to about 153 mm.

In certain embodiments, the piezoelectric material comprises a thickness of at least about 10 μm. The piezoelectric material can comprise a thickness of up to about 3 mm.

In embodiments, the electrode layer comprises at least one working electrode. The at least one working electrode comprises a conductive film. The conductive film comprises gold, indium tin oxide (ITO), or a combination thereof.

In certain embodiments, the at least one working electrode is greater than about 1 nm thick. The at least one working electrode comprise a thickness of between about 1 nm and 500 nm, inclusive. The at least one working electrode can comprise a diameter of at least 10 μm. In embodiments, the at least one working electrode comprises a diameter of up to 150 mm.

In certain embodiments, the sensing device comprises a thickness shear mode (TSM) transducer. The sensing device can comprise a disposable sensor cartridge. In embodiments, the sensing layer comprises an antigen or an antibody that is specific for the at least one biomarker.

In embodiments, the disease or condition is caused by a coronavirus. The disease or condition can comprise COVID-19, severe acute respiratory syndrome, middle-east respiratory syndrome (MERS), a tissue inflammation or a combination thereof. In certain embodiments, at least one biomarker comprises IgG antibodies, IgM antibodies, or a combination thereof.

The sensing device can comprise at least two disposable sensor cartridges. In embodiments, one of the at least two sensor cartridges comprises a means for detecting IgG antibodies in the fluid sample, and the other sensor cartridge comprises a means for detecting IgM antibodies in the fluid sample.

In embodiments, the sensing layer comprises a severe acute respiratory syndrome coronavirus 2 (SARS-CoV-2) structural protein or an antibody thereto immobilized on a surface of the at least one electrode layer, and IgG, IgM, or a combination thereof, wherein the IgG, IgM, or a combination thereof is tethered to the SARS-CoV-2 structural protein. The SARS-CoV-2 structural protein or the antibody thereto can be immobilized to the surface of the at least one electrode layer via a self-assembled monolayer (SAM). The SAM can comprise a streptavidin-biotin bond, a thiol-bond, or a combination thereof.

In certain embodiments, the SARS-CoV-2 structural protein comprises an S Protein, an N protein, an M protein, or a combination thereof.

In embodiments, the diagnostic platform can comprise at least one stabilizing solution that is configured to extend the shelf life of the diagnostic platform for up to at least 12 months.

The sensing device can be communicatively linked with the electronic reading platform via a USB connection. In embodiments, the computing device comprises a mobile computing device. In one embodiment, the diagnostic platform further comprises an application running on a processor of the mobile computing device, wherein the electronic reading platform is communicatively linked to the mobile computing device, and the electronic reading platform is configured to transmit sensor data to the mobile computing device. The electronic reading platform can be communicatively linked to the mobile computing device through one or more wireless communications protocols. The mobile computing device can comprise a portable digital assistant, a tablet, a smartphone, a laptop, or a combination thereof.

In another aspect, the invention comprises a method of predicting the existence or progression of a disease or condition or level of immunity in a patient. The method can comprise obtaining a fluid sample from the patient; placing the fluid sample on any of the various sensing device embodiments disclosed herein; permitting the diagnostic platform to determine the presence, absence, or amount of the at least one biomarker for the disease or condition; permitting the diagnostic platform to generate a sensor data report; reviewing the sensor data report; and predicting the presence or progression of the disease or condition. In embodiments, the method comprises two biomarkers, wherein the disease or condition comprises COVID-19, MERS, SARS, or a combination thereof; one of the two biomarkers comprises IgM antibodies and the remaining biomarker comprises IgG antibodies. In certain embodiments, the presence of IgM antibodies but not IgG antibodies indicates that the patient is in an intermediate stage of infection. The presence of IgG antibodies but not IgM antibodies can indicate that either the patient is in a late stage or an early stage of recurring infection or the patient is in a convalescent stage of infection. The presence of both IgM antibodies and IgG antibodies can indicate that either the patient is in a late phase of the infection, or the patient is in recovery stage of infection. In embodiments, the absence of IgG and IgM antibodies indicates that the patient does not have COVID-19.

In certain embodiments, the disease or condition comprises COVID-19, MERS, SARS, or a combination thereof. A first biomarker can comprise an S protein, a second biomarker can comprise an N protein, and a third biomarker can comprise an M protein, and the presence of any one or more of the biomarkers indicates the presence of the disease or condition.

BRIEF DESCRIPTION OF THE DRAWINGS

FIG. 2A shows an exploded version of the system under one embodiment. FIG. 2B provides a detailed view of a sensor cartridge under one embodiment. FIG. 2C provides a top view of the full system in this embodiment. As shown in FIG. 2D, the system can be integrated with a software application on a portable device. FIG. 2E provides an illustration of a wearable embodiment of the presently disclosed.

FIG. 3 panel B provides a close-up view of a micro TSM under an embodiment of the present invention. FIG. 3 panel C a graphical plot showing regions under each curve combinations of electrode thicknesses and diameters that will suppress inharmonic modes of vibration. FIG. 3 panel D provides a schematic example of various steps involved in immobilizing GABA on the surface for anti-GABA sensing using TSM. This shows experience four group in anti-body sensing and immobilization chemistry FIG. 3 panel E provides a calibration curve for detection of anti-GABA antibody in PBS buffer (chemistry in FIG. 3 panel D). Maximum sensitivity of sensor to anti-GABA antibody is determined as the slope (red line) at the midpoint. The sensing interface consists of SAM/dextran/GABA on a gold electrode. [2, 3]. The curve in FIG. 3 panel E is be fitted to the equation: $\Delta f = \Delta f0 + \Delta fmax/(1 + Keq/C)$, where C is concentration, Keq equilibrium association constant[2].

FIG. 4 panel B—EIS shows impact of PEDOT:PSS electrode diameter on electrode impedance and phase angle. FIG. 4 panel C provides a close-up view of 16 Ag/PEDOT:PSS electrode leads printed with 50 μm line width on Polycaprolactone (PCL) under one embodiment (Left). A close-up view of recording sites where AgNPs leads terminate with PEDOT:PSS electrodes of 50 μm (Right). In this embodiment, the leads are passivated with PCL (Right). A 16-electrode neural interface printed on Polyimide (PI). Closeup of AgNPs lead terminate with graphene/PEDOT:PSS and PEDOT:PSS-coated electrodes of 50 μm. The leads are passivated with PVPh (Middle). FIG. 4 panel D provides a schematic showing a fabrication schematic that can be utilized when employing inkjet devices.

Figure 1:
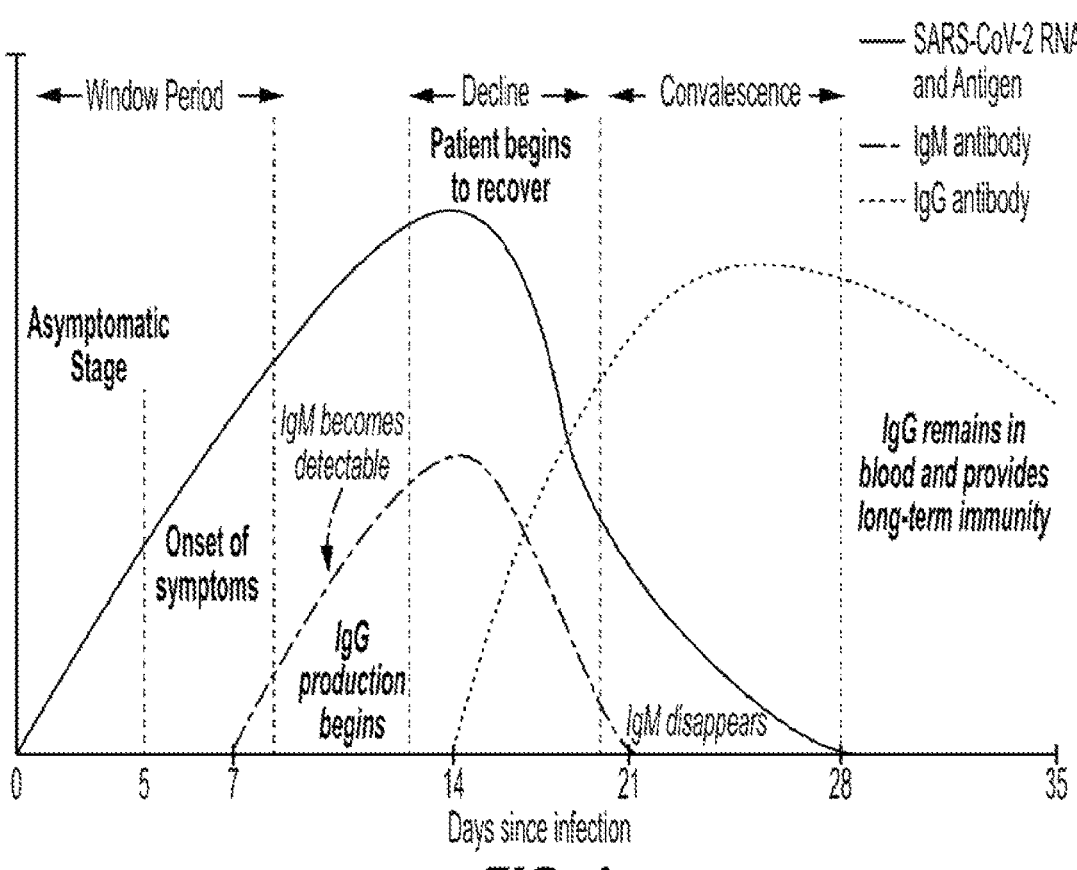
FIG. 1 shows a graphical representation of data collected from a literature survey showing the timeline of the COVID-19 with respect to the level of different known COVID-19 biomarkers.

Molecular adhesion to the gold electrodes on the quartz resonator causes a decrease in the resonant frequency of the resonator, in direct proportion to the mass of adhered molecules. We will use surface immobilization chemistry for Nucleocapsid (N-protein) and NSP5 proteins.

DETAILED DESCRIPTION OF THE INVENTION

The present invention relates to a sensor device for detection of biomarkers associated with a particular condition, disease, or disorder and methods of making and using the same. In embodiments, the invention comprises a highly sensitive diagnostic platform for rapid detection of seroprevalence of a disease or condition is caused by a coronavirus. The disease or condition can comprise COVID-19, severe acute respiratory syndrome, middle-east respiratory syndrome (MERS), a tissue inflammation or a combination thereof. The diagnostic platform can be configured to permit rapid detection of antigens of SARS-CoV-2.

Before the present disclosure is described in greater detail, it is to be understood that this disclosure is not limited to particular embodiments described, and as such can, of course, vary. It is also to be understood that the terminology used herein is for the purpose of describing particular embodiments only, and is not intended to be limiting.

The discussion of the background to the invention herein is included to explain the context of the present invention. This is not to be taken as an admission that any of the material referred to was published, known, or part of the common general knowledge in any country as of the priority date of any of the claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges can independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein can have the same meaning as commonly understood by one of ordinary skill in the art to which this disclosure belongs. Any methods and materials similar or equivalent to those described herein can also be used in the practice or testing of the present disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Abbreviations and Definitions

Detailed descriptions of one or more embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it can modify that range by extending the boundaries above and below the numerical values set forth. In general, the term "about" is used herein to modify a numerical value above and below the stated value by a variance of 20 percent up or down (higher or lower).

The terms "sufficient" and "effective", as used interchangeably herein, can refer to an amount (e.g. mass, volume, dosage, concentration, and/or time period) needed to achieve one or more desired result(s).

The term "administration" can refer to introducing a composition of the present disclosure into a subject. For example, one route of administration of the composition is intracranial administration. As another example, the composition can be administered by intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", and/or "treating" can refer to acting upon a condition (e.g., inflammation), a disease or a disorder with a composition to affect the condition (e.g., inflammation), disease or disorder by improving or altering it. The improvement or alteration can include an improvement in symptoms or an alteration in the physiologic pathways associated with the condition (e.g., inflammation), disease, or disorder. "Treatment" can refer to one or more treatments of the disease or condition in a subject (e.g., a mammal, typically a human or non-human animal of veterinary interest), and can include: (a) reducing the risk of occurrence in a subject determined to be predisposed to the condition or disease but not yet diagnosed with it (b) impeding the development of the condition or disease, and/or (c) relieving the condition or disease, e.g., causing regression of the condition or disease and/or relieving one or more condition or disease symptoms. As used herein, the terms "prophylactically treat" or "prophylactically treating" can refer to completely or partially preventing (e.g., about 50% or more, about 60% or more, about 70% or more, about 80% or more, about 90% or more, about 95% or more, or about 99% or more) a condition (e.g., condition or disease), a disease, or a symptom thereof and/or can be therapeutic in terms of a partial or complete cure for a condition (e.g., condition or disease), a disease, and/or adverse effect attributable to the disease.

As used herein, "therapeutic" can refer to curing or treating a symptom of a disease or condition.

As used herein, the term "subject," or "patient," can include humans and mammals (e.g., mice, rats, pigs, cats, dogs, and horses), and non-mammals (e.g., aves such as chickens etc.). Typical subjects to which compounds of the present disclosure can be administered will be mammals, particularly primates, especially humans. For veterinary applications, a wide variety of subjects will be suitable, non-limiting examples of which comprise livestock such as cattle, sheep, goats, cows, swine; poultry such as chickens, ducks, geese, turkeys; and domesticated animals particularly pets such as dogs and cats. For diagnostic or research applications, a wide variety of mammals can be suitable subjects, non-limiting examples of which comprise rodents (e.g., mice, rats, hamsters), rabbits, primates, and swine such as inbred pigs and the like. The term "living subject" can refer to a subject noted above or another organism that is alive.

As used herein, the term "fluid sample" can refer to a body fluid sample including, without limitation blood, plasma, cerebrospinal fluid, and other body fluids. The fluid sample can comprise a serologic sample. The body fluid sample can be diluted with, e.g., buffer or other reagents that facilitate handling. As used herein, the term "vapor sample" is intended to mean a sample containing a non-liquid component and optionally entrained liquid component. A preferred vapor sample is exhaled breath, which can be diluted with additional gas prior to detection or concentrated by removing certain components of the vapor sample. Both fluid samples and vapor samples can be used to detect the drug or metabolite concentration. As used herein, the term "sample" without further description is intended to encompass both fluid samples and vapor samples.

Before explaining at least one embodiment of the disclosure in detail, it is to be understood that the disclosure is not necessarily limited in its application to the details set forth in the following description or exemplified by the examples.

The disclosure is capable of other embodiments or of being practiced or carried out in various ways. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Accordingly, a first aspect of the present invention relates to a diagnostic platform for the detection of at least one biomarker in a fluid sample. In embodiments, the diagnostic platform comprises a sensing device and an electronic reading platform. Under certain embodiments, the sensing device comprises a layer of piezoelectric material, at least one electrode layer, a sensing layer, or a combination thereof. In embodiments, the sensing layer is disposed upon the electrode layer and is configured to bind at least one biomarker of a particular disease or condition.

In one embodiment, the diagnostic platform is configured to test for the serological prevalence of COVID-19.

Sensors

In various embodiments, the sensing device disclosed herein comprises an acoustic sensor configured to detect the presence of certain biomarkers of a disease or condition. In embodiments, the sensor comprises a piezoelectric material that operates as a transducer of a detection event. The piezoelectric material can comprise quartz crystals or any piezoelectric material known in the art. Exemplary piezoelectric material includes, but is not limited to, Sucrose (table sugar), Rochelle salt, Topaz, Tourmaline, Berlinite ($AlPO_4$), Barium titanate ($BaTiO_3$), Lead titanate ($PbTiO_3$), Lead zirconate titanate (PZT), Piezoelectric ceramic, Potassium niobate ($KNbO_3$), Lithium niobate ($LiNbO_3$), Lithium tantalate ($LiTaO_3$), Sodium tungstate ($NazWO_4$), Sodium potassium niobate (NaKNb), Bismuth ferrite ($BiFeO_3$), Sodium niobate ($NaNbO_3$), Collagen, Gallium orthophosphate ($GaPO_4$), Langasite ($La_3Ga_5SiO_{14}$), lead magnesium titanate-lead titanate (PMNPT), zinc Oxide, aluminum nitride (AlN), polyvinylidene difluoride, polyvinylidene fluoride (PVDF), or a combination thereof.

In certain embodiments, AT-cut quartz produces bulk transverse shear waves with particle displacements parallel to the surface of the crystal and its electrodes. The application of an electric field across the thickness of AT-cut quartz can lead to particle movement, which in turn results in two types of standing waves—a transverse wave in the thickness direction referred to as the thickness shear wave $TS_1$ and a wave traveling in the radial direction known as the thickness twist $TT_3$ wave. In one embodiment, the path length of $TS_1$ waves is the plate thickness with nodes along the diameter of the plate, while the path length for $TT_3$ is the electrode radius with concentric nodal lines along the center of the plate. When the length of the path is an integral number of wavelengths, a standing wave occurs and results in resonance [20]. The fundamental resonant frequency of AT-cut quartz is a result of the $TS_1$ standing wave and is a reliable and large wave of this type of acoustic systems. These AT-cut quartz oscillators can also be called thickness shear mode (TSM) resonator given the displacement direction. In operation, when a small mass, such as a biomarker for a particular disease or condition is deposited on the surface of a quartz crystal oscillator, the oscillator's resonance frequency decreases in direct proportion to the deposited mass as described by the classic Sauerbrey equation for sensitivity of the resonator, which is provided below as Equation 1:

$$\Delta f_o = \frac{2f_o^2}{(\rho_Q \mu_Q)^{1/2}} \frac{\Delta m}{A}$$

Wherein $f_o$ is the fundamental resonant frequency of the quartz crystal, A is the surface area of the electrode on top of the crystal, $\mu_Q$ and $\rho_Q$ are the shear modulus and the density of quartz. While m is the mass deposited on sensor.

As noted herein, the acoustic sensor is intended to be in contact with a fluid sample. As such, during use, the electrochemical sensor is intended to be exposed to a fluid sample. To facilitate exposure to the fluid sample, a fluid sample can be drawn from the patient and then exposed ex vivo to the sensor or sensing device. The sensor or sensor device according to any embodiment described herein is suitable for ex vivo detection of a biomarker for a particular disease or condition.

As discussed herein, the sensing device can comprise a sensing layer configured to bind at least one biomarker for a disease, infection, or condition. In embodiments, the sensing layer comprises a probe for detection of a biomarker, wherein the probe is immobilized, fixed, anchored, or otherwise tethered to a solid support. The probe can comprise a polypeptide, a polynucleotide, or a combination thereof. For example, in embodiments, the probe can be an antibody, an antibody fragment, an antigen (such as a portion of a viral spike protein or cell wall protein), or a fragment of antigen. The term "antibody fragment", as used herein, can be a portion of an antibody such as $F_{(ab')2}$, $F_{(ab)2}$, $F_{ab}'$, $F_{ab}$, Fv, scFv and the like. Non-limiting examples of antibody fragments that can be attached to a support include Fab, Fab' and F(ab')2, Fd, Fvs, single-chain Fvs (scFv), single-chain antibodies, dAb (domain antibody), minibodies, disulfide-linked Fvs (sdFv), fragments comprising either a VL or VH domain, fragments produced by a Fab expression library, and anti-idiotypic (anti-Id) antibodies.

Figure 5:
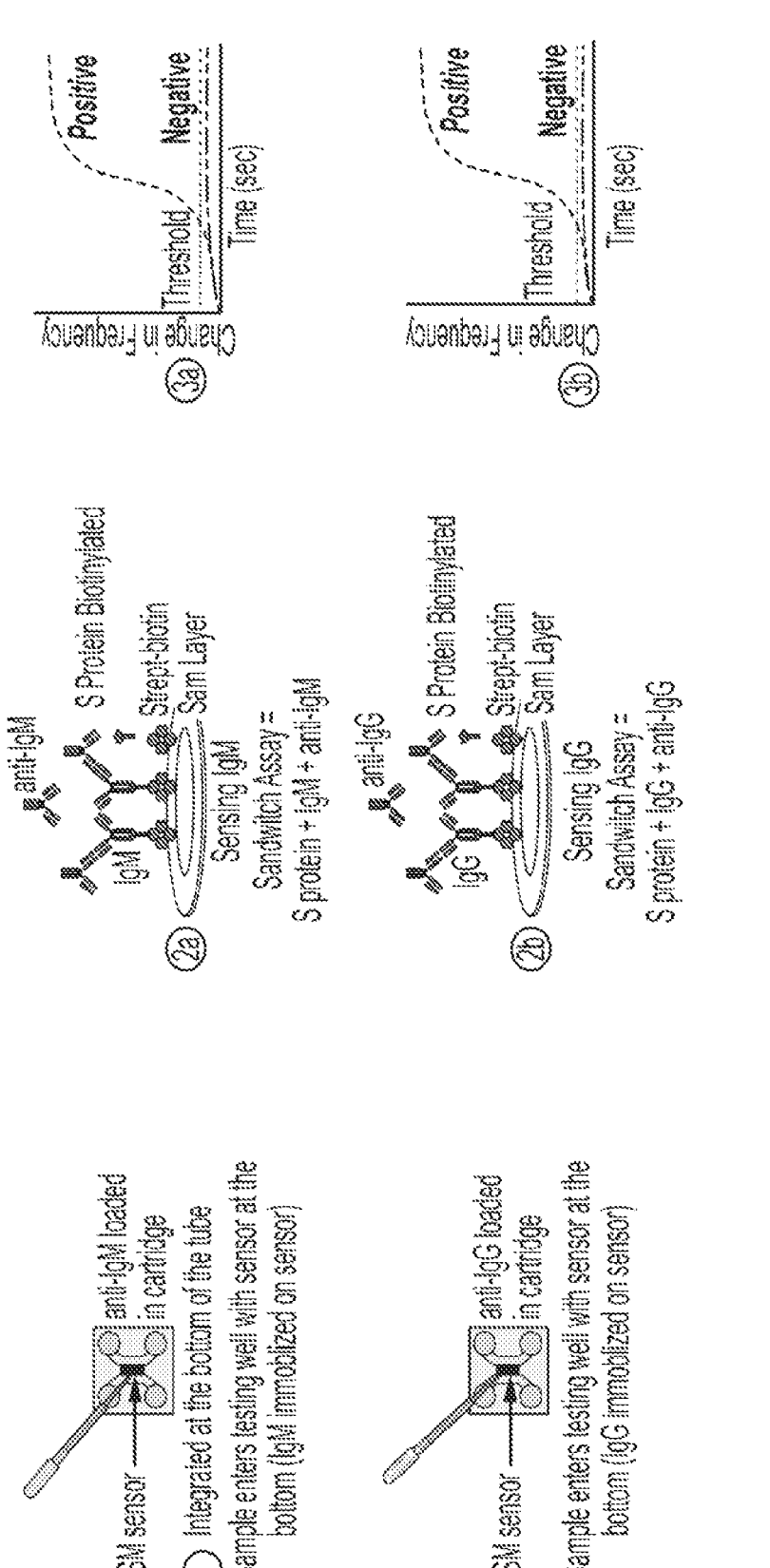
FIG. 5 provides a schematic workflow of the sensor device and associated diagnostic test under one embodiment. As shown, the system can be configured to diagnose COVID-19 according to the presence of IgM (top), IgG (bottom), or a combination thereof.
Figure 6:
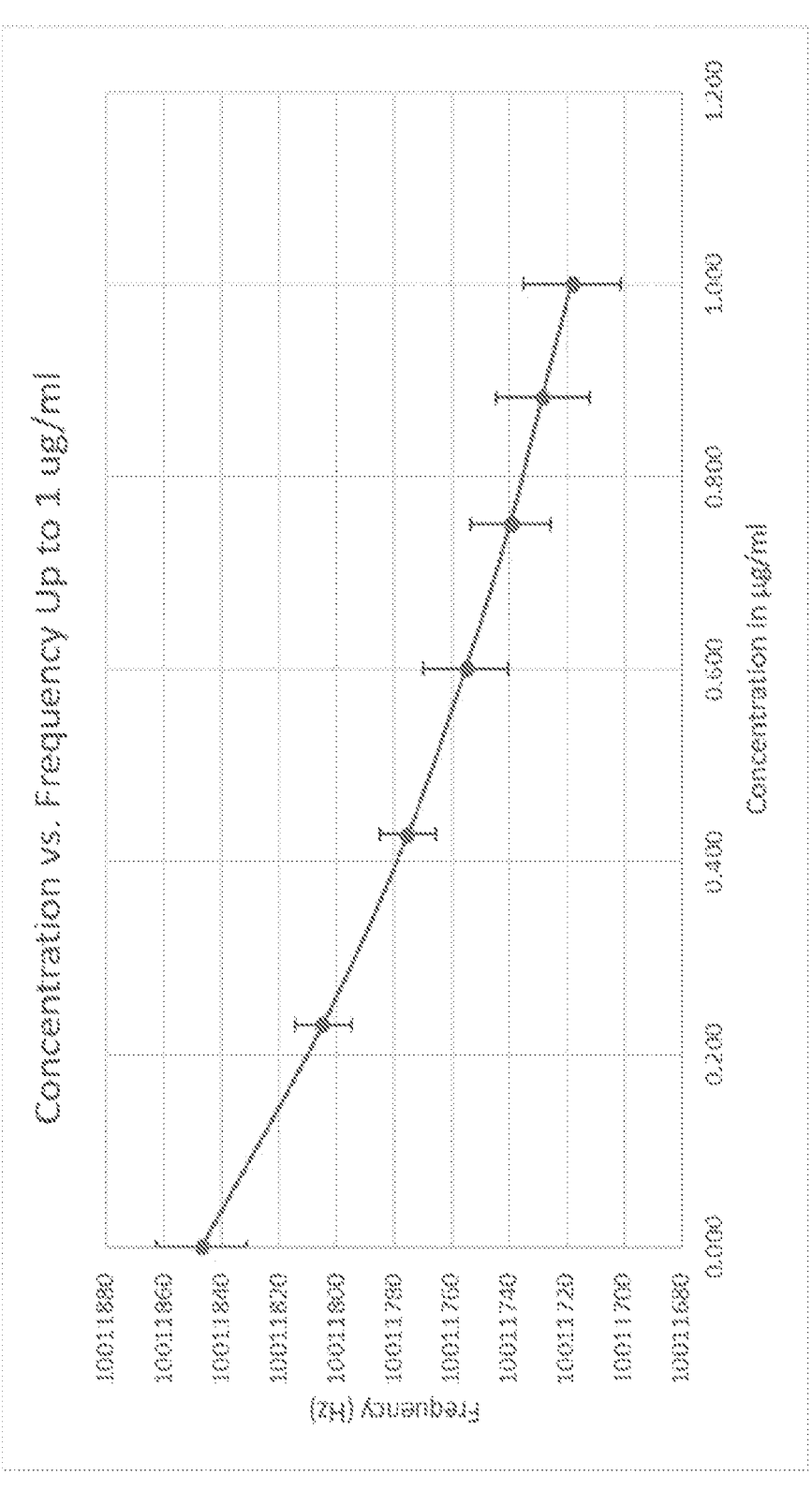
FIG. 6 shows the response of a miniaturized point-of-care, in vitro diagnostic sensor to different concentrations of monoclonal antibody to the nucleocapsid protein of the SARS-CoV-2 virus, under one embodiment. The early sensitivity assessment was performed without any optimization of the resonator or electrode dimensions. The monoclonal antibodies were in a solution of bovine serum albumin and added to the sensor surface that had 60 μl of phosphate buffered saline solution.

The probe can be covalently or non-covalently attached to the support. In some embodiments, the probe (such as the antibody, antigen, or fragment thereof) can be cross-linked to the solid support for immobilization. The skilled artisan understands it can use a crosslinker to aim at the primary amine (—$NH_2$) and carboxyl (—COOH) groups since they are abundant and well distributed over the protein surface. Non-limiting examples of cross-linkers include NHS esters, imidoesters, or glutaraldehyde for amine-to-amine conjugation, carbodiimide for carboxyl-to-amine linking, maleimide or epoxide for sulfhydryl groups, and hydrazides for aldehyde groups (see also, Shen at al., Methods. 2017 Mar. 1; 116: 95-111; which is incorporated by reference in its entirety). In some embodiments, the solid support can comprise one or more amine(s), hydroxyl(s) or epoxide(s) to immobilize the probe. For example, the probe can be an antibody or antibody fragment that is attached to the support. For example, the probe can be an antigen or antigen fragment that is attached to the support. In some embodiments, the support can be porous or non-porous. Examples of non-porous supports include polystyrene, polyethylene, dextran, polypropylene, plastic, and glass. In some embodiments, the support can be transparent. The probe can be tethered to the solid support via a sandwich assay. In embodiments, the probe is tethered to an amino acid sequence or a polynucleotide sequence that is immobilized the support surface. In one embodiment, the sandwich assay comprises immobilized S protein on the surface and ant-IgM and IgG in buffer topping the sensor to detect IgM and IgG (as illustrated in FIG. 5—panels 2a & 2b). In embodiments, the probe is immobilized utilizing a conjugation of biotin and streptavidin, biotin and avidin, a sugar and lectin, or a combination thereof. One embodiment comprises amination of the electrode surface via self-assembled mono-layer (SAM) of 11-amino-1-undecanethiol or 9-amino-1-undecanethiol. This can be followed by covalent attachment of streptavidin and then biotinylated S protein are attached via streptavidin-biotin bond. Such a process of electrode surface amination followed by a streptavidin-biotin bridge can be utilized to attach any protein to the sensor surface. Another embodiment comprises amination of the electrode surface via SAM of 11-amino-1-undecanethiol or 9-amino-1-undecanethiol. This can be followed by covalent attachment of antibodies to S-protein or N-protein or M-protein or E protein.

Wherein the diameter of the sensing electrode (non-liming examples include about 10 μm-about 15 mm) is optimized along with the thickness of the sensing layer above the electrode (non-limiting examples include about 30-about 150 nm), and the operating resonant frequency (e.g. about 1-about 100 MHz) of the piezoelectric substrate for a given viscosity (e.g. about 0.1-about 10 cP) of the sample fluid (blood, saliva, nasal swab or other biofluid) to achieve the desired Q-factor (e.g. about 100-about 100,000), sensitivity (e.g. about 1 pg/ml-about 100 μg/ml) and detection limits. Additionally, for a given operating resonant frequency, the diameter and thickness of the sensing electrode (e.g. about 1-about 500 nm) can be optimized to maximize energy trapping and mitigate inharmonic modes of oscillation under fluid. The number of sensing electrodes (e.g. about 1-about 100,000) on the piezoelectric substrate is determined by the number of independent, simultaneous measurements that need to be performed. In embodiments, the thickness, diameter size, or both of the at least one working electrode can be configured to optimize energy trapping, mitigate inharmonic modes in the bulk piezoelectric with standing liquid (serum or buffer or saliva or any other sample fluid) on top of the working electrode.

Biomarkers

As discussed herein, various embodiments of the disclosure permit the detection of biomarkers in a sample as an indicator of a particular disease, infection, or condition. In embodiments, biomarkers include any biological marker whose presence or absence is known to be associated with a particular disease, infection, or condition. Biomarkers can be useful for diagnosing a patient with a particular disease, infection, or condition; predicting clinical outcomes of a patient suffering from a disease, infection, or condition, directing individualized treatment decisions for a patient suffering from a particular disease, infection, or condition, predicting the likelihood that a particular treatment will be effective, assessing the effectiveness of a particular treatment response, or a combination thereof. Biomarkers can be specific for a particular disease, infection, or condition, showing little to no cross-over to alternate disease states.

In embodiments, biomarkers can comprise biological indicators of infectious disease caused by a microorganism (such as the presence of antigens or antibodies). In some embodiments, the infectious disease can be caused by a microorganism, such as a DNA virus, RNA virus, or reverse transcribing virus. Non-limiting examples of viruses include Adenovirus, Coxsackievirus, Epstein-Barr virus, Hepatitis A virus, Hepatitis B virus, Hepatitis C virus, Herpes simplex virus, type 1, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Rubella virus, Varicella-zoster virus. In embodiments, biomarkers can comprise biological indicators of a coronavirus, such as SARS-CoV-2 or COVID-19. Representative coronaviruses include but are not limited to human coronavirus NL63 (HCoV-NL63), porcine transmissible gastroenteritis coronavirus (TGEV), porcine epidemic diarrhea coronavirus (PEDV), and porcine respiratory coronavirus (PRCV) in the genus Alphacoronavirus; severe acute respiratory syndrome coronavirus (SARS-CoV), Middle East respiratory syndrome coronavirus (MERS-COV), bat coronavirus HKU4, mouse hepatitis coronavirus (MHV), bovine coronavirus (BCOV), and human coronavirus OC43 in the genus Betacoronavirus; avian infectious bronchitis coronavirus (IBV) in the genus Gammacoronavirus; and porcine deltacoronavirus (PdCV) in the genus Deltacoronavirus Embodiments can also include biomarkers for Influenza A, Influenza B, and its different sub-types, or for any other disease condition for which appropriate biomarkers can be found.

In some embodiments, the infectious disease can be caused by a microorganism, such as a Gram-positive bacterium, a Gram-negative bacterium, a protozoa, or a fungus. Non-limiting examples of disease-causing bacteria include: *Bacillus anthracis, Bacillus cereus, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenza, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholera, Yersinia pestis, Yersinia enterocolitica, Yersinia pseudotuberculosis*. Non-limiting examples of disease-causing protozoa include: *Plasmodium falciparum* (malaria), *Toxoplasma gondii* (toxoplasmosis), *Leishmania* species (leishmaniases), *Trypanosoma brucei* (African sleeping sickness), *Trypanosoma cruzi* (Chagas disease), and *Giardia intestinalis* (giardiasis). Non-limiting examples of disease-causing fungi include *Candida albicans, Aspergillus fumigatus, Aspergillus flavus, Cryptococcus neoformans, Cryptococcus gattii, Histoplasma capsulatum, Pneumocystis carinii, Stachybotrys chartarum*.

For example, the biomarkers described herein can be found in saliva, nasal swabs, blood samples or other biological samples.

The SARS-CoV-2 genome encodes for four major structural proteins: the spike (S, QHD43416.1), membrane (M, QHD43419.1), envelope (E, QHD43418.1) and nucleocapsid (N, QHD43423.2) proteins, each of which can serve as a biomarker for COVID-19. The S protein comprises 2 subunits, S1 and S2. S1 mediates the binding of the virus to the host cell receptor, while S2 contains other elements required for membrane fusion. The M protein is the most abundant structural protein that defines the shape of the virus. The N protein is the most abundantly shed viral protein during infection and can be detected in serum and urine samples within the first 2 weeks of infection. The smallest major structural protein, E protein, participates in viral assembly and pathogenesis.

Exemplary COVID-19 biomarkers include SARS-CoV-2 RNA detected via envelope (E), RNA-dependent RNA polymerase (RdRp) genes (YP_009725307, RdRp/helicase (H) genes (YP_009725308). Additional COVID-19 biomarkers include nucleocapsid protein (N, QHD43423.2), and ORF1b (BCN86436.1), which are highly conserved among other respiratory viruses. An additional exemplary biomarker comprises ORF1a. In some embodiments, the technology described herein can be useful for the detection of SARS-CoV2 variants. For example, the variants can be: the UK variant B.1.1.7 (such as B.1.1.7 with S:E484K); the South African variant B.1.351; the California variant B.1.427; the California variant B.1.429; the Brazilian variant P.1; the Brazilian variant P.2; the New York variant B.1.526 (such as B.1.526 with S:E484K or B.1.526 with S:S477N); the New York variant B.1.526.1; the New York variant B.1.526.2, the amino acid mutations of each strain which can be accessed at https://outbreak.info/situation-reports #Lineage_Mutation, and is incorporated by reference in their entireties. For example, a variant of SARS-CoV2 has accession number YP_009724390.1. For example, a variant of SARS-CoV2 has accession number QHD43416.1.

Antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, $IgG_3$, $IgG_4$. Furthermore, in humans, the light chain can be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" can refer to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In embodiments, additional biomarkers include antibodies for SARS-CoV-2 that can be present in the serum or plasma of patients. In certain embodiments, such antibodies include IgG, IgM, IgA antibodies, or a combination thereof. IgG can be detectable starting 13 to 21 days after infection and persists for long durations. IgM response on the other hand occurs earlier, at around 10 days after infection, but then decreases rapidly after 35 days and disappears. Data in FIG. 1 is collected from a literature survey showing the timeline of the disease with respect to the level of biomarkers (citations to the data points are in the references cited in Example 1).

Biomarkers can include any isotopes, fragments, variants, derivatives, or other modifications of any of the foregoing.

Biomarkers can include any one or more of the following amino acid and nucleotide sequence.

The amino acid sequence of the spike protein (S) (Severe acute respiratory syndrome coronavirus 2; GenBank: QHD43416.1; SEQ ID NO: 1) is:

```
MFVFLVLLPLVSSQCVNLTTRTQLPPAYTNSFTRGVYYPDKVFRSSVLHSTQDLF

LPFFSNVTWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVYSSANN

CTFEYVSQPFLMDLEGKQGNFKNLREFVFKNIDGYFKIYSKHTPINLVRDLPQGF

SALEPLVDLPIGINITRFQTLLALHRSYLTPGDSSSGWTAGAAAYYVGYLQPRTFL

LKYNENGTITDAVDCALDPLSETKCTLKSFTVEKGIYQTSNFRVQPTESIVRFPNIT

NLCPFGEVFNATRFASVYAWNRKRISNCVADYSVLYNSASFSTFKCYGVSPTKL

NDLCFTNVYADSFVIRGDEVRQIAPGQTGKIADYNYKLPDDFTGCVIAWNSNNL

DSKVGGNYNYLYRLFRKSNLKPFERDISTEIYQAGSTPCNGVEGENCYFPLQSYG

FQPTNGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITPGTNTSNQ

VAVLYQDVNCTEVPVAIHADQLTPTWRVYSTGSNVFQTRAGCLIGAEHVNNSYE

CDIPIGAGICASYQTQTNSPRRARSVASQSIIAYTMSLGAENSVAYSNNSIAIPTNF

TISVTTEILPVSMTKTSVDCTMYICGDSTECSNLLLQYGSFCTQLNRALTGIAVEQ

DKNTQEVFAQVKQIYKTPPIKDFGGFNFSQILPDPSKPSKRSFIEDLLFNKVTLAD

AGFIKQYGDCLGDIAARDLICAQKFNGLTVLPPLLTDEMIAQYTSALLAGTITSG

WTFGAGAALQIPFAMQMAYRFNGIGVTQNVLYENQKLIANQFNSAIGKIQDSLS

STASALGKLQDVVNQNAQALNTLVKQLSSNFGAISSVLNDILSRLDKVEAEVQID
```

-continued

RLITGRLQSLQTYVTQQLIRAAEIRASANLAATKMSECVLGQSKRVDFCGKGYH

LMSFPQSAPHGVVFLHVTYVPAQEKNFTTAPAICHDGKAHFPREGVFVSNGTHW

FVTQRNFYEPQIITTDNTFVSGNCDVVIGIVNNTVYDPLQPELDSFKEELDKYFKN

HTSPDVDLGDISGINASVVNIQKEIDRLNEVAKNLNESLIDLQELGKYEQYIKWP

WYIWLGFIAGLIAIVMVTIMLCCMTSCCSCLKGCCSCGSCCKFDEDDSEPVLKGV

KLHYT

The amino acid sequence of the membrane (M) protein (Severe acute respiratory syndrome coronavirus 2; GeneBank: QHD43419.1; SEQ ID NO: 2) is:

MADSNGTITVEELKKLLEQWNLVIGFLFLTWICLLQFAYANRNRFLYIIK

LIFLWLLWPVTLACFVLAAVYRINWITGGIAIAMACLVGLMWLSYFIASF

RLFARTRSMWSFNPETNILLNVPLHGTILTRPLLESELVIGAVILRGHLR

IAGHHLGRCDIKDLPKEITVATSRTLSYYKLGASQRVAGDSGFAAYSRYR

IGNYKLNTDHSSSSDNIALLVQ

The amino acid sequence of the envelope (E) protein (Severe acute respiratory syndrome coronavirus 2; GeneBank Accession No. QHID43418.1; SEQ ID NO: 3) is:

MYSFVSEETGTLIVNSVLLFLAFVVFLLVTLAILTALRLCAYCCNIVNVS

LVKPSFYVYSRVKNLNSSRVPDLLV

The amino acid sequence of the nucleocapsid (N) protein (Severe acute respiratory syndrome coronavirus 2; GeneBank: QHD43423.2; SEQ ID NO: 4) is:

MSDNGPQNQRNAPRITFGGPSDSTGSNQNGERSGARSKQRRPQGLPNNTA

SWFTALTQHGKEDLKFPRGQGVPINTNSSPDDQIGYYRRATRRIRGGDGK

MKDLSPRWYFYYLGTGPEAGLPYGANKDGIIWVATEGALNTPKDHIGTRN

PANNAAIVLQLPQGTTLPKGFYAEGSRGGSQASSRSSSRSRNSSRNSTPG

SSRGTSPARMAGNGGDAALALLLLDRLNQLESKMSGKGQQQQGQTVTKKS

AAEASKKPRQKRTATKAYNVTQAFGRRGPEQTQGNFGDQELIRQGTDYKH

WPQIAQFAPSASAFFGMSRIGMEVTPSGTWLTYTGAIKLDDKDPNFKDQV

ILLNKHIDAYKTFPPTEPKKDKKKKADETQALPQRQKKQQTVILLPAADL

DDFSKQLQQSMSSADSTQA

The amino acid sequence of helicase (H) (Severe acute respiratory syndrome coronavirus 2; NCBI Reference Sequence: YP_009725308.1; SEQ ID NO: 5) is:

AVGACVLCNSQTSLRCGACIRRPFLCCKCCYDHVISTSHKLVLSVNPYVC

NAPGCDVTDVTQLYLGGMSYYCKSHKPPISFPLCANGQVFGLYKNTCVGS

DNVTDFNAIATCDWTNAGDYILANTCTERLKLFAAETLKATEETFKLSYG

IATVREVLSDRELHLSWEVGKPRPPLNRNYVFTGYRVTKNSKVQIGEYTF

EKGDYGDAVVYRGTTTYKLNVGDYFVLTSHTVMPLSAPTLVPQEHYVRIT

GLYPTLNISDEFSSNVANYQKVGMQKYSTLQGPPGTGKSHFAIGLALYYP

-continued

SARIVYTACSHAAVDALCEKALKYLPIDKCSRIIPARARVECFDKFKVNS

TLEQYVFCTVNALPETTADIVVFDEISMATNYDLSVVNARLRAKHYVYIG

DPAQLPAPRTLLTKGTLEPEYFNSVCRLMKTIGPDMFLGTCRRCPAEIVD

TVSALVYDNKLKAHKDKSAQCFKMFYKGVITHDVSSAINRPQIGVVREFL

TRNPAWRKAVFISPYNSQNAVASKILGLPTQTVDSSQGSEYDYVIFTQTT

ETAHSCNVNRFNVAITRAKVGILCIMSDRDLYDKLQFTSLEIPRRNVATL

Q

The amino acid sequence of RNA-Dependent RNA polymerase (RdRp) (Severe acute respiratory syndrome coronavirus 2; NCBI Reference Sequence: YP_009725307.1; SEQ ID NO: 6) is:

SADAQSFLNRVCGVSAARLTPCGTGTSTDVVYRAFDIYNDKVAGFAKFLK

TNCCRFQEKDEDDNLIDSYFVVKRHTFSNYQHEETIYNLLKDCPAVAKHD

FFKFRIDGDMVPHISRQRLTKYTMADLVYALRHFDEGNCDTLKEILVTYN

CCDDDYFNKKDWYDFVENPDILRVYANLGERVRQALLKTVQFCDAMRNAG

IVGVLTLDNQDLNGNWYDFGDFIQTTPGSGVPVVDSYYSLLMPILTLTRA

LTAESHVDTDLTKPYIKWDLLKYDFTEERLKLFDRYFKYWDQTYHPNCVN

CLDDRCILHCANFNVLFSTVFPPTSFGPLVRKIFVDGVPFVVSTGYHFRE

LGVVHNQDVNLHSSRLSFKELLVYAADPAMHAASGNLLLDKRTTCFSVAA

LTNNVAFQTVKPGNFNKDFYDFAVSKGFFKEGSSVELKHFFFAQDGNAAI

SDYDYYRYNLPTMCDIRQLLFVVEVVDKYFDCYDGGCINANQVIVNNLDK

SAGFPFNKWGKARLYYDSMSYEDQDALFAYTKRNVIPTITQMNLKYAISA

KNRARTVAGVSICSTMTNRQFHQKLLKSIAATRGATVVIGTSKFYGGWHN

MLKTVYSDVENPHLMGWDYPKCDRAMPNMLRIMASLVLARKHTTCCSLSH

RFYRLANECAQVLSEMVMCGGSLYVKPGGTSSGDATTAYANSVFNICQAV

TANVNALLSTDGNKIADKYVRNLQHRLYECLYRNRDVDTDFVNEFYAYLR

KHFSMMILSDDAVVCFNSTYASQGLVASIKNFKSVLYYQNNVFMSEAKCW

TETDLTKGPHEFCSQHTMLVKQGDDYVYLPYPDPSRILGAGCFVDDIVKT

DGTLMIERFVSLAIDAYPLTKHPNQEYADVFHLYLQYIRKLHDELTGHML

DMYSVMLINDNTSRYWEPEFYEAMYTPHTVLQ

The amino acid sequence of ORF1b (Severe acute respiratory syndrome coronavirus 2; NCBI Sequence: BCN86436.1; SEQ ID NO: 7) is:

```
# 5'3' Frame 1
VQPVLHRAAQALVLMSYTGLLTSTMIK-LVLLNS-KLIVVASKKRTKMTI-LILTL-LRDTLSLTTNMKKQFIIYLR

IVQLLLNMTSLSLE-TVTWYHIYHVNVLLNTQWQTSSML-GILMKVIVTH-KKYLSHTIVVMMIISIKRTGMIL-KT

QIYYAYTPT-VNVYAKLC-KQYNSVMPCEMLVLLVY-H-IIKISMVTGMISVISYKPRQVVEFLL-ILIIHC-CLY-

P-PGL-LQSHMLTLT-QSLTLSGIC-NMTSRKRG-NSLTVILNIGIRHTTQIVLTVWMTDAFCIVQTLMFYSLQCSH

LQVLDH--EKYLLMVFHL-FQLDTTSES-VLYIIRM-TYIALDLVLRNYLCMLLTLLCTLLLVIYY-INALRAFQ-L

HLLTMLLFKLSNPVILTKTSMTLLCLRVSLRKEVLLN-NTSSLLRMVMLLSAIMTTIVIIYQQCVISDNYYL-LKLL

ISTLIVTMVAVLMLTKSSSTT-TNQLVFHLINGVRLDFIMIQ-VMRIKMHFSHIQNVMSSLL-LK-ILSMPLVQRIE

LAP-LVSLSVVL-PIDSFIKNY-NQ-PPLEELL--LEQANSMVVGTTC-KLFIVM-KTLTLWVGIILNVIEPCLTCL

ELWPHLFLLANIQRVVACHTVSID-LMSVLKY-VKWSCVAVHYMLNQVEPHQEMPQLLMLIVFLTFVKLSRPMLMHF

YLLMVTKLPISMSAIYNTDEMSVSIEIEMLTQTL-MSFTHICVNISQ--YSLTMLLCVSIALMHLKV-WLA-RTLSQ

FFIIKTMFLCLKQNVGLRLTLLKDLMNFALNIQC-LNRVMIMCTFLTQIHQES-GPAVL-MIS-KQMVHL-LNGSCL

-L-MLTHLLNILIRSMLMSFICTYNT-ESYMMS-QDTC-TCILLCLLMITLQGIGNLSFMRLCTHRIQSYRLLGLVF

FAIHRLH-DVVLAYVDHSYVVNAVTTMSYQHHIN-SCLLIRMFAMLQVVMSQM-LNFT-EV-AIIVNHINHPLVFHC

VLMDKFLVYIKIHVLVAIMLLTLMQLQHVTGQMLVITE-LTPVLKDSSFLQQKRSKLLRRHLNCLMVLLLYVKCCLT

ENYIFHGKLVNLDHHLTEIMSLLVIV-LKTVKYK-ESTPLKKVTMVMLLFTEVQQLTN-MLVIILC-HHIQ-CH-VH

LH-CHKSTMLELLAYTQHSISQMSFLAMLQIIKRLVCKSILHSRDHLVLVRVILLLA-LSTTLLLA-CIQLALMPLL

MHYVRRH-NICL-INVVELYLHVLV-SVLINSK-IQH-NSMSFVL-MHCLRRQQI-LSLMKFQWPQIMI-VLSMPDY

VLSTMCTLATLLNYLHHAHC-LRAH-NQNISIQCVDL-KL-VQTCSSELVGVVLLKLLTL-VLWFMIISLKHIKTNQ

LNALKCFIRVLSRMMFHLQLTGHK-AW-ENSLHVTLLGEKLSLFHLIIHRML-PQRFWDYQLKLLIHHRAQNMTMSY

SLKPLKQLTLVM-TDLMLLLPEQK-AYFA-CLIETFMTSCNLQVLKFHVGMWQLYKLKM-QDSLKIVVR-SLGYILH

RHLHTSVLTLNSKLKVYVLTYLAYLRT-PIEDSSL-WVLK-IIKLMVTLTCLSPAKKL-DMYVHGLASMSRGVMLLE

KLLVPIYLYS-VFLQVLT-LLYLQVMLIHLIIQIFPELVLNHRLEINLNTSYHLCTKDFLGM-CV-RLYKC-VTHLK

ISLTESYLSYGHMALS-HL-SIL-K-DLSAPVVYVIDVPHAFPLLQTLMPVGIILLDLITSIIRL-LMENNGVLQVT

YKATMICIVKSMVMHM-LVVMQS-LGV-LSTSALLSVLTGLLNIL-LVMN-RLMRLVERFNTWLLKLHY-QTNSQFF

TTLVTLKLLSVYLKLM-NGSSMMHSLVVTKLIK-KNYSILMPHILTNSQMVYAYFGIAMSIDILLIPLFVDLTLECY

LTLTCLVVMVAVCM-INMHSTHQLLIKVLLLI-NNYHFSITLTVHVSLMENK-CQI-IMYH-SLLRV-HVAI-VVLS

VDIMLMSTDCISMLIT--SQLALACGFTNNLILITSGTLLQDFRV-KMWLLML-IRDTLMDNRVKYQFLSLITLFTQ

KLMVLM-NCLKIKQHYLLM-HLSFGLSATLNQYQR-KYSIIWVWTLLLIL-SGTTKEMLQHIYLLLVFVL-LT-PRN

QLKRFVHHSLSFLMVELMVK-TYLEMPVMVFLLQKVVLKVYNHL-VPNKLVLMESH-LEKP-KHSSIIIRKLMVLSN

NYLKLTLLRVEIYKNLNPGVKWKLIS-N-LWMNSLNGIN-KAMPSNISFMEILVIVS-VVYIY-LD-LNVLRNHLLN

-KILFLWTVQLKTIS-QMRKQVHLSVCVLLLIYYLMILLK--NPKIYL-FLRLSK-LLTIQKFHLCFGVKMAM-KHF

TQNYNLVKRGNRVLLCLIFTKCKECY-KSVTFKIMVIVQHYLKA---MSQNILNCVNI-TH-H-LYPII-ELYILVL

VLIKELHQVQLF-DSGCLRVRCLSIQILMTLSLMQIQL-LVIVQLYIQLINGISLLVICTTLRLKMLQKKMTLKRVE

SLTFVGLYNKS-LLEVPWL-R-QNILGMLIFISSWDTSHGGQPLLLM-MRHHLKHF-LDVIILANHANK-MVMSCMQ

ITYFGGIQIQFSCLPILYLT-VNFPLN-GVLLLCL-KKVKSMI-FYLFLVKVDL-LEKTTELLFLVMELLTT

# 5'3' Frame 2
CSPSYTVRHRH-Y-CRIQGF-HLQ--SSWFC-IPKN-LLSLPRKGRR-QFN-FLLCS-ETHFL-LPT-RNNL-FT-G

LSSCC-T-LL-V-NRR-HGTTYITSTSY-IHNGRPRLCFKAF--R-L-HIKRNTCHIQLL---LFQ-KGLV-FCRKP

RYITRIRQLR-TCTPSFVKNSTIL-CHAKCWYCWCTDIR-SRSQW-LV-FR-FHTNHAR-WSSCCRFLLFIVNAYIN

LDQGFNCRVTC-H-LNKALH-VGFVKI-LHGREVKTL-PLF-ILGSDIPPKLC-LFG-QMHSALCKL-CFILYSVPT

YKFWTTSEKNIC-WCSICSENWIPLORARCCT-SGCKLT-L-T-F-GITCVCC-PCYARCFW-SITR-THYVLFSSC
```

-continued

TY-QCCFSNCQTR-F-QRLL-LCCV-GFL-GRKFC-IKTLLLCSGW-CCYQRL-LLSL-STNNV-YQTTTICS-SC-

-VL-LLRWWLY-C-PSHRQQPRQISWFSI--MG-G-TLL-FNEL-GSRCTFRIYKT-CHPYYNSNES-VCH-CKE-S

SHRSWCLYL-YYDQ-TVSSKIIEINSRH-RSYCSNWNKQILWWLAQHVKNCL--CRKPSPYGLGLS-M--SHA-HA-

NYGLTCSCSQTYNVL-LVTPFL-IS--VCSSIE-NGHVWRFTIC-TRWNLIRRCHNCLC--CF-HLSSCHGQC-CTF

IY-W-QNCR-VCPQFTTOTL-VSL-K-RC-HRLCE-VLRIFA-TFLNDDTL-RCCCVFQ-HLCISRSSG-HKEL-VS

SLLSKQCFYV-SKMLD-D-PY-RTS-ILLSTYNAS-TG--LCVPSLPRSIKNPRGRLFCR-YRKNRWYTYD-TVRVF

SYRCLPTY-TS-SGVC-CLSFVLTIHKKAT--VNRTHVRHVFCYAY---HFKVLGT-VL-GYVHTAYSLTGCWGLCS

LQFTDFIKMWCLHT-TILML-MLLRPCHINIT-ISLVC-SVCLQCSRL-CHRCDSTLLRRYELLL-IT-TTH-FSIV

C-WTSFWFI-KYMCW-R-CY-L-CNCNM-LDKCW-LHES-HLY-KTOAFCSRNAQSY-GDI-TVLWYCYCT-SAV-Q

RITSFMGSW-T-TTT-PKLCLYWLSCN-KQ-STNRRVHL-KR-LW-CCCLPRYNNLQIKCW-LFCADITYSNAIKCT

YTSATRALC-NYWLIPNTQYLR-VF-QCCKLSKGWYAKVFYTPGTTWYW-ESFCYWPSSLLPFCSHSVYSLLSCRC-

CTM-EGIKIFAYR-M--NYTCTCSCRVF--IQSEFNIRTVCLLYCKCIA-DDSRYSCL--NFNGHKL-FECCQCQIT

C-ALCVHWRPCSITCTTHIAN-GHTRTRIFQFSV-TYENYRSRHVPRNLSALSC-NC-HCECFGL---A-ST-RQIS

SML-NVL-GCYHA-CFICN-QATNRRGKRIPYT-PCLEKSCLYFTL-FTECCSLKDFGTTNSNC-FITGLRI-LCHI

HSNH-NSSLL-CKQI-CCYYQSKSRHTLHNV--RPL-QVAIYKS-NST-ECGNFTS-KCNRTL-RL--GNHWVTSYT

GTYTPQC-H-IQN-RFMC-HTWHT-GHDL-KTHLYDGF-NELSS-WLP-HVYHPRRSYKTCTCMDWLRCRGVSCY-R

SCWYQFTFTARFFYRC-PSCCTYRLC-YT--YRFFQS-C-TTAWRSI-TPHTTYVORTSLECSAYKDCTNVK-HT-K

SL-QSRICLMGTWL-VDIYEVFCENRT-AHLLSM--TCHMLFHCFRHLCLLASFYWI-LRL-SVYD-CSTMGFYR-P

TKQP-SVLSSPW-CTCS-L-CNHD-VSSCPRVLC-AC-LDY-ISYNW--TED-CGL-KGSTHGC-SCIISRQIPSSS

RHW-P-SY-VCTSS-CRMEVL-CTAL--QSL-NRRIILFLCHTF-QIHRWCMPILELQCR-ISC-FHCL-I-H-SAI

-P-LAWL-WWQFVCK-TCIPHTSF--KCFC-FKTITIFLLL-QSM-VSWKTSSVRYRLCTTKVCYVYNTLQFRWCCL

-TSC--VOIVSRCL-HDDLSWL-LVGLQTI-YL-PLEHFYKTSEFRKCGF-CCK-GTL-WTTG-STSFYH--HCLHK

S-WC-CRIV-K-NNITC-CSI-ALG-AQH-TSTRGENTQ-FGCGHCC-YCDLGLOKRCSSTYIYYWCLFYD-HSQET

N-NDLCTTHCLF-W-S-WSSRLI-KCP-WCSYYRR-C-RFTTICRSQTS-S-WSHINWRSRKNTVOLL-ES-WCCPT

IT-NLLYSE-KFTRI-TQESNGN-FLRISYG-IH-TV-IRRLCLRTYRLWRF-S-SVRWFTSTDWTS-TF-GITF-I

RRFYSYGQYS-KLFHNRCANRFI-VCVFCY-FIT--FC-NNKIPRFICSF-GCQSDY-LYRNFIYALV-RWPCRNIL

PKITI-SSVATGCCYA-SLONAKNAIRKV-PSKLW--CNIT-RHNDECRKIYSTVSIFKHINISCTL-YESYTFWCW

F--RSCTRYSCFKTVVAYGYAACRFRS--LCL-CRFNFDW-LCNCTYS--MGSHY--YVRP-D-KCYKRK-L-RGFF

HLHLWVYTTKASSWRFRGYKDNRTFLEC-SL-AHGTLRMVDSLCY-CECVII-SIFNWM-LSWQTTRTNRWLCHACK

LHILEEYKSNSVVFLFFI-HE-ISP-IKGYCCYVFKRRSNQ-YDFISS--R-TYN-RKQQSCYF--CSC-QL

5'3' Frame 3 (longest ORF)
AARLTPCGTGTSTDVVYRAFDIYNDKVAGFAKFLKTNCCRFQEKDEDDNLIDSYFVVKRHTFSNYQHEETIYNLLKD

CPAVAKHDFFKFRIDGDMVPHISRORLTKYTMADLVYALRHFDEGNCDTLKEILVTYNCCDDDYENKKDWYDFVENP

DILRVYANLGERVRQALLKTVQFCDAMRNAGIVGVLTLDNQDLNGNWYDFGDFIQTTPGSGVPVVDSYYSLLMPILT

LTRALTAESHVDTDLTKPYIKWDLLKYDFTEERLKLFDRYFKYWDQTYHPNCVNCLDDRCILHCANFNVLFSTVFPP

TSFGPLVRKIFVDGVPFVVSTGYHFRELGVVHNQDVNLHSSRLSFKELLVYAADPAMHAASGNLLLDKRTTCFSVAA

LTNNVAFQTVKPGNFNKDFYDFAVSKGFFKEGSSVELKHFFFAQDGNAAISDYDYYRYNLPTMCDIRQLLFVVEVVD

KYFDCYDGGCINANQVIVNNLDKSAGFPFNKWGKARLYYDSMSYEDQDALFAYTKRNVIPTITQMNLKYAISAKNRA

RTVAGVSICSTMTNRQFHQKLLKSIAATRGATVVIGTSKFYGGWHNMLKTVYSDVENPHLMGWDYPKCDRAMPNMLR

IMASLVLARKHTTCCSLSHRFYRLANECAQVLSEMVMCGGSLYVKPGGTSSGDATTAYANSVENICQAVTANVNALL

STDGNKIADKYVRNLQHRLYECLYRNRDVDTDFVNEFYAYLRKHFSMMILSDDAVVCENSTYASQGLVASIKNFKSV

-continued

LYYQNNVFMSEAKCWTETDLTKGPHEFCSQHTMLVKQGDDYVYLPYPDPSRILGAGCFVDDIVKTDGTLMIERFVSL

AIDAYPLTKHPNQEYADVFHLYLQYIRKLHDELTGHMLDMYSVMLINDNTSRYWEPEFYEAMYTPHTVLQAVGACVL

CNSQTSLRCGACIRRPFLCCKCCYDHVISTSHKLVLSVNPYVCNAPGCDVTDVTOLYLGGMSYYCKSHKPPISFPLC

ANGQVFGLYKNTCVGSDNVTDFNAIATCDWTNAGDYILANTCTERLKLFAAETLKATEETFKLSYGIATVREVLSDR

ELHLSWEVGKPRPPLNRNYVFTGYRVTKNSKVQIGEYTFEKGDYGDAVVYRGTTTYKLNVGDYFVLTSHTVMPLSAP

TLVPQEHYVRITGLYPTLNISDEFSSNVANYQKVGMQKYSTLQGPPGTGKSHFAIGLALYYPSARIVYTACSHAAVD

ALCEKALKYLPIDKCSRIIPARARVECFDKFKVNSTLEQYVFCTVNALPETTADIVVFDEISMATNYDLSVVNARLR

AKHYVYIGDPAQLPAPRTLLTKGTLEPEYFNSVCRLMKTIGPDMFLGTCRRCPAEIVDTVSALVYDNKLKAHKDKSA

QCFKMFYKGVITHDVSSAINRPQIGVVREFLTRNPAWRKAVFISPYNSQNAVASKILGLPTQTVDSSQGSEYDYVIF

TQTTETAHSCNVNRENVAITRAKVGILCIMSDRDLYDKLQFTSLEIPRRNVATLQAENVTGLFKDCSKVITGLHPTQ

APTHLSVDTKFKTEGLCVDIPGIPKDMTYRRLISMMGFKMNYQVNGYPNMFITREEAIRHVRAWIGEDVEGCHATRE

AVGTNLPLQLGFSTGVNLVAVPTGYVDTPNNTDFSRVSAKPPPGDQFKHLIPLMYKGLPWNVVRIKIVOMLSDTLKN

LSDRVVFVLWAHGFELTSMKYFVKIGPERTCCLCDRRATCESTASDTYACWHHSIGFDYVYNPFMIDVQQWGFTGNL

QSNHDLYCQVHGNAHVASCDAIMTRCLAVHECFVKRVDWTIEYPIIGDELKINAACRKVQHMVVKAALLADKFPVLH

DIGNPKAIKCVPQADVEWKFYDAQPCSDKAYKIEELFYSYATHSDKFTDGVCLFWNCNVDRYPANSIVCREDTRVLS

NLNLPGCDGGSLYVNKHAFHTPAFDKSAFVNLKQLPFFYYSDSPCESHGKQVVSDIDYVPLKSATCITRONLGGAVC

RHHANEYRLYLDAYNMMISAGFSLWVYKQFDTYNLWNTFTRLQSLENVAFNVVNKGHFDGQQGEVPVSIINNTVYTK

VDGVDVELFENKTTLPVNVAFELWAKRNIKPVPEVKILNNLGVDIAANTVIWDYKRDAPAHISTIGVCSMTDIAKKP

TETICAPLTVFFDGRVDGQVDLFRNARNGVLITEGSVKGLQPSVGPKQASLNGVTLIGEAVKTQFNYYKKVDGVVQQ

LPETYFTQSRNLQEFKPRSQMEIDFLELAMDEFIERYKLEGYAFEHIVYGDFSHSQLGGLHLLIGLAKRFKESPFEL

EDFIPMDSTVKNYFITDAQTGSSKCVCSVIDLLLDDFVEIIKSQDLSVVSKVVKVTIDYTEISFMLWCKDGHVETFY

PKLQSSQAWQPGVAMPNLYKMQRMLLEKCDLQNYGDSATLPKGIMMNVAKYTQLCQYLNTLTLAVPYNMRVIHFGAG

SDKGVAPGTAVLRQWLPTGTLLVDSDLNDFVSDADSTLIGDCATVHTANKWDLIISDMYDPKTKNVTKENDSKEGFF

TYICGFIQQKLALGGSVAIKITEHSWNADLYKLMGHFAWWTAFVTNVNASSSEAFLIGCNYLGKPREQIDGYVMHAN

YIFWRNTNPIQLSSYSLFDMSKFPLKLRGTAVMSLKEGQINDMILSLLSKGRLIIRENNRVVISSDVLVNN

The nucleotide sequence of the spike protein (S) (Severe acute respiratory syndrome coronavirus 2; GenBank: QHD43416.1; SEQ ID NO: 8) is:

atggatttgtttatgagaatcttcacaattggaactgtaacttttgaagca aggtgaaatcaaggatgctactccttcagattttgttcgcgctactgcaa cgataccgatacaagcctcactcccttcggatggcttattgttggcgtt gcacttcttgctgttttttcagagcgcttccaaaatcataaccctcaaaaa gagatggcaactagcactctccaagggtgttcactttgtttgcaacttgc tgttgttgtttgtaacagtttactcacaccttttgctcgttgctgctggc cttgaagcccctttttctctatctttatgctttagtctacttcttgcagag tataaactttgtaagaataataatgaggctttggctttgctggaaatgcc gttccaaaaacccattactttatgatgccaactattttctttgctggcat actaattgttacgactattgtataccttacaatagtgtaacttcttcaat tgtcattacttcaggtgatggcacaacaagtcctatttctgaacatgact accagattggtggttatactgaaaaatgggaatctggagtaaaagactgt -continued gttgtattacacagttacttcacttcagactattaccagctgtactcaac tcaattgagtacagacactggtgttgaacatgttaccttcttcatctaca ataaaattgttgatgagcctgaagaacatgtccaaattcacacaatcgac ggttcatccggagttgttaatccagtaatggaaccaatttatgatgaacc gacgacgactactagcgtgcctttgtaa The nucleotide sequence of the membrane (M) protein (Severe acute respiratory syndrome coronavirus 2; GeneBank: QHD43419.1; SEQ ID NO: 9) is:

atgtttcatctcgttgactttcaggttactatagcagagatattactaat tattatgaggacttttaaagtttccatttggaatcttgattacatcataa acctcataattaaaaatttatctaagtcactaactgagaataaatattct caattagatgaagagcaaccaatggagattgattaa The nucleotide sequence of the envelope (E) protein (Severe acute respiratory syndrome coronavirus 2; GeneBank Accession No. QHD43418.1; SEQ ID NO: 10) is:

atggcagattccaacggtactattaccgttgaagagcttaaaaagctcct tgaacaatggaacctagtaataggtttcctattccttacatggatttgtc ttctacaatttgcctatgccaacaggaataggttttttgtatataattaag ttaattttcctctggctgttatggccagtaactttagcttgttttgtgct tgctgctgtttacagaataaaattggatcaccggtggaattgctatcgcaa tggcttgtcttgtaggcttgatgtggctcagctacttcattgcttctttc agactgtttgcgcgtacgcgttccatgtggtcattcaatccagaaactaa cattcttctcaacgtgccactccatggcactattctgaccagaccgcttc tagaaagtgaactcgtaatcggagctgtgatccttcgtggacatcttcgt attgctggacaccatctaggacgctgtgacatcaaggacctgcctaaaga aatcactgttgctacatcacgaacgctttcttattacaaattgggagctt cgcagcgtgtagcaggtgactcaggttttgctgcatacagtcgctacagg attggcaactataaattaaacacagaccattccagtagcagtgacaatat tgctttgcttgtacagtaa The nucleotide sequence of the nucleocapsid (N) protein (Severe acute respiratory syndrome coronavirus 2; GeneBank: QHID43423.2; SEQ ID NO: 11) is:

atgtctgataatggaccccaaaatcagcgaaatgcaccccgcattacgtt tggtggaccctcagattcaactggcagtaaccagaatggagaacgcagtg gggcgcgatcaaaacaacgtcggccccaaggtttacccaataatactgcg tcttggttcaccgctctcactcaacatggcaaggaagaccttaaattccc tcgaggacaaggcgttccaattaacaccaatagcagtccagatgaccaaa ttggctactaccgaagagctaccagacgaattcgtggtggtgacggtaaa atgaaagatctcagtccaagatggtatttctactacctaggaactgggcc agaagctggacttccctatggtgctaacaaagacggcatcatatgggttg caactgagggagccttgaatacaccaaaagatcacattggcacccgcaat cctgctaacaatgctgcaatcgtgctacaacttcctcaaggaacaacatt gccaaaaggcttctacgcagaagggagcagaggcggcagtcaagcctctt ctcgttcctcatcacgtagtcgcaacagttcaagaaattcaactccaggc agcagtaggggaacttctcctgctagaatggctggcaatggcggtgatgc tgctcttgctttgctgctgcttgacagattgaaccagcttgagagcaaaa tgtctggtaaaggccaacaacaacaaggccaaactgtcactaagaaatct gctgctgaggcttctaagaagcctcggcaaaaacgtactgccactaaagc atacaatgtaacacaagctttcggcagacgtggtccagaacaaacccaag gaaattttggggaccaggaactaatcagacaaggaactgattacaaacat tggccgcaaattgcacaatttgcccccagcgcttcagcgttcttcggaat gtcgcgcattggcatggaagtcacaccttcgggaacgtggttgacctaca caggtgccatcaaattggatgacaaagatccaaatttcaaagatcaagtc attttgctgaataagcatattgacgcatacaaaacattcccaccaacaga gcctaaaaaggacaaaaagaagaaggctgatgaaactcaagccttaccgc agagacagaagaaacagcaaactgtgactcttcttcctgctgcagatttg -continued gatgatttctccaaacaattgcaacaatccatgagcagtgctgactcaac tcaggcctaa The nucleotide sequence for the protein coding sequence (CDS) of the helicase (H) (Severe acute respiratory syndrome coronavirus 2; NCBI Reference Sequence: YP_009725308.1; SEQ ID NO: 12)

gctgttggggcttgtgttctttgcaattcacagacttcattaagatgtgg tgcttgcatacgtagaccattcttatgttgtaaatgctgttacgaccatg tcatatcaacatcacataaattagtcttgtctgttaatccgtatgtttgc aatgctccaggttgtgatgtcacagatgtgactcaactttacttaggagg tatgagctattattgtaaatcacataaaccacccattagttttccattgt gtgctaatggacaagttttttggtttatataaaaatacatgtgttggtagc gataatgttactgactttaatgcaattgcaacatgtgactggacaaatgc tggtgattacatttttagctaacacctgtactgaaagactcaagcttttg cagcagaaacgctcaaagctactgaggagacatttaaactgtcttatggt attgctactgtacgtgaagtgctgtctgacagagaattacatctttcatg ggaagttggtaaacctagaccaccacttaaccgaaattatgtctttactg gttatcgtgtaactaaaaacagtaaagtacaaataggagagtacacctt gaaaaaggtgactatggtgatgctgttgtttaccgaggtacaacaacta caaattaaatgttggtgattattttgtgctgacatcacatacagtaatgc cattaagtgcacctacactagtgccacaagagcactatgttagaattact ggcttataccccaacactcaatatctcagatgagttttctagcaatgttgc aaattatcaaaaggttggtatgcaaaagtattctacactccagggaccac ctggtactggtaagagtcattttgctattggcctagctctctactaccct tctgctcgcatagtgtatacagcttgctctcatgccgctgttgatgcact atgtgagaaggcattaaaatatttgcctatagataaatgtagtagaatta tacctgcacgtgctcgtgtagagtgtttgataaattcaaagtgaattca acattagaacagtatgtctttgtactgtaaatgcattgcctgagacgac agcagatatagttgtctttgatgaaatttcaatggccacaaattatgatt tgagtgttgtcaatgccagattacgtgctaagcactatgtgtacattggc gaccctgctcaattacctgcaccacgcacattgctaactaagggcacact agaaccagaatatttcaattcagtgtgtagacttatgaaaactataggtc cagacatgttcctcggaacttgtcggcgttgtcctgctgaaattgttgac actgtgagtgctttggtttatgataataagcttaaagcacataaagacaa atcagctcaatgctttaaaatgtttttataagggtgttatcacgcatgatg tttcatctgcaattaacaggccacaaataggcgtggtaagagaattcctt acacgtaaccctgcttggagaaaagctgtctttatttcaccttataattc acagaatgctgtagcctcaaagatttttgggactaccaactcaaactgttg attcatcacagggctcagaatatgactatgtcatattcactcaaaccact gaaacagctcactcttgtaatgtaaacagatttaatgttgctattaccag agcaaaagtaggcatactttgcataatgtctgatagagacctttatgaca

```
agttgcaatttacaagtcttgaaattccacgtaggaatgtggcaacttta caa
```

The nucleotide sequence for the CDS of RNA-Dependent RNA polymerase (RdRp) (Severe acute respiratory syndrome coronavirus 2; NCBI Reference Sequence: YP_009725307.1; SEQ ID NO: 13) is:

```
tcagctgatgcacaatcgttttttaaacgggtttgcggtgtaagtgcagcc cgtcttacaccgtgcggcacaggcactagtactgatgtcgtatacagggc ttttgacatctacaatgataaagtagctggttttgctaaattcctaaaaa ctaattgttgtcgcttccaagaaaaggacgaagatgacaatttaattgat tcttactttgtagttaagagacacactttctctaactaccaacatgaaga aacaatttataatttacttaaggattgtccagctgttgctaaacatgact tctttaagtttagaatagacggtgacatggtaccacatatatcacgtcaa cgtcttactaaatacacaatggcagacctcgtctatgctttaaggcatttt tgatgaaggtaattgtgacacattaaaagaaatacttgtcacatacaatt gttgtgatgatgattatttcaataaaaaggactggtatgattttgtagaa aacccagatatattacgcgtatacgccaacttaggtgaacgtgtacgcca agctttgttaaaaacagtacaattctgtgatgccatgcgaaatgctggta ttgttggtgtactgacattagataatcaagatctcaatggtaactggtat gatttcggtgatttcatacaaaccacgccaggtagtggagttcctgttgt agattcttattattcattgttaatgcctatattaaccttgaccagggctt taactgcagagtcacatgttgacactgacttaacaaagccttacattaag tgggatttgttaaaatatgacttcacggaagagaggttaaaactctttga ccgttattttaaatattgggatcagacataccacccaaattgtgttaact gtttggatgacagatgcattctgcattgtgcaaactttaatgtttttattc tctacagtgttcccacctacaagttttggaccactagtgagaaaaatatt tgttgatggtgttccatttgtagtttcaactggataccacttcagagagc taggtgttgtacataatcaggatgtaaacttacatagctctagacttagt tttaaggaattacttgtgtatgctgctgaccctgctatgcacgctgcttc tggtaatctattactagataaacgcactacgtgcttttcagtagctgcac ttactaacaatgttgcttttcaaactgtcaaacccggtaattttaacaaa gacttctatgactttgctgtgtctaagggtttctttaaggaaggaagttc
```

```
tgttgaattaaaacacttcttctttgctcaggatggtaatgctgctatca gcgattatgactactatcgttataatctaccaacaatgtgtgatatcaga caactactatttgtagttgaagttgttgataagtactttgattgttacga tggtggctgtattaatgctaaccaagtcatcgtcaacaacctagacaaat cagctggttttccatttaataaatggggtaaggctagacttttattatgat tcaatgagttatgaggatcaagatgcacttttcgcatatacaaaacgtaa tgtcatccctactataactcaaatgaatcttaagtatgccattagtgcaa agaatagagctcgcaccgtagctggtgtctctatctgtagtactatgacc aatagacagtttcatcaaaaattattgaaatcaatagccgccactagagg agctactgtagtaattggaacaagcaaattctatggtggttggcacaaca tgttaaaaactgtttatagtgatgtagaaaaccctcaccttatgggttgg gattatcctaaatgtgatagagccatgcctaacatgcttagaattatggc ctcacttgttcttgctcgcaaacatacaacgtgttgtagcttgtcacacc gtttctatagattagctaatgagtgtgctcaagtattgagtgaaatggtc atgtgtggcggttcactatatgttaaaccaggtggaacctcatcaggaga tgccacaactgcttatgctaatagtgttttttaacatttgtcaagctgtca cggccaatgttaatgcactttttatctactgatggtaacaaaattgccgat aagtatgtccgcaatttacaacacagactttatgagtgtctctatagaaa tagagatgttgacacagactttgtgaatgagttttacgcatatttgcgta aacatttctcaatgatgatactctctgacgatgctgttgtgtgtttcaat agcacttatgcatctcaaggtctagtggctagcataaagaactttaagtc agttctttattatcaaaacaatgttttttatgtctgaagcaaaatgttgga ctgagactgaccttactaaaggacctcatgaattttgctctcaacataca atgctagttaaacaggtgatgattatgtgtaccttccttacccagatcc atcaagaatcctaggggccggctgtttttgtagatgatatcgtaaaaacag atggtacacttatgattgaacggttcgtgtctttagctatagatgcttac ccacttactaaacatcctaatcaggagtatgctgatgtctttcatttgta cttacaatacataagaaagctacatgatgagttaacaggacacatgttag acatgtattctgttatgcttactaatgataacacttcaaggtattgggaa cctgagtttttatgaggctatgtacacaccgcatacagtcttacag
```

The nucleic sequence of ORF 1b) (Severe acute respiratory syndrome coronavirus 2; NCBI Sequence: BCN86436.1; SEQ ID NO: 14) is:

```
gtgcagcccgtcttacaccgtgcggcacaggcactagtactgatgtcgtatacagggcttttgacatctacaatgat aaagtagctggttttgctaaattcctaaaaactaattgttgtcgcttccaagaaaaggacgaagatgacaatttaat tgattcttactttgtagttaagagacacactttctctaactaccaacatgaagaaacaatttataatttacttaagg attgtccagctgttgctaaacatgacttctttaagtttagaatagacggtgacatggtaccacatatatcacgtcaa cgtcttactaaatacacaatggcagacctcgtctatgctttaaggcattttgatgaaggtaattgtgacacattaaa agaaatacttgtcacatacaattgttgtgatgatgattatttcaataaaaaggactggtatgattttgtagaaaacc cagatatattacgcgtatacgccaacttaggtgaacgtgtacgccaagctttgttaaaaacagtacaattctgtgat
```

-continued

```
gccatgcgaaatgctggtattgttggtgtactgacattagataatcaagatctcaatggtaactggtatgatttcgg tgatttcatacaaaccacgccaggtagtggagttcctgttgtagattcttattattcattgttaatgcctatattaa ccttgaccagggctttaactgcagagtcacatgttgacactgacttaacaaagccttacattaagtgggatttgtta aaatatgacttcacggaagagaggttaaaactctttgaccgttattttaaatattgggatcagacataccacccaaa ttgtgttaactgtttggatgacagatgcattctgcattgtgcaaactttaatgttttattctctacagtgttcccac ctacaagttttggaccactagtgagaaaaatatttgttgatggtgttccatttgtagtttcaactggataccacttc agagagctaggtgttgtacataatcaggatgtaaacttacatagctctagacttagtttttaaggaattacttgtgta tgctgctgaccctgctatgcacgctgcttctggtaatctattactagatadaacgcactacgtgcttttcagtagctg cacttactaacaatgttgcttttcaaactgtcaaacccggtaattttaacaaagacttctatgactttgctgtgtct aagggtttctttaaggaaggaagttctgttgaattaaaaacacttcttctttgctcaggatggtaatgctgctatcag cgattatgactactatcgttataatctaccaacaatgtgtgatatcagacaactactatttgtagttgaagttgttg ataagtactttgattgttacgatggtggctgtattaatgctaaccaagtcatcgtcaacaacctagacaaatcagct ggttttccatttaataaatggggtaaggctagactttattatgattcaatgagttatgaggatcaagatgcacttttt cgcatatacaaaacgtaatgtcatccctactataactcaaatgaatcttaagtatgccattagtgcaaagaatagag ctcgcaccgtagctggtgtctctatctgtagtactatgaccaatagacagtttcatcaaaaattattgaaatcaata gccgccactagaggagctactgtagtaattggaacaagcaaattctatggtggttggcacaacatgttaaaaactgt ttatagtgatgtagaaaaccctcaccttatgggttgggattatcctaaatgtgatagagccatgcctaacatgctta gaattatggcctcacttgttcttgctcgcaaacatacaacgtgttgtagcttgtcacaccgtttctatagattagct aatgagtgtgctcaagtattgagtgaaatggtcatgtgtggcggttcactatatgttaaaccaggtggaacctcatc aggagatgccacaactgcttatgctaatagtgttttttaacatttgtcaagctgtcacggccaatgttaatgcacttt tatctactgatggtaacaaaattgccgataagtatgtccgcaatttacaacacagactttatgagtgtctctataga aatagagatgttgacacagactttgtgaatgagtttttacgcatatttgcgtaaacatttctcaatgatgatactctc tgacgatgctgttgtgtgtttcaatagcacttatgcatctcaaggtctagtggctagcataaagaactttaagtcag ttctttattatcaaaacaatgttttttatgtctgaagcaaaatgttggactgagactgaccttactaaaggacctcat gaattttgctctcaacatacaatgctagttaaacagggtgatgattatgtgtaccttccttacccagatccatcaag aatcctaggggccggctgttttgtagatgatatcgtaaaaacagatggtacacttatgattgaacggttcgtgtctt tagctatagatgcttacccacttactaaacatcctaatcaggagtatgctgatgtctttcatttgtacttacaatac ataagaaagctacatgatgagttaacaggacacatgttagacatgtattctgttatgcttactaatgataacacttc aaggtattgggaacctgagttttatgaggctatgtacacaccgcatacagtcttacaggctgttggggcttgtgttc tttgcaattcacagacttcattaagatgtggtgcttgcatacgtagaccattcttatgttgtaaatgctgttacgac catgtcatatcaacatcacataaattagtcttgtctgttaatccgtatgtttgcaatgctccaggttgtgatgtcac agatgtgactcaactttacttaggaggtatgagctattattgtaaatcacataaaccacccattagttttccattgt gtgctaatggacaagttttttggtttatataaaaatacatgtgttggtagcgataatgttactgactttaatgcaatt gcaacatgtgactggacaaatgctggtgattacattttagctaacacctgtactgaaagactcaagcttttttgcagc agaaacgctcaaagctactgaggagacatttaaactgtcttatggtattgctactgtacgtgaagtgctgtctgaca gagaattacatcttttcatgggaagttggtaaacctagaccaccacttaaccgaaattatgtgtcttactggttatcgt gtaactaaaaacagtaaagtacaaataggagagtacacctttgaaaaaggtgactatggtgatgctgttgtttaccg aggtacaacaacttacaaattaaatgttggtgattattttttgtgctgacatcacatacagtaatgccattaagtgcac ctacactagtgccacaagagcactatgttagaattactggcttatacccaacactcaatatctcagatgagttttct agcaatgttgcaaattatcaaaaggttggtatgcaaaagtattctacactccagggaccacctggtactggtaagag tcattttgctattggcctagctctctactacccttctgctcgcatagtgtatacagcttgctctcatgccgctgttg
```

-continued atgcactatgtgagaaggcattaaaatatttgcctatagataaatgtagtagaattatacctgcacgtgctcgtgta gagtgtttgataaattcaaagtgaattcaacattagaacagtatgtctttgtactgtaaatgcattgcctgagac gacagcagatatagttgtctttgatgaaatttcaatggccacaaattatgatttgagtgttgtcaatgccagattac gtgctaagcactatgtgtacattggcgaccctgctcaattacctgcaccacgcacattgctaactaagggcacacta gaaccagaatatttcaattcagtgtgtagacttatgaaaactataggtccagacatgttcctcggaacttgtcggcg ttgtcctgctgaaattgttgacactgtgagtgctttggtttatgataataagcttaaagcacataaagacaaatcag ctcaatgctttaaaatgtttttataagggtgttatcacgcatgatgtttcatctgcaattaacaggccacaaataggc gtggtaagagaattccttacacgtaaccctgcttggagaaaagctgtctttatttcaccttataattcacagaatgc tgtagcctcaaagattttgggactaccaactcaaactgttgattcatcacagggctcagaatatgactatgtcatat tcactcaaaccactgaaacagctcactcttgtaatgtaaacagatttaatgttgctattaccagagcaaagtaggc atactttgcataatgtctgatagagacctttatgacaagttgcaatttacaagtcttgaaattccacgtaggaatgt ggcaactttacaagctgaaaatgtaacaggactctttaaagattgtagtaaggtaatcactgggttacatcctacac aggcacctacacacctcagtgttgacactaaattcaaaactgaaggtttatgtgttgacatacctggcatacctaag gacatgacctatagaagactcatctctatgatgggtttttaaaatgaattatcaagttaatggttaccctaacatgtt tatcacccgcgaagaagctataagacatgtacgtgcatggattggcttcgatgtcgaggggtgtcatgctactagag aagctgttggtaccaatttacctttacagctaggttttttctacaggtgttaacctagttgctgtacctacaggttat gttgatacacctaataatacagattttttccagagttagtgctaaaccaccgcctggagatcaatttaaacacctcat accacttatgtacaaaggacttccttggaatgtagtgcgtataaagattgtacaaatgttaagtgacacacttaaaa atctctctgacagagtcgtatttgtcttatgggcacatggctttgagttgacatctatgaagtattttgtgaaaata ggacctgagcgcacctgttgtctatgtgatagacgtgccacatgcttttccactgcttcagacacttatgcctgttg gcatcattctattggatttgattacgtctataatccgtttatgattgatgttcaacaatggggtttttacaggtaacc tacaaagcaaccatgatctgtattgtcaagtccatggtaatgcacatgtagctagttgtgatgcaatcatgactagg tgtctagctgtccacgagtgctttgttaagcgtgttgactggactattgaatatcctataattggtgatgaactgaa gattaatgcggcttgtagaaaggttcaacacatggttgttaaagctgcattattagcagacaaattcccagttcttc acgacattggtaaccctaaagctattaagtgtgtacctcaagctgatgtagaatggaagttctatgatgcacagcct tgtagtgacaaagcttataaaatagaagaattattctattcttatgccacacattctgacaaattcacagatggtgt atgcctattttggaattgcaatgtcgatagatatcctgctaattccattgtttgtagatttgacactagagtgctat ctaaccttaacttgcctggttgtgatggtggcagtttgtatgtaaataaacatgcattccacacaccagctttttgat aaaagtgcttttgttaatttaaaacaattaccattttttctattactctgacagtccatgtgagtctcatggaaaaca agtagtgtcagatatagattatgtaccactaaagtctgctacgtgtataacacgttgcaatttaggtggtgctgtct gtagacatcatgctaatgagtacagattgtatctcgatgcttataacatgatgatctcagctggctttagcttgtgg gtttacaaacaatttgatacttataacctctggaacacttttacaagacttcagagtttagaaaatgtggctttttaa tgttgtaaataagggacactttgatggacaacagggtgaagtaccagtttctatcattaataacactgtttacacaa aagttgatggtgttgatgtagaattgtttgaaaataaaacaacattacctgttaatgtagcatttgagctttgggct aagcgcaacattaaaccagtaccagaggtgaaaatactcaataatttgggtgtggacattgctgctaatactgtgat ctgggactacaaaagagatgctccagcacatatatctactattggtgtttgttctatgactgacatagccaagaaac caactgaaacgatttgtgcaccactcactgtctttttttgatggtagagttgatggtcaagtagacttatttagaaat gcccgtaatggtgttcttattacagaaggtagtgttaaaggtttacaaccatctgtaggtcccaaacaagctagtct taatggagtcacattaattggagaagccgtaaaaacacagttcaattattataagaaagttgatggtgttgtccaac aattacctgaaacttactttactcagagtagaaatttacaagaatttaaacccaggagtcaaatggaaattgatttc -continued

```
ttagaattagctatggatgaattcattgaacggtataaattagaaggctatgccttcgaacatatcgtttatggaga ttttagtcatagtcagttaggtggtttacatctactgattggactagctaaacgttttaaggaatcacctttttgaat tagaagatttattcctatggacagtacagttaaaaactatttcataacagatgcgcaaacaggttcatctaagtgt gtgtgttctgttattgatttattacttgatgattttgttgaaataataaaatcccaagatttatctgtagtttctaa ggttgtcaaagtgactattgactatacagaaatttcatttatgctttggtgtaaagatggccatgtagaaacatttt acccaaaattacaatctagtcaagcgtggcaaccgggtgttgctatgcctaatctttacaaaatgcaaagaatgcta ttagaaaagtgtgaccttcaaaattatggtgatagtgcaacattacctaaaggcataatgatgaatgtcgcaaaata tactcaactgtgtcaatatttaaacacattaacattagctgtaccctataatatgagagttatacattttggtgctg gttctgataaaggagttgcaccaggtacagctgtttttaagacagtggttgcctacgggtacgctgcttgtcgattca gatcttaatgactttgtctctgatgcagattcaactttgattggtgattgtgcaactgtacatacagctaataaatg ggatctcattattagtgatatgtacgaccctaagactaaaaatgttacaaaagaaaatgactctaaagagggtttt tcacttacatttgtgggtttatacaacaaaagctagctcttggaggttccgtggctataaagataacagaacattct tggaatgctgatctttataagctcatgggacacttcgcatggtggacagcctttgttactaatgtgaatgcgtcatc atctgaagcatttttaattggatgtaattatcttggcaaaccacgcgaacaaatagatggttatgtcatgcatgcaa attacatattttggaggaatacaaatccaattcagttgtcttcctattctttatttgacatgagtaaatttccccctt aaattaaggggtactgctgttatgtctttaaaagaaggtcaaatcaatgatatgattttatctcttcttagtaaagg tagacttataattagagaaaacaacagagttgttatttctagtgatgttcttgttaacaactaa
```

The amino sequence of ORF1a (SEQ ID NO: 15) is:

```
# 5'3' Frame 1 (longest ORF)
MESLVPGFNEKTHVQLSLPVLQVRDVLVRGFGDSVEEVLSEARQHLKDGTCGLVEVEKGVLPOLEQPYVFIKRSDAR

TAPHGHVMVELVAELEGIQYGRSGETLGVLVPHVGEIPVAYRKVLLRKNGNKGAGGHSYGADLKSFDLGDELGTDPY

EDFQENWNTKHSSGVTRELMRELNGGAYTRYVDNNFCGPDGYPLECIKDLLARAGKASCTLSEQLDFIDTKRGVYCC

REHEHEIAWYTERSEKSYELQTPFEIKLAKKFDTENGECPNFVFPLNSIIKTIQPRVEKKKLDGFMGRIRSVYPVAS

PNECNQMCLSTLMKCDHCGETSWQTGDFVKATCEFCGTENLTKEGATTCGYLPQNAVVKIYCPACHNSEVGPEHSLA

EYHNESGLKTILRKGGRTIAFGGCVFSYVGCHNKCAYWVPRASANIGCNHTGVVGEGSEGLNDNLLEILQKEKVNIN

IVGDFKLNEEIAIILASFSASTSAFVETVKGLDYKAFKQIVESCGNFKVTKGKAKKGAWNIGEQKSILSPLYAFASE

AARVVRSIFSRTLETAQNSVRVLQKAAITILDGISQYSLRLIDAMMFTSDLATNNLVVMAYITGGVVOLTSQWLTNI

FGTVYEKLKPVLDWLEEKFKEGVEFLRDGWEIVKFISTCACEIVGGQIVTCAKEIKESVQTFFKLVNKFLALCADSI

IIGGAKLKALNLGETFVTHSKGLYRKCVKSREETGLLMPLKAPKEIIFLEGETLPTEVLTEEVVLKTGDLQPLEQPT

SEAVEAPLVGTPVCINGLMLLEIKDTEKYCALAPNMMVTNNTFTLKGGAPTKVTFGDDTVIEVQGYKSVNITFELDE

RIDKVLNEKCSAYTVELGTEVNEFACVVADAVIKTLQPVSELLTPLGIDLDEWSMATYYLFDESGEFKLASHMYCSF

YPPDEDEEEGDCEEEEFEPSTQYEYGTEDDYQGKPLEFGATSAALQPEEEQEEDWLDDDSQQTVGQQDGSEDNQTTT

IQTIVEVQPQLEMELTPVVQTIEVNSFSGYLKLTDNVYIKNADIVEEAKKVKPTVVVNAANVYLKHGGGVAGALNKA

TNNAMQVESDDYIATNGPLKVGGSCVLSGHNLAKHCLHVVGPNVNKGEDIQLLKSAYENFNQHEVLLAPLLSAGIFG

ADPIHSLRVCVDTVRTNVYLAVFDKNLYDKLVSSFLEMKSEKQVEQKIAEIPKEEVKPFITESKPSVEQRKODDKKI

KACVEEVTTTLEETKELTENLLLYIDINGNLHPDSATLVSDIDITFLKKDAPYIVGDVVQEGVLTAVVIPTKKAGGT

TEMLAKALRKVPTDNYITTYPGQGLNGYTVEEAKTVLKKCKSAFYILPSIISNEKQEILGTVSWNLREMLAHAEETR

KLMPVCVETKAIVSTIQRKYKGIKIQEGVVDYGARFYFYTSKTTVASLINTLNDLNETLVTMPLGYVTHGLNLEEAA

RYMRSLKVPATVSVSSPDAVTAYNGYLTSSSKTPEEHFIETISLAGSYKDWSYSGQSTQLGIEFLKRGDKSVYYTSN

PTTFHLDGEVITFDNLKTLLSLREVRTIKVFTTVDNINLHTQVVDMSMTYGQQFGPTYLDGADVTKIKPHNSHEGKT
```

-continued

FYVLPNDDTLRVEAFEYYHTTDPSFLGRYMSALNHTKKWKYPQVNGLTSIKWADNNCYLATALLTLQQIELKENPPA

LQDAYYRARAGEAANFCALILAYCNKTVGELGDVRETMSYLFQHANLDSCKRVLNVVCKTCGQQQTTLKGVEAVMYM

GTLSYEQFKKGVQIPCTCGKQATKYLVQQESPFVMMSAPPAQYELKHGTFTCASEYTGNYQCGHYKHITSKETLYCI

DGALLTKSSEYKGPITDVFYKENSYTTTIKPVTYKLDGVVCTEIDPKLDNYYKKDNSYFTEQPIDLVPNQPYPNASF

DNFKFVCDNIKFADDLNQLTGYKKPASRELKVTFFPDLNGDVVAIDYKHYTPSFKKGAKLLHKPIVWHVNNATNKAT

YKPNTWCIRCLWSTKPVETSNSFDVLKSEDAQGMDNLACEDLKPVSEEVVENPTIQKDVLECNVKTTEVVGDIILKP

ANNSLKITEEVGHTDLMAAYVDNSSLTIKKPNELSRVLGLKTLATHGLAAVNSVPWDTIANYAKPFLNKVVSTTTNI

VTRCLNRVCTNYMPYFFTLLLQLCTFTRSTNSRIKASMPTTIAKNTVKSVGKFCLEASFNYLKSPNFSKLINIIIWF

LLLSVCLGSLIYSTAALGVLMSNLGMPSYCTGYREGYLNSTNVTIATYCTGSIPCSVCLSGLDSLDTYPSLETIQIT

ISSFKWDLTAFGLVAEWFLAYILFTRFFYVLGLAAIMQLFFSYFAVHFISNSWLMWLIINLVQMAPISAMVRMYIFF

ASFYYVWKSYVHVVDGCNSSTCMMCYKRNRATRVECTTIVNGVRRSFYVYANGGKGFCKLHNWNCVNCDTFCAGSTF

ISDEVARDLSLQFKRPINPTDQSSYIVDSVTVKNGSIHLYFDKAGQKTYERHSLSHFVNLDNLRANNTKGSLPINVI

VFDGKSKCEESSAKSASVYYSQLMCQPILLLDQALVSDVGDSAEVAVKMFDAYVNTFSSTENVPMEKLKTLVATAEA

ELAKNVSLDNVLSTFISAARQGFVDSDVETKDVVECLKLSHQSDIEVTGDSCNNYMLTYNKVENMTPRDLGACIDCS

ARHINAQVAKSHNIALIWNVKDFMSLSEQLRKQIRSAAKKNNLPFKLTCATTRQVVNVVTTKIALKGGKIVNNWLKQ

LIKVTLVFLFVAAIFYLITPVHVMSKHTDFSSEIIGYKAIDGGVTRDIASTDTCFANKHADFDTWFSQRGGSYTNDK

ACPLIAAVITREVGFVVPGLPGTILRTTNGDFLHFLPRVFSAVGNICYTPSKLIEYTDFATSACVLAAECTIFKDAS

GKPVPYCYDTNVLEGSVAYESLRPDTRYVLMDGSIIQFPNTYLEGSVRVVTTFDSEYCRHGTCERSEAGVCVSTSGR

WVLNNDYYRSLPGVFCGVDAVNLLTNMFTPLIQPIGALDISASIVAGGIVAIVVTCLAYYFMRFRRAFGEYSHVVAF

NTLLFLMSFTVLCLTPVYSFLPGVYSVIYLYLTFYLTNDVSFLAHIQWMVMFTPLVPFWITIAYIICISTKHFYWFF

SNYLKRRVVFNGVSFSTFEEAALCTFLLNKEMYLKLRSDVLLPLTQYNRYLALYNKYKYFSGAMDTTSYREAACCHL

AKALNDFSNSGSDVLYQPPQTSITSAVLOSGFRKMAFPSGKVEGCMVQVTCGTTTLNGLWLDDVVYCPRHVICTSED

MLNPNYEDLLIRKSNHNFLVQAGNVOLRVIGHSMONCVLKLKVDTANPKTPKYKFVRIQPGQTFSVLACYNGSPSGV

YQCAMRPNFTIKGSFLNGSCGSVGFNIDYDCVSFCYMHHMELPTGVHAGTDLEGNFYGPFVDRQTAQAAGTDTTITV

NVLAWLYAAVINGDRWFLNRFTTTLNDENLVAMKYNYEPLTQDHVDILGPLSAQTGIAVLDMCASLKELLQNGMNGR

TILGSALLEDEFTPFDVVRQCSGVTFQSAVKRTIKGTHHWLLLTILTSLLVLVQSTQWSLFFFLYENAFLPFAMGII

AMSAFAMMFVKHKHAFLCLFLLPSLATVAYFNMVYMPASWVMRIMTWLDMVDTSLSGFKLKDCVMYASAVVLLILMT

ARTVYDDGARRVWTLMNVLTLVYKVYYGNALDQAISMWALIISVTSNYSGVVTTVMFLARGIVEMCVEYCPIFFITG

NTLQCIMLVYCFLGYFCTCYFGLFCLLNRYFRLTLGVYDYLVSTQEFRYMNSQGLLPPKNSIDAFKLNIKLLGVGGK

PCIKVATVQSKMSDVKCTSVVLLSVLQQLRVESSSKLWAQCVQLHNDILLAKDTTEAFEKMVSLLSVLLSMQGAVDI

NKLCEEMLDNRATLQAIASEFSSLPSYAAFATAQEAYEQAVANGDSEVVLKKLKKSLNVAKSEFDRDAAMQRKLEKM

ADQAMTQMYKQARSEDKRAKVTSAMQTMLFTMLRKLDNDALNNIINNARDGCVPLNIIPLTTAAKLMVVIPDYNTYK

NTCDGTTFTYASALWEIQQVVDADSKIVQLSEISMDNSPNLAWPLIVTALRANSAVKLONNELSPVALROMSCAAGT

TQTACTDDNALAYYNTTKGGRFVLALLSDLQDLKWARFPKSDGTGTIYTELEPPCRFVTDTPKGPKVKYLYFIKGLN

NLNRGMVLGSLAATVRLOAGNATEVPANSTVLSFCAFAVDAAKAYKDYLASGGQPITNCVKMLCTHTGTGQAITVTP

EANMDQESFGGASCCLYCRCHIDHPNPKGFCDLKGKYVQIPTTCANDPVGFTLKNTVCTVCGMWKGYGCSCDQLREP

MLQSADAQSFLNGFAV-

5'3' Frame 2
WRALSLVSTRKHTSNSVCLFYRFATCSYVALETPWRRSYQRHVNILKMALVA--KLKKAFCLNLNSPMCSSNVRMLE

LHLMVMLWLSW-QNSKAFSTVVVVRHLVSLSLMWAKYQWLTARFFFVRTVIKELVAIVTAPI-SHLT-ATSLALILM

KIFKKTGTLNIAVVLPVNSCVSLTEGHTLAMSITTSVALMATLLSALKTF-HVLVKLHALCPNNWTLLTLRGVYTAA

-continued

```
VNMSMKLLGTRNVLKRAMNCRHLLKLNWQRNLTPSMGNVQILYFP-IP-SRLFNQGLKRKSLMALWVEFDLSIQLRH

QMNATKCAFQLS-SVIIVVKLHGRRAILLKPLANFVALRI-LKKVPLLVVTYPKMLLLKFIVQHVTIQK-DLSIVLP

NTIMNLA-KPFFVRVVALLPLEAVCSLMLVAITSVPIGFHVLALT-VVTIQVLLEKVPKVLMTTFLKYSKKRKSTSI

LLVTLNLMKRSPLFWHLFLLPQVLLWKL-KVWIIKHSNKLLNPVVILKLQKEKLKKVPGILVNRNQY-VLFMHLHQR

LLVLYDQFSPALLKLLKILCVFYRRPL-QY-MEFHSIH-DSLML-CSHLIWLLTI-L-WPTLQVVLES-LRSG-LTS

LALFMKNSNPSLIGLKRSLRKV-SFLETVGKLLNLSQPVLVKLSVDKLSPVQRKLRRVFRHSLSL-INFWLCVLTLS

LLVELNLKP-I-VKHLSRTQRDCTESVLNPEKKLAYSCL-KPQKKLSS-REKHFPQKC-QRKLS-KLVIYNH-NNLL

VKLLKLHWLVHQFVLTGLCCSKSKTQKSTVPLHLI-W-QTIPSHSKAVHQQRLLLVMTL--KCKVTRV-ISLLNLMK

GLIKYLMRSALPIQLNSVQK-MSSPVLWQMLS-KLCNQYLNYLHHWALI-MSGVWLHTTYLMSLVSLNWLHICIVLS

TLQMRMKKKVIVKKKSLSHQLNMSMVLKMITKVNLWNLVPLLLLFNLKKSKKKIG-MMIVNKLLVNKTAVRTIRQLL

FKQLLRENLN-RWNLHQLFRLLK-IVLVVI-+NLNLLTMYTLKMQTLWKKLKR-NQQWLLMQPMFTLNMEEVLQEP-

IRLLTMPCKLNLMIT-LLMDHLKWVVVVF-ADTILLNTVFMLSAQMLTKVKTENFLRVLMKILISTKFYLHHYYQLV

FLVLTLYIL-EFV-ILFAQMST-LSLIKISMTNLFQAFWK-RVKSKLNKRSLRFLKRKLSHL-LKVNLQLNRENKMI

RKSKLVLKKLQQLWKKLSSSQKTCYFILTLMAIFIQILPLLLVTLTSLS-RKMLHI-WVMLFKRVF-LLWLYLLKRL

VALLKC-RKL-EKCQQTII-PLTRVRV-MVTL-RRQRQCLKSVKVPFTFYHLLSLMRSKKFLELFLGICEKCLHMQK

KHAN-CLSVWKLKP-FQLYSVNIRVLKYKRVWLIMVLDFTFTPVKQL-RHLSTHLTI-MKLLLQCHLAM-HMA-IWK

KLLGI-DLSKCQLQFLFLHLMLLQRIMVILLLLLKHLKNILLKPSHLLVPIKIGPILDNLHN-V-NFLREVIKVYIT

LVILPHST-MVKLSPLTILRHFFL-EK-GLLRCLQQ-TTLTSTRKLWTCQ-HMDNSLVQLIWMELMLLK-NLIIHMK

VKHFMFYLMMTLYVLRLLSTTTQLILVFWVGTCQH-ITLKSGNTHKLMV-LLLNGQITTVILPLHC-HSNK-S-SLI

HLLYKMLITEQGLVKLLTFVHLS-PTVIRQ-VS-VMLEKQ-VTCFNMPI-ILAKES-TWCVKLVDNSRQPLRV-KLL

CTWAHFLMNNLRKVFRYLVRVVNKLQNI-YNRSHLLL-CQHHLLSMNLSMVHLLVLVSTLVITSVVTINI-LLKKLC

IA-TVLYLQSPQNTKVLLRMFSTKKTVTQQP-NQLLINWMVLFVQKLTLSWTIIIRKTILISQSNQLILYQTNHIQT

QASIILSLYVIISNLLMI-TS-LVIRNLLQESLKLHFSLT-MVMWWLLIINTTHPLLRKELNCYINLLFGMLTMQLI

KPRINQIPGVYVVFGAQNQLKHQIRLMY-SQRTRREWIILPAKI-NQSLKK-WKILPYRKTFLSVM-KLPKL-ETLY

LNQQIIV-KLQKRLATQI-WLLM-TILVLLLRNLMNYLEY-V-KPLLLMV-LLLIVSLGIL-LIMLSLFLTKLLVQL

LT-LHGV-TVFVLIICLISLLYCYNCVLLLEVQILELKHLCRLL-QRILLRVSVNFV-RLHLII-SHLIFLN--IL-

FGFYY-VFA-VL-STQPLL-VF-CLI-ACLLTVLVTEKAI-TLLMSLLQPTVLVLYLVVFVLVV-IL-TPILL-KLY

KLPFHLINGI-LLLA-LQSGFWHIFFSLGFSMYLDWLQSCNCFSAILQYILLVILGLCG--LILYKWPRFQLWLECT

SSLHHFIMYGKVMCML-TVVIHQLV-CVTNVIEQQESNVQLLLMVLEGPFMSMLMEVKAFANYTIGIVLIVIHSVLV

VHLLVMKLRETCHYSLKDQ-ILLTSLLTSLIVLQ-RMVPSIFTLIKLVKRLMKDILSLILLT-TT-ELITLKVHCLL

ML-FLMVNQNVKNHLQNQRLFTTVSLCVNLYCY-IRH-CLMLVIVRKLQLKCLMLTLIRFHQLLTYQWKNSKH-LQL

QKLNLQRMCP-TMSYLLLFQQLGKGLLIQM-KLKMLLNVLNCHINLT-KLLAIVVITICSPITKLKT-HPVTLVLVL

TVVRVILMRR-QKVTTLL-YGTLKISCHCLNNYENKYVVLLKRITYLLS-HVQLLDKLLML-QQR-HLRVVKLLIIG

-SS-LKLHLCSFLLLLFSI--HLFMSCLNILTFQVKS-DTRLLMVVSLVT-HLQILVLLTNMLILTHGLASVVVVIL

MTKLAH-LLQS-QEKWVLSCLVCLARYYAQLMVTFCISYLEFLVQLVTSVTHHQNL-STLTLQHQLVFWLLNVQFLK

MLLVSQYHIVMIPMY-KVLLLMKVYALTHVMCSWMALLENFLTPTLKVLLEW-QLLILSTVGTALVKDQKLVFVYLL

VVDGYLTMIITDLYQEFSVV-ML-IYLLICLHH-FNLLVLWTYQHL--LVVL-LS--HALPTIL-GLEELLVNTVM-

LPLILYYSLCHSLYSV-HQFTHSYLVFILLFTCT-HFILLMMFLF-HIFSGWLCSHL-YLSG-QLLISFVFPQSISI

GSLVIT-RDV-SLMVFPLVLLKKLRCAPFC-IKKCI-SCVVMCYYLLRNIIDT-LFIISTSILVEQWIQLATEKLLV

VISQRLSMTSVTQVLMFFTNHHKPLSPQLFCRVVLEKWHSHLVKLRVVWYK-LVVQLHLTVFGLMT-FTVQDM-SAP

LKTCLTLIMKIYSFVSLIIISWYRLVMENSGLLDILCKIVYLSLRLIQPILRHLSISLEAFNQDRLFQC-LVTMVHH
```

-continued

LVFTNVL-GPISLLRVHSLMVHVVVLVLT-IMTVSLFVTCTIWNYQLEFMLAQT-KVTFMDLLLLTGKQHKQLVRTQL

LQLMF-LGCTLLL-METGGFSIDLPQLLMTLTLWL-STIMNL-HKTMLTY-DLFLLKLELPF-ICVLH-KNYCKMV-

MDVPYWVVLY-KMNLHLLMLLDNAQVLLSKVQ-KEQSRVHTTGCYSQF-LHF-F-SRVLNGLCSFFCMKMPFYLLLW

VLLLCLLLQ-CLSNISMHFSVCFCYLLLPL-LILIWSICLLVG-CVL-HGWIWLILVCLVLS-KTVLCMHQL-CY-S

L-QQELCMMMVLGECGHL-MS-HSFIKFIMVML-IKPFPCGLL-SLLLLTTQV-LQLSCFWPEVLFLCVLSIALFSS

-LVIHFSV-C-FIVS-AIFVLVTLASFVYSTATLD-LLVFMIT-FLHRSLDI-IHRDYSHPRIA-MPSNSTLNCWVL

VANLVSK-PLYSLKCQM-SAHQ-SYSQFCNNSE-NHHLNCGLNVSSYTMTFS-LKILLKPLKKWFHYFLFCFPCRVL

-T-TSFVKKCWTTGQPYKL-PQSLVPFHHMQLLLLLKKLMSRLLLMVILKLFLKS-RSL-MWLNLNLTVMQPCNVSW

KRWLIKL-PKCINRLDLRTRGQKLLVLCRQCFSLCLESWIMMHSTTLSTMQEMVVFP-T-YLLQQQPN-WLSYQTIT

HIKIRVMVQHLLMHQHCGKSNRL-MQIVKLENLVKLVWTIHLI-HGLLL-QL-GPILLSNYRIMSLVLLHYDRCLVL

PVLHKLLALMTMR-LTTTQQREVGLYLHCYPIYRI-NGLDSLRVMELVLSIQNWNHLVGLLQTHLKVLK-SIYTLLK

D-TT-IEVWYLVV-LPQYVYKLVMQQKCLPIQLYYLSVLLL-MLLKLTKII-LVGDNQSLIVLRCCVHTLVLVRQ-Q

LHRKPIWIKNPLVVHRVVCTAVAT-IIQILKDFVT-KVSMYKYLQLVLMTLWVLHLKTQSVPSAVCGKVMAVVVINS

ANPCFSQLMHNRF-TGLRC

5'3' Frame 3
GEPCPWFQRENTRPTQFACFTGSRRARTWLWRLRGGGLIRGTSTS-RWHLWLSRS-KRRFAST-TALCVHQTFGCSN

CTSWSCYG-AGSRTRRHSVRS-W-DTWCPCPSCGRNTSGLPQGSSS-ER--RSWWP-LRRRSKVI-LRRRAWH-SL-

RFSRKLEH-T-QWCYP-THA-A-RRGIHSLCR-QLLWP-WLPS-VH-RPSSTCW-SFMHFVRTTGLY-H-EGCILLP

-T-A-NCLVHGTF-KEL-IADTF-N-IGKEI-HLQWGMSKFCISLKFHNQDYSTKG-KEKA-WLYG-NSICLSSCVT

K-MQPNVPFNSHEV-SLW-NFMADGRFC-SHLRILWH-EFD-RRCHYLWLLTPKCCC-NLLSSMSQFRSRT-A-SCR

IP--IWLENHSS-GWSHYCLWRLCVLLCWLP-QVCLLGSTC-R-HRL-PYRCCWRRFRRS--QPS-NTPKRESQHQY

CW-L-T--RDRHYFGIFFCFHKCFCGNCERFGL-SIQTNC-ILW-F-SYKRKS-KRCLEYW-TEINTESSLCICIRG

CSCCTINFLPHS-NCSKFCACFTEGRYNNTRWNFTVFTETH-CYDVHI-FGY-QSSCNGLHYRWCCSVDFAVAN-HL

WHCL-KTQTRP-LA-REV-GRCRVS-RRLGNC-IYLNLCL-NCRWTNCHLCKGN-GECSDIL-ACK-IFGFVC-LYH

YWWS-T-SLEFR-NICHALKGIVQKVC-IQRRNWPTHASKSPKRNYLLRGRNTSHRSVNRGSCLENW-FTTIRTTY-

-SC-SSIGWYTSLY-RAYVARNQRHRKVLCPCT-YDGNKQYLHTQRRCTNKGYFW--HCDRSARLQECEYHF-T--K

D--ST--EVLCLYS-TRYRSK-VRLCCGRCCHKNFATSI-ITYTTGH-FR-VEYGYILLI---VW-V-IGFTYVLFFL

PSR-G-RRR-L-RRRV-AINSI-VWY-R-LPR-TFGIWCHFCCSST-RRARRRLVR---STNCWSTRRQ-GQSDNYY

SNNC-GSTSIRDGTYTSCSDY-SE-F-WLFKTY-QCIH-KCRHCGRS-KGKTNSGC-CSQCLP-TWRRCCRSLK-GY

-QCHAS-I--LHSY-WTT-SGW-LCFKRTQSC-TLSSCCRPKC-QR-RHSTS-ECL-KF-SARSSTCTIIISWYFWC

-PYTFFKSLCRYCSHKCLLSCL--KSL-QTCFKLFGNEE-KAS-TKDR-DS-RGS-AIYN-K-TFS-TEKTR--ENQ

SLC-RSYNNSGRN-VPHRKLVTLY-H-WQSSSRFCHSC--H-HHFLKERCSIYSG-CCSRGCFNCCGYTY-KGWWHY

-NASESFEKSANRQLYNHLPGSGFKWLHCRGGKDSA-KV-KCLLHSTIYYL--EARNSWNCFLEFARNACTCRRNTQ

INACLCGN-SHSFNYTA-I-GY-NTRGCG-LWC-ILLLHQ-NNCSVTYQHT-RSK-NSCYNATWLCNTWLKFGRSCS

VYEISQSASYSFCFFT-CCYSV-WLSYFFF-NT-RTFY-NHLTCWFL-RLVLFWTIYTTRYRIS-ER--KCILH--S

YHIPPRW-SYHL-QS-DTSFFERSEDY-GVYNSRQH-PPHASCGHVNDIWTTVWSNLFGWS-CY-NKTS-FT-R-NI

LCFT---HSTC-GF-VLPHN-S-FSG-VHVSIKSH-KVEIPTS-WFNFY-MGR-QLLSCHCIVNTPTNRVEV-STCS

TRCLLQSKGW-SC-LLCTYLSLL--DSR-VR-C-RNNELLVSTCQFRFLQKSLERGV-NLWTTADNP-GCRSCYVHG

HTFL-TI-ERCSDTLYVW-TSYKISSTTGVTFCYDVSTTCSV-T-AWYIYLC--VHW-LPVWSL-TYNF-RNFVLHR

RCFTYKVLRIQRSYYGCFLQRKQLHNNHKTSYL-IGWCCLYRN-P-VGQLL-ERQFLFHRATN-SCTKPTISKRKLR

-F-VCM--YQIC--FKPVNWL-ETCFKRA-SYIFP-LKW-CGGY-L-TLHTLF-ERS-IVT-TYCLAC-QCN--SHV

-continued

-TKYLVYTLSLEHKTS-NIKFV-CTEVRGRAGNG-SCLRRSKTSL-RSSGKSYHTERRS-V-CENYRSCRRHYT-TS

K--FKNYRRGWPHRSNGCLCRQF-SYY-ET--II-SIRFENPCYSWFSCC--CPLGYYS-LC-AFS-QSC-YNY-HS

YTVFKPCLY-LYALFLYFIATIVYFY-KYKF-N-SIYADYYSKEYC-ECR-ILSRGFI-LFEVT-FF-TDKYYNLVF

TIKCLPRFFNLLNRCFRCFNV-FRHAFLLYWLQRRLFELY-CHYCNLLYWFYTL-CLS-WFRFFRHLSFFRNYTNYH

FIF-MGFNCFWLSCRVVFGIYSFH-VFLCTWIGCNHAIVFQLFCSTFY--FLAYVVNN-SCTNGPDFSYG-NVHLLC

IILLCMEKLCACCRRL-FINLYDVLQT--SNKSRMYNYC-WC-KVLLCLC-WR-RLLQTTQLELC-L-YILCW-YIY

---SCERLVTTV-KTNKSY-PVFLHR--CYSEEWFHPSLL--SWSKDL-KTFSLSFC-LRQPES--H-RFIAY-CYS

F-W-IKM-RIICKISVCLLQSAYVSTYTVTRSGISV-CW--CGSCS-NV-CLR-YVFINF-RINGKTQNTSCNCRS-

TCKECVLRQCLIYFYFSSSARVC-FRCRN-RCC-MS-IVTSI-HRSYWR-L--LYAHL-QS-KHDTP-PWCLY-L-C

ASY-CAGSKKSQHCFDMER-RFHVIV-TTTKTNT-CC-KE-LTF-VDMCNY-TSC-CCNNKDST-GW-NC--LVEAV

N-SYTCVPFCCCYFLFNNTCSCHV-TY-LFK-NHRIQGY-WWCHS-HSIYRYLFC-QTC-F-HMV-PAWW-LY--QS

LPIDCCSHNKRSGFCRAWFAWHDITHN-W-LFAFLT-SF-CSW-HLLHTIKTYRVH-LCNISLCFGC-MYNF-RCFW

-ASTILL-YQCTRRFCCL-KFTP-HTLCAHGWLYYSIS-HLP-RFC-SGNNF-F-VL-ARHL-KIRSWCLCIY-W-M

GT-Q-LLQIFTRSFLWCRCCKFTY-YVYTTNSTYWCFGHISIYSSWWYCSYRSNMPCLLFYEV-KSFW-IQSCSCL-

YFTIPYVIHCTLFNTSLLILTWCLFCYLLVLDILSY--CFFFSTYSVDGYVHTFSTFLDNNCLYHLYFHKAFLLVL-

-LPKETCSL-WCFL-YF-RSCAVHLFVK-RNVSKVA--CAITSYAI--ILSSL--VQVF-WSNGYN-LQRSCLLSSR

KGSQ-LQ-LRF-CSLPTTTNLYHLSCFAEWF-KNGIPIW-S-GLYGTSNLWYNYT-RSLA--RSLLSKTCDLHL-RH

A-P-L-RFTHS-V-S-FLGTGW-CSTQGYWTFYAKLCT-A-G-YSQS-DT-V-VCSHSTRTDFFSVSLLQWFTIWCL

PMCYEAQFHY-GFIP-WFMW-CWF-HRL-LCLFLLHAPYGITNWSSCWHRLRR-LLWTFC-QANSTSSWYGHNYYS-

CFSLVVRCCYKWRQVVSQSIYHNS--L-PCGYEVQL-TSNTRPC-HTRTSFCSNWNCRFRYVCFIKRITAKWYEWTY

HIG-CFIRR-IYTF-CC-TMLRCYFPKCSEKNNQGYTPLVVTHNFDFTFSFSPEYSMVFVLFFV-KCLFTFCYGYYC

YVCFCNDVCQT-ACISLFVFVTFSCHCSLF-YGLYAC-LGDAYYDMVGYG-Y-FVWF-AKRLCYVCISCSVTNPYDS

KNCV--WC-ESVDTYECLDTRL-SLLW-CFRSSHFHVGSYNLCYF-LLRCSYNCHVFGQRYCFYVC-VLPYFLHNW-

YTSVYNASLLFLRLFLYLLLWPLLFTQPLL-TDSWCL-LLSFYTGV-IYEFTGTTPTQE-HRCLQTQH-IVGCWWQT

LYQSSHCTV-NVRCKVHISSLTLSFATTQSRIII-IVGSMCPVTQ-HSLS-RYY-SL-KNGFTTFCFAFHAGCCRHK

QAL-RNAGQQGNLTSYSLRV-FPSIICSFCYCSRSL-AGCC-W-F-SCS-KVEEVFECG-I-I-P-CSHAT-VGKDG

-SSYDPNV-TG-I-GQEGKSY-CYADNAFHYA-KVG--CTQQHYQQCKRWLCSLEHNTSYNSSQTNGCHTRL-HI-K

YV-WYNIYLCISIVGNPTGCRCR--NCST--N-YGQFT-FSMASYCNSFKGQFCCQITE--A-SCCTTTDVLCCRYY

TNCLH--QCVSLLQHNKGR-VCTCTVIRFTGFEMG-IP-E-WNWYYLYRTGTTL-VCYRHT-RS-SEVFILY-RIKQ

PK-RYGTW-FSCHSTSTSW-CNRSACQFNCIIFLCFCCRCC-SLQRLSS-WGTTNH-LC-DVVYTHWYWSGNNSYTG

SQYGSRILWWCIVLSVLPLPHRSSKS-RIL-LKR-VCTNTYNLC--PCGFYT-KHSLYRLRYVERLWL-L-STPRTH

ASVS-CTIVEKRVCGV

The nucleic acid sequence of ORF1a); SEQ ID NO: 1 6)
is:

atggagagccttgtccctggtttcaacgagaaaacacacgtccaactcagtttgcctgtttttacaggttcgcgacgt gctcgtacgtggctttggagactccgtggaggaggtcttatcagaggcacgtcaacatcttaaagatggcacttgtg gcttagtagaagttgaaaaaggcgtttttgcctcaacttgaacagccctatgtgttcatcaaacgttcggatgctcga actgcacctcatggtcatgttatggttgagctggtagcagaactcgaaggcattcagtacggtcgtagtggtgagac acttggtgtccttgtccctcatgtgggcgaaataccagtggcttaccgcaaggttcttcttcgtaagaacggtaata -continued

```
aaggagctggtggccatagttacggcgccgatctaaagtcatttgacttaggcgacgagcttggcactgatccttat gaagattttcaagaaaactggaacactaaacatagcagtggtgttacccgtgaactcatgcgtgagcttaacggagg ggcatacactcgctatgtcgataacaacttctgtggccctgatggctaccctcttgagtgcattaaagaccttctag cacgtgctggtaaagcttcatgcactttgtccgaacaactggactttattgacactaagaggggtgtatactgctgc cgtgaacatgagcatgaaattgcttggtacacggaacgttctgaaaagagctatgaattgcagacacctttgaaat taaattggcaaagaaatttgacaccttcaatgggaatgtccaaattttgtatttcccttaaattccataatcaaga ctattcaaccaagggttgaaaagaaaaagcttgatggctttatgggtagaattcgatctgtctatccagttgcgtca ccaaatgaatgcaaccaaatgtgcctttcaactctcatgaagtgtgatcattgtggtgaaacttcatggcagacggg cgattttgttaaagccacttgcgaattttgtggcactgagaatttgactaaagaaggtgccactacttgtggttact taccccaaaatgctgttgttaaaatttattgtccagcatgtcacaattcagaagtaggacctgagcatagtcttgcc gaataccataatgaatctggcttgaaaaccattcttcgtaagggtggtcgcactattgcctttggaggctgtgtgtt ctcttatgttggttgccataacaagtgtgcctattgggttccacgtgctagcgctaacataggttgtaaccatacag gtgttgttggagaaggttccgaaggtcttaatgacaaccttcttgaaatactccaaaaagagaaagtcaacatcaat attgttggtgactttaaacttaatgaagagatcgccattattttggcatcttttctgcttccacaagtgctttttgt ggaaactgtgaaaggtttggattataaagcattcaaacaaattgttgaatcctgtggtaattttaaagttacaaaag gaaaagctaaaaaaggtgcctggaatattggtgaacagaaatcaatactgagtcctctttatgcatttgcatcagag gctgctcgtgttgtacgatcaatttctcccgcactcttgaaactgctcaaaattctgtgcgtgtttttacagaaggc cgctataacaatactagatggaatttcacagtattcactgagactcattgatgctatgatgttcacatctgatttgg ctactaacaatctagttgtaatggcctacattacaggtggtgttgttcagttgacttcgcagtggctaactaacatc tttggcactgtttatgaaaaactcaaacccgtccttgattggcttgaagagaagtttaaggaaggtgtagagtttct tagagacggttgggaaattgttaaatttatctcaacctgtgcttgtgaaattgtcggtggacaaattgtcacctgtg caaaggaaattaaggagagtgttcagacattctttaagcttgtaaataaattttttggctttgtgtgctgactctatc attattggtggagctaaacttaaagccttgaatttaggtgaaacatttgtcacgcactcaaagggattgtacagaaa gtgtgttaaatccagagaagaaactggcctactcatgcctctaaaagccccaaaagaaattatcttcttagagggag aaacacttcccacagaagtgttaacagaggaagttgtcttgaaaactggtgatttacaaccattagaacaacctact agtgaagctgttgaagctccattggttggtacaccagtttgtattaacgggcttatgttgctcgaaatcaaagacac agaaaagtactgtgcccttgcacctaatatgatggtaacaaacaataccttcacactcaaaggcggtgcaccaacaa aggttacttttggtgatgacactgtgatagaagtgcaaggttacaagagtgtgaatatcacttttgaacttgatgaa aggattgataaagtacttaatgagaagtgctctgcctatacagttgaactcggtacagaagtaaatgagttcgcctg tgttgtggcagatgctgtcataaaaactttgcaaccagtatctgaattacttacaccactgggcattgatttagatg agtggagtatggctacatactacttatttgatgagtctggtgagtttaaattggcttcacatatgtattgttctttc taccctccagatgaggatgaagaagaaggtgattgtgaagaagaagagtttgagccatcaactcaatatgagtatgg tactgaagatgattaccaaggtaaacctttggaatttggtgccacttctgctgctcttcaacctgaagaagagcaag aagaagattggttagatgatgatagtcaacaaactgttggtcaacaagacggcagtgaggacaatcagacaactact attcaaacaattgttgaggttcaacctcaattagagatggaacttacaccagttgttcagactattgaagtgaatag ttttagtggttatttaaaacttactgacaatgtatacattaaaaatgcagacattgtggaagaagctaaaaaggtaa aaccaacagtggttgttaatgcagccaatgtttaccttaaacatggaggaggtgttgcaggagccttaaataaggct actaacaatgccatgcaagttgaatctgatgattacatagctactaatgaccacttaaagtgggtggtagttgtgt tttaagcggacacaatcttgctaaacactgtcttcatgttgtcggcccaaatgttaacaaaggtgaagacattcaac ttcttaagagtgcttatgaaaattttaatcagcacgaagttctacttgcaccattattatcagctggtatttttggt gctgaccctatacattctttaagagtttgtgtagatactgttcgcacaaatgtctacttagctgtctttgataaaaa
```

-continued

```
tctctatgacaaacttgtttcaagcttttttggaaatgaagagtgaaaagcaagttgaacaaaagatcgctgagattc ctaaagaggaagttaagccatttataactgaaagtaaaccttcagttgaacagagaaaacaagatgataagaaaatc aaagcttgtgttgaagaagttacaacaactctggaagaaactaagttcctcacagaaaacttgttactttatattga cattaatggcaatcttcatccagattctgccactcttgttagtgacattgacatcactttcttaaagaaagatgctc catatatagtgggtgatgttgttcaagagggtgtttaactgctgtggttatacctactaaaaaggctggtggcact actgaaatgctagcgaaagctttgagaaaagtgccaacagacaattatataaccacttacccgggtcagggtttaaa tggttacactgtagaggaggcaaagacagtgcttaaaaagtgtaaaagtgcctttacattctaccatctattatct ctaatgagaagcaagaaattcttggaactgtttcttggaatttgcgagaaatgcttgcacatgcagaagaaacacgc aaattaatgcctgtctgtgtggaaactaaagccatagtttcaactatacagcgtaaatataagggtattaaaataca agagggtgtggttgattatggtgctagattttacttttacaccagtaaaacaactgtagcgtcacttatcaacacac ttaacgatctaaatgaaactcttgttacaatgccacttggctatgtaacacatggcttaaatttggaagaagctgct cggtatatgagatctctcaaagtgccagctacagtttctgtttcttcacctgatgctgttacagcgtataatggtta tcttacttcttcttctaaaacacctgaagaacatttttattgaaaccatctcacttgctggttcctataaagattggt cctattctggacaatctacacaactaggtatagaatttcttaagagaggtgataaaagtgtatattacactagtaat cctaccacattccacctagatggtgaagttatcacctttgacaatcttaagacacttctttctttgagagaagtgag gactattaaggtgtttacaacagtagacaacattaacctccacacgcaagttgtggacatgtcaatgacatatggac aacagtttggtccaacttatttggatggagctgatgttactaaaataaaacctcataattcacatgaaggtaaaaca ttttatgtttacctaatgatgacactctacgtgttgaggctttttgagtactaccacacaactgatcctagttttct gggtaggtacatgtcagcattaaatcacactaaaaagtggaaatacccacaagttaatggtttaacttctattaaat gggcagataacaactgttatcttgccactgcattgttaacactccaacaaatagagttgaagtttaatccacctgct ctacaagatgcttattacagagcaagggctggtgaagctgctaacttttgtgcacttatcttagcctactgtaataa gacagtaggtgagttaggtgatgttagagaaacaatgagttacttgtttcaacatgccaatttagattcttgcaaaa gagtcttgaacgtggtgtgtaaaacttgtggacaacagcagacaacccttaagggtgtagaagctgttatgtacatg ggcacactttcttatgaacaatttaagaaaggtgttcagataccttgtacgtgtggtaaacaagctacaaaatatct agtacaacaggagtcacctttttgttatgatgtcagcaccacctgctcagtatgaacttaagcatggtacatttactt gtgctagtgagtacactggtaattaccagtgtggtcactataaacatataacttctaaagaaactttgtattgcata gacggtgctttacttacaaagtcctcagaatacaaaggtcctattacggatgttttctacaaagaaaacagttacac aacaaccataaaaccagttacttataaaattggatggtgttgtttgtacagaaattgaccctaagttggacaattatt ataagaaagacaattcttatttcacagagcaaccaattgatcttgtaccaaaccaaccatatccaaacgcaagcttc gataattttaagtttgtatgtgataatatcaaatttgctgatgatttaaaccagttaactggttataagaaacctgc ttcaagagagcttaaagttacattttttccctgacttaaatggtgatgtggtggctattgattataaacactacacac cctcttttaagaaaggagctaaattgttacataaacctattgtttggcatgttaacaatgcaactaataaagccacg tataaaccaaatacctggtgtatacgttgtctttggagcacaaaaccagttgaaacatcaaattcgtttgatgtact gaagtcagaggacgcgcagggaatggataatcttgcctgcgaagatctaaaaccagtctctgaagaagtagtggaaa atcctaccatacagaaagacgttcttgagtgtaatgtgaaaactaccgaagttgtaggagacattatacttaaacca gcaaataatagtttaaaaattacagaagaggttggccacacagatctaatggctgcttatgtagacaattctagtct tactattaagaaacctaatgaattatctagagtattaggtttgaaaacccttgctactcatggtttagctgctgtta atagtgtcccttgggatactatagctaattatgctaagccttttcttaacaaagttgttagtacaactactaacata gttacacggtgtttaaaccgtgtttgtactaattatatgcccttattttctttactttattgctacaattgtgtacttt tactagaagtacaaattctagaattaaagcatctatgccgactactatagcaaagaatactgttaagagtgtcggta
```

-continued

```
aattttgtctagaggcttcatttaattatttgaagtcacctaatttttctaaactgataaatattataatttggttt ttactattaagtgtttgcctaggttctttaatctactcaaccgctgctttaggtgtttttaatgtctaatttaggcat gccttcttactgtactggttacagagaaggctatttgaactctactaatgtcactattgcaacctactgtactggtt ctataccttgtagtgtttgtcttagtggtttagattctttagacacctatccttctttagaaactatacaaattacc atttcatcttttaaatgggatttaactgcttttggcttagttgcagagtggttttttggcatatattcttttcactag gttttctatgtacttggattggctgcaatcatgcaattgtttttcagctattttgcagtacattttattagtaatt cttggcttatgtggttaataattaatcttgtacaaatggccccgatttcagctatggttagaatgtacatcttctttt gcatcattttattatgtatggaaaagttatgtgcatgttgtagacggttgtaattcatcaacttgtatgatgtgtta caaacgtaatagagcaacaagagtcgaatgtacaactattgttaatggtgttagaaggtcctttttatgtctatgcta atggaggtaaaggcttttgcaaactacacaattggaattgtgttaattgtgatacattctgtgctggtagtacattt attagtgatgaagttgcgagagacttgtcactacagtttaaaagaccaataaatcctactgaccagtcttcttacat cgttgatagtgttacagtgaagaatggttccatccatctttactttgataaagctggtcaaaagacttatgaaagac attctctctctcattttgttaacttagacaacctgagagctaataacactaaaggttcattgcctattaatgttata gtttttgatggtaaatcaaaatgtgaagaatcatctgcaaaatcagcgtctgtttactacagtcagcttatgtgtca acctatactgttactagatcaggcattagtgtctgatgttggtgatagtgcggaagttgcagttaaaatgtttgatg cttacgttaatacgttttcatcaacttttaacgtaccaatggaaaaactcaaaacactagttgcaactgcagaagct gaacttgcaaagaatgtgtccttagacaatgtcttatctactttatttcagcagctcggcaagggtttgttgattc agatgtagaaactaaagatgttgttgaatgtcttaaattgtcacatcaatctgacatagaagttactggcgatagtt gtaataactatatgctcacctataacaaagttgaaaacatgacaccccgtgaccttggtgcttgtattgactgtagt gcgcgtcatattaatgcgcaggtagcaaaaagtcacaacattgctttgatatggaacgttaaagatttcatgtcatt gtctgaacaactacgaaaacaaatacgtagtgctgctaaaaagaataacttaccttttaagttgacatgtgcaacta ctagacaagttgttaatgttgtaacaacaaagatagcacttaagggtggtaaaattgttaataattggttgaagcag ttaattaaagttacacttgtgttcctttttgttgctgctattttctatttaataacacctgttcatgtcatgtctaa acatactgacttttcaagtgaaatcataggatacaaggctattgatggtggtgtcactcgtgacatagcatctacag atacttgtttttgctaacaaacatgctgattttgacacatggtttagccagcgtggtggtagttatactaatgacaaa gcttgcccattgattgctgcagtcataacaagagaagtgggtttttgtcgtgcctggtttgcctggcacgatattacg cacaactaatggtgactttttgcatttcttacctagagttttttagtgcagttggtaacatctgttacacaccatcaa aacttatagagtacactgactttgcaacatcagcttgtgtttttggctgctgaatgtacaattttttaaagatgcttct ggtaagccagtaccatattgttatgataccaatgtactagaaggttctgttgcttatgaaagtttacgccctgacac acgttatgtgctcatggatggctctattattcaatttcctaacacctaccttgaaggttctgttagagtggtaacaa cttttgattctgagtactgtaggcacggcacttgtgaaagatcagaagctggtgtttgtgtatctactagtggtaga tgggtacttaacaatgattattacagatctttaccaggagtttttctgtggtgtagatgctgtaaatttacttactaa tatgtttacaccactaattcaacctattggtgctttggacatatcagcatctatagtagctggtggtattgtagcta tcgtagtaacatgccttgcctactatttatgaggtttagaagagctttttggtgaatacagtcatgtagttgccttt aatactttactattccttatgtcattcactgtactctgtttaacaccagtttactcattcttacctggtgtttattc tgttatttacttgtacttgacattttatcttactaatgatgtttcttttttagcacatattcagtggatggttatgt tcacacctttagtacctttctggataacaattgcttatatcatttgtatttccacaaagcatttctattggttcttt agtaattacctaaagagacgtgtagtcttaatggtgtttcctttagtacttttgaagaagctgcgctgtgcacctt tttgttaaataaagaaatgtatctaaagttgcgtagtgatgtgctattacctcttacgcaatataatagatacttag ctctttataataagtacaagtattttagtggagcaatggatacaactagctacagagaagctgcttgttgtcatctc gcaaaggctctcaatgacttcagtaactcaggttctgatgttctttaccaaccaccacaaacctctatcacctcagc
```

-continued

```
tgttttgcagagtggttttagaaaaatggcattcccatctggtaaagttgagggttgtatggtacaagtaacttgtg gtacaactacacttaacggtctttggcttgatgacgtagtttactgtccaagacatgtgatctgcacctctgaagac atgcttaaccctaattatgaagatttactcattcgtaagtctaatcataatttcttggtacaggctggtaatgttca actcagggttattggacattctatgcaaaattgtgtacttaagcttaaggttgatacagccaatcctaagacaccta agtataagtttgttcgcattcaaccaggacagacttttttcagtgttagcttgttacaatggttcaccatctggtgtt taccaatgtgctatgaggcccaatttcactattaagggttcattccttaatggttcatgtggtagtgttggttttaa catagattatgactgtgtctcttttttgttacatgcaccatatggaattaccaactggagttcatgctggcacagact tagaaggtaacttttatggacctttttgttgacaggcaaacagcacaagcagctggtacggacacaactattacagtt aatgttttagcttggttgtacgctgctgttataaatggagacaggtggtttctcaatcgatttaccacaactcttaa tgactttaaccttgtggctatgaagtacaattatgaacctctaacacaagaccatgttgacatactaggacctcttt ctgctcaaactggaattgccgtttttagatatgtgtgcttcattaaaagaattactgcaaaatggtatgaatggacgt accatattgggtagtgcttattagaagatgaatttacacctttttgatgttgttagacaatgctcaggtgttactttt ccaaagtgcagtgaaaagaacaatcaagggtacacaccactggttgttactcacaattttgacttcactttttagttt tagtccagagtactcaatggtctttgttcttttttttgtatgaaaatgccttttttacctttttgctatgggtattatt gctatgtctgcttttgcaatgatgtttgtcaaacataagcatgcatttctctgtttgttttttgttaccttctcttgc cactgtagcttattttaatatggtctatatgcctgctagttgggtgatgcgtattatgacatggttggatatggttg atactagtttgtctggtttttaagctaaaagactgtgttatgtatgcatcagctgtagtgttactaatccttatgaca gcaagaactgtgtatgatgatggtgctaggagagtgtggacacttatgaatgtcttgacactcgtttataaagttta ttatggtaatgctttagatcaagccatttccatgtgggctcttataatctctgttacttctaactactcaggtgtag ttacaactgtcatgttttttggccagaggtattgtttttatgtgtgttgagtattgccctattttcttcataactggt aatacacttcagtgtataatgctagtttattgtttcttaggctatttttgtacttgttactttggcctcttttgttt actcaaccgctactttagactgactcttggtgtttatgattacttagtttctacacaggagtttagatatatgaatt cacagggactactcccacccaagaatagcatagatgccttcaaactcaacattaaattgttgggtgttggtggcaaa ccttgtatcaaagtagccactgtacagtctaaaatgtcagatgtaaagtgcacatcagtagtcttactctcagtttt gcaacaactcagagtagaatcatcatctaaattgtgggctcaatgtgtccagttacacaatgacattctcttagcta aagatactactgaagcctttgaaaaaatggtttcactactttctgtttttgctttccatgcagggtgctgtagacata aacaagctttgtgaagaaatgctggacaacagggcaacctttacaagctatagcctcagagtttagttcccttccatc atatgcagcttttgctactgctcaagaagcttatgagcaggctgttgctaatggtgattctgaagttgttcttaaaa agttgaagaagtctttgaatgtggctaaatctgaatttgaccgtgatgcagccatgcaacgtaagttggaaaagatg gctgatcaagctatgacccaaatgtataaacaggctagatctgaggacaagagggcaaaagttactagtgctatgca gacaatgctttttcactatgcttagaaagttggataatgatgcactcaacaacattatcaacaatgcaagagatggtt gtgttcccttgaacataatacctcttacaacagcagccaaactaatggttgtcataccagactataacacatataaa aatacgtgtgatggtacaacatttacttatgcatcagcattgtgggaaatccaacaggttgtagatgcagatagtaa aattgttcaacttagtgaaattagtatggacaattcacctaatttagcatggcctcttattgtaacagctttaaggg ccaattctgctgtcaaattacagaataatgagcttagtcctgttgcactacgacagatgtcttgtgctgccggtact acacaaactgcttgcactgatgacaatgcgttagcttactacaacacaacaaagggaggtaggtttgtacttgcact gttatccgatttacaggatttgaaatgggctagattccctaagagtgatggaactggtactatctatacagaactgg aaccaccttgtaggtttgttacagacacacctaaaggtcctaaagtgaagtatttatactttattaaaggattaaac aacctaaatagaggtatggtacttggtagtttagctgccacagtacgtctacaagctggtaatgcaacagaagtgcc tgccaattcaactgtattatctttctgtgctttttgctgtagatgctgctaaagcttacaaagattatctagctagtg
```

-continued

```
ggggacaaccaatcactaattgtgttaagatgttgtgtacacacactggtactggtcaggcaataacagttacaccg gaagccaatatggatcaagaatcctttggtggtgcatcgtgttgtctgtactgccgttgccacatagatcatccaaa tcctaaaggattttgtgacttaaaaggtaagtatgtacaaatacctacaacttgtgctaatgaccctgtgggtttta cacttaaaaacacagtctgtaccgtctgcggtatgtggaaaggttatggctgtagttgtgatcaactccgcgaaccc atgcttcagtcagctgatgcacaatcgttttttaaacgggtttgcggtgtaa
```

As demonstrated in the accompanying examples, the sensing device presently disclosed is capable of detecting various biomarkers in a fluid sample, even when the biomarkers are present in very low concentrations. In particular, detection limits of 1-10 pg/ml of IgG and IgM antibodies can be achieved with millimeter scale electrode dimensions; both detection limits and sensitivities can be improved by several orders of magnitude by changes in the thickness and lateral dimensions of the electrode and thickness of the vibrating substrate.

Electrodes

In embodiments, the electrode layer comprises at least one working electrode. The electrode lay can comprise working electrode, auxiliary or counter electrode, a reference electrode, or any combination thereof. In embodiments, any one or more of the reference electrode, counter electrode, and working electrode, can be formed out of a suitable electrically conductive material. The electrically conductive material can comprise titanium, titanium nitride, iridium oxide, platinum, gold, aluminum, stainless steel, indium tin ox, silver, mercury, platinum, ruthenium, rhodium, or a combination thereof. In certain embodiments, the conductive material comprises a conductive polymer. Exemplary conductive polymers include polyethylenedioxythiophene (PEDOT), polypyrrole, polyaniline, carbon-nanotube infused poly-dimethylsiloxane (PDMS) or a combination thereof. The electrode layer is coated with micro-porous platinum, nano-porous platinum, nano-gold, or a combination thereof. In embodiments, the particular form, function, and number of electrodes will vary depending on the specific application, the disease or condition-of-interest, the biomarker, the type of sensing device, or a combination thereof.

Figure 4:
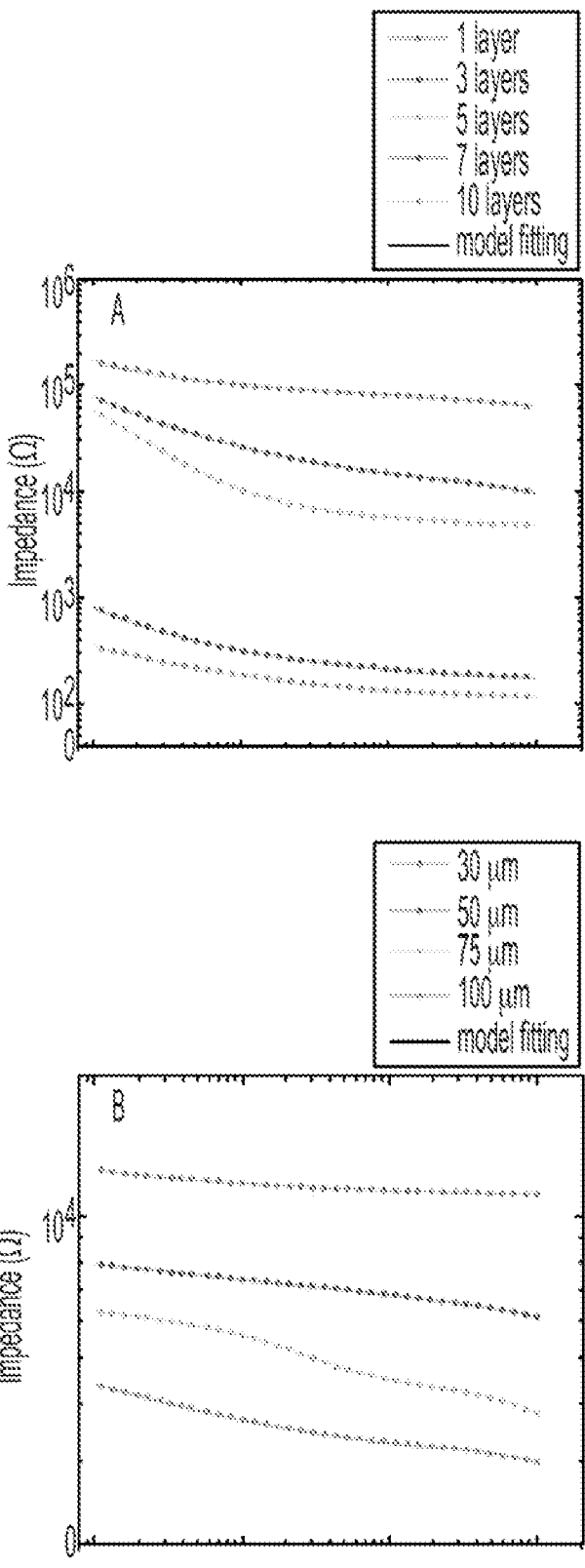
FIG. 4 panel A provides Electrochemical Impedance Spectroscopy (EIS) data that show impact of poly(3,4-ethylenedioxythiophene) polystyrene sulfonate (PEDOT:PSS) multiple layer printing on 50 μm electrode impedance.
Figure 4:
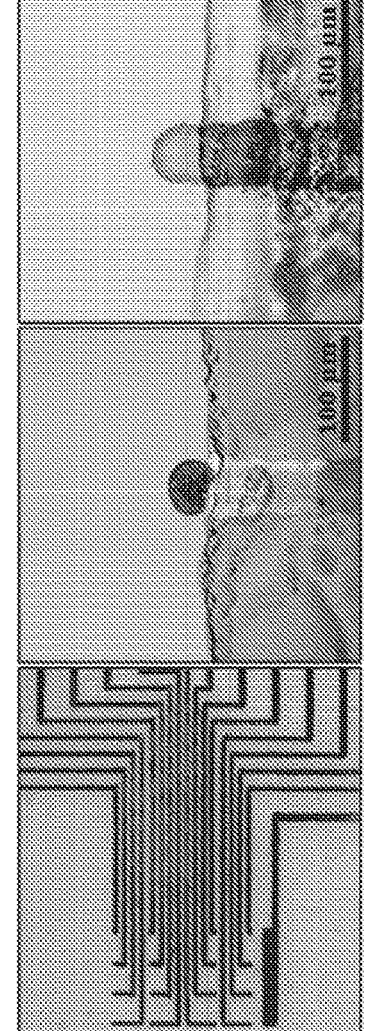
Figure 4:
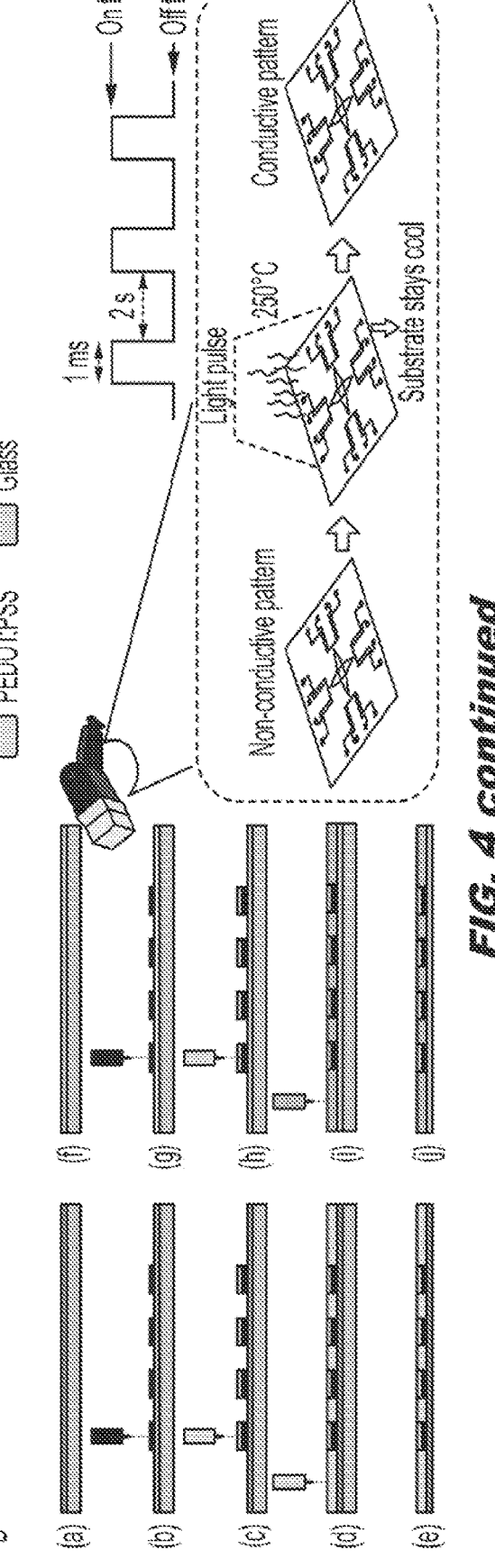

The electrodes can be constructed, patterned, or coated via any of method known in the art. By way of example and as illustrated in FIG. 4, one embodiment comprises the use of inkjet techniques to pattern the electrode layer on the surface of a quartz crystal.

Application of the coating over the electrode can be carried out by first forming a mixture of the component ingredients, which are dissolved in a suitable solvent such as THF, and then applying the dissolved solution using any of a variety of means including, without limitation, spray-coating, spin-coating, dip-coating, roller-coating, blade-coating, etc. The particular choice of coating technique will depend on its compatibility with the structure of the electrochemical cell that forms part of the sensing device of the present invention. During and subsequent to application the solvent used to disperse the components is removed, leaving the coating applied to a surface of the electrode(s).

In embodiments, the physical parameters of the electrodes can vary with fluid the sample volumes, and the biomarker in question. In embodiments, at least one electrode comprises a diameter of at least about 600 nm. At least one electrode can have a diameter or up to about 10 mm. Embodiments can comprise an electrode with a diameter that is greater than about 10 mm. In one embodiment, an electrode has a diameter of up to 30 mm. In certain embodiments the diameter of at least one electrode is less than about 600 nm.

In embodiments, at least one electrode comprises a thickness of at least about 10 nm. At least one electrode can have a thickness of up to about 500 nm. Embodiments can comprise an electrode thickness of greater than about 500 nm.

In certain embodiments, the at least one working electrode is greater than about 1 nm thick. The at least one working electrode can comprise a thickness of between about 1 nm and 500 nm, inclusive. The working electrode can be greater about 25 nm, about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, or about 500 nm. The at least one working electrode can comprise a diameter of at least 10 μm. In embodiments, the at least one working electrode comprises a diameter of up to 150 mm. the diameter of the at least one working electrodes can be about 25 μm, about 50 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, about 475 μm, about 500 μm, about 525 μm, about 550 μm, about 575 μm, about 600 μm, about 625 μm, about 650 μm, about 675 μm, about 700 μm, about 725 μm, about 750 μm, about 775 μm, about 800 μm, about 825 μm, about 850 μm, about 875 μm, about 900 μm, about 925 μm, about 950 μm, about 975 μm, about 1000 μm, about 1025 μm, about 1050 μm, about 1075 μm, about 1200 μm, about 1225 μm, about 1250 μm, about 1275 μm, about 1300 μm, about 1325 μm, about 1350 μm, about 1375 μm, about 1400 μm, about 1425 μm, about 1450 μm, about 1475 μm, about 1500 μm. In certain embodiments, the at least one working electrode comprises a diameter of greater than about 1 mm, about 10 mm, about 20 mm, about 30 mm, about 40 mm, about 50 mm, about 60 mm, about 70 mm, about 80 mm, about 90 mm, about 100 mm, about 110 mm, about 120 mm, about 130 mm, about 140 mm, or about 150 mm. The at least one working electrode can comprise a diameter of greater than about 150 mm.

The piezoelectric material can comprise a diameter of at least about 1 mm. In embodiments, the piezoelectric material comprises a diameter of up to about 200 mm. The diameter of the piezoelectric material can be up to about 190, up to about 180, up to about 170, up to about 160, up to about 150 mm, up to about 140 mm, up to about 130 mm, up to about 120 mm, up to about 110 mm, or up to about 100 mm. In certain embodiments, the diameter of the piezoelectric material is less than about 1 mm. The diameter of the piezoelectric material can be at least about 1 mm, at least about 2 mm, at least about 3 mm, at least about 4 mm, at least about 5 mm, at least about 6 mm, at least about 7 mm, at least about 8 mm, at least about 9 mm, or at least about 10 mm. In certain embodiments, the piezoelectric material can comprise a diameter of at least about 10 mm, at least about 15 mm, at least about 20 mm, at least about 25 mm, at least about 30 mm, at least about 35 mm, at least about 40 mm, at least about 45 mm, at least about 50 mm, at least about 55 mm, at least about 60 mm, at least about 65 mm, at least about 70 mm, at least about 75 mm, at least about 80 mm, at least about 85 mm, at least about 90 mm, at least about 95 mm, or at least about 100 mm.

In certain embodiments, the piezoelectric material comprises a thickness of at least about 10 $\mu$m. The piezoelectric material can comprise a thickness of up to about 5 mm. the thickness of the piezoelectric material can comprise up to about 1 mm, up to about 2 mm, up to about 3 mm, up to about 4 mm, or up to about 5 mm. In embodiments, the thickness of the piezoelectric material can be at least about 1 $\mu$m, at least about 2 $\mu$m, at least about 3 $\mu$m, at least about 4 $\mu$m, at least about 5 $\mu$m, at least about 6 $\mu$m, at least about 7 $\mu$m, at least about 8 $\mu$m, at least about 9 $\mu$m, or at least about 10 $\mu$m.

The embodiments disclosed herein are exemplary—the electrodes and piezoelectric material can have varying dimensions to provide for preferred sensitivities Stabilizers In embodiments, the diagnostic platform disclosed herein can be shelf stable at room temperature for up to at least 18 months. In certain embodiments, the diagnostic platform is shelf stable for at least 12 months.

In embodiments, the diagnostic platform comprises at least one stabilizing solution. Non-limiting examples of such stabilizers comprise sucrose, LB Medium and Blocking buffer, Lipidure, glycerin.

In embodiments, the sensing cartridge is stabilized by via stabilizing the surface bound S protein and IgG/IgM antibodies.

In embodiments, the process for adding the stabilizers comprises covering the prepared sensor surface with 1) blocking buffer (Thermo Fisher Scientific, USA) 0.15 M. 2) (5% w/v) sucrose (Acros). 3) coating stabilizer and blocking buffer diluted 1:1 with water. The devices can then be aspirated and dried. All devices can be stored at 50° C. to age the coating (1 day at 50° C. is equal to about 6.5 days at room temperature). We can assess the stability of the coating at 10 days, 3 weeks, 3 months & 6 months [27]. Without being bound by theory, embodiments can comprise an 18-month shelf life. Besides the in-use stability assessment of reagents in the above experiments, the stability of reagents can also be assessed under the following conditions:

Shelf-life stability—Reagent shelf life can be assessed by real-time stability testing, with reagents stored at the specified storage temperature.

Stress testing—the reagents can be cycled through a temperature of 4° C. and ambient temperature to mimic shipping conditions. A separate group of reagents can be cycled through light conditions to mimic shipping conditions. They can then be placed under normal storage conditions and their in-use stability assessed.

As discussed herein the presently disclosed diagnostic platform can obtain data regarding the presence or absence of certain biomarkers that identify a particular condition, disease, or disorder. In embodiments, the sensing device can be communicatively linked to a mobile device application running on a processor of a mobile computing device. In embodiments, the sensing device is communicatively coupled with the mobile device application through one or more wireless communications protocols.

Transmission/Communication of Data

In embodiments, the mobile device application can present collected data directly to a user through a smartphone application display. The mobile device can be communicatively coupled to one or more applications running on at least one processor of a remote server. The mobile device application can transmit data or results of data analysis (as described below) to the remote server. Third party clients such as health care professionals or researchers can (with appropriate consents and compliance with HIPPA and other federal and state privacy legislation) receive application data through requests to remote server applications. In embodiments, such third party health care provider can then recommend or prescribe a therapeutic agent or other treatment option as appropriate according to the data received.

As indicated above, sensor data can be communicated to a mobile device application which can then be presented to a user, a health professional, a researcher, or a combination thereof. However, the mobile device application can initially analyze and interpret raw sensor data to determine the user's likelihood of having a particular condition, disease, or disorder. The application can then send analytical results to remote server applications for third party access. Under an embodiment, data analytics can be performed by the mobile device application, remote server applications, or a combination thereof.

In embodiments, the diagnostic platform can comprise a microcontroller. The microcontroller monitors and receives data from transducers/sensors. In embodiments, the microcontroller can also send and receive data to memory. Under an embodiment, the microcontroller transmits transducer/sensor data through a transceiver to a mobile device application running on a processor of a smartphone.

As indicated above, the sensor device can be communicatively coupled with the mobile device application through one or more wireless communications protocols. The communicative coupling can comprise a wireless local area network (WLAN). A WLAN connection can implement WiFi™ communications protocols. Alternatively, the communicative coupling can comprise a wireless personal area network WPAN. A WPAN connection can implement Bluetooth™ communications protocols.

Under an embodiment, the sensing device can additionally comprise a data port for relaying data from the sensor device to the mobile device application or other computing device. The data port can comprise a USB connection or any other type of data port. In embodiments, the data port allows for a wired communication between the sensing device and separate computing devices. The data port can be used alone or in combination with the wireless transceiver of the sensing device described above.

In certain embodiments, the sensing device and mobile application are communicatively couple through a local router. The router can comprise a component of the WLAN or WPAN. The router can further communicate with wide area networks, metropolitan area networks, and/or other private/public networks and communication services providing general internet connectivity. Accordingly, in certain embodiments, the sensing device and/or mobile device application can send data to remote server applications. As indicated above, a remote server application can receive raw data from a sensing device and/or mobile device application. Alternatively, the remote server can receive data analytics performed by the mobile device application. Under an embodiment, the remote server application can offer access to third parties and/or systems, i.e., health care practitioners, electronic health records systems, or researchers (assuming consents and compliance with HIPPA and other state/federal privacy legislation). Under an embodiment, a user can access the remote server application and retrieve/review raw data and data analytics using a desktop HTML client application.

In embodiments, a mobile computing device can be configured to receive data from the sensing device. The mobile computing device can comprise a portable digital assistant, a tablet, a smartphone (such as iOS™ and Android™ based devices), a laptop, or similar computing device. The mobile computing device can comprise a wearable device. Under an alternative embodiment, a wearable device can represent an additional component of the network. In other words, an additional wearable device can couple with the communications network and communicate with the sensing device, mobile computing device, and local router. A wearable device application can comprise some or all functionality presented by the mobile device application.

Upon receipt of the data, a mobile device application can relay the data directly to the user, the health professional, a researcher, or a combination thereof. The application can, alternatively or in combination, relay the data to be included within the patient's electronic medical records (EMR) for later diagnosis or evaluation.

In one embodiment, the mobile device application compares the data received to historical patient data. The historical patient data can include data reported through prior scientific publications, data compiled from the health professional's own patient records, data from EMR systems that represent diverse patient populations, or any other source of patient data or combinations thereof. Of course, all such data comply with HIPPA and state/federal data privacy legislation.

Using such information, the application can detect similarities and differences in the patient's data with historical patient data and uses statistical methods to calculate the probability that the user is suffering from a particular condition, disease, or disorder. Using this probability data, a health care professional can make certain recommendations or prescriptions to treat or otherwise alleviate the condition, disease, or disorder or any symptoms associated therewith.

Data can be reported to users via a dashboard type view for the user to see results and receive recommendations. These results are under an embodiment viewable through the application interface. As indicated above, data and data analysis can additionally reside on a remote server. A user can access such data and analysis through a desktop client.

Computer networks suitable for use with the embodiments described herein include local area networks (LAN), wide area networks (WAN), Internet, or other connection services and network variations such as the world wide web, the public internet, a private internet, a private computer network, a public network, a mobile network, a cellular network, a value-added network, and the like. Computing devices coupled or connected to the network can be any microprocessor-controlled device that permits access to the network, including terminal devices, such as personal computers, workstations, servers, mini-computers, main-frame computers, laptop computers, mobile computers, palm top computers, hand-held computers, mobile phones, TV set-top boxes, or combinations thereof. The computer network can include one of more LANs, WANs, Internets, and computers. In embodiments, the computers serve as servers, clients, or a combination thereof.

The systems and methods of the presently disclosed diagnostic platform can be a component of a single system, multiple systems, and/or geographically separate systems. The systems and methods of the presently disclosed diagnostic platform can also be a subcomponent or subsystem of a single system, multiple systems, and/or geographically separate systems. The components of systems and methods of the presently disclosed diagnostic platform can be coupled to one or more other components (not shown) of a host system or a system coupled to the host system.

In certain embodiments, one or more components of the systems and methods of the presently disclosed diagnostic platform and/or a corresponding interface, system or application to which the systems and methods are coupled or connected includes and/or runs under and/or in association with a processing system. The processing system can include any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein can refer to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that include the systems and methods of the presently disclosed diagnostic platform can be located together or in separate locations. Communication paths couple the components and include any medium for communicating or transferring files among the components. The communication paths can include wireless connections, wired connections, and hybrid wireless/wired connections. The communication paths also include couplings or connections to networks including local area networks (LANs), metropolitan area networks (MANs), wide area networks (WANs), proprietary networks, interoffice or back-end networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Aspects of the systems and methods of the presently disclosed diagnostic platform described herein can be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the systems and methods of the presently disclosed diagnostic platform can include: microcontrollers with memory (such as electronically erasable programmable read only memory (EEPROM)), embedded microprocessors, firmware, software, etc. Furthermore, aspects of the systems and methods of the presently disclosed diagnostic platform can be embodied in microprocessors having software-based circuit emulation, discrete logic (sequential and combinatorial), custom devices, fuzzy (neural) logic, quantum devices, and hybrids of any of the above device types. The underlying device technologies can be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein can be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions can be embodied include, but are not limited to, non-volatile storage media in various forms (e.g., optical, magnetic or semiconductor storage media) and carrier waves that can be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components can be processed by a processing entity (e.g., one or more processors) within the computer system in conjunction with execution of one or more other computer programs.

The Kit

The invention also provides for a kit for using any of the various sensing devices or diagnostic platforms described herein.

The kit can be used to carry out any of the various methods as described herein.

In embodiments, the kit can comprise any one or more of the following: a sensing device, an electronic reading platform, a negative control, a positive control, sample buffer, a lancet (for use with fingerstick procedures), a nasal swab, a vial for collection of saliva, packing materials, and instructions for use. In embodiments, the sensing device can comprise a sensing cartridge with acousto-IgG™ or acousto-IgM™ sensor.

The instructions generally include one or more of: a description of the genetically engineered cells; methods for thawing or preparing cells; precautions; warnings; animal pharmacology; clinical studies; and/or references. The instructions can be printed directly on the container (when present), or as a label applied to the container, or as a separate sheet, pamphlet, card, or folder supplied in or with the container. Generally, a kit as described herein also includes packaging. In some embodiments, the kit includes a sterile container which contains a genetically engineered cells; such containers can be boxes, ampules, bottles, vials, tubes, bags, pouches, blister-packs, or other suitable container forms known in the art. Such containers can be made of plastic, glass, laminated paper, metal foil, or other materials suitable for holding cells or medicaments.

56

EXAMPLES

The Examples set forth below are for illustrative purposes only and are not intended to limit, in any way, the scope of the present invention.

Example 1

Background

Severe acute respiratory syndrome coronavirus 2 (SARS-CoV-2) leads to the infectious disease COVID-19, which was first reported in Wuhan, China in December 2019. The disease has since spread across the globe infecting over 200 countries. The lack of cheap, scalable, and rapid testing platform has contributed significantly to the spread of the diseases as countries struggle to identify patients and isolate them to prevent the wide spread of the disease before health care systems are overwhelmed. The problem is exacerbated by the presence of many asymptomatic infected patients. In the absence of proven antiviral drug therapies and vaccines, the current pandemic containment and mitigation strategy depends on isolation of the infected individuals and their close contacts in addition to social distancing through large scale lockdowns for the entire countries or communities. The latter has strained economies across the world, currently risks the availability of resources and has paralyzed the world in ways that will take years to recover from[5]. However, to mitigate the risk of having resurge in cases, increasing testing capacity and access is fundamental for the rapid identification and isolation of COVID-19 cases and containment of any new clusters.

The current technologies require skilled healthcare workers to operate, large, qualitative error-prone techniques that cannot be deployed in the field.

In this proposal, we aim to equip soldiers with a wearable (belt mounted) COVID-19 testing kit, one that tests for disease immunity. The proposed platform is a high throughput, high sensitivity point-of-care diagnostic platform for rapid detection of COVID-19 seroprevalence that covers necessary testing throughout the disease cycle.

SARS-CoV-2 Virology and Pathophysiology

SARS-CoV-2 is an enveloped large positive-sense single-stranded RNA virus with genome of ~30 kb. It belongs to the genus betacoronavirus and has a diameter of 50-200 nm and spikes on its surface of length 20 nm that gives it a crown-like structure, a characteristic of coronaviruses (Zhou et al. 2020, Cascella et al., 2020). The SARS-CoV-2 genome encodes for four major structural and function proteins: the spike (S), membrane (M), envelope (E) and nucleocapsid (N) proteins [6]. The S protein consists of 2 functional subunits, S1 and S2; S1 mediates the binding of the virus to the host cell receptor, while S2 contains other elements required for viral and cellular membrane fusion. The M protein is the most abundant structural protein that defines the shape of the virus. The N protein is the most abundantly shed viral protein during infection and can be detected in serum and urine samples within the first 2 weeks of infection. The smallest major structural protein, E protein, participates in viral assembly and pathogenesis [7]. COVID-19 patients show clinical manifestations in the form of fever, nonproductive cough, dyspnea, fatigue, and radiographic evidence of pneumonia. In addition, they show high production of leukocytes and elevated levels of cytokines, chemokines, and proinflammatory [8]. The immune response triggered against this virus involves the secretion of 3 types of immunoglobulins, IgG, IgM, and IgA, which are produced prior to a prolonged infection, and are essential to diagnose the presence of the virus within the body [9].
Biomarkers The SARS-CoV-2 genome encodes for four major structural proteins: the spike (S), membrane (M), envelope (E) and nucleocapsid (N) proteins [6]. The S protein consists of 2 subunits, S1 and S2. S1 mediates the binding of the virus to the host cell receptor, while S2 contains other elements required for membrane fusion. The M protein is the most abundant structural protein that defines the shape of the virus. The N protein is the most abundantly shed viral protein during infection and can be detected in serum and urine samples within the first 2 weeks of infection. The smallest major structural protein, E protein, participates in viral assembly and pathogenesis [7].

Current RT-PCR assays detect the SARS-CoV-2 RNA via envelope (E) and RNA-dependent RNA polymerase (RdRp) gene assays [10]. The assay is highly specific for SARS-CoV-2 RNA and presents no cross-reactivity with other coronaviruses. In another approach, an RT-PCR assay was employed for the detection of RdRp/helicase (H) genes, which did not cross-react with other viruses [11]. Other RT-PCR assays were also developed that detect nucleocapsid protein (N) and ORF1b, which are highly conserved among other respiratory viruses. Thus, the assay could also bind to SARS-CoV and other viruses [12].

Serological immunoassays have also been developed to detect antibodies for SARS-CoV-2 in the serum or plasma of patients. These assays include rapid lateral flow immunoassay tests, ELISA, automated chemiluminescence immunoassay (CLIA) and others. These assays are mostly used to detect IgG and IgM antibodies. IgG is detectable starting 13 to 21 days after infection and persists for long durations. IgM response on the other hand occurs earlier, at around 10 days after infection, but then decreases rapidly after 35 days and disappears [13]. Data in FIG. 1 is collected from a literature survey showing the timeline of the disease with respect to the level of biomarkers (citations to the data points are in the appendix).
Serological Testing Serological or antibody-based testing can be complementary to real-time polymerase chain reaction (RT-PCR), which is the current gold standard for COVID-19 detection. These assays are good for determining seroprevalence and thus exposure in the community but unlike RT-PCR, are not suitable for diagnosis of patients in the acute phase of infection. First, antibodies are only released after the first week or infection. Second, current antibody-based rapid assays suffer in terms of their sensitivity and thus active cases can be easily missed. Misdiagnosis of active cases can have dire impacts on outbreak containment The term "antibody" herein is used in the broadest sense and encompasses various antibody structures. Non-limiting examples of antibodies comprise monoclonal antibodies, polyclonal antibodies, multispecific antibodies (e.g., bispecific antibodies), humanized antibodies, fully human antibodies fully human antibodies as is understood in the art, and antibody fragments so long as they exhibit the desired antigen-binding activity. Antibodies can comprise comprises a monospecific antibody, a bispecific antibody, a trispecific antibody, or a multi-specific antibody. Non-limiting examples of antibody fragments comprise Fv, Fab, Fab', Fab'-SH, F(ab')2; diabodies; linear antibodies; single-chain antibody molecules (e.g. scFv); and multispecific antibodies formed from antibody fragments. In one embodiment, the invention comprise scFVs directed towards (and specific for) a target antigen or biomarker.

Thickness Shear Mode (TSM) Biosensors

Quartz crystals are the most commonly used piezoelectric material for building transducers for gravimetry due to their desirable mechanical, thermal, chemical and electrical properties. AT-cut quartz produces bulk transverse shear waves with particle displacements parallel to the surface of the crystal and its electrodes [3, 15-17]. These AT-cut quartz oscillators are commonly termed thickness shear mode (TSM) resonators. When a small mass is deposited on the surface of a quartz crystal oscillator, the oscillator's resonance frequency decreases in direct proportion to the deposited mass as described by the classic Sauerbrey equation [4] for sensitivity of the resonator, which is provided below as Equation 1:

$$\Delta f_o = \frac{2f_o^2}{(\rho_Q \mu_Q)^{1/2}} \frac{\Delta m}{A}$$

Wherein $f_o$ is the fundamental resonant frequency of the quartz crystal, A is the surface area of the electrode on top of the crystal, $\mu_Q$ and $\rho_Q$ are the shear modulus and the density of quartz [4]. While m is the mass deposited on sensor.

The novelty of mass sensing led to several thousand applications of TSM in biosensing, especially in point-of-care diagnostics. The specificity of the sensor relies on binding the molecular or protein of choice to the surface of the sensor for detection [18-21].

High Sensitivity Molecular and Proteins Sensing μTSM Sensor

Figure 2:
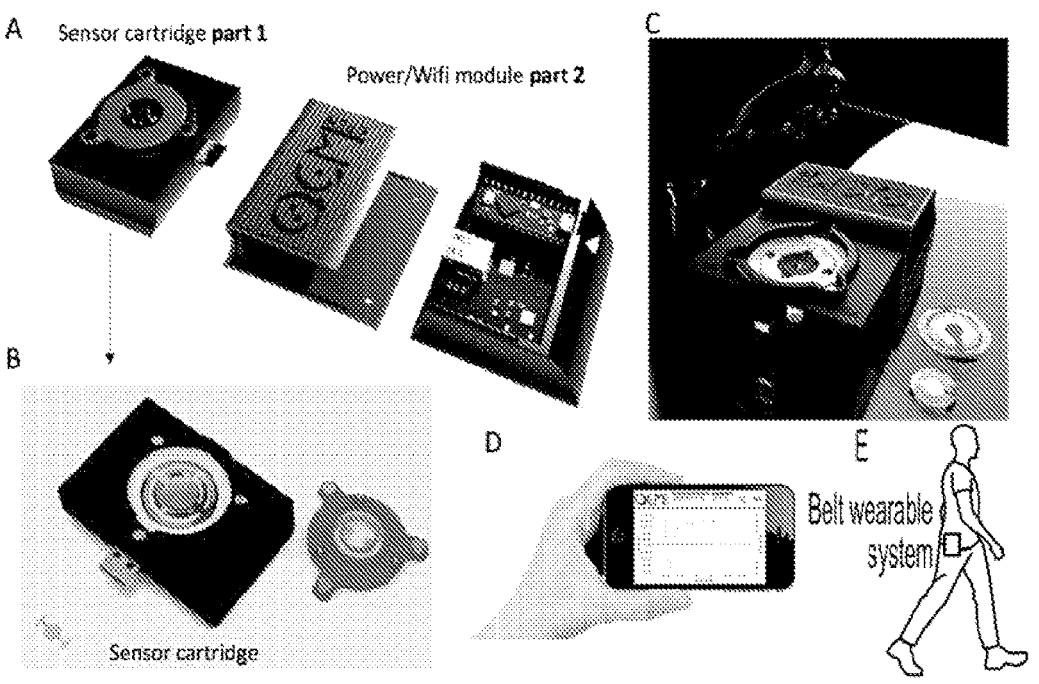
FIG. 2 shows the presently disclosed system under one embodiment.

Our group has extensive experience using TSM sensors for biological sensing [2, 17, 18, 20, 22]. Recent work by our group has outlined the theoretical basis for increasing the sensitivity of TSM sensors validated by microfabricated prototypes used for biological experiments. Our work showed that high frequency quartz can be used to build miniaturized high sensitivity TSM sensors that operate at high Q-factors not damped by inharmonic modes. The loss of energy from inharmonic dampening was reduced by an optimal combination of sensor active area diameter, metal thickness and resonant frequency to create μTSM sensors with sensitivities that were orders of magnitude higher than commercially available TSM sensors[3, 18].
Wearable, Miniaturized μTSM Systems Advances in high efficiency and high frequency circuits for driving resonators has enabled a new generation of small and compact data acquisitions devices that can be also be Wi-Fi/Mobile phone connected, battery operated and light and small enough to be wearable. One embodiment of the present invention can utilize the openQCM™ system (Novaetech S.r.l., Pompei, Italy) a simultaneous frequency, dissipation and phase measurements platform based on AD8302 RF/IF Gain and Phase Detector™ (Analog Devices, Inc, Wilmington, Massachusetts). The platform provides fully integrated system for measuring gain/loss in the quartz sensor and phase difference between actuation and sensor response. In embodiments, the platform is designed to include a modular measurement cell allowing for testing a plurality of biomarkers on a single system, as shown in FIG. 2.

TABLE 1

| Comparison of proposed Acousto-IgG ™ and Acousto-IgM ™ with current approaches | | | | |
|---|---|---|---|---|
| | Acousto-IgG ™/ Acousto-IgM ™ | Antigen | Lateral Flow | Enzyme linked Tests |
| Target | IgG & IgM antibodies | N protein | IgG & IgM antibodies | IgG, IgM and IgA antibodies |
| Sample preparation | No user required sample prep. | Sampling processing for 1 minute Mix the sample gently by pipetting Transfer the sample to test cassette Fluorescent signal readout preceded by lateral flow | Separate plasma or serum from specimen by centrifugation Transfer whole blood, serum or plasma to the test cassette for lateral flow capillary movement Lateral flow visual readout | Separate plasma or serum from specimen by centrifugation or sampling tubes with separation gel sample processing and coating with magnetic particles signal readout by a plate reader |
| Assay-to-result time | 5-10 min | 15 mins | 15-20 min | 35 min |
| Size of system | Wearable | Large | Small | Large |
| Sample-to-result time | 10 min | ~20 minutes | 30 min | 1-5 hrs |
| Result type | Quantitative | Qualitative | Qualitative | Quantitative |
| Sensitivity | 100% | 80% | 82-93.8% | 87.5-100% |
| Specificity | To be determined | 100% | 90.63-100% | 95-100% |
| Cost (high, low) | Low | Low | low | High-Moderate |

Figure 3:
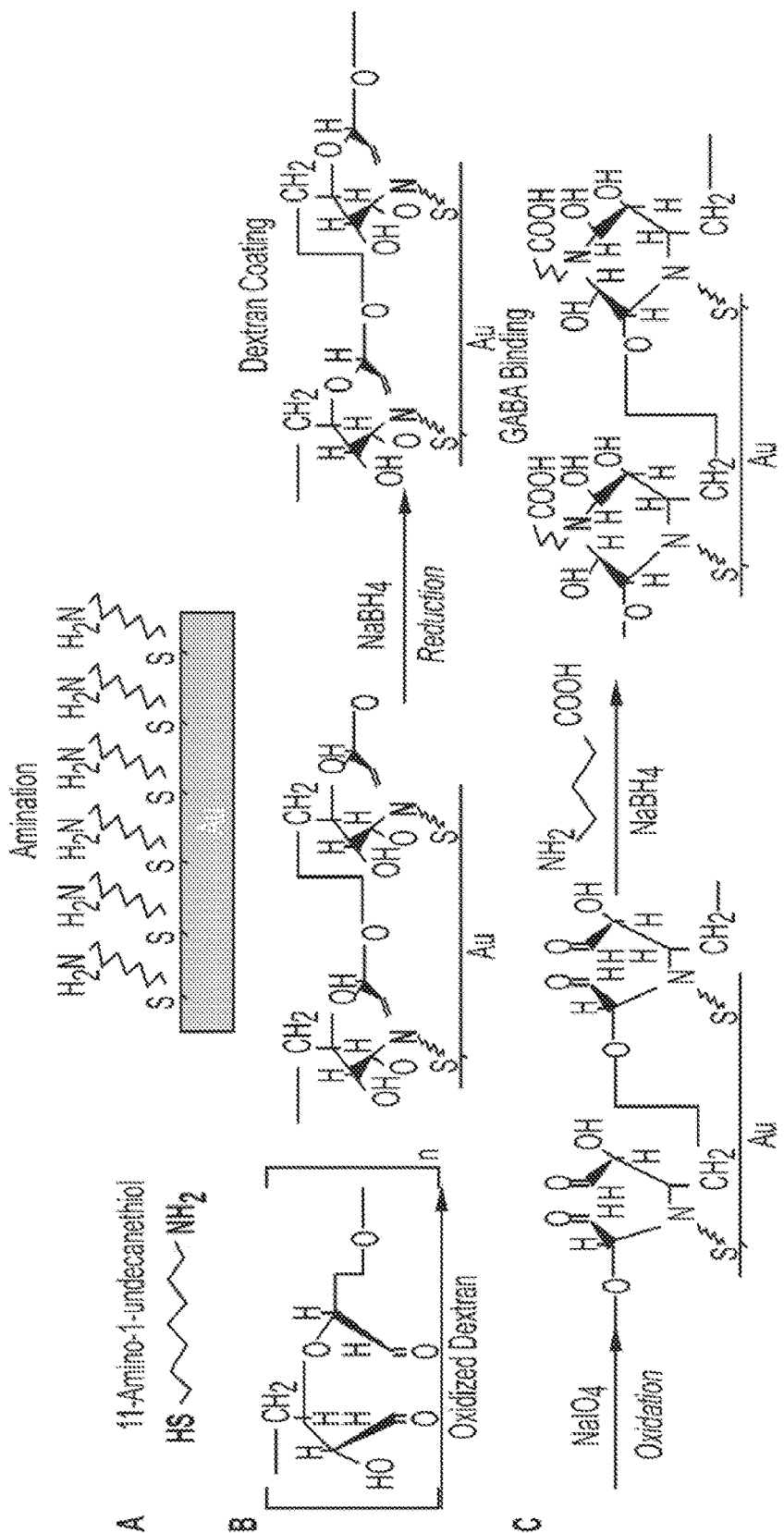
FIG. 3 panel A shows fabricated TSM sensors under one embodiment of the present invention. A US penny is shown next to the TSM sensor for scale.
Figure 3:
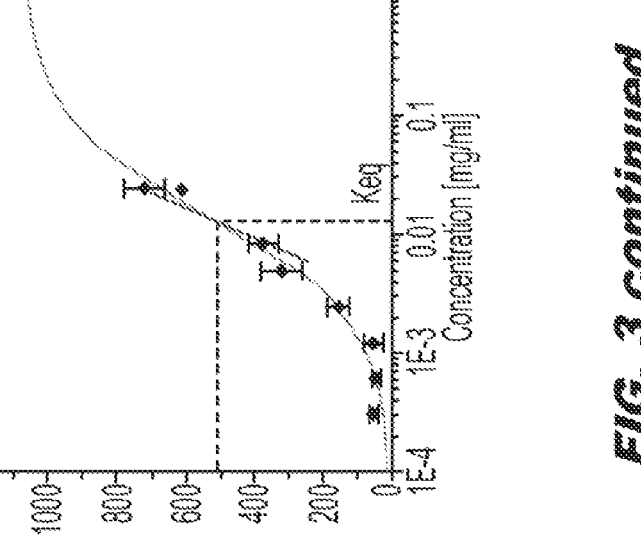

TSM piezoelectric sensors have shown great promise in bio-sensing applications but commercial TSM currently fall short in sensitivity and detection area as compared to competing sensing modalities such as surface plasmon resonance (SPR). We have investigated the design principles for improving sensitivity and lowering the detection area for TSM sensors operating in liquids for the purposes of monitoring cell adhesion in real time. The theoretical predictions were validated with fabricated prototypes operating in liquid and published [3, 18] as shown in FIG. 3A, B, C and table 1. Prior to that, we have developed TSM immunosensors to sense neurotransmitter gamma-aminobutyric acid (GABA) [2, 15]. Some of the key results are shown in FIGS. 3D and E.

Ink-Jet Processes for the Fabrication of Biosensors

Our group is engaged in developing inkjet processes for building microscale biosensors that are highly sensitive and cheap. Inkjet printers deposit small droplets of functional material, accurately and directly on a substrate. The resolution and capability of inkjet printing have greatly improved with recent advances in material dispensing technologies and electronic alignment. This method has several advantages over conventional photolithography techniques. This technique does not require masks or cumbersome cleanroom equipment and requirements and has the ability to sequentially deposit multiple layers of different materials without perturbing the previously deposited layers. Accordingly, the deposition process is reduced to just few steps. To enable such fabrication, powerful machines capable of inkjet printing on a large-scale substrate can be used. One example of such a machine includes the Fluid FM® BOT (Cytosurge AG, Glattbrugg, Switzerland), a system capable of nanoinjection with a vast variety of materials of choice selectively into any substrate at nanoscale resolution. An alternate system is the Dimatix® Materials Printer (Fujifilm, Minato City, Tokyo, Japan) which is capable of scaling designs to 8×11 inch areas while maintaining a micron resolution printing with 8 materials printed simultaneously [23, 24]. Preliminary results from this inkjet printing approach are shown in FIG. 4. Without being bound by theory, such inkjet techniques can pattern electrodes of desired thickness and dimensions on the quartz resonators and achieve the desired sensitivities.

Without being bound by theory, disclosed herein is a low cost, high sensitivity wearable diagnostic platform for rapid detection of seroprevalence of COVID-19 that covers necessary testing throughout the disease cycle (FIG. 5). Embodiments of the presently disclosed platform perform serological blood test via fingerstick using a belt mounted system. The sensor cartridge comprises a thickness shear mode (TSM) transducer where mass sensing can be used for detection. In embodiments, a sandwich assay is utilized that comprises immobilized S protein on the surface and ant-IgM and IgG in buffer topping the sensor to detect IgM and IgG separately (as illustrated in FIG. 5-2a&b).

Aim #1: Without being bound by theory, the presently disclosed serological blood test assay permits low cost, high throughput, high sensitivity point-of-care diagnostic platform for rapid detection of antibodies to COVID-19. In embodiments, the diagnostic platform can be used to assess seroprevalence in the community and recovery stage in COVID-19 patients.

Without wishing to be bound by theory, TSM sensors can utilize a sandwich assay (S protein immobilized on the sensor surface loaded with IgG/IgM and IgG/IgM antibodies using commercially available 10 MHz quartz crystals. Without being bound by theory, a high sensitivity antibody COVID-19 sensor can be incorporated into a millimeter scale TSM biosensor. In embodiments, assays can comprise at two antibodies for SARS-Cov-2 as a hand-held, point-of-care diagnostic.

Impact: Without being bound by theory, embodiments include a quantitative bioelectronic antibody assay for COVID19 that can comprise a hand-held sensor usable by military personnel deployed in a mission.

Aim #2: Without being bound by theory, the Acousto-IgG™ and Acousto-IgM™ platform will be highly specific and stable.

Aim #2A: The cross reactivity of the platform to human IgG and IgM can be tested. The aim targets testing the serologic cross reactivity of available anti-IgG and anti-IgM antibodies.

Innovation: In embodiments, high specificity anti-IgG and anti-IgM ensures high accuracy of the platform.

Challenge: Cross reactivity can significantly impact the sensitivity of platform especially when the sensing is in blood.

Impact: Without being bound by theory, the optimal choice of anti-IgG and anti-IgM enables accurate estimation of disease progression.

Aim #2B: Without wishing to be bound by theory, the shelf life of the sensing cartridge in room can be stabilized via stabilizing the surface bound S protein and IgG/IgM antibodies.

Innovation: Without wishing to be bound by theory, several stabilizing solutions for the capture surface device will extend the shelf life at room temperature. In embodiments, such stabilizers include, Sucrose, LB Medium and Blocking buffer.

Deploying the IVD platform in the field requires accounting for the conditions that can affect the stability of the antibodies.

Impact: Without being bound by theory, this disclosure provides for a long shelf life of the sensor cartridges in Acousto-IgG™ and Acousto-IgM™ platform.

Aim 3—Without being bound by theory, a functional product can be developed using appropriate ISO design map, regulatory map, software architecture map, risk management studies, manufacturing processes etc.

Without being bound by theory, the sensor hardware and accompanying software can comprise a wearable, point-of-care in vitro diagnostic platform.

Strategy

Aim #1: Develop and test the sensitivity of TSM sensors to sandwich assay (S protein immobilized on the sensor surface loaded with IgG/IgM and IgG/IgM antibodies using commercially available 10 MHz quartz crystals.

Experimental Design: Without being bound by theory, we can utilize immobilization methodology to produce stable anchoring of bioactive antigen molecules with reproducible orientations to ensure consistency in coating. Briefly, amination of gold surface via self-assembly mono-layer (SAM) of 11-amino-1-undecanethiol. This is followed by covalent attachment of streptavidin and then biotinylated S protein are attached via streptavidin-biotin bond. Each stage can be monitored via TSM sensor response, atomic force microscopy (AFM) and X-ray photoelectron spectroscopy (XPS) [25]. The sensor can be topped with 1 mg/ml anti-IgG or anti-IgM (depending on what sensor cartridge we are testing). We can test various concentrations IgG/IgM (1λ10−4-1 mg/ml) and build a frequency/concentrations curve to help predict antibody concentration FIG. 4E. Data Acquisition: We can openQCM devices and software during this phase [3, 18].

Sensitivity to anti-bodies: Effectively, the sensor can measure the binding of anti-IgG/IgM to the S protein bound IgM/IgG. Although the concentration of IgM and IgG vary widely among different patients, the median has been reported as reaching peaks at 16-20 days after illness onset at 7.25 µg/mL for IgM, while median concentration of IgG peaked during 21-25 days after illness onset at 16.47 µg/mL. Our data show the linear regime of the sensor is centered around 10 µg/ml as shown in the dose-response curve of FIG. 3. For a 10-MHz AT-cut quartz crystal at room temperature, sensitivity is approximately equal to 4.4 ng/(cm2·Hz). Crystals are typically 10 mm in diameter resulting in a sensitivity of 3.45 ng/Hz. A drop of blood from a pin prick is estimated to be 50 µL which would contain 362 ng & 882 ng of IgM and IgG, respectively. Also, without being bound by theory, our platform can reach frequency of 60 MHz while reducing the sensing area of TSM to 30 µm which can achieve 7 orders of magnitude increase in sensitivity [3, 18]. The latter ensures a high sensitivity platform with a small sample of blood (obtained by finger prick).

Prophetic Results and Interpretation: Without being bound by theory, we can determine a calibration curve for Acousto-IgG™ and Acousto-IgG™ using different concentrations of IgG and IgM antibodies in standard solutions. Under experimental conditions, this calibration curve can be used to determine the concentrations of IgG and IgM in the blood sample. Replicates of 5 each for 10 distinct concentrations of IgG and IgM, at an $\alpha=0.05$ results in statistical power of 0.89.

TABLE 2

| Desirable specifications for imprecision, bias and total error | | | | | |
|---|---|---|---|---|---|
| Analyte | $CV_W$ | $CV_G$ | I (%) | B (%) | TE (%) |
| IgG | 4.5 | 16.5 | 2.3 | 4.3 | 8.0 |
| IgM | 5.9 | 47.3 | 3.0 | 11.9 | 16.8 |

The desirable specifications for imprecision, bias and total error are listed in Table 2 (from Biological variations references database https://www.westgard.com/biodatabase2.htm). Imprecision or analytical variation should be less than half of the within-patient coefficient of variation (CVW). I<0.5 CVw. This same specification has to be maintained for screening, diagnosis and case finding when a fixed cut-off point is used to define a pathological or healthy condition [EK Harris, Am J Clin Path, 1979]. Analytical bias can be maintained within one quarter of within—plus between-subject components. We can determine the (+) or (−) for the presence of IgM or IgG from the lowest concentration recorded frequency/concentrations curve (Table 3).

TABLE 3

| The result of the patient test using the disclosed platform can fit with the table to better assess the clinical significance of the test and state of the patient. | | |
|---|---|---|
| IgM | IgG | Clinical Significance |
| − | − | Patient potentially is in the early window of infection |
| + | − | Patient may be in intermediate stage of infection |
| + | + | Patient in late phase of infection |
| − | + | Patient may be in late stage or early stage of recurring infection |
| + | − | Patient may be in intermediate stage of infection |
| − | + | Patient is in the convalescent stage (recovered) |

TABLE 3-continued

The result of the patient test using the disclosed
platform can fit with the table to better assess the
clinical significance of the test and state of the patient.

| IgM | IgG | Clinical Significance |
|-----|-----|-----------------------|
| + | + | Patient may be in recovery stage of infection |

Alternative Approaches: Without being bound by theory, the calculated sensitivity of the commercial crystals can be capable of sensing IgM and IgM from COVID-19 positive patients as indicated by our estimates in the previous section. In the event, we need to enhance the sensitivity due to variations between patients, we can use the techniques outlined in our most recent publication [3] build our own sensors with enhanced sensitivity (see background and significance section). We can obtain blank quartz crystals (such as those from Xeco Inc., Cedar city, UT, USA). Inkjet printing can be used to pattern electrodes on surface of the crystal (see preliminary data for layer and electrode control). The same technology can pattern an interface board. The printing process can be done via a commercially available material printer (e.g., DMP-2850, Fujifilm Dimatix, USA) fitted with a piezo-driven 16-nozzle print-head. The conductive patterns and coatings can be printed using a 1 pL cartridge, while the passivation layers can be printed using a 10 pL cartridge as shown in FIG. 4.

Aim #2A: Test the cross reactivity of the platform to human IgG and IgM. The aim targets testing the serologic cross reactivity of commercially available anti-IgG and anti-IgM antibodies. More rigorous cross-reactivity assessments can be performed under aim #3.

Experimental Design: Surfaces can be coated as described in aim #1. Without being bound by theory, cell-free blood samples can be used to test the specificity of the Acousto-IgG™ and Acousto-IgM™ diagnostic platforms. Human serum samples from healthy individuals can be spiked with low, mid and high concentrations of human IgG and human IgM (concentration range 1×10–4-1 mg/ml). We can then test for the impact of endogenous interferences such hemoglobin, biotin, bilirubin, human anti-mouse antibody (HAMA), intralipid and rheumatoid factor, human IgG (for the samples with IgM), human IgM (for serum samples with IgG) and human IgA. Each sample can be tested in duplicate. More detailed interference assessments with exogenous molecules and assessments of hook effect can be also be performed.

Membrane for isolating cells from blood: We can incorporate an electrospun filter that efficiently removes blood cells from whole blood. The design is based on poly (ethylene terephthalate) (PET)/poly(vinyl pyrrolidone) (PVP) blend. Previous work has shown 80%/20% blend of PET/PVP respectively produces a mean fiber diameter of 0.92 μm with a mean pore size of 4.67 μm, which is sufficient to retain WBCs and RBCs [26]. The additional decrease in pore size could retain platelets as well.

Prophetic Results and Interpretation: Interference can be considered significant if response of the sensor in the presence of the interfering agent exceeds ±10% of initial value. We will then determine the highest concentration of the interference that showed a non-significant effect.

Aim #2B: Without being bound by theory, the shelf life of the sensing cartridge in room can be stabilized via stabilizing the S protein and anti-IgG and IgM.

Experimental Design: The process for adding the stabilizers comprises covering the prepared sensor surface with 1) blocking buffer (Thermo Fisher Scientific, USA) 0.15 M. 2) (5% w/v) sucrose (Acros). 3) coating stabilizer and blocking buffer diluted 1:1 with water. The devices can then be aspirated and dried. All devices can be stored at 50° C. to age the coating (1 day at 50° C. is equal to about 6.5 days at room temperature). We can assess the stability of the coating at 10 days, 3 weeks, 3 months & 6 months [27]. Without being bound by theory, embodiments can comprise an 18-month shelf life. Besides the in-use stability assessment of reagents in the above experiments, we can also assess the stability of the reagents under the following conditions:

Shelf-life stability—Reagent shelf life can be assessed by real-time stability testing, with reagents stored at the specified storage temperature.

Stress testing—the reagents can be cycled through a temperature of 4° C. and ambient temperature to mimic shipping conditions. A separate group of reagents can be cycled through light conditions to mimic shipping conditions. They can then be placed under normal storage conditions and their in-use stability assessed.

Prophetic Results and Interpretation: Without being bound by theory, the samples covered by sucrose have the highest stability.

Aim 3—Without being bound by theory, a functional product can be developed using appropriate ISO design map, regulatory map, software architecture map, risk management studies, manufacturing processes etc.

In embodiments, the biosensor product can comprise a wearable form factor under 100-150 g. The biosensor can be configured for military use conditions with disposable serology cartridges under variable weather conditions not limited to temperature, humidity, and atmospheric pressure.

Aim 4—Testing and validation of the Acousto-IgG™ and Acousto-IgM™ diagnostic systems towards.

We can use the Serology template for manufacturers provided by the FDA (guidance document issued May 2020—Policy for Coronavirus Disease-2019 Tests During the Public Health Emergency (Revised)—Immediately in Effect Guidance for Clinical Laboratories, Commercial Manufacturers, and Food and Drug Administration Staff) for validation of the acousto-IgG™ and acousto-IgM™ diagnostic systems. Validation can be performed using blood samples obtained from 2 different sites—the CLIA-waived laboratory at the Biodesign Institute in ASU, Tempe, AZ and from Dr. Zaraket lab in AUB, Beirut, Lebanon. Control solutions that will accompany the diagnostic systems include solutions with low & high IgG (positive controls) and no IgG (negative control), low & high IgM (positive control) and no IgM (negative control).

| Kit components (example) | Manufacturer |
|--------------------------|--------------|
| Test cartridge with acousto-IgG ™ or acousto-IgM ™ sensor | Open-QCM and Grace Microsystems LLC |
| acoust-IgG ™ or acousto-IgM ™ reader platform | Open-QCM |
| Negative control | Agrisera AB, Sweden |
| Positive control | Agrisera AB, Sweden |
| Sample buffer (bottle) | Grace Microsystems LLC |
| Lancet (for fingerstick only) | Grace Microsystems LLC |
| Instructions for Use leaflet | Grace Microsystems LLC |

65

-continued

| Kit components (example) | Manufacturer |
|---|---|
| Packing materials | Grace Microsystems LLC |

Cross-reactivity—The FDA recommends testing for cross-reactivity against the following antibodies—anti-influenza A (IgG and IgM), anti-influenza B (IgG and IgM), anti-HCV (IgG and IgM), anti-HBV (IgG and IgM), anti-*Haemophilus influenzae* (IgG and IgM), anti-229E (alpha coronavirus), anti-NL63 (alpha coronavirus), anti-OC43 (beta coronavirus), anti-HKU1 (beta coronavirus), ANA, anti-respiratory syncytial virus (IgG and IgM) and anti-HIV. We can test a minimum of 5 individual samples for each disease/infectious agent/antibody class listed above (as per FDA recommendation). We can prepare spiked samples with the IgM or IgG antibodies for the underlying conditions. We can use commercially available IgM or IgG antibodies for the underlying conditions panels collected prior to the COVID-19 pandemic to ensure the panels are SARS-CoV-2 antibody negative.

Power analysis—For n=5 trials, and a of 0.05, 10% variability and a difference in means of 20%, the statistical power of the above comparison was estimated to be 0.89.

If a significant false positive rate (>5%) is observed, we can test different anti-human-IgG and anti-human-IgM identify the candidate anti-human-IgG and anti-human-IgM that minimizes the cross-reactivity.

Class-specificity testing—Since our Acousto-IgG™ or Acousto-IgM™ will quantitatively assess the different classes of immunoglobulins, we can perform the following class-specificity testing as recommended by the FDA. We can use the dithiothrietol (DTT) assay on both of the above diagnostic systems to assess their class-specificity, where the signal due to IgM either decreases or becomes negative upon application of DTT while the signal due to IgG remains unaffected. We can test both Acousto-IgG™ and Acousto-IgM™ with 5 samples (IgG/IgM, +/+) and 2 replicates each (as recommended by the FDA template). Without being bound by theory, we will see 100% agreement between the results of the diagnostic systems and the expected result of DTT treatment (−/+) to IgM/IgG, +/+. To confirm DTT activity, a positive control test can also be included.

Clinical agreement study—We can test prospectively collected SARS-CoV-2 antibody positive specimens from patients that have been previously confirmed infected by SARS-CoV-2 RT PCR. These specimens can be purchased either from the CLIA-waived laboratory in the Biodesign Institute at ASU or directly from the CDC. The specimens can be accompanied by basic information such as the population from which the sample was drawn and the comparator method, specimen collection date, date of onset of symptoms (if present/known), and comparator method to confirm patients as SARS-CoV-2 infected or not infected.

Patient samples eligible for this study ca be from patients who are 18-99 years old, of all sexes including healthy volunteers.

Criteria for Inclusion and Exclusion

Inclusion Criteria:

Individuals who have experienced symptoms of COVID-19 and have been tested using a CDC approved or FDA registered and listed nucleic acid based test within 1 year of Feb. 1, 2020.

Individuals who are at the time of enrollment in the study currently or in the recent past (3 weeks) exhibiting symptoms of COVID-19.

Individuals capable of performing a finger stick blood drop draw and placing it on the sample well.

Individuals that have interacted with a COVID-19 positive individual and are still exhibiting symptoms will be tested by the Arizona Department of Health Services with a CDC approved or FDA registered nucleic acid-based device.

Exclusion Criteria:

Individuals incapable of pricking their finger and placing a drop of blood into a sample well.

Pregnant woman are not excluded if they meet the inclusion criteria and age requirements.

We can collect a minimum of 30 IgG positive and 30 IgM positive samples and 30 IgG negative and 30 IgM negative samples as deemed acceptable by the FDA. The samples can be generated, collected and sourced from the CLIA-waived laboratory in the Biodesign Institute at ASU and will be collected prospectively after an IRB approval from ASU, Tempe, AZ.

In addition, we can also place an Acousto-IgG™ and Acousto-IgM™ system in the above laboratory. We can have the patients perform a blood draw using a lancet and use the above diagnostic systems. Both the patients and the laboratory personnel can be blinded to the results from the above diagnostic systems. The results of the blood samples collected by the lab personnel can be independently analyzed from the blood samples drawn by the patients using a lancet. As recommended by the serology template for manufacturers from FDA, we can use the following tables to quantitatively assess the positive percent agreement (PPA) and negative percent agreement (NPA):

| | | Comparator method/Clinical truth | |
|---|---|---|---|
| | | Positive | Negative |
| Acousto-IgG ™ | Positive | A | B |
| | Negative | C | D |

| | | Comparator method/Clinical truth | |
|---|---|---|---|
| | | Positive | Negative |
| Acousto-IgM ™ | Positive | A | B |
| | Negative | C | D |

The PPA for each of the above diagnostics is determined by A/(A+C) and the NPA for each of the above diagnostics is determined by D/(D+B). Independent analysis of NPA and PPA from the blood samples collected by the lab personnel and corresponding blood samples obtained by fingerstick from patients using the lancet will allow us to validate the point-of-care claim.

Matrix equivalency—We can test 4 different sample matrices—(a) fingerstick cell-free, whole blood (b) EDTA plasma (c) anti-coagulant 1 and (d) anti-coagulant 2. Each of the sample(s) can come from the same donor from the CLIA-waived laboratory in the Biodesign institute at ASU. As required by the FDA template for serology manufacturers, samples that were assessed negative with the above 2 Acousto-IgG™ and Acousto-IgM™ diagnostics can subsequently be spiked with low SARS-Cov-2 IgG & IgM antibodies (separate samples) and moderate SARS-Cov-2 IgG & IgG (separate samples). Negative samples for each of the 4 specimen matrices can be spiked with the same amount of SARS-Cov-2 IgG and IgM (separate samples) to allow for comparison. We can test 2 replicates of 5 samples under each condition (concentration of antibodies)—negative, low and moderate. Therefore, we will have 30 samples to be tested under each matrix/specimen condition. We can repeat this for each of the 4 specimen conditions each for IgG and IgM respectively.

| Specimen matrix 1 (IgG) | | | | |
|---|---|---|---|---|
| Sample | replicate | Negative | Low postive | Moderate positive |
| Sample 1 | 1 | | | |
| | 2 | | | |
| Sample 2 | 1 | | | |
| . . . | 2 | | | |
| Sample 5 | 1 | | | |
| | 2 | | | |

| Specimen matrix 1 for (IgM) | | | | |
|---|---|---|---|---|
| Sample | replicate | Negative | Low postive | Moderate positive |
| Sample 1 | 1 | | | |
| | 2 | | | |
| Sample 2 | 1 | | | |
| . . . | 2 | | | |
| Sample 3 | 1 | | | |
| | 2 | | | |

Aim 5—Optimize the hardware and accompanying software to a wearable, point-of-care in vitro diagnostic platform.

In various embodiments, sensing cartridge of the presently disclosed platform comprise molecular moieties on the sensor, given dimensions of the gold electrode (thickness of the gold film and diameter of the gold electrode), given acoustic parameters of the sensor (resonant frequency, Q-factor etc), or a combination thereof. The hardware (the electronic reading platform) and the software interface can be further configured to comprise a wearable in vitro diagnostic.

In embodiments, the electronic reading platform interfaces with the sensing cartridge through an USB interface and with an external mobile phone through a wireless Bluetooth interface. The electronic reading platform can be optimized for any one or more of the following features:

Form factor that will allow the attachment of the electronic reading platform to be attached to a belt in the waist while allowing for free movement of the wearer. In some embodiments, the wearer can comprise a soldier. It can also be optimized for ease of hand-held operation and improved robustness against damages during physical handling, out in the open field.

Reduce the weight of the device to a few tens of grams excluding battery.

Enhance battery-life such as through a combination of software and hardware enhancements that minimizes power consumption during use and allows the device to operate in a low-power sleep mode when not in use.

Eliminate temperature rise due to electronic heating when it is used to analyze a large batch of samples that could potentially corrupt the sensor performance.

Enhance the user experience through improved graphical user interface (GUI) and improve reliability of wireless communication between the hand-held electronic reader and the mobile phone; and In a limited number of patients (50 positive samples and 50 negative samples each for IgG and IgM), we will run validation experiments with similar inclusion and exclusion criteria used in the "clinical agreement study" detailed in aim #3 to verify the point-of-care claim for both the Acousto-IgG™ and Acousto-IgM™ diagnostic systems subsequent to all the above enhancements.

References Cited in this Example

1. Lauer, S. A., et al., The Incubation Period of Coronavirus Disease 2019 (COVID-19) From Publicly Reported Confirmed Cases: Estimation and Application. Ann Intern Med, 2020.
2. Wang, T. and J. Muthuswamy, Immunosensor for detection of inhibitory neurotransmitter gammaaminobutyric acid using quartz crystal microbalance. Anal Chem, 2008. 80(22): p. 8576-82.
3. Khraiche, M. L., J. Rogul, and J. Muthuswamy, Design and Development of Microscale Thickness Shear Mode (TSM) Resonators for Sensing Neuronal Adhesion. Front Neurosci, 2019. 13: p. 518.
4. Sauerbrey, G., The use of quartz crystal oscillators for weighing thin layers and for microweighing applications. Z. Phys, 1959. 155: p. 206-222.
5. Li, R., et al., Substantial undocumented infection facilitates the rapid dissemination of novel coronavirus (SARS-CoV2). Science, 2020.
6. Li, X., et al., Molecular immune pathogenesis and diagnosis of COVID-19. J Pharm Anal, 2020.
7. Vashist, S. K., In Vitro Diagnostic Assays for COVID-19: Recent Advances and Emerging Trends. Diagnostics, 2020. 10(4): p. 202.
8. Rothan, H. A. and S. N. Byrareddy, The epidemiology and pathogenesis of coronavirus disease (COVID-19) outbreak. J Autoimmun, 2020. 109: p. 102433.
9. Jacofsky, D., E. M. Jacofsky, and M. Jacofsky, Understanding Antibody Testing for COVID-19. J Arthroplasty, 2020.
10. Corman, V. M., et al., Detection of 2019 novel coronavirus (2019-nCOV) by real-time RT-PCR. Euro Surveill, 2020. 25(3).
11. Chan, J. F., et al., Improved molecular diagnosis of COVID-19 by the novel, highly sensitive and specific COVID-19-RdRp/Hel real-time reverse transcription-polymerase chain reaction assay validated in vitro and with clinical specimens. J Clin Microbiol, 2020.
12. Chu, D. K. W., et al., Molecular Diagnosis of a Novel Coronavirus (2019-nCOV) Causing an Outbreak of Pneumonia. Clin Chem, 2020. 66(4): p. 549-555.
13. Tan, W., et al., Viral Kinetics and Antibody Responses in Patients with COVID-19. medRxiv, 2020: p. 2020.03.24.20042382.
14. To, K. K., et al., Temporal profiles of viral load in posterior oropharyngeal saliva samples and serum antibody responses during infection by SARS-CoV-2: an observational cohort study. Lancet Infect Dis, 2020.
15. Ergezen, E., et al., Real time monitoring of the effects of Heparan Sulfate Proteoglycan (HSPG) and surface charge on the cell adhesion process using thickness shear mode (TSM) sensor. Biosensors and Bioelectronics, 2007. 22(9-10): p. 2256-2260.

16. Lu, F., et al., Finite element analysis of interference for the laterally coupled quartz crystal microbalances. Sensors and Actuators a-Physical, 2005. 119(1): p. 90-99.

17. Wang, T. T., et al., Immobilization and characterization of gamma-aminobutyric acid on gold surface. Journal of Biomedical Materials Research Part A, 2006. 79A(1): p. 201-209.

18. Khraiche, M. and J. Muthuswamy, Multi-modal biochip for simultaneous, real-time measurement of adhesion and electrical activity of neurons in culture. Lab Chip, 2012. 12(16): p. 2930-41.

19. Khraiche, M. L., N. Jackson, and J. Muthuswamy, Early onset of electrical activity in developing neurons cultured on carbon nanotube immobilized microelectrodes. Conf Proc IEEE Eng Med Biol Soc, 2009. 2009: p. 777-80.

20. Khraiche, M. L., A. Zhou, and J. Muthuswamy, Acoustic sensor for monitoring adhesion of Neuro-2A cells in real-time. J Neurosci Methods, 2005. 144(1): p. 1-10.

21. M L Khraiche, A Zhou, and J Muthuswamy, Acoustic sensor for monitoring adhesion of Neuro-2A cells in real-time Journal of neuroscience methods, 2004. 144(1): p. 1.

22. Zhou, A. and J. Muthuswamy, Acoustic biosensor for monitoring antibody immobilization and neurotransmitter GABA in real-time. Sensors and Actuators B: Chemical, 2004. 101(1): p. 8-19.

23. Qiu, S. and C. Zhou, Organic Printable Electronic Materials. Printed Electronics, 2016: p. 21-53.

24. Su, W., Encapsulation Technology for Organic Electronic Devices. Printed Electronics, 2016: p. 287-315.

25. Wang, T., et al., Immobilization and characterization of gamma-aminobutyric acid on gold surface. J Biomed Mater Res A, 2006. 79(1): p. 201-9.

26. Shahrabi, S. S., J. Barzin, and P. Shokrollahi, Blood cell separation by novel PET/PVP blend electrospun membranes. Polymer Testing, 2018. 66: p. 94-104.

27. Standard Guide for Accelerated Aging of Sterile Medical Device Packages. ASTM International Designation. F 1980-02.

Example 2

Brief Summary: The world continues to struggle to contain the spread of COVID19, first reported in Wuhan, China in December 2019. This global public health crisis risks overwhelming healthcare systems everywhere with a highly contagious acute respiratory syndrome that has to date claimed the lives of hundreds of thousands of people. The lack of cheap, scalable, and rapid testing platform has contributed significantly to the continued lockdown measures as we struggle to identify patients that have acquired an immunity to the disease to quantitively assess the state of herd immunity. This disease also has huge national security implications. The lack of readily available test kits and the need for specialized laboratory equipment for testing can have a significant impact on the military along the entire chain of command. Therefore, there is a need for a point-of-care in vitro diagnostic system that is wearable (or easily deployable in remote areas), readily available and can be used by untrained personnel. It becomes important to have tests that can identify the prevalence of the disease at every stage of progression. Therefore, CDC in partnership with state, local and territorial health agencies, public and private healthcare providers routinely conducts seroprevalence studies to track the status of disease in the population.

In various embodiments, the invention reported here includes a hand-held/wearable, high accuracy and easy to use diagnostic platform to enable the assessment of serological prevalence of COVID19. The current testing technologies are often qualitative, require healthcare workers to operate, prone to error and too large to be deployed in the field. In embodiments, the disclosed diagnostic platform comprises two distinct variants, Acousto-IgG™ and Acousto-IgM™ for the detection of IgG and IgM antibodies to SARS-CoV-2 and requires no medical training to operate, performs the test in minutes using a fingerstick and transmits data directly to Wi-Fi enabled devices. The core technology involves the use of acoustic waves to achieve sensitivities that are orders of magnitude higher than the current techniques such as enzyme linked immunosorbent assay (ELISA), chemi-luminescent immunoassay (CLIA) or lateral flow assays that are often semi-quantitative. Other advantages over current technologies include a rapid, quantitative read-out (within minutes), as opposed to the qualitative read-out that take 15-30 min with current techniques. The hand-held, point-of-care nature of this invention will mitigate the need for samples to be transported over long distances to specialized laboratories or for patients to make risky trips to local diagnostic laboratories.

Introduction: The invention builds on the successful experience of the inventors in developing highly sensitive, label-free, acoustic sensors for monitoring cellular adhesion, neurotransmitter concentrations and other biomolecular events. We have successfully developed highly sensitive acoustic sensors for the detection of anti-bodies to GABA (gamma-aminobutyric acid, a widely prevalent neurotransmitter in the brain). The invention reported here pertains to the fields of—in vitro diagnostics, acoustic sensors, biomolecular detection, millimeter and microscale electromechanical systems. Most recently, the inventors developed a technique (M. Khraiche, J. Rogul, and J. Muthuswamy, Design and Development of Microscale Thickness Shear Mode (TSM) Resonators for Sensing Neuronal Adhesion, Front. Neurosci., 4 Jun. 2019) to enhance the sensitivity of the acoustic sensors using physical principles of bulk wave resonators leading to optimal design of electrode dimensions and thickness of the quartz resonators for achieving desired sensitivity. The invention reported here builds on all of this work.

In embodiments, the disclosed invention comprises a wearable, in vitro diagnostic platform for detecting SARS-CoV-2 antibodies. Without wishing to be bound by theory, the disclosed diagnostic platforms and disposable sensor cartridges will equip soldiers with a much needed point-of-care technology to identify immune individuals and serological prevalence in a population regardless of proximity or access to medical centers.

SUMMARY OF THE INVENTION

Serological or antibody-based testing for SARS-CoV-2 (Severe Acute Respiratory Stress—Coronavirus—2) is critical to assess seroprevalence and also track efficacy in vaccine development. Here, we disclose a point-of-care in vitro diagnostic (IVD) technology that will address current challenges in access/availability, deployment and communication of results, ease of use, scalability to large and remote populations.

OPPORTUNITY: Public and private health services, contract research organizations (CROs), and pharmaceutical companies need regular data on seroprevalence to track disease progression and also assess the efficacy of new vaccines and therapeutics currently under development. Current diagnostic technologies require skilled workforce to operate and interpret results, often 24-48 hr turnaround times, and hard to deploy in remote locations. Patients are often reluctant to visit diagnostic laboratories and health care providers during this pandemic significantly increasing the time, cost and failure rates of such seroprevalence studies.

SOLUTION: We disclose here a hand-held or wearable, rapid (<1 min), low-cost IVD. In embodiments, the IVD detects IgG and IgM antibodies for the SARS-Cov-2 virus, with high sensitivity and specificity that can be rapidly deployed and operated without the requirement of skilled laboratory personnel. The proposed technology can also communicate results back to health care providers through mobile phone or other hand-held computing platforms. This IVD technology can enable virtual clinical trials of new vaccines and therapeutics. In embodiments, the IVD platform can also be adapted at a later stage to track other biomarkers.

The Assure system is a qualitative assessment using lateral flow assays. The presently disclosed IVD will provide rapid, quantitative assessment of both IgG & IgM.

In various embodiments, the present invention comprises one or more of the following:

Millimeter or microscale electrodes on bulk acoustic wave resonators allow for tuning of sensitivity of conventional acoustic sensors to what is optimal to detect IgG and IgM antibodies in blood samples.

The chemistry on surface of the electrodes of the resonators determines the selectivity of the sensor to the antibodies to SARS-Cov-2.

In embodiments, the presently disclosed technology provides for any one or more of the following advantages:

Significantly enhanced sensitivity to antibody detection

Eliminate transporting blood samples.

Reduce time from sample collection to result from several hours to <10 min.

Reduce time and cost for clinical trials by enabling virtual clinical trials.

Quantitative assessment that will allow advanced informatic tools for predictive modeling.

As easy to use as a glucometer.

Eliminates the need for trained personnel and patient visits to labs.

In various embodiments the presently disclosed invention provides a quantitative assessment of both IgG and IgM antibodies rapidly within seconds. In addition, compared to most of the competition, embodiments require no trained personnel (will be as easy to use as a glucometer).

Example 3

Figure 7:
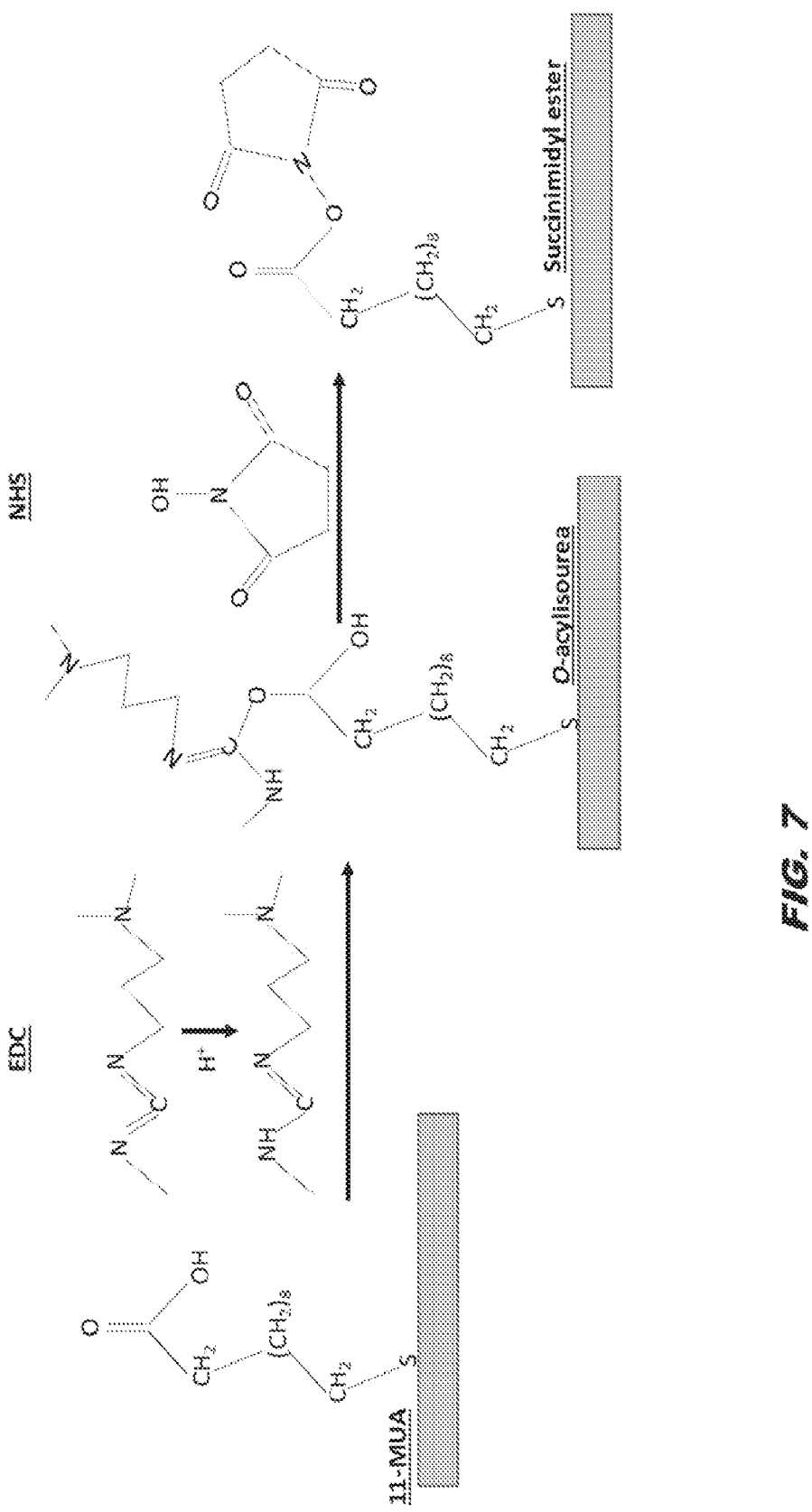
FIG. 7 shows a reaction scheme of embodiments of immobilization chemistry to sense antibodies to Spike-protein of the SARS-CoV-2 virus.
Figure 8:
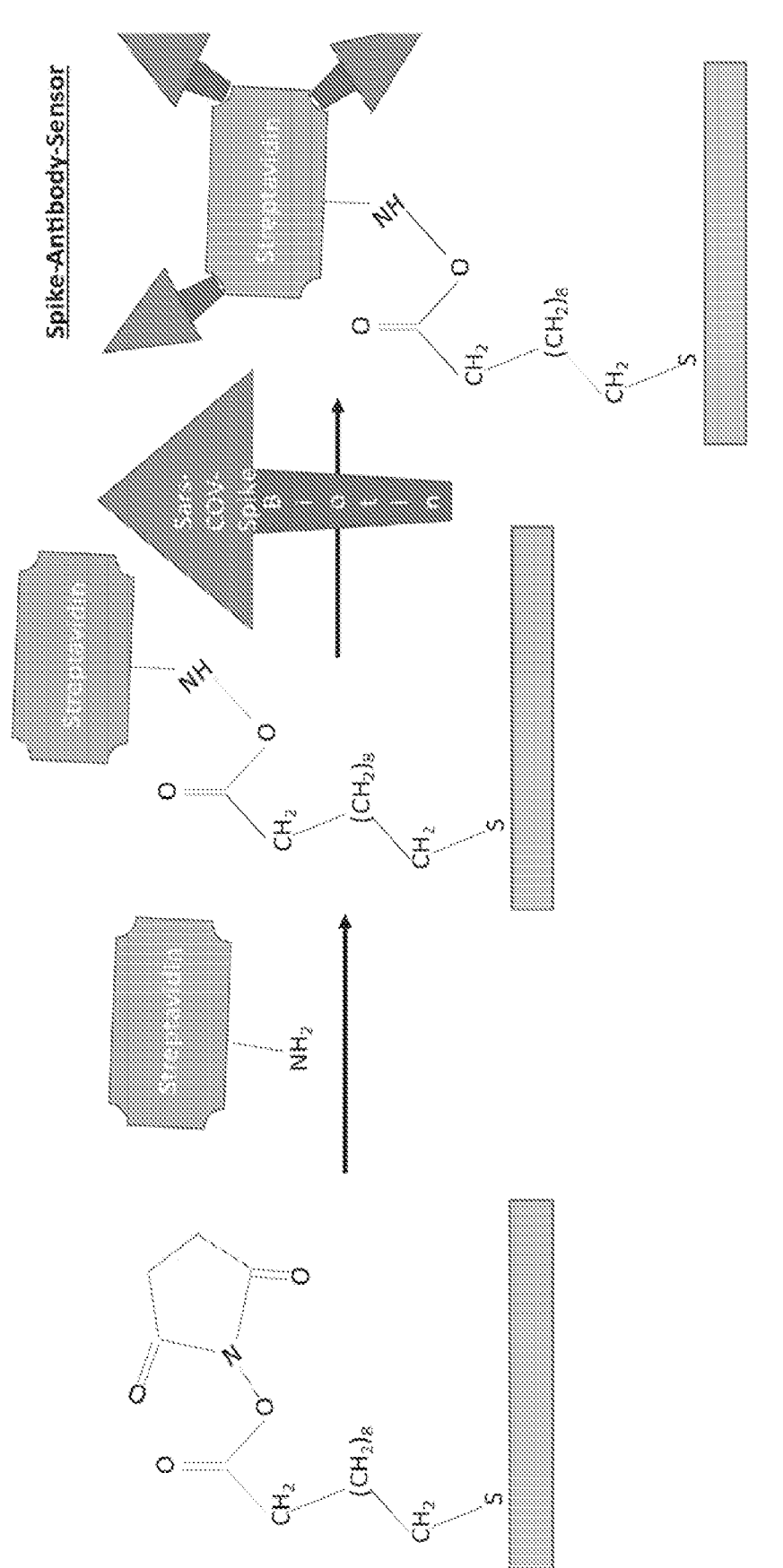
FIG. 8 shows a reaction scheme of embodiments of immobilization chemistry to sense antibodies to Spike-protein of the SARS-CoV-2 virus.
Figure 9:
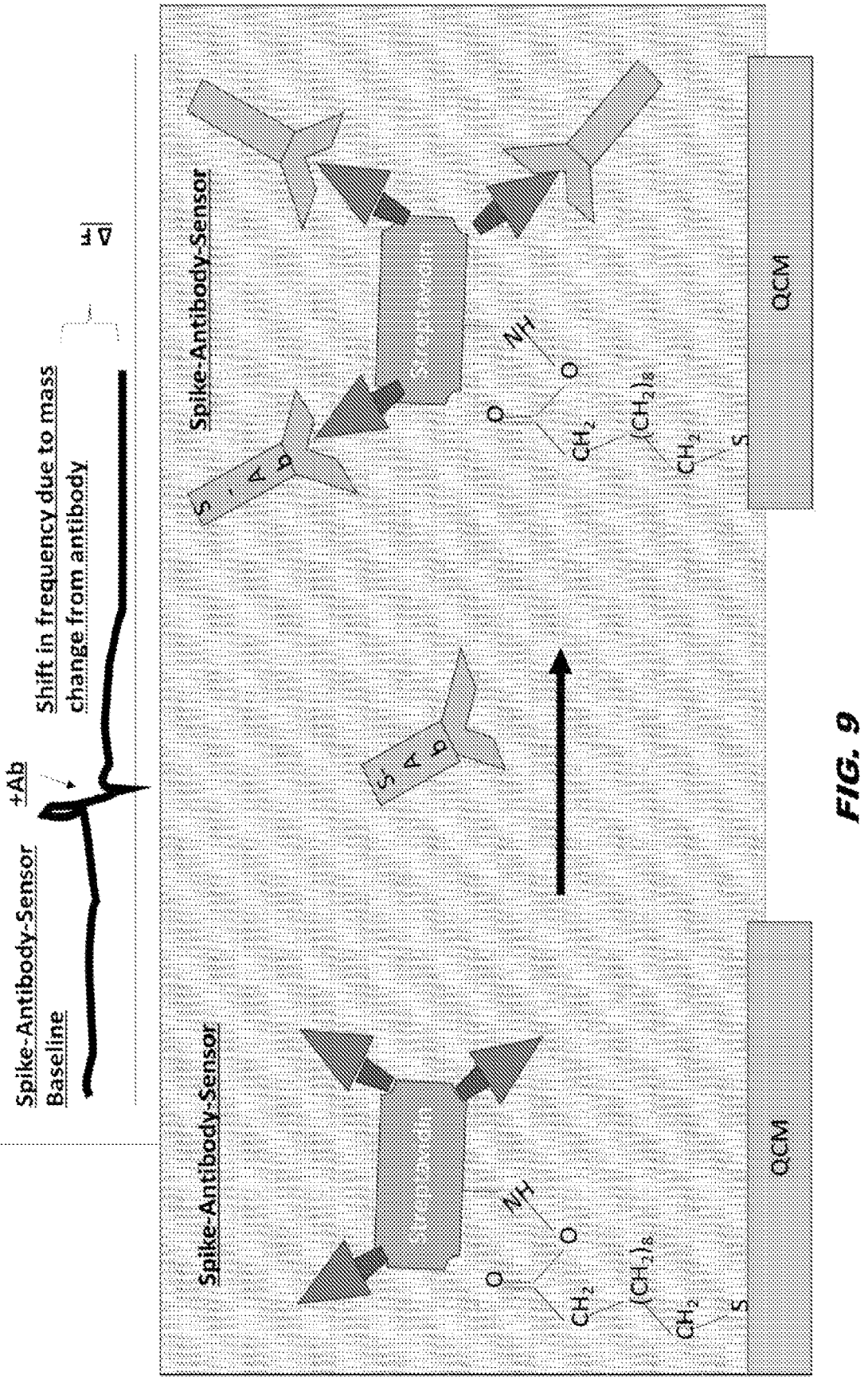
FIG. 9 shows a reaction scheme of embodiments of immobilization chemistry to sense antibodies to Spike-protein of the SARS-CoV-2 virus.

Non-Limiting, Exemplary Data for the Acoustic Resonator-Based Sensor to Detect Antibody to Spike RBD Protein of SARS-CoV-2 Virus Summary: Effect of Alkanethiol Composition on QCM Response to Covid-19 Spike RBD Antibody FIGS. 7-9 show immobilization chemistry to sense antibodies to Spike-protein of the SARS-CoV-2 virus QCM sensor chemistry can be tailored to desired dynamic range.

Figure 12:
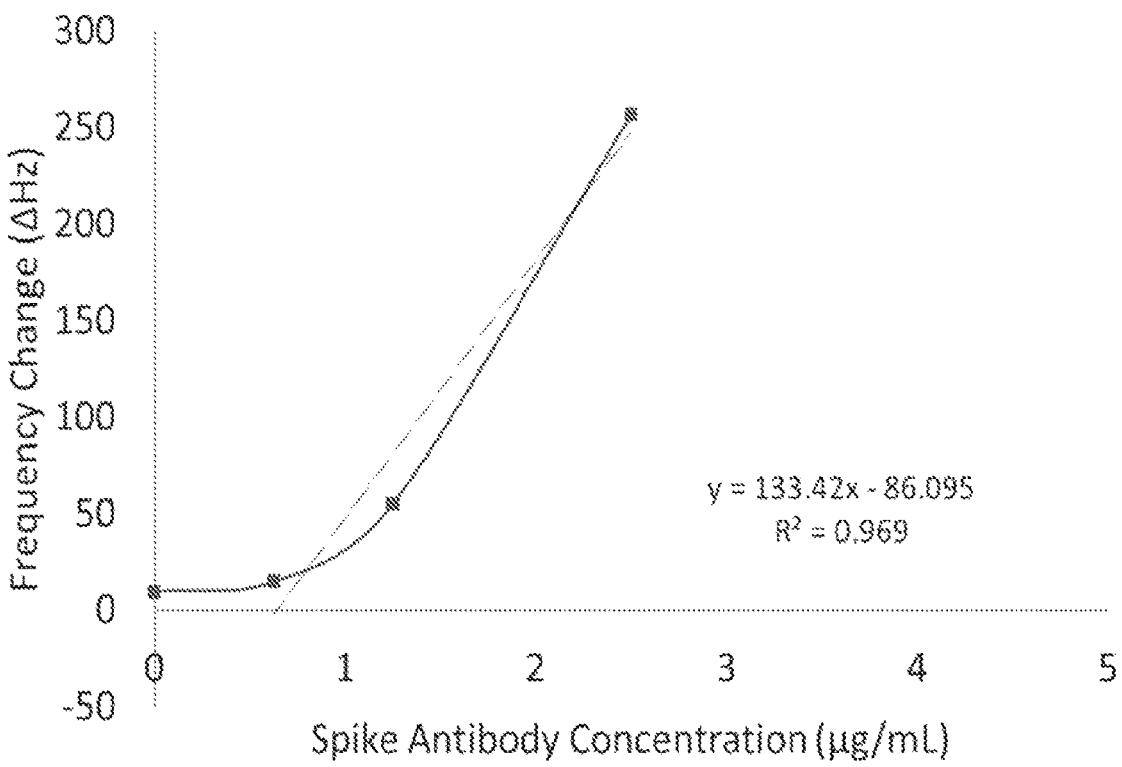
FIG. 12 shows a graph of QCM sensor data. Testing sensor with spike antibody in calf blood plasma diluted in PBS.
Figure 13:
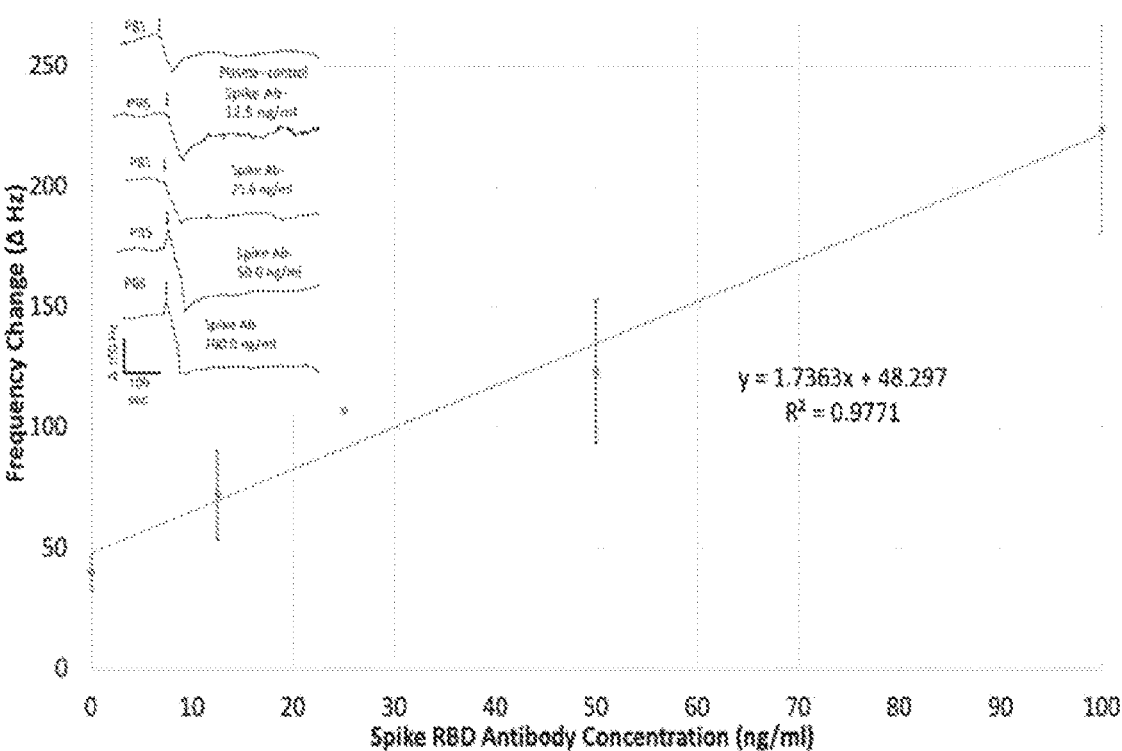
FIG. 13 shows a graph of QCM sensor data. QCM sensor was responsive to [Spike Ab] in plasma when diluted in PBS. Results of sensitivity analysis show the sensor demonstrating a linear response to increasing concentrations of anti-S IgG in plasma from calf-blood. (Inset) Time series responses of the sensor (change in frequency) to 4 different concentrations of anti-S IgG in plasma from calf blood. A response of ~48.3 Hz at 0 ng/ml indicates the response of the Acousto-Ab sensor to non-specific binding of plasma proteins in calf blood.

FIGS. 12-13 indicate QCM sensor was responsive to [Spike Ab] in plasma when diluted in PBS.

Figure 14:
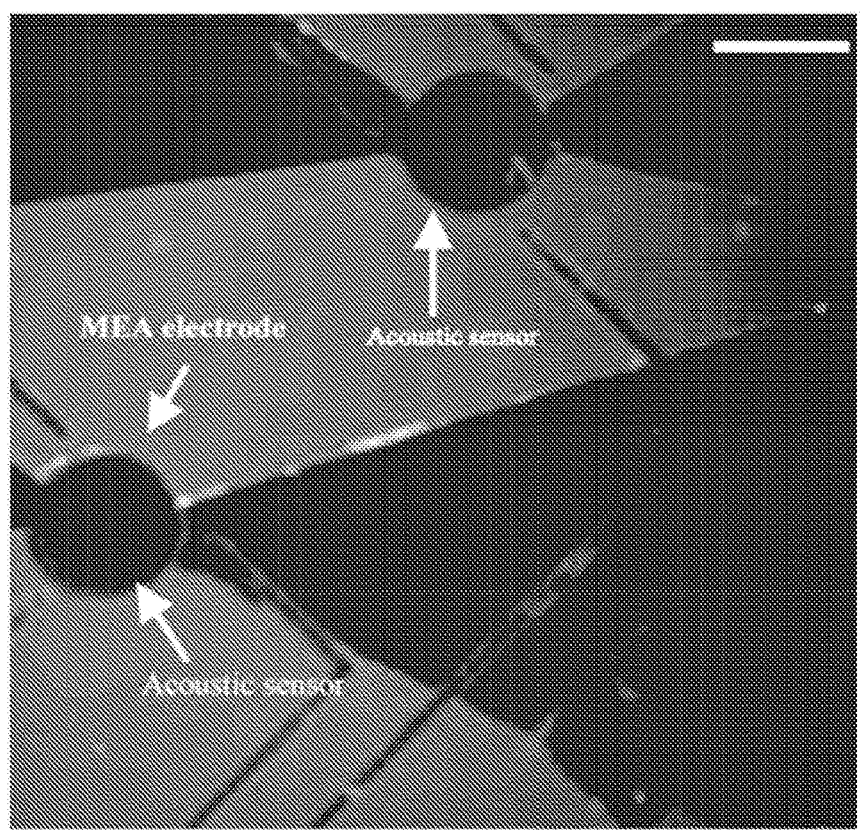
FIG. 14 shows a photograph of a two channel quartz resonators fabricated on a glass substrate. Scale bar=300 mm. Data published in Khraiche and Muthuswamy, *Lab on Chip,* 2012, 12, 2930-2941.
Figure 15:
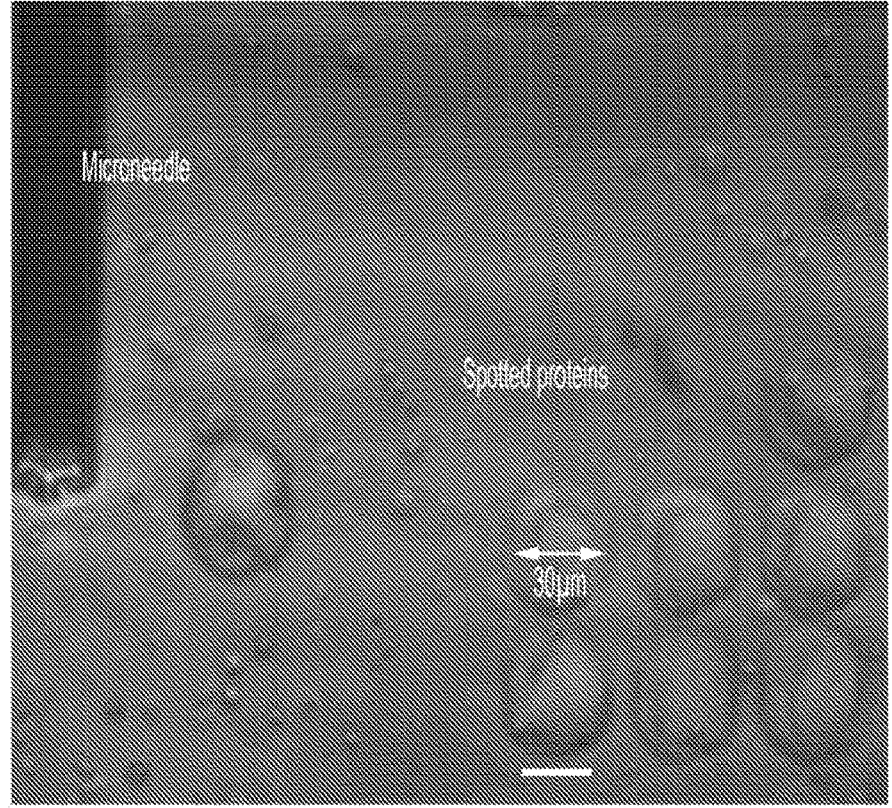
FIG. 15 shows a photograph of an example of fluid spotting precision on 30 μm diameter electrodes.

FIGS. 14-15 show multi-channel micro-resonators and spotting process

Figure 16:
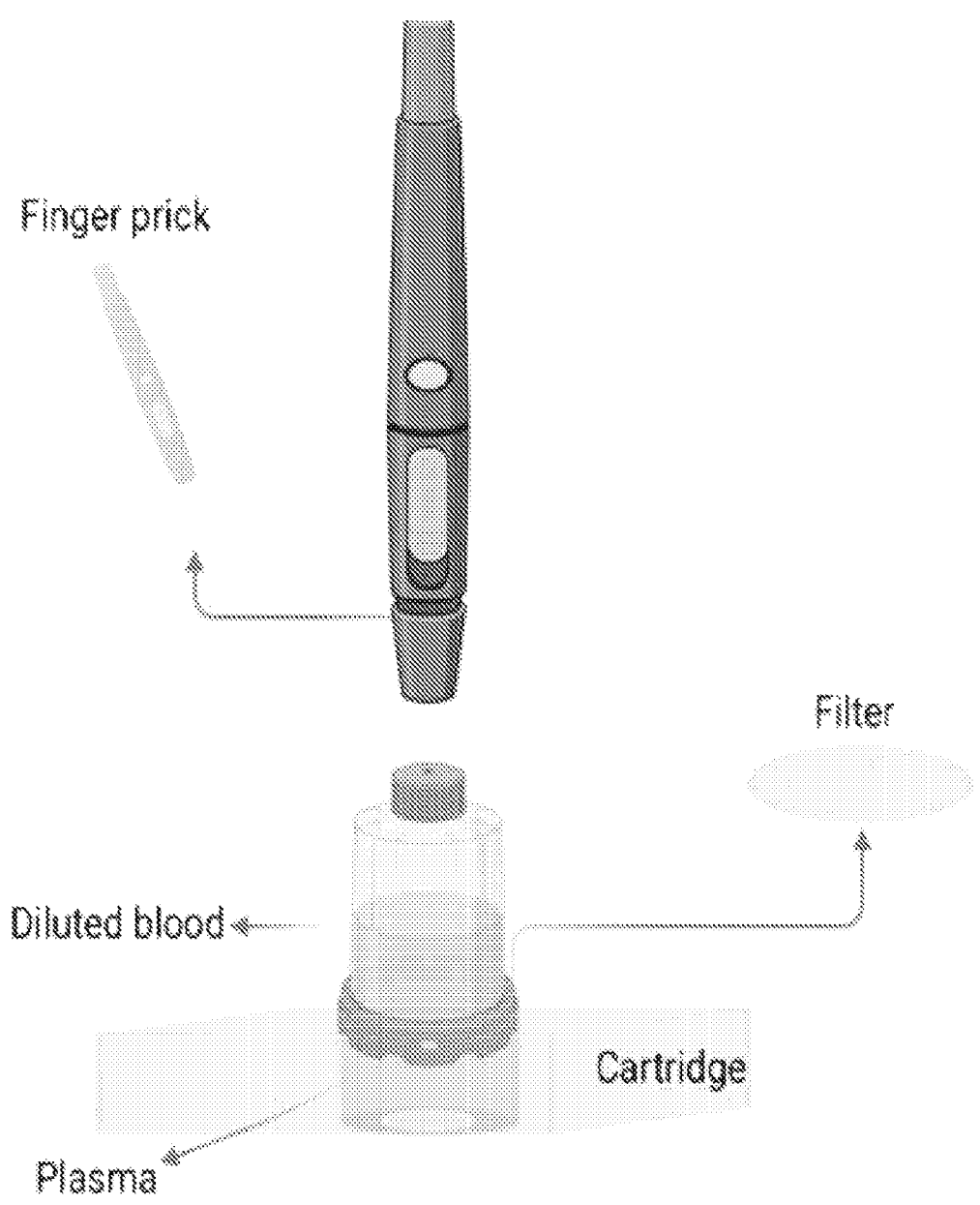
FIG. 16 shows an illustration of blood being sampled by a lancet pen and dispensed into a dilution well (filled with PBS). It is then filtered using a graphene filter before releasing plasma into the sensor well in the cartridge. Illustration of blood being sampled by a lancet pen and dispensed into a dilution well. It is then filtered using a graphene filter before releasing plasma into the sensor well in the cartridge.

FIG. 16 shows scheme for blood draw using lancet and filtration before sensing Chemicals Used:

EDC—1-ethyl-3-(-3-dimethylaminopropyl) carbodiimide

NHS-N-Hydroxysuccinimide

11-Mercaptoundecanoic acid (MUA)

9-Mercapto-1-nonanol

PBS-phosphate buffered saline

Figure 10:
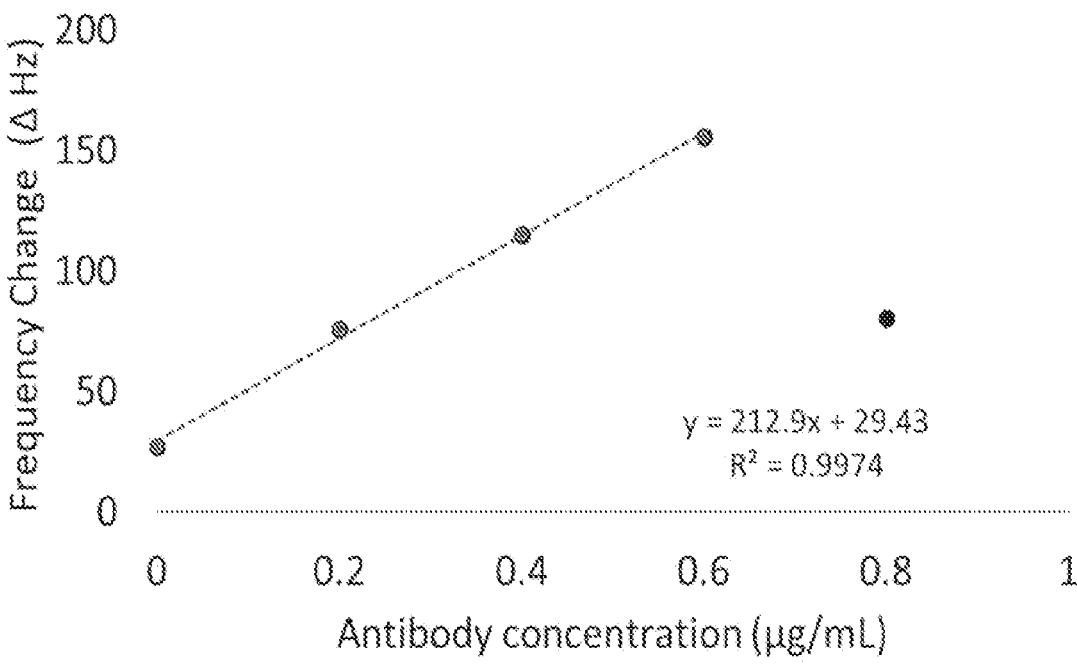
FIG. 10 shows a graph of QCM sensor data. In PBS, using 100% 11-MUA as the initial alkanethiol layer (SAM), the dynamic range of the sensor was ~0-0.8 μg/ml.

FIG. 10 shows Version 1—In PBS, using 100% 11-MUA as the initial alkanethiol layer (SAM), the dynamic range of the sensor was ~0-0.8 µg/ml.

100% 11-MUA as alkanethiol layer

Spike antibody (Ab) was added to PBS 0-0.8 µg/mL concentrations

At higher concentrations, response seems to decline or saturate.

Figure 11:
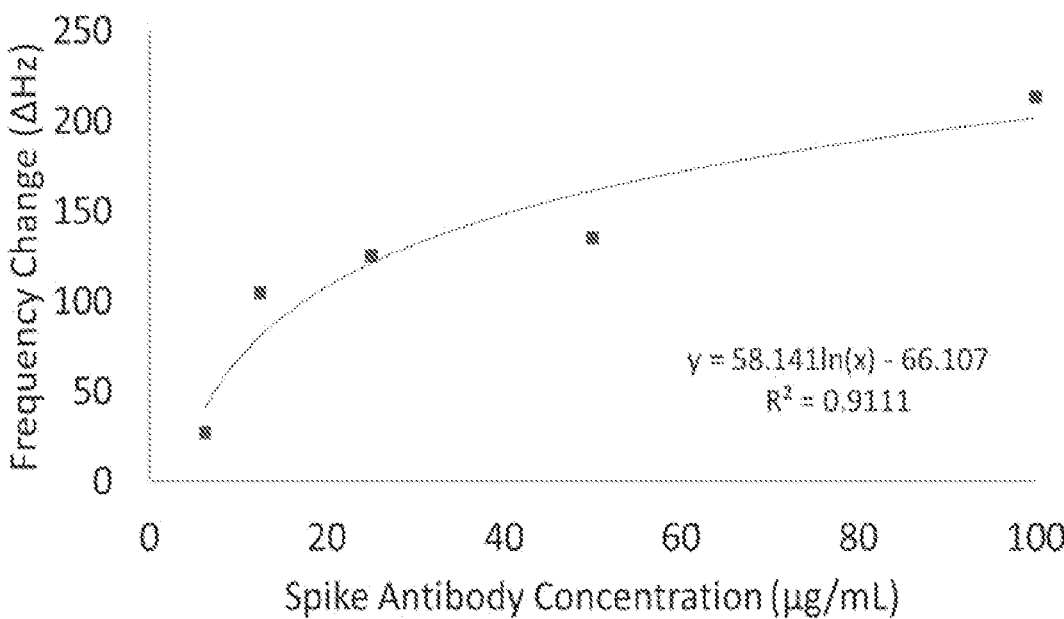
FIG. 11 shows a graph of QCM sensor data. In PBS, using 50% 11-MUA and 50% 9-Mercapto-1-nonanol as the initial alkanethiol layer (SAM), the dynamic range of the sensor increased to ~0-100 g/ml.

FIG. 11 shows Version 2—In PBS, using 50% 11-MUA and 50% 9-Mercapto-1-nonanol as the initial alkanethiol layer (SAM), the dynamic range of the sensor increased to ~0-100 µg/ml.

100% 11-MUA as alkanethiol layer

Spike antibody (Ab) was added to PBS 0-0.8 µg/mL concentrations

At higher concentrations, response seems to decline or saturate.

FIG. 12 shows Testing sensor with spike antibody in calf blood plasma diluted in PBS Version 3—However, in calf blood plasma, using 20% 11-MUA and 80% 9-Mercapto-1-nonanol as the initial alkanethiol layer (SAM), the dynamic range of the sensor decreased to ~0.625-3 µg/ml.

20% MUA/80% nonanol as alkanethiol layer

Spike antibody (Ab) was added to Calf Blood Plasma and serially diluted in PBS to give 0.625-10 µg/mL concentrations At higher concentrations, response seems to decline, but overall dynamic range seems similar to 100% MUA (QCM1).

At lower concentrations, response is non-linear

FIG. 13 shows raw data from our most recent sensor using the above immobilization chemistry on a conventional 10 MHz quartz resonator shows high sensitivity in measuring 12-100 ng/ml of anti-S IgG antibody in 100 µl of plasma from calf blood. Sensitivity analysis of the above Acousto-Ab sensors using their responses to different concentrations of anti-S IgG antibody shows a sensitivity of 1.74 Hz/ng/ml. There was a measurable response of 48.3 Hz to non-specific binding of plasma proteins (in calf blood) on the surface of the sensor. A drop of blood from a finger stick (~50 µl) is estimated to contain 362 ng & 882 ng of IgM and IgG, respectively, which is far larger than the values tested in the above experiments. Therefore, preliminary experiments indicate that the sensitivity of the current Acousto-Ab system appears to be more than adequate for human blood samples.

Results of sensitivity analysis show the sensor demonstrating a linear response to increasing concentrations of anti-S IgG in plasma from calf-blood. (Inset) Typical time series responses of the sensor (change in frequency) to 4 different concentrations of anti-S IgG in plasma from calf blood. A response of ~48.3 Hz at 0 ng/ml indicates the response of the Acousto-Ab sensor to non-specific binding of plasma proteins in calf blood.

Multi-channel resonators. FIG. 14 shows a photograph of a two channel quartz resonators fabricated on a glass substrate. Scale bar=300 mm. Data published in Khraiche and Muthuswamy, Lab on Chip, 2012, 12, 2930-2941.

Protein spotting on micro-scale sensors. New capabilities developed in the lab of Dr. Khraiche at American University of Beirut in Lebanon that help us realize precision spotting of proteins on micro-scale electrodes. FIG. 15 shows an image of Example of fluid spotting precision on 30 μm diameter electrodes.

Scheme for Blood Sample Collection

FIG. 16 shows Illustration of blood being sampled by a lancet pen and dispensed into a dilution well (filled with PBS). It is then filtered using a graphene filter before releasing plasma into the sensor well in the cartridge.

Example 4

Serological testing for antibodies to SARS-CoV-2 (Severe Acute Respiratory Stress—Coronavirus—2) or other viruses that can be pandemic, is critical for a variety of important purposes. These include critical assessment of immunity levels, tracking the efficacy of vaccines during their development process and after vaccine administration, seroprevalence, and plasma evaluation.

This example addresses the need for point of care, rapid, and quantitative antibody readout among immune-compromised individuals, vaccine developers, doctor's offices, and blood banks that screen and evaluate plasma for convalescent therapy. The serological tests that are EUA (emergency use authorization from FDA) approved do not meet the needs of being both point of care and quantitative. Without wishing to be bound be theory, we can develop a point-of-care, rapid, quantitative in vitro diagnostic (IVD) with high sensitivity, specificity, and scalability based on innovations in acoustic. The IVD will address current challenges in precise quantitation, access, availability, deployment, and communication of results, ease of use, and scalability to large and remote populations.

Acousto-Ab series, will be a portable point-of-care IVD device consisting of a cell phone-sized measurement unit and replaceable cartridges. The device will quantitatively assess IgG, IgM and IgA antibodies separately on different platforms or sequentially on the same platform for the SARS-Cov-2 virus rapidly (~5 min) in a droplet of blood from a finger stick, with high sensitivity and specificity. A multi-channel version of Acousto-Ab will simultaneously assess antibodies to Spike (S), Nucleocapsid (N) and NSP5 proteins that will enable the detection of antibodies to emerging variants also. The system will be designed to be quickly deployed and as easy to use as a home blood glucose meter and will communicate results back to health care providers through a mobile phone or other hand-held computing platforms. The system can be readily adapted in future modifications to track over 30 or more biomarkers simultaneously. Comparable systems available in the marketplace today that use enzyme-linked immunosorbent assays (ELISA) require trained personnel, extensive instrumentation and often take multiple hours between sample collection and reporting of test results. In addition, current FDA-approved point-of-care systems for serological tests provide only a qualitative assessment of antibodies using lateral flow assays.

Background and Significance

Recent developments in serological testing for antibodies to SARS-CoV-2 (Severe Acute Respiratory Stress—Coronavirus—2) are moving towards addressing the critical need for a point-of-care IVD capable of simultaneously providing rapid and quantitative readouts of antibodies [3-7]. A recent study on a limited number of patients who were seropositive for COVID-19 reported median IgG antibody titers in the range 0.29-1.38 μg/ml depending on the number of symptoms (0-5) exhibited by the patients [8]. The minimum and maximum antibody titers ranged from 0.001-0.746 μg/ml and 5.45-11.12 μg/ml, respectively, depending on the number of symptoms (0 to 5 symptoms) [8]. Quantitative assays are therefore essential for state and federal health agencies to determine the seroprevalence and thus immunity levels of the target community, and to better understand the immune mechanisms for example, in immune compromised individuals. For instance, concentrations of antibodies in blood to spike protein of SARS-CoV-2 were found to be either unaltered post-vaccination or significantly lowered post-vaccination in immune-compromised patients than those of normal people [9]. For vaccine developers, it is crucial to obtain a rapid, quantitative readout of levels of antibodies in the blood samples to track their production rate immediately after vaccine administration and subsequent decay in the following months. A point-of-care, rapid, quantitative assay will ease the compliance burden on the patients involved in clinical trials by not requiring them to repeatedly report to a central laboratory.

Figure 17:
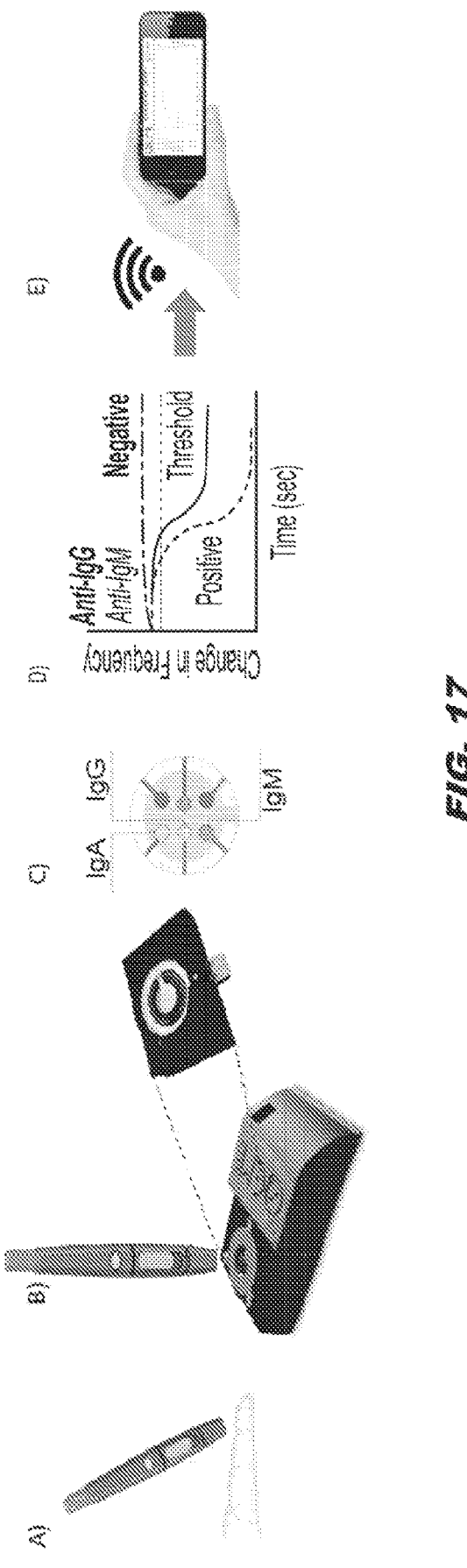
FIG. 17 provides an illustration of the overall concept of Acousto-Ab systems for sensing antibodies in blood. (Panel A) The user will use a lancet to draw a drop of blood. (Panel B) the blood sample will be added to the sensor well in a cartridge (inset) that is integrated to an electronic reader. (Panel C) Multiple sensing electrodes defined on a resonating platform will enable simultaneous detection of multiple antibodies to proteins in the blood sample. (Panel D) Changes in resonant frequency of the resonator under a given sensing electrode is directly proportional to the concentration of the target antibody and (Panel E) will be transmitted wirelessly by the reader to an external hand-held device.
Figure 18:
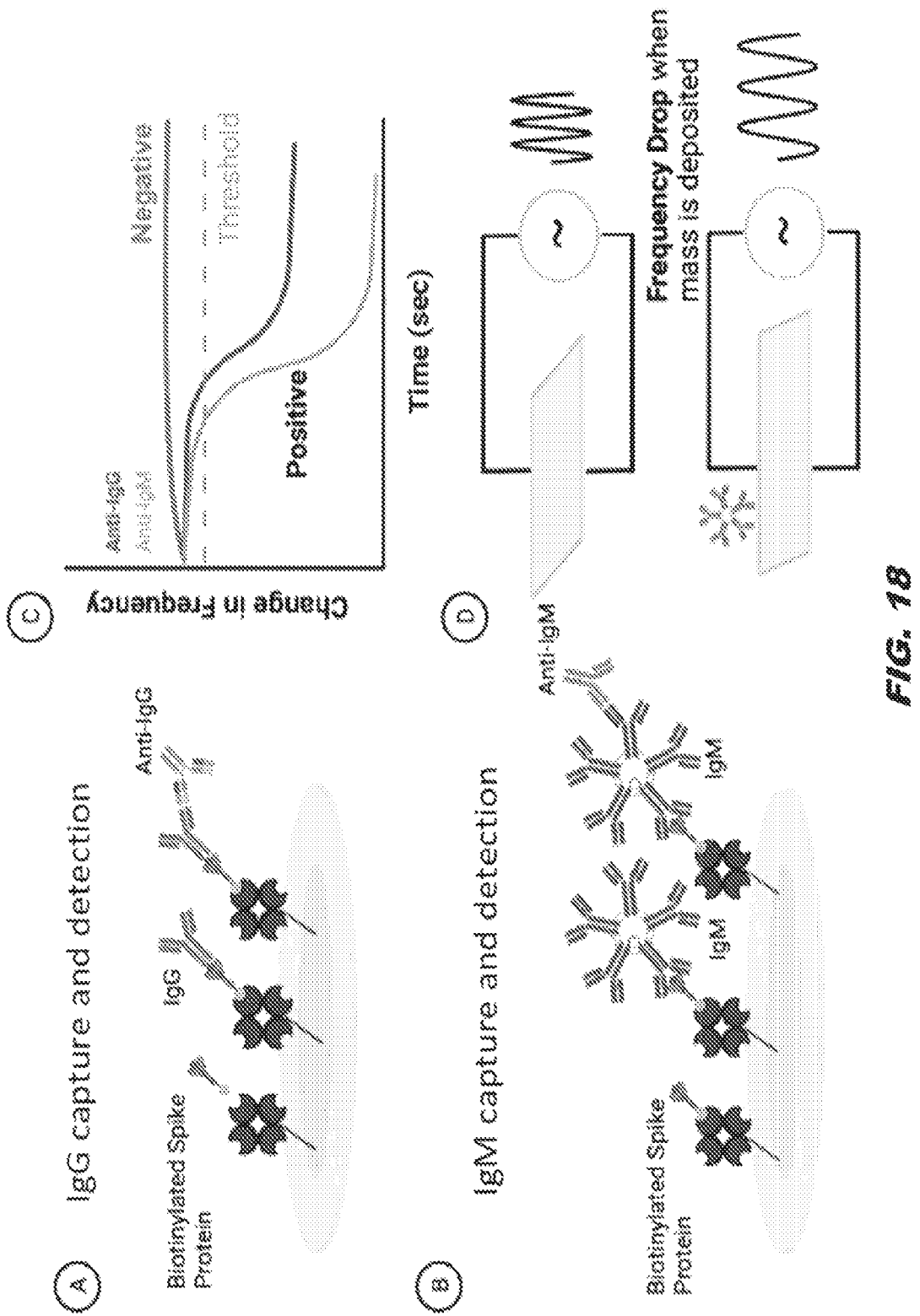
FIG. 18 provides an illustration of the surface immobilization chemistry and the operating principle of the Acousto-Ab system—(Panel A) biotynlated Spike protein are bound to a self-assembled monolayer terminating in streptavidin. Any IgG captured from serum or plasma sample is detected by the subsequent addition of anti-IgG. (Panel B) similar scheme for the detection of IgM. (Panel C) & (Panel D).

Herein, we describe a new, hand-held, point-of-care, rapid quantitative assay, which we call Acousto-Ab, to detect IgG, IgM and IgA antibodies for the SARS-Cov-2 virus, respectively, with high sensitivity and specificity in blood samples to track immunity levels. The approach uses a new gravimetric detection system for antibodies to SARS-Cov-2 proteins that relies on changes in the resonant frequency of an acoustic resonator in response to binding events between the immobilized antigen (receptor-binding domain of the spike S-protein or other sub-units of the S-protein or the nucleocapsid N-protein from SARS-CoV-2) on the surface of the sensor and the antibody that needs to be detected. Such molecular binding events cause changes in mass adhered on the resonator and viscosity of the resonator-liquid interface. We will track energy dissipation changes in addition to changes in resonant frequency of the resonator to simultaneously track mass and viscosity changes in the interface. The overall concept is illustrated in FIG. 17 and the sensing principle is illustrated in FIG. 18. The gravimetric approach using resonators will allow our platform to integrate sensing of multiple biomarkers from the same blood sample in a single sensor cartridge. The approach will go a long way to future-proof the technology to new discoveries of immune biomarkers for COVID19, resulting in new emerging point-of-care disease screening markets.

Herein centers on physical and chemical methods to track changes in the resonant frequencies (in response to biomolecular binding events) of multiple millimeter- or micrometer-scale acoustic resonators on a single substrate reliably and simultaneously while operating in a highly viscous liquid medium such as blood. This allows label-free detection from one sample without the need for microfluidics.

The effort is a systematic application of our prior knowledge and experience designing and developing acoustic resonators platforms for sensing neurotransmitter γ-aminobutyric acid (GABA) & anti-GABA, and also monitoring the dynamics of cell adhesion [10-15]. We will use this experience to develop our prototype Acousto-Ab point-of-care diagnostic and systematically optimize the sensitivity, cross-reactivity or specificity, and stability.

Work measuring anti-GABA using commercially-available acoustic resonators demonstrated a detection limit of 10 nM and a change in frequency of 500 Hz for 10 μg/ml of anti-GABA [14, 15]. A virtue of the proposed sensing platform is that the sensitivity of the acoustic resonator operating under viscous fluids can be further optimized for resonant frequency and the dimensions of the sensing area, as we have demonstrated in our studies [11, 12]. We have shown that we can achieve increases in sensitivity of over seven orders of magnitude by increasing the resonant frequency (up to 60 MHZ) and the dimensions of the sensing area of the electrode (minimum diameter of 30 μm). In phase I of this project proposal, we will focus on the deployment of the α-prototype in a commercial laboratory that meets the FDA's requirement for sensitivity, specificity, and stability for LDT approval to achieve business feasibility. Subsequently, we will file point-of-care FDA Class II or EUA in phase II whichever meets our business needs.

Project 1—We will design, develop and test an α-prototype of Acousto-Ab system to detect antibodies to a S-protein in human blood samples and obtain early customer feedback.

Rationale—We have demonstrated that the approach will work for antibodies to neurotransmitter GABA and in sensing purified samples of monoclonal IgG antibodies to the N-protein in PBS and S1-protein of SARS-CoV-2 in calf serum. The method will be validated in sero-positive human blood samples with IgG, IgM and IgA levels typically observed in COVID-19 patients in the weeks following infection. The acoustic sensors can be optimized for dynamic range and sensitivity to perform under varying levels of viscosity typically seen in blood, sample volumes, and sample injection methods. The temporal levels of different classes of antibodies (IgM, IgG, IgA) in blood are a powerful biomarker panel that can be used to understand temporal progression of pathology and can help to both classify disease stage and severity and focus treatment approaches.

IgM can be an indicator of early immune response, after which class-switching is observed. Additionally, in human Covid-19 pathology, IgA is a potent, neutralizing antibody that plays a crucial role in the immune response, especially toward viral and other pathogens. Although it can be found in mucosal linings, IgA is the second-most abundant antibody in serum and has a proinflammatory role in activating astrocytes and myeloid lineage cells that include macrophages, monocytes, microglia, neutrophils. However, recent studies show that high IgA levels correspond to disease severity in Covid-19 patients and are expressed persistently in serum up to 365 days post infection [16, 17]. Serum IgA is 3-fold higher in patients with severe COVID [18] In human Covid-19 pathology, IgA is a potent, neutralizing antibody that plays a crucial role in the immune response, for example toward viral and other pathogens.

We will integrate 10 and 25 MHz quartz crystal resonators with a sandwich assay involving biotinylated S-protein or N-protein from SARS-CoV-2 immobilized on the sensor surface as shown in FIG. 18. The test serum samples will have unknown quantities of IgG, IgM or IgA antibodies and will be mixed with known amounts of human anti-IgG or human anti-IgM or human anti-IgA to detect IgG, IgM or IgA respectively. We will utilize proven immobilization methods, illustrated in FIG. 18, to produce stable anchoring of bioactive antigen molecules with reproducible orientations to ensure consistent coating on the gold electrodes (yellow oval in FIG. 18) on the quartz resonator (blue oval in FIG. 18). In embodiments, commercially available biotinylated SAM will be applied to the gold surface. This is followed by the attachment of streptavidin and then biotinylated sub-units or receptor-binding domain (RBD) of S-protein or N-protein. The N-protein (amino acid residues 1-419, Genbank accession QHD43423.2), the spike protein (Genbank accession QHD43416.1), S1 domain composed of amino acid residues 16-690, the S2 domain (amino acid residues 698-1213), and the RBD region of the S1 (amino acid residues 319-541), will be tested as antigens. We will use protein BLAST analysis (blast.ncbi.nlm.nih.gov/Blast) to determine the sequence homologies of N and S proteins to the corresponding protein sequences from other SARS-CoV-2 isolates deposited in the GenBank database (taxonomy id 694009), and to try to achieve >98% homology. We will also try to minimize the sequence homology to the respective N and S proteins from four human coronaviruses (strains OC43, HKU1, 229E, and NL63) that cause common cold symptoms to minimize interferents and enhance specificity. The Human SARS-Cov-2 Serology Standard (a pool of plasma from four donors) will be obtained from Fredrick National laboratory for cancer research for final testing. Alternatively, we will buy commercially available human blood samples (Covid+/-) from Innovative Research Inc. (Novi, MI).

Filtering blood samples—The disposable cartridge housing the sensor will have a sealed well into which a drop (~50 μl) of blood sample will be dispensed as illustrated in FIG. 16 using a commercially available blood lancet pen. The sealed well will contain heparinized dilution buffer (10× dilution factor) and a commercial graphene filter at the bottom to separate plasma from cells. Studies in our lab indicate the 10× dilution factor allows for (1) detection of anti-S protein antibody levels within the published dynamic range for human pathology and (2) minimizes non-specific binding effects on the sensor. The diluted plasma with the anti-S antibodies will then be filtered into the QCM-sensor well in the disposable cartridge via gravity flow (~100 μl volume) and tested for virus-antibody binding events in both single and multi-channel Acousto-Ab platforms.

Finally, the sensor will be topped with 20 μg/ml of anti-human IgG or IgM or IgA (depending on whether we are sensing IgG, IgM or IgA respectively) that will elicit a change in resonant frequency proportional to the concentration of IgG, IgM or IgA from the sample that is already bound to the sensor. Alternatively, all three (anti-human IgG, IgM and IgA) will be added in sequence on the same sensor to give a sequential read-out of IgG, IgM and IgA respectively. Each stage will be monitored via response of the Acousto-Ab sensor, atomic force microscopy (AFM), and X-ray photoelectron spectroscopy (XPS) available at ASU for industrial users for a service fee. We will validate various concentrations of IgG/IgM/IgA ($1 \times 10^{-4}$-100 μg/ml) and build dose-response curves with change in resonant frequency plotted as a function of antibody concentration (FIG. 13). We will use commercial open-QCM systems during the initial prototyping phase to obtain rapid customer feedback.

Sensitivity to antibodies: In embodiments, the sensor will measure anti-IgG (or anti-IgM or anti-IgA) binding to any IgG (or IgM or IgA) from the serum sample once the antibodies bind to the immobilized S-protein on the sensor surface. Raw data (in FIG. 13) from our most recent Acousto-Ab sensor using the immobilization chemistry described herein on a conventional 10 MHz quartz resonator shows high sensitivity in measuring 12-100 ng/ml of anti-S IgG antibody in 100 μl of plasma from calf blood. Sensitivity analysis of the above Acousto-Ab sensors using their responses to different concentrations of anti-S IgG antibody shows a sensitivity of 1.74 Hz/ng/ml. There was a measurable response of 48.3 Hz to non-specific binding of plasma proteins (in calf blood) on the surface of the sensor. A drop of blood from a finger stick (~50 μl) is estimated to contain 362 ng & 882 ng of IgM and IgG, respectively, which is far larger than the values tested in other experiments described herein. Therefore, experiments indicate that the sensitivity of the current Acoust-Ab system appears to be more than adequate for human blood samples. Typical half-life (in days) and serum levels of IgG, IgM and IgA in humans are summarized in Table 4. A recent study reported the antibody-titers of 120 seropositive individuals ranged 0.001-11 μg/ml [8].

TABLE 4

| Comparison of IgG, IgM & IgA in Normal Human Serum | | | |
|---|---|---|---|
| Antibody Type | Approximate Molecular Weight (g/mol) | Typical Half-life in Blood (days) | Typical Serum Levels (mg/ml) *age-dependent |
| IgG | ~150,000 | ~25 | 3.5-47 |
| IgM (pentamer) | ~900,000 | ~5-6 | 0.5-2.0 |
| IgA | ~160,000 (monomer, serum) ~320,000 (dimer, secretory, mucosa) | ~4-6 | 2-3 |

We will perform expanded versions of such sensitivity analyses to determine calibration curves for Acousto-Ab for a wide range of concentrations of IgG, IgM and IgA antibodies to the RBD domain of the spike protein (S-protein) in plasma. Under experimental conditions, these calibration curves will be used to determine the concentrations of IgG, IgM and IgA in plasma sample from the measured responses of Acousto-Ab. Replicates of 5 each for ten distinct concentrations of IgG, IgM and IgA, at an $\alpha$=0.05, is expected to result in a statistical power of 0.89. IgG can be found in monomeric form, whereas IgM can be found in pentamers, which is reflected in the 6-fold relative change in molecular weight (Table 4). This change is expected to result in a higher sensitivity.

Testing for cross-reactivity or specificity—We will validate the serologic cross-reactivity of the diagnostic platform for human IgG, IgM, IgA antibodies to available anti-human IgG, IgM, and IgA.

Power analysis—For n=5 trials, and a of 0.05, 10% variability and a difference in means of 20%, the statistical power of the above comparison is estimated to be 0.89.

The FDA also recommends testing for cross-reactivity against the following antibodies—anti-influenza A (IgG and IgM), anti-influenza B (IgG and IgM), anti-HCV (IgG and IgM), anti-HBV (IgG and IgM), anti-*Haemophilus* influenza (IgG and IgM), anti-229E (alpha coronavirus), anti-NL63 (alpha coronavirus), anti-OC43 (beta coronavirus), anti-HKU1 (beta coronavirus), ANA, anti-respiratory syncytial virus (IgG and IgM) and anti-HIV. We will test a minimum of 5 individual samples for each disease/infectious agent/ antibody class listed above (as per FDA recommendation). In addition, we will prepare plasma samples spiked with the IgM or IgG or IgA antibodies for the underlying conditions. We will use commercially-available IgM or IgG antibodies panels for the underlying conditions collected before the COVID-19 pandemic to ensure the panels are SARS-CoV-2 antibody negative.

Class-specificity testing—Since our Acousto-Ab devices will quantitatively assess the different classes of immunoglobulins, we will perform the following class-specificity testing as recommended by the FDA. We will use the dithiothreitol (DTT) assay on all configurations of the Acousto-Ab diagnostic systems to assess their class-specificity, where the signal due to IgM either decreases or becomes negative upon application of DTT but the signal due to IgG remains unaffected. We will test the Acousto-Ab systems with five samples each of (IgG/IgM, +/+), (IgG/IgA, +/+), (IgA/IgM, +/+) and two replicates each (as recommended by the FDA template). We expect to see 100% agreement between the results of the diagnostic systems and the expected outcome of DTT treatment (−/+) to IgM/IgG, +/+. To confirm DTT activity, a positive control test will also be included.

Milestone 1—Completion of $\alpha$-Prototype of Acousto-Ab Platform.

Project 2—we Will Optimize and Test β-Prototypes of Acousto-Ab Platform for S- and N-Proteins Based on Early Customer Feedback from Our $\alpha$-Prototypes.

Based on our reading of the literature and user interviews, without wishing to be bound by theory, we will see the following—(1) improvement in sensitivity and detection limit to match those of ELISA with a detection limit of 0.1 ng/ml and sensitivity of at least 1-5 Hz/ng/ml for IgG, IgM and IgA to S-protein and N-protein in blood samples. (2) expand the repertoire of Acousto-Ab to assess IgG, IgM and IgA to S- & N-protein of SARS-Cov-2.

Enhanced sensitivities—Without wishing to be bound by theory, the calculated sensitivity of the commercial crystals can sense IgG, IgM and IgA from COVID-19 positive patients, as indicated by our estimates herein. However, estimates from seropositive patients indicate antibody titers as low as one ng/ml in asymptomatic patients[7]. If lower detection limits emerge as being important in our customer interviews, we will use the techniques outlined previously[13] to validate electrode diameters in the range of 50 μm-5 mm and resonant frequencies (10, 25, and 60 MHz) to enhance sensitivities and detection limits. The sensitivity of the resonator is directly proportional to the square of electrode diameter if the resonator is operating in the air, as given by the classic Sauerbrey equation. Another way to explain this electrode diameter-sensitivity relationship is through an improvement in the Q-factor of the resonator that is caused by a decrease in electrical resistance of the electrodes as its diameter increases. However, when the resonators operate in liquid, particularly in a viscous liquid such as blood or plasma (at room temperature), the viscous interface on the electrode adds further resistance to the crystal resulting in dampening of oscillations, decrease in Q-factor, and loss of sensitivity. We will use the theoretical equations and experimental results outlined in our most recent publication to achieve up to seven orders of magnitude increase in sensitivity to counter any loss of sensitivity due to the viscosity of blood.

We will purchase blank quartz crystals from Xeco Inc., Cedar City, UT, USA and use ink-jet printing to pattern electrodes on the surface of the crystal. The printing process will be done for a service fee via an ink-jet printer (DMP-2850, Fujifilm Dimatix, USA) fitted with a piezo-driven 16-nozzle print-head available in the lab of MK in AUB. The conductive patterns and coatings will be printed using a 1 pL cartridge, while the passivation layers will be printed using a 10 pL cartridge.

Expanded repertoire of antibody sensing—Current antibody assays for COVID-19 usually detect anti-S protein or anti-N protein antibodies since the S- and N-proteins are considered highly immunogenic [5, 19]. Therefore, in a separate diagnostic, we will expand the repertoire of Acousto-Ab platform to sense IgG, IgM & IgA antibodies to the N-protein.

If a significant false-positive rate (>5%) is observed, we will validate different anti-human-IgG, anti-human-IgM and anti-human IgA to identify candidates that minimize response of the sensor to cross-reactivity. We will also validate alternate antigen sequences with lower homologies to other human antibodies that are potential cross-reactants.

Testing and improving the stability of the sensing cartridge—We will validate methods to extend the shelf life of the sensing cartridge at room temperature via stabilizing the surface-bound S1-protein or N-protein.

Rationale—Deploying embodiments described herein in the field requires accounting for conditions that may affect the stability and lifetime of the anti-IgG, anti-IgM and anti-IgA in the sensing cartridge.

Experimental Design—The process for adding stabilizers will consist of covering the surface with (a) 0.15 M blocking buffer (Thermo Fisher Scientific, USA), (b) 5% w/v sucrose (catalog #AC177142500, Acros organics), and (c) coating stabilizer and blocking buffer diluted 1:1 with water. The devices will then be aspirated and dried. All devices will be stored at 50° C. to age the coating (1 day at 50° C. is equal to 6.5 days at room temperature). We will assess the stability of the coating at ten days, three weeks, and three months. We will attempt to achieve an 18-month shelf life at room temperature. Besides the in-use stability assessment of reagents in the above experiments, we will also assess the stability of the reagents under the following conditions:

Shelf-life stability—Reagent shelf life will be assessed by real-time stability testing, with reagents stored at the specified storage temperature.

Stress testing—The reagents will be cycled through temperatures of 4° C. and ambient temperature to mimic shipping conditions. A separate cohort of reagents will be cycled through different light conditions to simulate shipping conditions. They will then be placed under normal storage conditions and their in-use stability assessed.

outcomes—Without wishing to be bound by theory, samples covered by sucrose will have the highest stability.

Milestone 2—Completion of α-prototype.

Milestone 3—Completion of cross-reactivity assessments for the α- & β-prototypes.

We will scale up the Acousto-Ab platforms to simultaneously sense more than one antibody from a single sample.

Rationale—A unique innovation of our system is to do multiplexed label-free assessment of antibodies from a single sample using multiple resonators fabricated on the same substrate (avoiding the need for fluidics). As new variants of the SARS-Cov-2 emerge, it is important to have a quantitative profile of antibodies to the different subdomains of the S-protein and other viral proteins. Such multi-dimensional profiling of blood biomarkers of immunity will not only be necessary to assess efficacies of neutralizing antibodies but also to assess the level of immunity and to track infection progression and severity of disease. Recent microarray studies[19] have also identified antibodies to other viral proteins such ORF9b and NSP5 as being activated in seropositive patients. Therefore, in addition to S-, N- and the RBD domain of S-proteins, we will validate the capability of the diagnostic to simultaneously measure NSP5 antibodies to assess the generalizability of the diagnostic platform.

Sensor design—Electrodes (sensing area) corresponding to multiple sensing sites will be spaced at least one electrode diameter apart to minimize interference in the acoustic waves between neighboring sites. In our prior studies, we have successfully demonstrated the use of multiple microscale acoustic sensors on the same quartz substrate to sense neuronal activity over a period of 9 days in culture, as shown in FIG. 14. The diameter and thickness of each electrode (along with sensor frequency) will determine final sensitivity. As in previous sections, we will use inkjet printing to build our electrodes (sensing area) on both sides of the quartz substrate. (FIG. 14).

Chemistry—We can pattern biomolecules on these microscale electrodes of gold and conductive polymers. Therefore, we can use that capability to pattern different proteins and their sub-units (S1-protein, N-protein, RBD domain of the spike protein, or NSP5) on each of the microscale electrodes using the same immobilization chemistry outlined in FIG. 18 except that the different proteins (S1, nucleocapsid (N), and the NSP5) will be spot printed on separate electrodes sequentially (as shown in FIG. 15). We can use a drop-on demand system (FluidFM BOT, Switzerland) which can be used for manipulating cells, that our team modified for liquid spotting, that allows for precision control when adding liquids to the surface.

Testing—We will add plasma samples directly to the sensor cartridge housing the quartz substrate with multiple sensors. After allowing for equilibration, we will add anti-human IgG or IgM or IgA depending on whether we are detecting IgG, IgM or IgA respectively.

Completion of Multi-Channel Prototype of Acousto-Ab Platform.

The relative proportions of IgM/IgG/IgA will also be validated by different fluorescently bound secondary antibodies. In the event, we don't achieve desired specificity with anti-human IgG, IgM and IgA, we will attempt to create a response profile of frequency changes at harmonics of the resonant frequency that will help distinguish between IgG/IgM/IgA due to differences in binding kinetics to antigen. We will monitor the above profile of frequency changes in response to a combinatorial application of different Ig-specific proteases such as Igase (specific to IgA), IdeZ (specific to IgG), serine proteases (specific to IgM). As the different proteases cleave their respective Ig, the profile of frequency changes in response to those events will determine the different fractions of IgG/IgM/IgA bound to the viral protein on the surface of the sensor. A second alternative is to use Protein A or G (binds to the Fc domain of IgG) to characterize the presence of IgG and jacalin (an IgA specific lectin) to characterize the presence of IgA and its corresponding change in resonant frequency of the resonator.

Testing with serological samples—We will test retrospectively-collected SARS-CoV-2 antibody-positive specimens from patients that have been previously confirmed infected by SARS-CoV-2 RT-PCR tests. These specimens will be purchased. The specimens will be accompanied by basic information such as the population from which the sample was drawn and the comparator method, specimen collection date, date of onset of symptoms (if present/known), and comparator method to confirm infection with SARS-CoV-2.

References Cited in this Example
1. Lee, C. Y. P., et al., Serological Approaches for COVID-19: Epidemiologic Perspective on Surveillance and Control. Frontiers in Immunology, 2020. 11(April): p. 1-7.
2. Harpaz, R., R. M. Dahl, and K. L. Dooling, Prevalence of Immunosuppression Among US Adults, 2013. JAMA, 2016. 316(23): p. 2547-2548.
3 Bastos, M. L., et al., Diagnostic accuracy of serological tests for covid-19: Systematic review and meta-analysis. The BMJ, 2020. 370.
4. Ainsworth, M., et al., Performance characteristics of five immunoassays for SARS-CoV-2: a head-to-head benchmark comparison. The Lancet Infectious Diseases, 2020. 20(12): p. 1390-1400.
5. Grzelak, L., et al., A comparison of four serological assays for detecting anti-SARS-CoV-2 antibodies in human serum samples from different populations. Science Translational Medicine, 2020. 12(559).

6. Li, Z., et al., Development and clinical application of a rapid IgM-IgG combined antibody test for SARS-CoV-2 infection diagnosis. Journal of Medical Virology, 2020. 92(9): p. 1518-1524.

7 Liu, G. and J. F. Rusling, COVID-19 Antibody Tests and Their Limitations. ACS Sensors, 2021. 6(3): p. 593-612.

8. Bartsch, Y. C., et al., Discrete SARS-CoV-2 antibody titers track with functional humoral stability. Nature Communications, 2021. 12(1).

9. Hagin, D., et al., Immunogenicity of Pfizer-BioNTech COVID-19 vaccine in patients with inborn errors of immunity. J Allergy Clin Immunol, 2021. 148(3): p. 739-749.

10. Zhou, A. and J. Muthuswamy, Acoustic biosensor for monitoring antibody immobilization and neurotransmitter GABA in real-time. Sensors and Actuators B: Chemical, 2004. 101(1): p. 8-19.

11. Khraiche, M. and J. Muthuswamy, Multi-modal biochip for simultaneous, real-time measurement of adhesion and electrical activity of neurons in culture. Lab on a Chip, 2012.

12. Khraiche, M. L., J. Rogul, and J. Muthuswamy, Design and development of microscale thickness shear mode (TSM) resonators for sensing neuronal adhesion. Frontiers in Neuroscience, 2019.

13. Khraiche, M. L., A. Zhou, and J. Muthuswamy, Acoustic sensor for monitoring adhesion of Neuro-2A cells in real-time. Journal of Neuroscience Methods, 2005.

14. Wang, T., et al., Immobilization and characterization of gamma-aminobutyric acid on gold surface. J Biomed Mater Res A, 2006. 79(1): p. 201-209.

15. Wang, T. and J. Muthuswamy, Immunosensor for detection of inhibitory neurotransmitter gamma-aminobutyric acid using quartz crystal microbalance. Anal Chem, 2008. 80(22): p. 8576-8582.

16. Dobano, C., et al., Persistence and baseline determinants of seropositivity and reinfection rates in health care workers up to 12.5 months after COVID-19. BMC Med, 2021. 19(1): p. 155.

17. Kulikowska, J., et al., The Significance of COVID-19 Immunological Status in Severe Neurological Complications and Multiple Sclerosis-A Literature Review. Int J Mol Sci, 2021. 22(11).

18. Ivanov, A. and E. Semenova, Long-term monitoring of the development and extinction of IgA and IgG responses to SARS-CoV-2 infection. J Med Virol, 2021. 93(10): p. 5953-5960.

19. Jiang, H. W., et al., SARS-CoV-2 proteome microarray for global profiling of COVID-19 specific IgG and IgM responses. Nat Commun, 2020. 11(1): p. 3581.

Example 5

Commercially available, 10 MHz crystals (14 mm diameter) with gold electrodes (QCM Open, Novaetech™ Srl) were sensitized with spike receptor binding domain (RBD) protein as the sensing element using carboiimide (EDC-NHS) chemistry (FIG. 7) and streptavidin-biotin linkage (FIG. 8). The QCM was placed in 20 mM 11-mercaptoundecanoic acid (11-MUA, Chemcruz™) in absolute ethanol for at least 24 hours at room temperature)(23° ° C. Next the 11-MUA treated QCM was incubated with 1:1 ratio (10 mg/ml) of 1-ethyl-3-(3-dimethylaminopropyl) carboiimide hydrochloride (EDC-HCL) and N-hydroxysuccinimide (NHS) in 0.1 M 4-morpholineethanesulfonic acid (MES) for 1 hour and washed once with MES buffer, followed by streptavidin (Millipore™) (200 µg/ml) in MES buffer for 1 hour. The streptavidin-immobilized surface was washed thrice in PBS (3 min each) followed by 1 M ethanolamine in phosphate buffered saline (0.01 M PBS, pH 8) to remove unreacted NHS for 30 min. After washing again in PBS thrice, the streptavidin immobilized QCM surface was incubated with 2 µg/ml of biotinylated-spike protein (Sino Biological, catalog number 40592-V27H-B) overnight. After washing in PBS, the QCM-Spike-Sensor was blocked in diluted calf-blood serum (1:10) overnight (~8 hours) to minimize non-specific adsorption and washed once in PBS prior to use.

(FIG. 9) For calibration, IgG-Spike was serially diluted (1 µg/ml, 100 ng/ml, 50 ng/ml, 25 ng/ml, 12.5 ng/ml) in diluted calf blood serum isolated by centrifuging heparinized, whole calf blood (Rockland, inc.™) for 60 min at approximately 1000×g, followed by dilution (1:10) in PBS. The QCM-Spike-Sensors were placed in the OpenQCM module and calibrated to their resonance frequency (~10 MHz) in 100 µl of PBS. Sensorograms were generated by manually pipetting in and replacing solutions (100 µl) in the sensor well every 5 min.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A diagnostic platform for detection of at least one biomarker in a fluid sample comprising:
   a quantitative sensing device configured to receive the fluid sample, wherein the fluid sample comprises blood, blood serum, or plasma;
   an electronic reading platform; and
   a computing device;
   wherein the sensing device comprises
      a layer of piezoelectric material comprising two faces;
      at least one electrode layer, wherein the at least one electrode layer is affixed to one face of the piezoelectric material, wherein the at least one electrode layer comprises
         a thickness of about 33 nm to about 300 nm, and
         a diameter of about 150 μm to about 350 μm;
      a second reference electrode layer that is affixed to a second face of the piezoelectric material;
      at least two disposable sensor cartridges, wherein one of the at least two sensor cartridges comprises a means for detecting IgG antibodies in the fluid sample and the other sensor cartridge comprises a means for detecting IgM antibodies in the fluid sample, wherein the IgG and IgM antibodies are quantitively detected;
      a Q-factor of at least 10,000;
      an operating frequency of about 10 MHz to about 90 MHz; and
      a sensing layer disposed upon the at least one electrode layer, wherein the sensing layer is configured to bind the at least one biomarker for a disease or condition, wherein the biomarker comprises an IgG antibody, an IgM antibody, or a combination thereof;
   wherein the quantitative sensing device is communicatively linked with the electronic reading platform,
   wherein the electronic reading platform is configured to receive sensor data from the sensing device and to communicate the data to the computing device,
and wherein the computing device is configured to determine the presence, absence, or amount of the at least one biomarker; and
   wherein the diagnostic platform quantitatively detects the at least one biomarker within about 10 minutes.

2. The diagnostic platform of claim 1, further comprising a fingerstick system configured to obtain the blood from a patient.

3. The diagnostic platform of claim 1, wherein the diagnostic platform comprises a portable, hand-held device.

4. The diagnostic platform of claim 3, wherein the portable, hand-held device is configured to be worn by a user.

5. The diagnostic platform of claim 1, wherein the diagnostic platform is configured to determine the presence, absence, or amount of the at least one biomarker within about 10 minutes after the fluid sample contacts the sensing device.

6. The diagnostic platform of claim 1, wherein the piezoelectric material comprises a quartz crystal, PZT (lead zirconate titanate), lead titanate, Barium titanate, Zinc Oxide, lead magnesium niobate lead titanate (PMNPT), polyvinylidene difluoride, polyvinylidene fluoride (PVDF), Aluminum nitride, Gallium nitride, or a combination thereof.

7. The diagnostic platform of claim 1, wherein the piezoelectric material comprises a diameter of up to about 153 mm.

8. The diagnostic platform of claim 1, wherein the piezoelectric material comprises a thickness of up to about 3 mm.

9. The diagnostic platform of claim 1, wherein the electrode layer comprises at least one working electrode.

10. The diagnostic platform of claim 9, wherein the at least one working electrode comprises a conductive film.

11. The diagnostic platform of claim 10, wherein the conductive film comprises gold, indium tin oxide (ITO), or a combination thereof.

12. The diagnostic platform of claim 1, wherein the sensing device comprises a thickness shear mode (TSM) transducer.

13. The diagnostic platform of claim 1, wherein sensing layer comprises an antigen or an antibody that is specific for the at least one biomarker.

14. The diagnostic platform of claim 13, wherein the antigen or antibody specific for the at least one biomarker is immobilized on the electrode layer.

15. The diagnostic platform of claim 14, wherein the at least one biomarker is immobilized by self-assembled monolayer (SAM).

16. The diagnostic platform of claim 1, wherein the disease or condition is caused by a coronavirus.

17. The diagnostic platform of claim 1, wherein the disease or condition comprises COVID-19, severe acute respiratory syndrome, a tissue inflammation or a combination thereof.

18. The diagnostic platform of claim 1, wherein the sensing layer comprises:

a severe acute respiratory syndrome coronavirus 2 (SARS-COV-2) structural protein or an antibody thereto immobilized on a surface of the at least one electrode layer; and IgG, IgM, or a combination thereof, wherein the IgG, IgM, or a combination thereof is tethered to the SARS-COV-2 structural protein.

19. The diagnostic platform of claim 18, wherein the SARS-COV-2 structural protein or the antibody thereto is immobilized to the surface of the at least one electrode layer via a self-assembled monolayer (SAM).

20. The diagnostic platform of claim 19, wherein the SAM comprises a streptavidin-biotin bond, a thiol-bond, or a combination thereof.

21. The diagnostic platform of claim 18, wherein the SARS-COV-2 structural protein comprises an S Protein, an N protein, an M protein, or a combination thereof.

22. The diagnostic platform of claim 1, comprising at least one stabilizing solution that is configured to extend the shelf life of the diagnostic platform for up to at least 12 months.

23. The diagnostic platform of claim 1, wherein the sensing device is communicatively linked with the electronic reading platform via a USB connection.

24. The diagnostic platform of claim 1, wherein the computing device comprises a mobile computing device, the diagnostic platform further comprising:

an application running on a processor of the mobile computing device, wherein the electronic reading platform is communicatively linked to the mobile computing device; and the electronic reading platform is configured to transmit sensor data to the mobile computing device.

25. The diagnostic platform of claim 1, wherein the electronic reading platform is communicatively linked to the mobile computing device through one or more wireless communications protocols.

26. The diagnostic platform of claim 24, wherein the mobile computing device comprises a portable digital assistant, a tablet, a smartphone, a laptop, or a combination thereof.

27. A method of predicting the existence or progression of a disease or condition or level of immunity in a patient, the method comprising:

obtaining a fluid sample from the patient;

placing the fluid sample on the sensing device of any one of claim 1, 3-12, 13-17, or 18-26;

permitting the diagnostic platform to determine the presence, absence, or amount of the at least one biomarker for the disease or condition;

permitting the diagnostic platform to generate a sensor data report;

reviewing the sensor data report; and predicting the presence or progression of the disease or condition.

28. The method of claim 27, comprising two biomarkers, wherein the disease or condition comprises COVID-19, SARS, or a combination thereof;

one of the two biomarkers comprises IgM antibodies and the remaining biomarker comprises IgG antibodies, wherein the presence of IgM antibodies but not IgG antibodies indicates that the patient is in an intermediate stage of infection;

the presence of IgG antibodies but not IgM antibodies indicates that either the patient is in a late stage or an early stage of recurring infection; or the patient is in a convalescent stage of infection;

the presence of both IgM antibodies and IgG antibodies indicates that either the patient is in a late phase of the infection; or the patient is in recovery stage of infection; and the absence of IgG and IgM antibodies indicates that the patient does not have COVID-19, SARS, or a combination thereof.

29. The method of claim 27, wherein the disease or condition comprises COVID-19, SARS, or a combination thereof;

the at least one biomarker comprises one or more monoclonal IgG or IgM antibodies for an S protein, an N protein, an M protein, or any combination thereof, wherein the presence of any one or more of the biomarkers indicates the presence of the disease or condition.

30. The diagnostic platform of claim 1, wherein the at least one electrode layer comprises a thickness of about 230 nm to about 300 nm, and a diameter of about 200 μm to about 350 μm;

and the piezoelectric material comprises a thickness of about 10 μm to about 3 mm.

* * * * *